United States Patent
Albone et al.

(10) Patent No.: US 11,572,414 B2
(45) Date of Patent: Feb. 7, 2023

(54) ERIBULIN ANTIBODY-DRUG CONJUGATES AND METHODS OF USE

(71) Applicant: EISAI R&D MANAGEMENT CO., LTD., Tokyo (JP)

(72) Inventors: Earl F. Albone, Blue Bell, PA (US); Jared Spidel, Downingtown, PA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 154 days.

(21) Appl. No.: 17/091,819

(22) Filed: Nov. 6, 2020

(65) Prior Publication Data

US 2021/0238304 A1 Aug. 5, 2021

Related U.S. Application Data

(60) Provisional application No. 62/932,373, filed on Nov. 7, 2019.

(51) Int. Cl.
| | |
|---|---|
| A61P 35/00 | (2006.01) |
| C07K 16/30 | (2006.01) |
| A61K 47/68 | (2017.01) |
| A61K 47/60 | (2017.01) |
| A61K 31/357 | (2006.01) |
| G01N 33/574 | (2006.01) |
| A61K 39/00 | (2006.01) |

(52) U.S. Cl.
CPC ........ *C07K 16/3076* (2013.01); *A61K 31/357* (2013.01); *A61K 47/60* (2017.08); *A61K 47/6803* (2017.08); *A61K 47/6851* (2017.08); *A61K 47/6889* (2017.08); *A61P 35/00* (2018.01); *G01N 33/57492* (2013.01); *A61K 2039/505* (2013.01); *C07K 2317/24* (2013.01); *C07K 2317/565* (2013.01); *C07K 2317/732* (2013.01); *C07K 2317/92* (2013.01)

(58) Field of Classification Search
CPC ............ C07K 16/3076; C07K 2317/24; C07K 2317/565; C07K 2317/732; C07K 2317/92; C07K 2317/34; C07K 2317/56; A61K 47/6803; A61K 2039/505; A61P 35/00
USPC ...................................................... 424/133.1
See application file for complete search history.

(56) References Cited

U.S. PATENT DOCUMENTS

| | | | |
|---|---|---|---|
| 4,816,567 | A | 3/1989 | Cabilly et al. |
| 5,290,540 | A | 3/1994 | Prince et al. |
| 5,855,913 | A | 1/1999 | Hanes et al. |
| 5,874,064 | A | 2/1999 | Edwards et al. |
| 5,934,272 | A | 8/1999 | Lloyd et al. |
| 5,985,309 | A | 11/1999 | Edwards et al. |
| 5,985,320 | A | 11/1999 | Edwards et al. |
| 6,019,968 | A | 2/2000 | Platz et al. |
| 6,214,865 | B1 | 4/2001 | Littlefield et al. |
| 6,653,341 | B1 | 11/2003 | Littlefield et al. |
| 10,322,192 | B2 | 6/2019 | Albone et al. |
| 10,548,986 | B2 | 2/2020 | Albone et al. |
| 2018/0193478 | A1 | 7/2018 | Albone et al. |
| 2020/0297860 | A1 | 9/2020 | Albone et al. |
| 2021/0101888 | A1 | 4/2021 | Pazolli et al. |
| 2021/0238304 | A1 | 8/2021 | Albone et al. |
| 2021/0299269 | A1 | 9/2021 | Pazolli et al. |
| 2022/0081486 | A1 | 3/2022 | Henry et al. |

FOREIGN PATENT DOCUMENTS

| | | |
|---|---|---|
| WO | WO 1990/005144 A1 | 5/1990 |
| WO | WO 1992/019244 A3 | 11/1992 |
| WO | WO 1997/032572 A2 | 9/1997 |
| WO | WO 1997/044013 A1 | 11/1997 |
| WO | WO 1998/031346 A1 | 7/1998 |
| WO | WO 1999/066903 A3 | 12/1999 |
| WO | WO 2016/205618 A1 | 12/2016 |
| WO | WO 2017/106643 | 6/2017 |
| WO | WO 2017/136769 | 8/2017 |
| WO | WO 2017/151979 A1 | 9/2017 |
| WO | WO 2019/232449 A9 | 12/2019 |
| WO | WO 2020/123836 A2 | 6/2020 |
| WO | WO 2021/090062 A1 | 5/2021 |
| WO | WO 2021/148003 A1 | 7/2021 |
| WO | WO 2021/248005 | 12/2021 |

OTHER PUBLICATIONS

Ab et al., (2015) "IMGN853, a Folate Receptor-a (FRa)—Targeting Antibody-Drug Conjugate, Exhibits Potent Targeted Antitumor Activity against FRa-Expressing Tumors", *Mol. Cancer Ther.*, 14:1605-1613.

Albone et al., (2017) "Generation of therapeutic immunoconjugates via Residue-Specific Conjugation Technology (RESPECT) utilizing a native cysteine in the light chain framework of Oryctolagus cuniculus", *Cancer Biol. Ther.*, 18(5):347-357.

Baldo et al., (2017) "Amatuximab and novel agents targeting mesothelin for solid tumors", *Onco Target Ther.*,10:5337-5353.

Bird et al., (1988) "Single-Chain Antigen-Binding Proteins", *Science*, 242:423-426.

(Continued)

*Primary Examiner* — Yan Xiao
(74) *Attorney, Agent, or Firm* — Finnegan, Henderson, Farabow, Garrett & Dunner LLP

(57) ABSTRACT

Antibodies, antigen-binding fragments, and conjugates (e.g., antibody-drug conjugates such as those comprising eribulin) thereof that bind to mesothelin are disclosed. The disclosure further relates to methods and compositions for use in the treatment of cancer by administering the compositions provided herein.

6 Claims, 34 Drawing Sheets
Specification includes a Sequence Listing.

(56) References Cited

OTHER PUBLICATIONS

Clackson et al., (1991) "Making antibody fragments using phage display libraries", *Nature*, 352:624-628.
Duke et al., (1992) "Morphological, Biochemical, and Flow Cytometric Assays of Apoptosis", *Current protocols in immunology*, 3.17.1-3.17.16.
Devereux et al., (1984) "A comprehensive set of sequence analysis programs for the VAX", *Nucl. Acid Res.* 12(1):387-395.
Dumontet et al., (2010) "Microtubule-binding agents: a dynamic field of cancer therapeutics", *Nat. Rev. Drug Discov.* 9:790-803.
Fitting et al., (2015) "Phage display-based generation of novel internalizing antibody fragments for immunotoxin-based treatment of acute myeloid leukemia", *MAbs* 7:390-402.
George et al., (1988) "Current Methods in Sequence Comparison and Analysis", *Macromolecule Sequencing and Synthesis, Selected Methods and Applications*, 12:127-149.
Gershoni et al., (2007) "Epitope Mapping: The First Step in Developing Epitope-Based Vaccines", *Biodrugs*, 21(3):145-156.
Hager-Braun et al., (2005) "Determination of protein-derived epitopes by mass spectrometry", *Expert Rev. Proteomics*, 2(5):745-756.
Han et al., (2017) "Mesothelin Expression in Gastric Adenocarcinoma and Its Relation to Clinical Outcomes", *J. Pathol. Transl. Med.*, 51(2):122-128.
Hassan et al., (2008) "Mesothelin targeted cancer immunotherapy", *Eur. J. Cancer*, 44(1):46-53.
Hassan et al., (2016) "Mesothelin Immunotherapy for Cancer: Ready for Prime Time?", *J. Clin. Oncol.*, 34(34):4171-4179.
He et al., (2010) "Targeting Prostate Cancer Cells In Vivo Using a Rapidly Internalizing Novel Human Single-Chain Antibody Fragment", *J. Nucl. Med.*, 51:427-432.
Hendriks et al., (2017) "Antibody-Based Cancer Therapy: Successful Agents and Novel Approaches", *International Review of Cell and Molecular Biology*, 331:289-383.
Holliger et al., (1993) "'Diabodies': Small bivalent and bispecific antibody fragments", *Proc. Natl. Acad. Sci. USA*, 90:6444-6448.
Huston et al., (1988) "Protein engineering of antibody binding sites: Recovery of specific activity in an antidigoxin single-chain Fv analogue produced in *Escherichia coli*", *Proc. Natl. Acad. Sci. USA*, 85:5879-5883.
International Application No. PCT/IB2020/000917, by Eisai R&D Management Co., Ltd, International Search Report and Written Opinion, dated Feb. 19, 2021, 16 pages.
Kabat, (1987 and 1991) "Sequences of Proteins of Immunological Interest", *National Institutes of Health*, Bethesda, Md.
Kachala et al., (2014) "Mesothelin Overexpression Is a Marker of Tumor Aggressiveness and Is Associated with Reduced Recurrence-Free and Overall Survival in Early-Stage Lung Adenocarcinoma", *Clin. Cancer. Res.*, 20(4):1020-1028.

Klein et al., (1997) "Progression of metastatic human prostate cancer to androgen independence in immunodeficient SCID mice", *Nature Medicine*, 3:402-408.
Kohler et al., (1975) "Continuous cultures of fused cells secreting antibody of predefined specificity", *Nature*, 256:495-497.
Marks et al., (1991) "By-passing immunization: Human antibodies from V-gene libraries displayed on phage", *Journal of Molecular Biology*, 222:581-597.
Needleman et al., (1970) "A general method applicable to the search for similarities in the amino acid sequence of two proteins",*Journal of Molecular Biology*, 48:443.
Nichetti et al., (2018) "The Role of Mesothelin as a Diagnostic and Therapeutic Target in Pancreatic Ductal Adenocarcinoma: A Comprehensive Review", *Target Oncol.* 13(3):333-351.
Page et al., (1993) "A new fluorometric assay for cytotoxicity measurements in-vitro", *International Journal of Oncology*, 3:473-476.
Pearson et al., (1988) "Improved tools for biological sequence comparison" *Proceedings of the National Academy of Sciences of the United States of America*, USA 85:2444.
Poljak et al., (1994) "Production and structure of diabodies", *Structure*, 2:1121-1123.
Skehan et al., (1990) "New colorimetric cytotoxicity assay for anticancer-drug screening", *Journal of National Cancer Institute*, 82:1107-12.
Smith et al., (1981) "Comparison of biosequences", *Advances in Applied Mathmatics*, 2:482-489.
Strohl et al., (2012) "Monoclonal antibody targets and mechanisms of action", *Therapeutic Antibody Engineering*, 163-196.
Tan et al. (2009) "Phase I Study of Eribulin Mesylate Administered Once Every 21 Days in Patients with Advanced Solid Tumors", *Clin Cancer Res.*, 15(12):4213-4219.
Tzartos, (1998) "Epitope Mapping by Antibody Competition", *In Methods in Molecular Biology: Epitope Mapping Protocols*, Morris ed., Humana Press, 66:55-66.
Vahdat et al., (2009) "Phase II Study of Eribulin Mesylate, a Halichondrin B Analog, in Patients With Metastatic Breast Cancer Previously Treated With an Anthracycline and a Taxane", *J. Clin. Oncol.*, 27(18):2954-2961.
Wang et al., (2012) "Inhibition of Mesothelin as a Novel Strategy for Targeting Cancer Cells", *PLoS ONE*, 7:e33214.
Ward et al., (1989) "Binding activities of a repertoire of single immunoglobulin variable domains secreted from *Escherichia coli*", *Nature*, 341(6242):544-546.
Weekes et al., (2016) "Phase I Study of DMOT4039A, an Antibody-Drug Conjugate Targeting Mesothelin, in Patients with Unresectable Pancreatic or Platinum-Resistant Ovarian Cancer", *Mol Cancer Ther.*, 15(3)439-447.
Zhao et al., (2016) "Novel Antibody Therapeutics Targeting Mesothelin in Solid Tumors", *Clin Cancer Drugs*, 3(2):76-86.
Zhu et al., (2010) "Identification of internalizing human single-chain antibodies targeting brain tumor sphere cells", *Molecular Cancer Therapeutics*, 9:2131-2141.

|   | 1 | 2 | 3 | 4 | 5 | 6 | 7 | 8 | 9 | 10 | 11 | 12 |
|---|---|---|---|---|---|---|---|---|---|---|---|---|
| A | 2012_10N8-HC | 2012_10N8-LC | 2012_106 A19-HC | 2012_106 A19-LC | 2012_172 K8-HC | 2012_172 K8-LC | 2012_311 N18-HC | 2012_311 N18-LC | 2012_28 O4-HC | 2012_28 O4-LC | 2012_11 2D7-HC | 2012_11 2D7-LC |
| B | 2012_33O1-HC | 2012_33O1-LC | 2012_105 O2-HC | 2012_105 O2-LC | 2012_172 I3-HC | 2012_172 I3-LC | 2012_308 H21-HC | 2012_308 H21-LC | 2012_43F8-HC | 2012_43F8-LC | 2012_201 C15-HC | 2012_201 C15-LC |
| C | 2012_43I12-HC | 2012_43I12-LC | 2012_110 J23-HC | 2012_110 J23-LC | 2012_175 D24-HC | 2012_175 D24-LC | 2012_324 F17-HC | 2012_324 F17-LC | 2012_82N2-HC | 2012_82N2-LC | 2012_238 B22-HC | 2012_238 B22-LC |
| D | 2012_55B4-HC | 2012_55B4-LC | 2012_111 J23-HC | 2012_111 J23-LC | 2012_176 J16-HC | 2012_176 J16-LC | 2012_345 A12-HC | 2012_345 A12-LC | 2012_92N19-HC | 2012_92N19-LC | 2012_250 P7-HC | 2012_250 P7-LC |
| E | 2012_62B10-HC | 2012_62B10-LC | 2012_131 F19-HC | 2012_131 F19-LC | 2012_204 E7-HC | 2012_204 E7-LC | 2012_346 C6-HC | 2012_346 C6-LC | 2012_97N24-HC | 2012_97N24-LC | 2012_246 F14-HC | 2012_246 F14-LC |
| F | 2012_82 M2-HC | 2012_82 M2-LC | 2012_145 D4-HC | 2012_145 D4-LC | 2012_215 O6-HC | 2012_215 O6-LC | 2012_347 H14-HC | 2012_347 H14-LC | 2012_161 O23-HC | 2012_161 O23-LC | 2012_262 H11-HC | 2012_262 H11-LC |
| G | 2012_99 B7-HC | 2012_99 B7-LC | 2012_147 F21-HC | 2012_147 F21-LC | 2012_264 B14-HC | 2012_264 B14-LC | 2012_360 I17-HC | 2012_360 I17-LC | 2012_102 A6-HC | 2012_102 A6-LC | 2012_264 E24-HC | 2012_264 E24-LC |
| H | 2012_95 B8-HC | 2012_95 B8-LC | 2012_101 L2-HC | 2012_101 L2-LC | 2012_300 O6-HC | 2012_300 O6-LC | 2012_390 A13-HC | 2012_390 A13-LC | 2012_120 N18-HC | 2012_120 N18-LC | 2012_342 P20-HC | 2012_342 P20-LC |

*FIG. 4*

| WELL | CLONE | TOTAL (μg) | WELL | CLONE | TOTAL (μg) | WELL | CLONE | TOTAL (μg) |
|---|---|---|---|---|---|---|---|---|
| A1 | 2012_10N8 | 492.4 | A3 | 2012_172K8 | 138.14 | A5 | 2012_28O4 | 637.2 |
| B1 | 2012_33O10 | 420.2 | B3 | 2012_172I3 | 166.4 | B5 | 2012_43F8 | 195.2 |
| C1 | 2012_43I12 | 459.8 | C3 | 2012_175D24 | 792.8 | C5 | 2012_82N2 | 236.4 |
| D1 | 2012_55B4 | 439.8 | D3 | 2012_176J16 | 830 | D5 | 2012_92N19 | 960.2 |
| E1 | 2012_62B10 | 423.6 | E3 | 2012_204E7 | TOO LOW | E5 | 2012_97N24 | 315.2 |
| F1 | 2012_82M2 | 327.6 | F3 | 2012_215O6 | 246.6 | F5 | 2012_161O23 | 671 |
| G1 | 2012_99B7 | 397 | G3 | 2012_264B14 | 160.16 | G5 | 2012_102A6 | 231.18 |
| H1 | 2012_95B8 | 466.4 | H3 | 2012_300O6 | 263.6 | H5 | 2012_120N18 | 408.8 |
| A2 | 2012_106A19 | 132.3 | A4 | 2012_311N18 | 139.68 | A6 | 2012_112D7 | 77.6 |
| B2 | 2012_105O2 | TOO LOW | B4 | 2012_308H21 | 397.8 | B6 | 2012_201C15 | 610 |
| C2 | 2012_110J23 | 521.8 | C4 | 2012_324F17 | 649.6 | C6 | 2012_238B22 | 333.6 |
| D2 | 2012_111J23 | TOO LOW | D4 | 2012_345A12 | 330.6 | D6 | 2012_250P7 | 361.6 |
| E2 | 2012_131F19 | 591 | E4 | 2012_346C6 | 262.2 | E6 | 2012_246F14 | 285.8 |
| F2 | 2012_145D4 | 439.4 | F4 | 2012_347H14 | 685.6 | F6 | 2012_262H11 | 282.4 |
| G2 | 2012_147F21 | 235.6 | G4 | 2012_360I17 | 78.82 | G6 | 2012_264E24 | 288.8 |
| H2 | 2012_101L2 | 319.4 | H4 | 2012_390A13 | 292.4 | H6 | 2012_342P20 | 341.4 |

*FIG. 5*

|  | | OVCAR3 | | A431-K5 | | A431 | |
|---|---|---|---|---|---|---|---|
|  | | EC50 (M) | MAX KILLING (%) | EC50 (M) | MAX KILLING (%) | EC50 (M) | MAX KILLING (%) |
| 2012_10N8 | A1 | 5.21E-09 | 95.5 | 7.885E-09 | 82.4 | ~5.359e-008 | 32.9 |
| 2012_33O10 | B1 | 2.273E-09 | 94.6 | 1.913E-09 | 76.7 | ~2.319e-007 | 21.3 |
| 2012_43I12 | C1 | 2.428E-09 | 91.8 | 1.301E-08 | 80.7 | ~1.562e-006 | 45.6 |
| 2012_55B4 | D1 | 2.922E-09 | 94.1 | 7.013E-10 | 69.0 | ~4.604e-006 | 21.9 |
| 2012_62B10 | E1 | 3.675E-09 | 96.2 | 5.753E-10 | 83.5 | ~3.956e-008 | 26.3 |
| 2012_82M2 | F1 | 1.644E-09 | 89.1 | 8.471E-10 | 77.3 | ~4.326e-007 | 16.4 |
| 2012_99B7 | G1 | 4.971E-09 | 89.3 | 2.499E-09 | 79.4 | ~6.102e-007 | 49.8 |
| 2012_95B8 | H1 | 4.154E-09 | 87.5 | 1.742E-08 | 77.5 | ~1.411e-007 | 34.0 |
| 2012_106A19 | A2 | 7.855E-10 | 87.8 | 1.063E-08 | 74.5 | ~2.509e-005 | 18.4 |
| 2012_10502 | B2 | 1.914E-09 | 88.6 | ~0.006310 | 77.5 | ~1.004e-005 | 20.3 |
| 2012_110J23 | C2 | 5.911E-09 | 85.3 | 4.272E-09 | 76.0 | ~3.027e-008 | 21.1 |
| 2012_111J23 | D2 | 6.658E-09 | 85.7 | ~1.946e-008 | 80.4 | ~7.776e-007 | 13.3 |
| 2012_131F19 | E2 | 6.894E-09 | 84.4 | 9.003E-10 | 79.9 | ~7.996e-007 | 22.9 |
| 2012_145D4 | F2 | 4.839E-09 | 84.0 | 1.19E-09 | 80.7 | ~9.026e-007 | 21.9 |
| 2012_147F21 | G2 | 4.91E-09 | 83.3 | 8.149E-09 | 84.2 | ~3.497e-006 | 30.7 |
| 2012_101L2 | H2 | 1.06E-08 | 83.1 | 5.102E-09 | 77.2 | ~6.119e-008 | 23.6 |
| 2012_172K8 | A3 | 7.714E-09 | 83.7 | 3.398E-09 | 84.6 | ~8.408e-008 | 15.9 |
| 2012_172I3 | B3 | 7.243E-09 | 83.2 | 2.204E-09 | 81.3 | ~8.136e-008 | 22.8 |
| 2012_175D24 | C3 | 6.611E-09 | 81.5 | ~2.570e-008 | 65.0 | ~6.087e-008 | 30.4 |
| 2012_176J16 | D3 | 2.392E-09 | 78.4 | 9.117E-09 | 69.8 | ~8.135e-008 | 42.6 |
| 2012_204E7 | E3 | 1.193E-08 | 88.5 | ~2.062e-008 | 63.5 | ~2.507e-008 | 8.6 |
| 2012_215O6 | F3 | ~2s981e-011 | 87.7 | 1.407E-08 | 70.2 | ~8.772e-007 | 14.3 |
| 2012_264B14 | G3 | 2.837E-09 | 85.9 | 1.776E-08 | 73.0 | ~3.077e-008 | 12.7 |
| 2012_300O6 | H3 | 5.156E-09 | 85.2 | 1.507E-08 | 75.0 | ~8.050e-008 | 29.2 |
| 2012_311N18 | A4 | 5.868E-09 | 83.6 | 6.931E-09 | 77.3 | ~7.831e-008 | 17.6 |

| | | OVCAR3 | | A431-K5 | | A431 | |
|---|---|---|---|---|---|---|---|
| | | EC50 (M) | MAX KILLING (%) | EC50 (M) | MAX KILLING (%) | EC50 (M) | MAX KILLING (%) |
| 2012_308H21 | B4 | 5.494E-09 | 84.2 | ~2.815e-08 | 61.5 | ~6.055e-008 | 14.2 |
| 2012_324F17 | C4 | 8.997E-09 | 84.6 | ~2.467e-08 | 66.2 | ~2.356e-006 | 15.4 |
| 2012_345A12 | D4 | 5.987E-09 | 87.3 | 1.468E-09 | 75.8 | ~8.451e-007 | 23.3 |
| 2012_346C6 | E4 | 4.411E-09 | 86.2 | 6.677E-10 | 77.7 | ~1.085e-006 | 21.6 |
| 2012_347H14 | F4 | 7.124E-09 | 88.3 | 1.869E-08 | 69.7 | ~6.063e-007 | 43.3 |
| 2012_360I17 | G4 | 5.161E-09 | 89.7 | 3.78E-09 | 83.0 | ~5.143e-007 | 22.1 |
| 2012_390A13 | H4 | 6.473E-09 | 87.5 | 2.004E-09 | 81.6 | ~5.892e-007 | 20.6 |
| 2012_28O4 | A5 | 3.674E-09 | 85.3 | 4.534E-09 | 83.2 | ~6.230e-007 | 23.4 |
| 2012_43F8 | B5 | 4.015E-09 | 85.7 | 1.076E-08 | 79.7 | ~2.064e-006 | 17.8 |
| 2012_82N2 | C5 | 3.307E-09 | 80.8 | 8.358E-09 | 81.6 | ~1.550e-006 | 27.4 |
| 2012_92N19 | D5 | 3.977E-10 | 89.6 | 4.74E-09 | 82.1 | ~3.785e-008 | 26.3 |
| 2012_97N24 | E5 | 2.382E-09 | 88.3 | 1.215E-08 | 83.1 | ~3.773e-007 | 55.2 |
| 2012_161O23 | F5 | 4.007E-09 | 87.5 | 3.466E-09 | 82.5 | ~3.762e-007 | 20.3 |
| 2012_102A6 | G5 | 9.218E-11 | 89.5 | 4.243E-10 | 86.1 | ~6.315e-007 | 45.8 |
| 2012_120N18 | H5 | 2.369E-09 | 86.6 | 6.946E-10 | 83.1 | ~1.582e-006 | 42.8 |
| 2012_112D7 | A6 | 2.601E-09 | 89.2 | ~2.380e-008 | 74.1 | ~3.334e-008 | 21.4 |
| 2012_201C15 | B6 | 3.515E-09 | 72.8 | 7.284E-10 | 80.3 | ~3.850e-007 | 23.4 |
| 2012_238B22 | C6 | 4.599E-09 | 87.5 | 1.292E-09 | 82.6 | ~4.032e-008 | 22.6 |
| 2012_250P7 | D6 | 1.086E-09 | 89.2 | 1.336E-08 | 73.0 | ~4.885e-007 | 20.8 |
| 2012_246F14 | E6 | 3.866E-09 | 87.9 | 2.296E-09 | 78.6 | ~8.035e-007 | 32.7 |
| 2012_262H11 | F6 | 1.89E-09 | 92.2 | 3.288E-09 | 86.2 | ~3.765e-008 | 33.2 |
| 2012_264E24 | G6 | 3.782E-09 | 90.3 | 1.75E-09 | 83.0 | ~8.320e-008 | 39.0 |
| 2012_342P20 | H6 | 1.232E-09 | 91.3 | 7.018E-10 | 83.0 | ~8.206e-008 | 25.0 |
| | #1 | ~1s529e+010 | 51.1 | 2.355E-10 | 78.9 | ~6.380e-008 | 34.0 |
| | #2 | ~0s0009O22 | 45.2 | ~3.878e-006 | 43.2 | ~2.823e-007 | 50.1 |

FROM FIG. 6

*FIG. 6 CONT.*

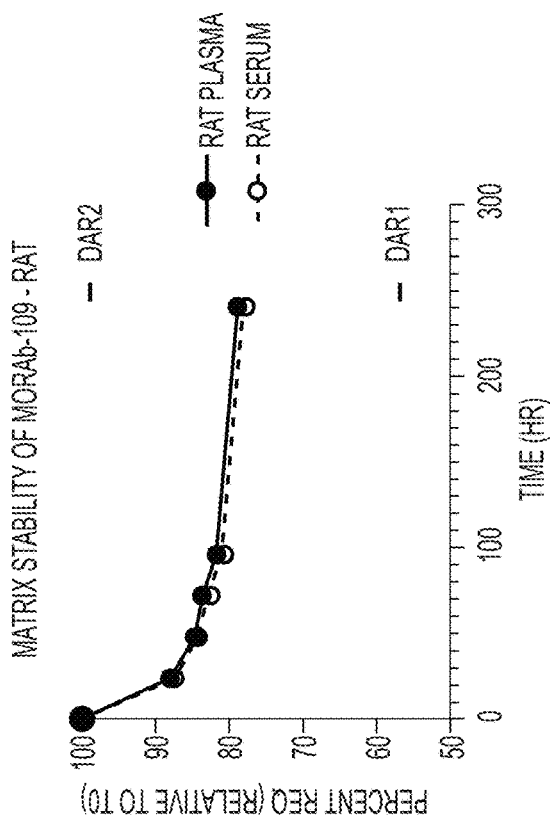
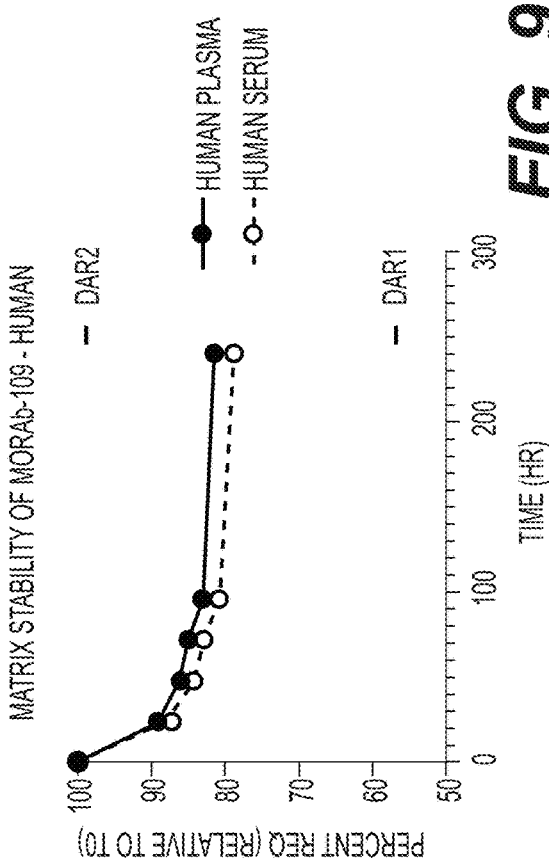
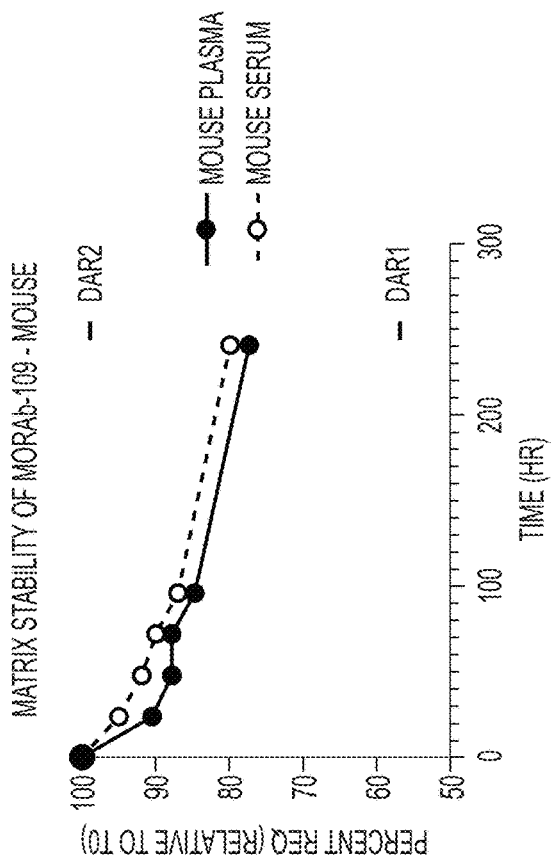
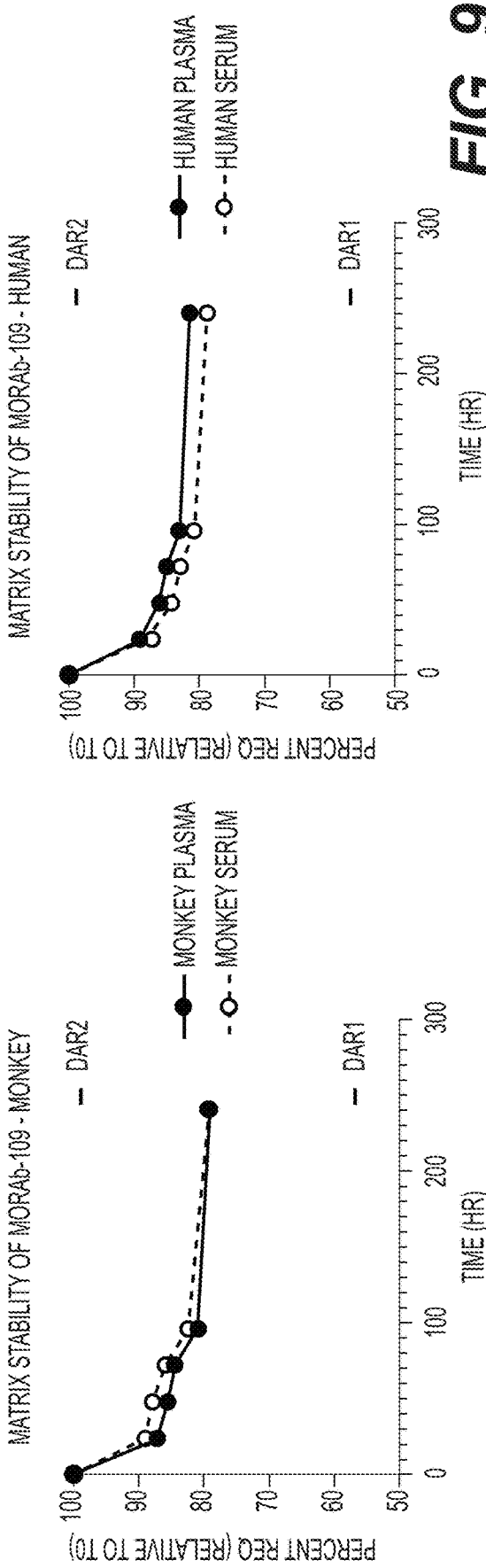
FIG. 9

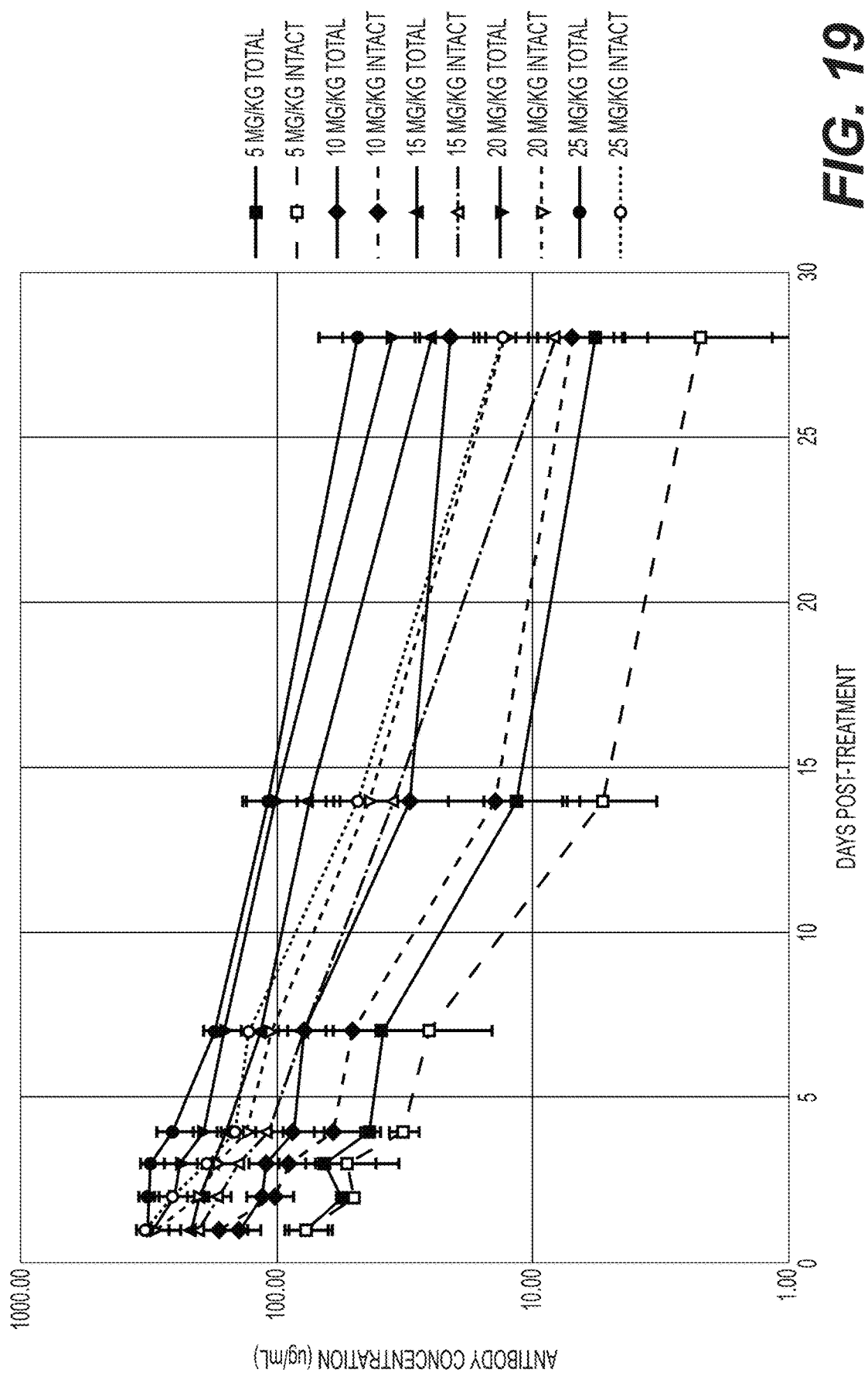

ERIBULIN ANTIBODY-DRUG CONJUGATES AND METHODS OF USE

The present disclosure claims the benefit of priority to U.S. Provisional Patent Application No. 62/932,373, filed Nov. 7, 2019, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 28, 2020, is named 08061_0043-00000_SL.txt and is 36,541 bytes in size.

The present disclosure relates to anti-mesothelin antibodies and antigen-binding fragments thereof, as well as conjugates such as antibody-drug conjugates (ADCs), e.g., those comprising eribulin, and their use in the treatment and diagnosis of cancers that express mesothelin and/or are amenable to treatment by disrupting tubulin or by administering a composition disclosed herein.

Cancer is among the leading causes of morbidity and mortality worldwide, with approximately 14 million new cases and 8.2 million cancer-related deaths in 2012. The most common causes of cancer death are cancers of: lung (1.59 million deaths); liver (745,000 deaths); stomach (723,000 deaths); colorectal (694,000 deaths); breast (521,000 deaths); and esophagus (400,000 deaths). The number of new cancer cases is expected to rise by about 70% over the next two decades, to approximately 22 million new cancer cases per year (World Cancer Report 2014).

Mesothelin, a glycosylphosphatidylinositol (GPI)-anchored cell surface protein, is an attractive target for antibody-based cancer therapy due to its high expression in various cancer types, including mesothelioma, ovarian cancer, and pancreatic adenocarcinomas (Tang et al. (2013) Anticancer Agents Med. Chem. 13(2):276-80). Although a full understanding of the biological functions of mesothelin is lacking given that mesothelin knockout mice do not show any detectable phenotype, it has been suggested that mesothelin plays a role in tumor adhesion and metastasis (Bera and Pastan (2000) Mol. Cell Biol. 20(8):2902-6; Rump et al. (2004) J. Biol. Chem. 279(10):9190-8). Mesothelin is also believed to confer resistance to certain forms of chemotherapy, and to contribute to tumor progression by having a proliferative effect on cells (Bharadwaj et al. (2011) Mol. Cancer. 10:106; Li et al. (2008) Mol. Cancer Ther. 7(2): 286-96).

Recent studies have shown that mesothelin may function as a master regulator of epithelial-mesenchymal transition (EMT), a process closely associated with cancer metastasis and recurrence (He et al. (2017). Mol Cancer. 16:63). Without wishing to be bound by theory, it is believed that inhibition of mesothelin, e.g., binding by an anti-mesothelin antibody, antigen-binding fragment, and/or ADC, may reduce EMT by inducing the reverse process, mesenchymal epithelial transition (MET), via suppression of TGF-β (transforming growth factor beta) signaling. Conversely, it is believed that overexpression of mesothelin may drive EMT through induction of cancer stem cell-like phenotypes associated with tumor progression and poor treatment response (He et al. (2017). Mol Cancer. 16:63; Koyama et al. (2017). J. Clin. Invest. 127(4): 1254-1270).

A commonly encountered challenge in cancer therapy is that the limited therapeutic index of chemotherapeutics results in significant toxicity to normal tissues and thus limits their therapeutic utility. One approach to achieve higher specificity for targeting cancer cells is by using antibodies to deliver cytotoxic effects to cells expressing certain tumor-specific antigens while sparing normal cells that express much lower levels or none of such antigens (Awwad et al. Pharmaceutics (2018) 10(3); Lambert and Berkenblit (2018) 69: 191-207). Such tumor-specific targeting can be exploited to both increase anti-tumor activity and decrease off-target cytotoxicity of therapeutics. Antibodies targeting tumor-specific antigens may deliver cytotoxic effects through a variety of mechanisms, including inhibiting the biological activity of the antigen, eliciting an immune effector activity, and/or inducing antibody-dependent cellular cytotoxicity (Hendrinks et al. International Review of Cell and Molecular Biology (2017); Therapeutic Antibody Engineering (2012): 163-196, 459-595).

Selection of tumor-specific antigens for an antibody-based therapeutic approach may involve specific expression of an antigen by tumor cells and robust killing of the antigen-expressing tumor cells. Several human cancers have been found to express high levels of mesothelin, including lung cancer, ovarian cancer, pancreatic cancer, and stomach cancer (Hassan et al. Eur. J. Cancer (2008) 44(1): 46-53; Hassan et al. J. Clin. Oncol. (2016) 34(34): 4171-4179). Mesothelin expression has also been found in drug resistant cancers such as lung cancers with KRAS and STK11 mutations with poor clinical response to checkpoint blockade immunotherapy, and HER2-negative gastric cancer. Additionally, correlation has been reported between mesothelin expression and the overall survival of patients with lung adenocarcinoma and of patients with gastric cancer metastasis, suggesting that high mesothelin expression may be a predictor of worse clinical outcome (Kachala et al. (2014) Clin. Cancer. Res. 20(4): 1020-1028; Han et al. (2017) J. Pathol. Transl. Med. 51(2): 122-128). The prevalence of mesothelin expression in human cancers and its association with poor clinical outcome render mesothelin a potential target for tumor antigen-specific drug delivery approaches, e.g., an antibody-mediated approach. Antibodies conjugated with cytotoxic compounds such as chemotherapeutics have also been explored to enhance the cell-killing activity of antibody-based drug delivery to tumor cells. Nevertheless, the need remains to provide suitable antibodies and/or ADCs that offer a combination of efficient tumor targeting, on-target effects, bystander killing, and/or reduced off-target effects.

Eribulin is a synthetic analog of the macrocyclic compound halichondrin B, which has been previously shown to be a potent inhibitor of tubulin polymerization, microtubule assembly, and tubulin-depend GTP hydrolysis. Tubulin makes up dynamic filamentous cytoskeletal proteins called microtubules that are involved in a variety of vital cellular functions, including intracellular migration and transport, cell signaling, the maintenance of cell shape, and cell division. The rapid dividing rate of cancer cells makes them particularly sensitive to the obstruction of tubulin function. As such, halichondrin B and eribulin have demonstrated notable anti-cancer activities in vitro and in vivo (Tan et al. (2009) Clin Cancer Res. 15(12): 4213-4219; Vandat et al. (2009) J. Clin. Oncol. 27(18): 2954-2961). The mesylate salt of eribulin (eribulin mesylate) is currently marketed under the trade name Halaven™ for the treatment of patients with refractory metastatic breast cancer.

While uses of eribulin have been reported in the art, including in the ADC context, there remains a need to better deliver eribulin in a targeted fashion to particular tissues, e.g., cancer tissues that express mesothelin. Likewise, there remains a need in the art for improved antibodies that bind mesothelin with superior properties, e.g., with respect to antigen-binding and/or the ability to effectively delivery payloads such as eribulin to a target cell or tissue expressing mesothelin.

In various embodiments, the present disclosure provides, in part, novel antibodies and antigen-binding fragments that may be used alone, linked to one or more additional agents (e.g., as ADCs), or as part of a larger macromolecule (e.g., a bispecific antibody, multispecific antibody, alone or as a multispecific antibody linked to a payload in an ADC format) and administered as part of pharmaceutical compositions or combination therapies. In some embodiments, the antibodies or antigen-binding fragments are humanized. In some embodiments, the antibodies or antigen-binding fragments contain minimal sequences derived from a non-human immunoglobulin and retain the reactivity of a non-human antibody while being less immunogenic in human. In certain embodiments, the antibodies and antigen-binding fragments may be useful for treating human cancer patients.

The present disclosure more specifically relates, in various embodiments, to antibodies and antibody-drug conjugate compounds that are capable of binding and/or killing tumor cells. In various embodiments, the compounds are also capable of internalizing into a target cell after binding. ADC compounds comprising a linker that attaches an eribulin drug moiety to an antibody moiety are disclosed. An antibody moiety may be a full-length antibody or an antigen-binding fragment.

In some embodiments, an antibody or antigen-binding fragment disclosed herein comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3), as defined by the Kabat numbering system (Kabat, Sequences of Proteins of Immunological Interest (National Institutes of Health, Bethesda, Md. (1987 and 1991))); or three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3), as defined by the IMGT numbering system (International ImMunoGeneTics Information System (IMGT®)).

In some embodiments, an antibody or antigen-binding fragment disclosed herein comprises three heavy chain complementarity determining regions (HCDRs) from a heavy chain variable region comprising an amino acid sequence of SEQ ID NO: 13 and three light chain complementarity determining regions (LCDRs) from a light chain variable region comprising an amino acid sequence of SEQ ID NO: 14.

In some embodiments, an antibody or antigen-binding fragment disclosed herein is an anti-mesothelin antibody or antigen-binding fragment. In various embodiments, the antibody or antigen-binding fragment comprises a heavy chain variable region comprising an amino acid sequence of SEQ ID NO: 13, and a light chain variable region comprising an amino acid sequence of SEQ ID NO: 14, or sequences that are at least 90% identical to the disclosed sequences. In various embodiments, the antibody or antigen-binding fragment comprises a human IgG1 heavy chain constant region comprising an amino acid sequence of SEQ ID NO: 15, and a human Ig kappa light chain constant region comprising an amino acid sequence of SEQ ID NO: 16. In various embodiments, the antibody or antigen-binding fragment comprises a heavy chain amino acid sequence of SEQ ID NO: 17, and a light chain amino acid sequence of SEQ ID NO: 18.

In various embodiments, an antibody or antigen-binding fragment disclosed herein comprises three heavy chain complementarity determining regions (HCDRs) comprising amino acid sequences encoded by nucleic acid sequences of SEQ ID NO: 19 (HCDR1), SEQ ID NO: 20 (HCDR2), and SEQ ID NO: 21 (HCDR3); and three light chain complementarity determining regions (LCDRs) comprising amino acid sequences encoded by nucleic acid sequences of SEQ ID NO: 22 (LCDR1), SEQ ID NO: 23 (LCDR2), and SEQ ID NO: 24 (LCDR3), as defined by the Kabat numbering system; or three heavy chain complementarity determining regions (HCDRs) comprising amino acid sequences encoded by nucleic acid sequences of SEQ ID NO: 25 (HCDR1), SEQ ID NO: 26 (HCDR2), and SEQ ID NO: 27 (HCDR3); and three light chain complementarity determining regions (LCDRs) comprising amino acid sequences encoded by nucleic acid sequences of SEQ ID NO: 28 (LCDR1), SEQ ID NO: 29 (LCDR2), and SEQ ID NO: 30 (LCDR3), as defined by the IMGT numbering system.

In various embodiments, the antibody or antigen-binding fragment comprises a heavy chain variable region comprising an amino acid sequence encoded by the nucleic acid sequence of SEQ ID NO: 31, and a light chain variable region comprising an amino acid sequence encoded by the nucleic acid sequence of SEQ ID NO: 32. In various embodiments, the antibody or antigen-binding fragment comprises a heavy chain constant region comprising an amino acid sequence encoded by the nucleic acid sequence of SEQ ID NO: 33, and a light chain constant region comprising an amino acid sequence encoded by the nucleic acid sequence of SEQ ID NO: 34. In various embodiments, the antibody or antigen-binding fragment comprises a heavy chain comprising an amino acid sequence encoded by the nucleic acid sequence of SEQ ID NO: 35, and a light chain comprising an amino acid sequence encoded by the nucleic acid sequence of SEQ ID NO: 36.

In some embodiments, the antibody or antigen-binding fragment is a full-length antibody. In some embodiments, the antibody or antigen-binding fragment is a monospecific antibody or antigen-binding fragment, a bispecific antibody or antigen-binding fragment, or a multispecific antibody or antigen-binding fragment. In some embodiments, the antibody or antigen-binding fragment is a single chain variable fragment (scFv), or a Fab fragment.

In various embodiments, the antibody or antigen-binding fragment is conjugated to a therapeutic agent, e.g., one or more small molecules and/or additional antibodies or antigen-binding fragments. In some embodiments, the therapeutic agent is eribulin. In some embodiments, the antibody or antigen-binding fragment is 345A12-HC15-LC4.

In various embodiments, an ADC disclosed herein comprises Formula (I):

$$Ab\text{-}(L\text{-}D)_p \quad (I)$$

wherein

Ab is an antibody or antigen-binding fragment, wherein the antibody or antigen-binding fragment is capable of binding to mesothelin and comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO:5 (LCDR2), and SEQ ID NO: 6 (LCDR3), as defined by the Kabat numbering system; or three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3), as defined by the IMGT numbering system;
D is a therapeutic agent, e.g., an eribulin moiety;
L is a cleavable linker that covalently attaches Ab to D; and
p is an integer from 1 to 8.

In some embodiments, p is an integer from 1 to 6. In some embodiments, p is 2 or 6.

In some embodiments, the ADC comprises a cleavable linker comprising a cleavable moiety that is positioned such that no part of the linker or the antibody or antigen-binding fragment remains bound to the therapeutic agent (e.g., eribulin) upon cleavage. In some embodiments, the cleavable linker comprises a cleavable peptide moiety that is cleavable by an enzyme such as cathepsin B. In some embodiments, the cleavable moiety comprises a cleavable peptide moiety, e.g., an amino acid unit such as Val-Cit. In some embodiments, the amino acid unit comprises valine-citrulline (Val-Cit).

In some embodiments, the cleavable linker comprises at least one spacer unit comprising at least one PEG moiety. In some embodiments, the spacer unit or linker comprises $(PEG)_2$. In some embodiments, a spacer unit attaches to the antibody moiety via a maleimide (Mal) moiety ("Mal-spacer unit"). In some embodiments, the Mal-spacer unit is joined to the antibody or antigen-binding fragment via a cysteine residue on the antibody or antigen-binding fragment (e.g., a LCcys80 residue on the antibody). In some embodiments, the Mal-spacer unit is joined to a cysteine residue (e.g., LCcys80) of a light chain variable region on the antibody or antigen-binding fragment. In some embodiments, p is 2, such that two -L-D moieties are attached to the antibody or antigen-binding fragment. In some embodiments, each -L-D moiety is attached to a cysteine residue (e.g., LCcys80) of a light chain variable region on the antibody or antigen-binding fragment. In some embodiments, the cysteine residue is a LCcys80, i.e., a cysteine residue at amino acid position 80 of a light chain variable region on an antibody or an antigen-binding fragment according to the Kabat numbering system. In some embodiments, the cleavable linker comprises the Mal-spacer unit and a cleavable peptide moiety and the cleavable peptide moiety comprises Val-Cit. In some embodiments, the Mal-spacer unit attaches the antibody or antigen-binding fragment to the cleavable moiety.

In some embodiments, the Mal-spacer unit comprises at least one PEG moiety. In some embodiments, the linker comprises Mal-$(PEG)_2$. In some embodiments, the Mal-spacer unit attaches the antibody moiety to the cleavable moiety in the linker. In some embodiments, the cleavable moiety in the linker is a cleavable peptide moiety, e.g., an amino acid unit. In some embodiments, the linker comprises Mal-$(PEG)_2$-Val-Cit.

In some embodiments, the cleavable moiety of the ADC is directly joined to eribulin, or a spacer unit attaches the cleavable moiety in the linker to the eribulin drug moiety and cleavage of the conjugate releases eribulin from the antibody or antigen-binding fragment and linker.

In some embodiments, the spacer unit that attaches the cleavable moiety to the eribulin drug moiety is self-immolative. In some embodiments, the self-immolative spacer unit comprises p-aminobenzyloxycarbonyl (pAB). In some embodiments, the pAB spacer unit attaches the cleavable moiety to the eribulin drug moiety via a C-35 amine. In some embodiments, the cleavable moiety is a cleavable peptide moiety, e.g., an amino acid unit. In some embodiments, the cleavable linker comprises Val-Cit-pAB. In some embodiments, the linker comprises Val-Cit-pAB and a PEG spacer unit joining the linker to the antibody moiety through a Mal moiety. In some embodiments, the linker comprises Mal-$(PEG)_2$-Val-Cit-pAB.

In various embodiments, the antibody or antigen-binding fragment of the ADC comprises human heavy and light chain variable region frameworks, or human heavy and light chain variable region frameworks with one or more back mutations. In various embodiments, the antibody or antigen-binding fragment of an ADC comprises a heavy chain variable region comprising an amino acid sequence of SEQ ID NO: 13 or that is at least 90% identical to the amino acid sequence of SEQ ID NO 13, and a light chain variable region comprising an amino acid sequence of SEQ ID NO: 14 or that is at least 90% identical to the amino acid sequence of SEQ ID NO: 14. In various embodiments, the antibody or antigen-binding fragment of an ADC comprises a human IgG1 heavy chain constant region comprising an amino acid sequence of SEQ ID NO: 15, and a human Ig kappa light chain constant region comprising an amino acid sequence of SEQ ID NO: 16. In various embodiments, the antibody or antigen-binding fragment of an ADC comprises the heavy chain amino acid sequence of SEQ ID NO: 17, and the light chain amino acid sequence of SEQ ID NO: 18.

In various embodiments, the ADC has Formula (I):

$$Ab-(L-D)_p \qquad (I)$$

wherein
Ab is an antibody or antigen-binding fragment, wherein the antibody or antigen-binding fragment is capable of binding to mesothelin and comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO:5 (LCDR2), and SEQ ID NO: 6 (LCDR3), as defined by the Kabat numbering system; or three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3), as defined by the IMGT numbering system;
D is an eribulin;
L is a cleavable linker comprising Mal-$(PEG)_2$-Val-Cit-pAB; and
p is an integer from 1 to 8, e.g., p is an integer from 2 to 6 or 3 to 4.

In some embodiments, p is an integer from 1 to 6. In some embodiments, p is 2 or 6.

In various embodiments, the antibody or antigen-binding fragment of the ADC (e.g., the ADC described above) comprises human heavy and light chain variable region frameworks, or human heavy and light chain variable region frameworks with one or more back mutations. In various embodiments, the antibody or antigen-binding fragment of the ADC comprises a heavy chain variable region comprising an amino acid sequence of SEQ ID NO: 13 or that is at least 90% identical to SEQ ID NO: 13, and a light chain variable region comprising an amino acid sequence of SEQ ID NO: 14 or that is at least 90% identical to SEQ ID NO: 14. In various embodiments, the antibody or antigen-binding fragment of the ADC comprises a human IgG1 heavy chain constant region comprising an amino acid sequence of SEQ ID NO: 15, and a human Ig kappa light chain constant region comprising an amino acid sequence of SEQ ID NO: 16. In various embodiments, the antibody or antigen-binding fragment of the ADC comprises the heavy chain amino acid sequence of SEQ ID NO: 17, and the light chain amino acid sequence of SEQ ID NO: 18.

In various embodiments, the ADC has Formula I:

$$Ab-(L-D)_p \qquad (I)$$

wherein Ab is an antibody or antigen-binding fragment, wherein the antibody or antigen-binding fragment is capable of binding to mesothelin and comprises a heavy chain variable region comprising an amino acid sequence of SEQ ID NO: 13, and a light chain variable region comprising an amino acid sequence of SEQ ID NO: 14;

D is eribulin;

L is a cleavable linker comprising Mal-(PEG)$_2$-Val-Cit-pAB; and p is an integer from 1 to 8, e.g., p is an integer from 2 to 6 or 3 to 4.

In some embodiments, p is an integer from 1 to 6. In some embodiments, p is 2 or 6.

In some embodiments, the antibody or antigen-binding fragment of the ADC comprises a human IgG1 heavy chain constant region, and a human Ig kappa light chain constant region. In some embodiments, the antibody or antigen-binding fragment comprises an IgG1 heavy chain constant region comprising an amino acid sequence of SEQ ID NO: 15, and an Ig kappa light chain constant region comprising an amino acid sequence of SEQ ID NO: 16. In some embodiments, the antibody or antigen-binding fragment comprises a heavy chain comprising an amino acid sequence of SEQ ID NO: 17, and a light chain comprising an amino acid sequence of SEQ ID NO: 18.

In various embodiments, provided herein are pharmaceutical compositions comprising the described antibodies, antigen-binding fragments, conjugates, and/or ADC compositions. In some embodiments, the pharmaceutical composition comprises one or more antibodies or antigen-binding fragments and/or one or more ADCs described herein along with at least a pharmaceutically acceptable carrier. In some embodiments, the pharmaceutical composition comprises multiple copies of the antibody, antigen-binding fragment, and/or ADC. In some embodiments, the pharmaceutical composition comprises multiple copies of an ADC disclosed herein, wherein the average p of the ADC is about 1 to about 6. In some embodiments, the average p of the ADC in the composition is about 1.7 or 2, or about 6.

In various embodiments, provided herein are therapeutic uses for the described antibodies, antigen-binding fragments, conjugates, and/or ADC compositions, e.g., in treating cancer. In certain aspects, the present disclosure provides methods of treating a cancer that expresses an antigen targeted by the antibody, antigen-binding fragment, and/or the antibody moiety of the conjugate or ADC, such as mesothelin. In certain aspects, the present disclosure provides methods of killing or inhibiting the proliferation of tumor cells or cancer cells by administering a therapeutically effective amount and/or regimen of any one of the antibodies, antigen-binding fragments, conjugates, and/or ADCs described herein. In some embodiments, the cancer is a mesothelin-expressing cancer, such as a mesothelioma, a breast cancer, a cervical cancer, a colorectal cancer, an endometrial cancer, a head and neck cancer, a liver cancer, a lung cancer (e.g., a non-small cell lung cancer), an ovarian cancer (e.g., a serous or a clear cell ovarian cancer), a pancreatic cancer, a prostate cancer, a renal cancer, a gastric cancer, a thyroid cancer, a urothelial cancer, a uterine cancer, a bile duct cancer, or a leukemia.

In certain aspects, the present disclosure provides uses for the described antibodies, antigen-binding fragments, conjugates, and/or ADC compounds and compositions, e.g., for determining whether a subject having or suspected of having a cancer (e.g., a mesothelin-expressing cancer) will be responsive to treatment with an agent targeting mesothelin, e.g., an antibody or antibody binding fragment, conjugate, or ADC disclosed herein. In some embodiments, the method comprises providing a biological sample from the subject; contacting the sample with an antibody or antigen-binding fragment disclosed herein; and detecting binding of the antibody or antigen-binding fragment to one or more cancer cells in the sample.

In certain other aspects, the present disclosure provides pharmaceutical compositions comprising an antibody or antibody binding fragment, conjugate, and/or ADC and a pharmaceutically acceptable diluent, carrier, and/or excipient. Methods of producing the disclosed antibody or antibody binding fragment, conjugate, or ADC compounds and compositions are also provided.

In some embodiments, nucleic acid sequence(s) encoding an antibody or antigen-binding fragment, a conjugate, or an ADC of the present disclosure are provided. The nucleic acid(s) may be in the form of an isolated nucleic acid, a nucleic acid incorporated into an isolated vector comprising, and/or an antibody or antigen-binding fragment expressed by a cell population under conditions suitable to produce the antibody or antigen-binding fragment.

BRIEF DESCRIPTION OF THE DRAWINGS

FIG. 4 shows anti-mesothelin clones for In-Fusion cloning and expression.

FIG. 5 shows a summary of purified 48 Rb-hu-xi anti-mesothelin antibodies.

FIG. 6 shows in-vitro cell-based potency results for anti-mesothelin-AuF conjugates.

FIG. 9 shows stability of MORAb-109 (345A12-HC15-LC4-VCP-eribulin) (DAR2) in various matrices.

FIG. 19 shows the concentrations (μg/mL) of total and intact MORAb-109 (DAR2) in NCI-N87 tumor-bearing mice following treatment with different doses of MORAb-109 (DAR2) ranging from 5 mg/kg to 25 mg/kg.

DETAILED DESCRIPTION

Figure 1:
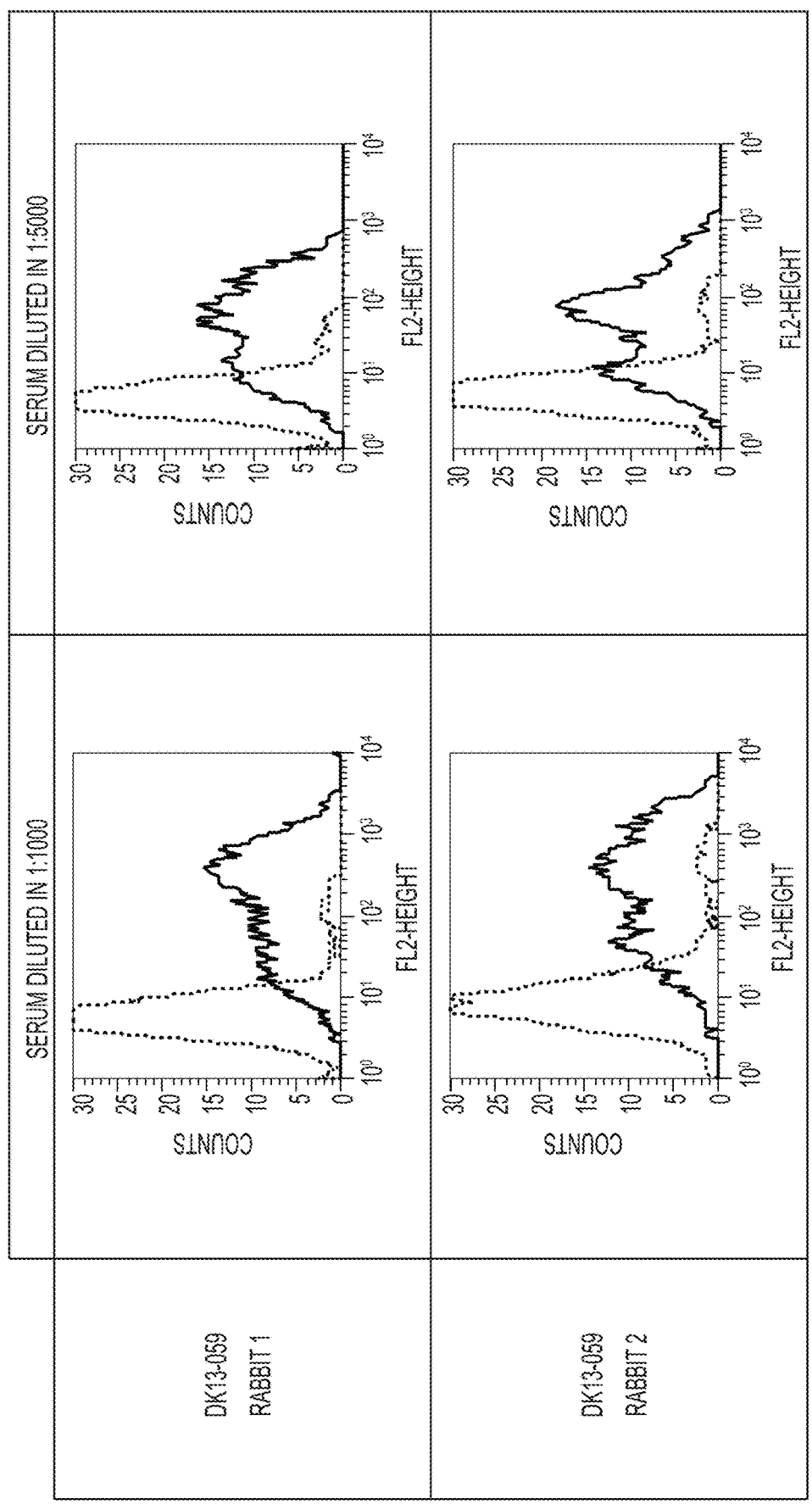
FIG. 1 shows detection of the specific reactivity of immune sera against human mesothelin by flow cytometry.

The disclosed compositions and methods may be understood more readily by reference to the following detailed description taken in connection with the accompanying figures, which form a part of this disclosure. It is to be understood that the terminology used herein is for the purpose of describing particular embodiments by way of example only and is not intended to be limiting of the claimed compositions and methods unless the context indicates otherwise.

Throughout this text, the descriptions refer to compositions and methods of using the compositions. Where the disclosure describes or claims a feature or embodiment associated with a composition, such a feature or embodiment is equally applicable to the methods of using the composition. Likewise, where the disclosure describes or claims a feature or embodiment associated with a method of using a composition, such a feature or embodiment is equally applicable to the composition.

When a range of values is expressed, it includes embodiments using any particular value within the range. Further, reference to values stated in ranges includes each and every value within that range. All ranges are inclusive of their endpoints and combinable. When values are expressed as approximations, by use of the antecedent "about," it will be understood that the particular value forms another embodiment. Reference to a particular numerical value includes at least that particular value, unless the context clearly dictates otherwise. The use of "or" will mean "and/or" unless the specific context of its use dictates otherwise. All references cited herein are incorporated by reference for any purpose. Where a reference and the specification conflict, the specification will control.

It is to be appreciated that certain features of the disclosed compositions and methods, which are, for clarity, described herein in the context of separate embodiments, may also be provided in combination in a single embodiment. Conversely, various features of the disclosed compositions and methods that are, for brevity, described in the context of a single embodiment, may also be provided separately or in any subcombination.

Definitions

Various terms relating to aspects of the description are used throughout the specification and claims. Such terms are to be given their ordinary meaning in the art unless otherwise indicated. Other specifically defined terms are to be construed in a manner consistent with the definitions provided herein.

As used herein, the singular forms "a," "an," and "the" include plural forms unless the context clearly dictates otherwise.

The terms "about" or "approximately" in the context of numerical values and ranges refers to values or ranges that approximate or are close to the recited values or ranges such that the embodiment may perform as intended, such as having a desired amount of nucleic acids or polypeptides in a reaction mixture, as is apparent to the skilled person from the teachings contained herein. Thus, these terms encompass values beyond those resulting from systematic error. In some embodiments, about means plus or minus 10% of a numerical amount.

The terms "antibody-drug conjugate," "antibody conjugate," "conjugate," "immunoconjugate," and "ADC" are used interchangeably, and refer to a therapeutic compound (e.g., an eribulin moiety) that is linked to an antibody moiety and is defined by the generic formula: Ab-(L-D)$_p$ (Formula I), wherein Ab is an antibody moiety (e.g., an antibody or antigen-binding fragment), L is a linker moiety, D is a drug moiety (e.g., an eribulin drug moiety), and p is the number of drug moieties per antibody moiety. In ADCs comprising an eribulin drug moiety, "p" refers to the number of eribulin moieties linked to the antibody moiety. In some embodiments, the linker L can include a cleavable moiety that can either directly attach to the antibody moiety and to the therapeutic compound, or the cleavable moiety can be attached to either or both the antibody moiety and therapeutic compound by spacer unit(s). In some embodiments, when a spacer unit attaches the cleavable moiety to the therapeutic compound, it is a self-immolative spacer unit.

The term "antibody" is used in the broadest sense to refer to an immunoglobulin molecule that recognizes and specifically binds to a target, such as a protein, polypeptide, carbohydrate, polynucleotide, lipid, or combinations of the foregoing through at least one antigen recognition site within the variable region of the immunoglobulin molecule. The heavy chain of an antibody is composed of a heavy chain variable domain (VH) and a heavy chain constant region (CH). The light chain is composed of a light chain variable domain (VL) and a light chain constant domain (CL). For the purposes of this application, the mature heavy chain and light chain variable domains each comprise three complementarity determining regions (CDR1, CDR2, and CDR3) within four framework regions (FR1, FR2, FR3, and FR4) arranged from N-terminus to C-terminus: FR1, CDR1, FR2, CDR2, FR3, CDR3, and FR4. An "antibody" can be naturally occurring or man-made, such as monoclonal antibodies produced by conventional hybridoma technology. The term "antibody" includes full-length monoclonal antibodies and full-length polyclonal antibodies, as well as antibody fragments such as Fab, Fab', F(ab')2, Fv, and single chain antibodies. An antibody can be any one of the five major classes of immunoglobulins: IgA, IgD, IgE, IgG, and IgM, or subclasses thereof (e.g., isotypes IgG1, IgG2, IgG3, IgG4). The term further encompasses human antibodies, chimeric antibodies, humanized antibodies and any modified immunoglobulin molecule containing an antigen recognition site, so long as it demonstrates the desired biological activity.

The term "monoclonal antibody," as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al. (1975) Nature 256:495, or may be made by recombinant DNA methods (see, e.g., U.S. Pat. No. 4,816,567). Monoclonal antibodies may also be isolated from phage antibody libraries using the techniques described in Clackson et al. (1991) Nature 352:624-8, and Marks et al. (1991) J. Mol. Biol. 222:581-97, for example.

The monoclonal antibodies described herein specifically include "chimeric" antibodies, in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they specifically bind the target antigen and/or exhibit the desired biological activity.

The term "chimeric antibody," as used herein, refers to antibodies wherein the amino acid sequence of the immunoglobulin molecule is derived from two or more species. In some instances, the variable regions of both heavy and light chains corresponds to the variable regions of antibodies derived from one species with the desired specificity, affinity, and activity while the constant regions are homologous to antibodies derived from another species (e.g., human) to minimize an immune response in the latter species.

As used herein, the term "humanized antibody" refers to forms of antibodies that contain sequences from non-human (e.g., rabbit) antibodies as well as human antibodies. Such antibodies are chimeric antibodies which contain minimal sequences derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the framework (FR) regions are those of a human immunoglobulin sequence. The humanized antibody optionally also will comprise at least a portion of an immunoglobulin constant region (Fc), typically that of a human immunoglobulin. The humanized antibody can be further modified by the substitution of residues, either in the Fv framework region and/or within the replaced non-human residues to refine and optimize antibody specificity, affinity, and/or activity.

The term "antigen-binding fragment," "antigen-binding domain," or "antigen-binding portion" of an antibody, as used herein, refers to one or more fragments of an antibody or protein that retain the ability to specifically bind to an antigen (e.g., mesothelin). Antigen-binding fragments may also retain the ability to internalize into an antigen-expressing cell. In some embodiments, antigen-binding fragments also retain immune effector activity. It has been shown that fragments of a full-length antibody can perform the antigen-binding function of a full-length antibody. Examples of binding fragments encompassed within the term "antigen-binding fragment," "antigen-binding domain," or "antigen-binding portion" of an antibody include (i) a Fab fragment, a monovalent fragment consisting of the VL, VH, CL, and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment, which comprises a single variable domain, e.g., a VH domain (see, e.g., Ward et al. (1989) Nature 341:544-6; and Intl. Pub. No. WO 1990/005144); and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). See, e.g., Bird et al. (1988) Science 242:423-6; and Huston et al. (1988) Proc. Natl. Acad. Sci. USA 85:5879-83. Such single chain antibodies are also intended to be encompassed within the term "antigen-binding fragment" or "antigen-binding portion" of an antibody, and are known in the art as an exemplary type of binding fragment that can internalize into cells upon binding (see, e.g., Zhu et al. (2010) 9:2131-41; He et al. (2010) J. Nucl. Med. 51:427-32; and Fitting et al. (2015) MAbs 7:390-402). In certain embodiments, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Holliger et al. (1993) Proc. Natl. Acad. Sci. USA 90:6444-8; and Poljak et al. (1994) Structure 2:1121-3). Antigen-binding fragments are obtained using conventional techniques known to those of skill in the art, and the binding fragments are screened for utility (e.g., binding affinity, internalization) in the same manner as are intact antibodies. Antigen-binding fragments may be prepared by cleavage of the intact protein, e.g., by protease or chemical cleavage.

"Internalizing" as used herein in reference to an antibody or antigen-binding fragment refers to an antibody or antigen-binding fragment that is capable of being taken through the cell's lipid bilayer membrane to an internal compartment (i.e., "internalized") upon binding to the cell, typically into a degradative compartment in the cell. For example, an internalizing anti-mesothelin antibody is one that is capable of being taken into the cell after binding to mesothelin on the cell membrane. In some embodiments, the antibody or antigen-binding fragment used in the ADCs disclosed herein targets a cell surface antigen (e.g., mesothelin) via an internalizing antibody or internalizing antigen-binding fragment (allowing the ADC to transfer through the cellular membrane after antigen-binding).

The term "mesothelin" or "MSLN," as used herein, refers to any native form of human mesothelin (MSLN). The term encompasses full-length mesothelin (e.g., NCBI Reference Sequence: AAC50348.1), as well as any form of human mesothelin that results from cellular processing. The term also encompasses naturally occurring variants of mesothelin, including but not limited to splice variants, allelic variants, and isoforms. Mesothelin can be isolated from a human, or may be produced recombinantly or by synthetic methods. The term may also encompass any synthetic variant to which an anti-mesothelin antibody, e.g., an antibody disclosed herein, and/or antigen-binding fragment, can specifically bind.

The term "anti-mesothelin antibody" or "antibody that specifically binds mesothelin" refers to any form of antibody or fragment thereof that specifically binds mesothelin, and encompasses monoclonal antibodies (including full-length monoclonal antibodies), polyclonal antibodies, and biologically functional antibody fragments so long as they specifically bind mesothelin. In some embodiments, the anti-mesothelin antibody used in the ADCs disclosed herein is an internalizing antibody or internalizing antibody fragment. 345A12 (e.g., 345A12-HC15-LC4) and 102A6A2 are exemplary internalizing anti-human mesothelin antibodies. As used herein, the terms "specific," "specifically binds," and "binds specifically" refer to the selective binding of the antibody to the target antigen epitope. Antibodies can be tested for specificity of binding by comparing binding to an appropriate antigen to binding to an irrelevant antigen or antigen mixture under a given set of conditions. If the antibody binds to the appropriate antigen with at least 2, 5, 7, or 10 times more affinity than to the irrelevant antigen or antigen mixture, then it is considered to be specific. A "specific antibody" or "target-specific antibody" is one that only binds the target antigen (e.g., mesothelin), but does not bind (or exhibits minimal binding) to other antigens.

The term "epitope" refers to the portion of an antigen capable of being recognized and specifically bound by an antibody. When the antigen is a polypeptide, epitopes can be formed from contiguous amino acids or noncontiguous amino acids juxtaposed by tertiary folding of the polypeptide. The epitope bound by an antibody may be identified using any epitope mapping technique known in the art, including X-ray crystallography for epitope identification by direct visualization of the antigen-antibody complex, as well as monitoring the binding of the antibody to fragments or mutated variations of the antigen, or monitoring solvent accessibility of different parts of the antibody and the antigen. Exemplary strategies used to map antibody epitopes include, but are not limited to, array-based oligo-peptide scanning, limited proteolysis, site-directed mutagenesis, high-throughput mutagenesis mapping, hydrogen-deuterium exchange, and mass spectrometry (see, e.g., Gershoni et al.

(2007) 21:145-56; and Hager-Braun and Tomer (2005) Expert Rev. Proteomics 2:745-56).

Competitive binding and epitope binning can also be used to determine antibodies sharing identical or overlapping epitopes. Competitive binding can be evaluated using a cross-blocking assay, such as the assay described in "Antibodies, A Laboratory Manual," Cold Spring Harbor Laboratory, Harlow and Lane (1$^{st}$ edition 1988, 2$^{nd}$ edition 2014). In some embodiments, competitive binding is identified when a test antibody or binding protein reduces binding of a reference antibody or binding protein to a target antigen such as mesothelin (e.g., a binding protein comprising CDRs and/or variable domains selected from those identified in Tables 1-3), by at least about 50% in the cross-blocking assay (e.g., 50%, 60%, 70%, 80%, 90%, 95%, 99%, 99.5%, or more, or any percentage in between), and/or vice versa. In some embodiments, competitive binding can be due to shared or similar (e.g., partially overlapping) epitopes, or due to steric hindrance where antibodies or binding proteins bind at nearby epitopes (see, e.g., Tzartos, Methods in Molecular Biology (Morris, ed. (1998) vol. 66, pp. 55-66)). In some embodiments, competitive binding can be used to sort groups of binding proteins that share similar epitopes. For example, binding proteins that compete for binding can be "binned" as a group of binding proteins that have overlapping or nearby epitopes, while those that do not compete are placed in a separate group of binding proteins that do not have overlapping or nearby epitopes.

The term "$k_{on}$" or "$k_a$" refers to the on-rate constant for association of an antibody to the antigen to form the antibody/antigen complex. The rate can be determined using standard assays, such as a surface plasmon resonance, biolayer inferometry, or ELISA assay.

The term "$k_{off}$" or "$k_d$" refers to the off-rate constant for dissociation of an antibody from the antibody/antigen complex. The rate can be determined using standard assays, such as a surface plasmon resonance, biolayer inferometry, or ELISA assay.

The term "$K_D$" refers to the equilibrium dissociation constant of a particular antibody-antigen interaction. $K_D$ is calculated by $k_d/k_a$. The rate can be determined using standard assays, such as a surface plasmon resonance, biolayer inferometry, or ELISA assay.

The term "p" or "drug loading" or "drug:antibody ratio" or "drug-to-antibody ratio" or "DAR" refers to the number of drug moieties per antibody moiety, i.e., drug loading, or the number of -L-D moieties per antibody or antigen-binding fragment (Ab) in ADCs of Formula (I). In ADCs comprising an eribulin drug moiety, "p" refers to the number of eribulin moieties linked to the antibody moiety. For example, if two eribulin moieties are linked to an antibody moiety, p=2. In compositions comprising multiple copies of ADCs of Formula (I), "average p" refers to the average number of -L-D moieties per antibody or antigen-binding fragment in a population of ADCs, also referred to as "average drug loading."

A "linker" or "linker moiety" is used herein to refer to any chemical moiety that is capable of covalently joining a compound, usually a drug moiety such as eribulin, to another moiety such as an antibody moiety. Linkers can be susceptible to or substantially resistant to acid-induced cleavage, peptidase-induced cleavage, light-based cleavage, esterase-induced cleavage, and/or disulfide bond cleavage, at conditions under which the compound or the antibody remains active.

The term "agent" is used herein to refer to a chemical compound, a mixture of chemical compounds, a biological macromolecule, or an extract made from biological materials. The term "therapeutic agent" or "drug" refers to an agent that is capable of modulating a biological process and/or has biological activity. The eribulin monomer described herein is an exemplary therapeutic agent.

The term "chemotherapeutic agent" or "anti-cancer agent" is used herein to refer to all agents that are effective in treating cancer regardless of mechanism of action. Inhibition of metastasis or angiogenesis is frequently a property of a chemotherapeutic agent. Chemotherapeutic agents include antibodies, biological molecules, and small molecules, and encompass eribulin, as described herein. A chemotherapeutic agent may be a cytotoxic or cytostatic agent. The term "cytostatic agent" refers to an agent that inhibits or suppresses cell growth and/or multiplication of cells. The term "cytotoxic agent" refers to a substance that causes cell death primarily by interfering with a cell's expression activity and/or functioning.

The term "eribulin" or "eribulin monomer," as used herein, refers to a synthetic analog of halichondrin B, a macrocyclic compound that was originally isolated from the marine sponge *Halichondria okadais*. Eribulin is a microtubule dynamics inhibitor, which is thought to bind tubulin and induce cell cycle arrest at the G2/M phase by inhibiting mitotic spindle assembly. The term "eribulin mesylate" refers to the mesylate salt of eribulin, which is marketed under the trade name Halaven™. Exemplary eribulin analogs include those shown and described in U.S. Pat. Nos. 6,214,865 and 6,653,341, which are incorporated herein by reference for the disclosed eribulin structures and methods of synthesizing those structures.

The term "eribulin dimer," as used herein, refers to a dimeric form of eribulin in which two eribulin monomers are attached via a covalent or non-covalent bond either directly or by a chemical linker (e.g., a secondary amine, a dihydroxyl secondary amine). Eribulin dimers may, in some embodiments, consist of two eribulin monomers covalently linked at the C-34 position by a secondary amine, or two eribulin monomers covalently linked at the C-35 position by a dihydroxyl secondary amine. An eribulin dimer consisting of two eribulin monomers covalently linked at the C-34 position by a secondary amine may be referred to herein as a "desOH eribulin dimer." An eribulin dimer consisting of two eribulin monomers covalently linked at the C-35 position by a dihydroxyl secondary amine may be referred to herein as a "diOH eribulin dimer." The term "eribulin dimer drug moiety" refers to the component of an ADC or composition that provides the structure of an eribulin dimer, e.g., the eribulin dimer (D) component in an ADC of Formula (I), or in a composition comprising -L-D. In some embodiments, a desOH eribulin dimer and/or a diOH eribulin dimer provides improved conjugatability over other eribulin dimer formats.

The term "cryptophycin," as used herein, refers to cryptophycin-1, a macrolide compound that was originally isolated from the cyanobacterium *Nostoc*, or to any synthetic analog thereof retaining anti-tubulin activity. Exemplary cryptophycin analogs include those shown and described in Intl. Publ. No. WO 2017/136769, which is incorporated herein by reference for all its disclosed cryptophycin structures and methods of synthesizing those structures. The term "cryptophycin drug moiety" refers to the component of an ADC or composition that has the structure of a cryptophycin.

The term "homolog" refers to a molecule which exhibits homology to another molecule, by for example, having sequences of chemical residues that are the same or similar at corresponding positions.

The term "inhibit" or "inhibition of," as used herein, means to reduce by a measurable amount, and can include but does not require complete prevention or inhibition.

The term "bystander killing" or "bystander effect" refers to the killing of target-negative cells in the presence of target-positive cells, wherein killing of target-negative cells is not observed in the absence of target-positive cells. Cell-to-cell contact, or at least proximity between target-positive and target-negative cells, enables bystander killing. This type of killing is distinguishable from "off-target killing," which refers to the indiscriminate killing of target-negative cells. "Off-target killing" may be observed in the absence of target-positive cells.

The term "cancer" refers to the physiological condition in mammals in which a population of cells is characterized by unregulated cell growth. Examples of cancers include, but are not limited to, a carcinoma, lymphoma, blastoma, sarcoma, and leukemia. Particular examples of such cancers include mesothelin-expressing cancers, such as a mesothelioma, a breast cancer, a cervical cancer, a colorectal cancer, an endometrial cancer, a head and neck cancer, a liver cancer, a lung cancer (e.g., a non-small cell lung cancer), an ovarian cancer (e.g., a serous, a clear cell, or an epithelial ovarian cancer), a pancreatic cancer, a prostate cancer, a renal cancer, a gastric cancer, a thyroid cancer, a urothelial cancer, a uterine cancer, a bile duct cancer, or a leukemia.

The terms "tumor" and "neoplasm" refer to any mass of tissue that results from excessive cell growth or proliferation, either benign or malignant, including precancerous lesions.

The terms "tumor cell" refer to individual cells or the total population of cells derived from a tumor, including both non-tumorigenic cells and cancer stem cells. As used herein, the term "tumor cell" will be modified by the term "non-tumorigenic" when referring solely to those tumor cells lacking the capacity to renew and differentiate to distinguish those tumor cells from cancer stem cells.

The terms "subject" and "patient" are used interchangeably herein to refer to any animal, such as any mammal, including but not limited to, humans, non-human primates, rodents, and the like. In some embodiments, the mammal is a mouse. In some embodiments, the mammal is a human.

A "pharmaceutical composition" refers to a preparation which is in such form as to permit administration and subsequently provide the intended biological activity of the active ingredient(s) and/or to achieve a therapeutic effect, and which contains no additional components which are unacceptably toxic to a subject to which the formulation would be administered. The pharmaceutical composition may be sterile.

A "pharmaceutical excipient" comprises a material such as an adjuvant, a carrier, pH-adjusting and buffering agents, tonicity adjusting agents, wetting agents, preservative, and the like.

"Pharmaceutically acceptable" means approved or approvable by a regulatory agency of the Federal or a state government, or listed in the U.S. Pharmacopeia or other generally recognized pharmacopeia, for use in animals, and more particularly in humans.

An "effective amount" of, e.g., an antibody, antigen-binding fragment, and/or ADC as disclosed herein is an amount sufficient to perform a specifically stated purpose, for example to produce a therapeutic effect after administration, such as a reduction in tumor growth rate or tumor volume, a reduction in a symptom of cancer, or some other indicia of treatment efficacy. An effective amount can be determined in a routine manner in relation to the stated purpose. The term "therapeutically effective amount" refers to an amount of an antibody, antigen-binding fragment, and/or an ADC effective to treat a disease or disorder in a subject. In the case of cancer, a therapeutically effective amount of an antibody, antigen-binding fragment, and/or ADC can reduce the number of cancer cells, reduce tumor size, inhibit (e.g., slow or stop) tumor metastasis, inhibit (e.g., slow or stop) tumor growth, and/or relieve one or more symptoms. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

As used herein, "to treat" or "therapeutic" and grammatically related terms, refer to any improvement of any consequence of disease, such as prolonged survival, less morbidity, and/or a lessening of side effects which are the byproducts of an alternative therapeutic modality. As is readily appreciated in the art, full eradication of disease is encompassed but not required for a treatment act. "Treatment" or "treat," as used herein, refers to the administration of a described antibody, antigen-binding fragment, and/or ADC to a subject, e.g., a patient. The treatment can be to cure, heal, alleviate, relieve, alter, remedy, ameliorate, palliate, improve or affect the disorder, the symptoms of the disorder or the predisposition toward the disorder, e.g., a cancer. In some embodiments, in addition to treating a subject with a condition, a composition disclosed herein can also be provided prophylactically to prevent or reduce the likelihood of developing that condition.

In some embodiments, a labeled antibody, antigen-binding fragment, and/or ADC is used. Suitable "labels" include radionuclides, enzymes, substrates, cofactors, inhibitors, fluorescent moieties, chemiluminescent moieties, magnetic particles, and the like.

By "protein," as used herein, is meant at least two covalently attached amino acids. The term encompasses polypeptides, oligopeptides, and peptides. In some embodiments, the two or more covalently attached amino acids are attached by a peptide bond. The protein may be made up of naturally occurring amino acids and peptide bonds, for example when the protein is made recombinantly using expression systems and host cells. Alternatively, the protein may include synthetic amino acids (e.g., homophenylalanine, citrulline, ornithine, and norleucine). A "recombinant protein" is a protein made using recombinant techniques using any techniques and methods known in the art, i.e., through the expression of a recombinant nucleic acid. Methods and techniques for the production of recombinant proteins are well known in the art.

For amino acid sequences, sequence identity and/or similarity may be determined using standard techniques known in the art, including, but not limited to, the local sequence identity algorithm of Smith and Waterman (1981) Adv. Appl. Math. 2:482, the sequence identity alignment algorithm of Needleman and Wunsch (1970) J. Mol. Biol. 48:443, the search for similarity method of Pearson and Lipman (1988) Proc. Nat. Acad. Sci. USA 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al. (1984) Nucl. Acid Res. 12:387-95, e.g., using the default settings, or by inspection. In some embodiments, percent identity is calculated by FastDB based upon the following parameters: mismatch penalty of 1; gap penalty of 1; gap size penalty of 0.33; and joining penalty of 30 ("Current Methods in Sequence Comparison and Analysis," Macromolecule Sequencing and Synthesis, Selected Methods and Applications, pp. 127-149 (1988), Alan R. Liss, Inc).

Generally, the amino acid homology, similarity, or identity between proteins disclosed herein and variants thereof, including variants of target antigens (such as mesothelin), variants of tubulin sequences, and variants of antibody variable domains (including individual variant CDRs), are at least 80% to the sequences depicted herein, e.g., homologies or identities of at least 85%, 90%, 91%, 92%, 93%, 94%, 95%, 96%, 97%, 98%, 99%, almost 100%, or 100%.

In a similar manner, "percent (%) nucleic acid sequence identity" with respect to the nucleic acid sequence of the antibodies and other proteins identified herein is defined as the percentage of nucleotide residues in a candidate sequence that are identical with the nucleotide residues in the coding sequence of the antigen-binding protein. A specific method utilizes the BLASTN module of WU-BLAST-2 set to the default parameters, with overlap span and overlap fraction set to 1 and 0.125, respectively.

While the site or region for introducing an amino acid sequence variation is predetermined, the mutation per se need not be predetermined. For example, in order to optimize the performance of a mutation at a given site, random mutagenesis may be conducted at the target codon or region and the expressed antigen-binding protein CDR variants screened for the optimal combination of desired activity. Techniques for making substitution mutations at predetermined sites in DNA having a known sequence are well known, for example, M13 primer mutagenesis and PCR mutagenesis.

Anti-Mesothelin Antibodies and Antigen-Binding Fragments

The present disclosure relates, in various embodiments, to antibodies or antigen-binding fragments thereof capable of binding and/or killing tumor cells (e.g., mesothelin-expressing tumor cells), as well as their use in conjugates and therapeutic compositions.

In some embodiments, the antibodies may be used alone, administered as part of pharmaceutical compositions or combination therapies, and/or as the antibody moiety in an ADC. In some embodiments, the anti-mesothelin antibodies and antigen-binding fragments disclosed herein are useful on their own (i.e., in unconjugated form) and as the antibody moiety in an ADC. In some embodiments, the anti-mesothelin antibodies and antigen-binding fragments are humanized. In some embodiments, the anti-mesothelin antibodies and antigen-binding fragments contain minimal sequence derived from a non-human immunoglobulin and retain the reactivity of a non-human (e.g., rabbit) antibody while being less immunogenic in human. In some embodiments, the anti-mesothelin antibodies and antigen-binding fragments disclosed herein provide one or more of improved stability, formulatability, aggregation, binding affinity, therapeutic efficacy, off-target toxicity, and/or metabolic profile as compared to one or more anti-mesothelin antibodies known to those of skill in the art.

In various embodiments, the antibodies or antigen-binding fragments disclosed herein bind specifically to mesothelin, e.g., as expressed on a cancer cell. The antibody or antigen-binding fragment may bind to a target antigen with a dissociation constant ($K_D$) of ≤1 mM, ≤100 nM or ≤10 nM, or any amount in between, as measured by, e.g., BIAcore® analysis. In certain embodiments, the $K_D$ is 1 pM to 500 pM. In some embodiments, the $K_D$ is between 500 pM to 1 μM, 1 μM to 100 nM, or 100 mM to 10 nM.

In some embodiments, the antibody moiety is a four-chain antibody (also referred to as an immunoglobulin), comprising two heavy chains and two light chains. In some embodiments the antibody moiety is a two-chain half body (one light chain and one heavy chain), or an antigen-binding fragment of an immunoglobulin.

In some embodiments, the antibody moiety is an antibody or antigen-binding fragment thereof. In some embodiments, the antibody moiety is an internalizing antibody or internalizing antigen-binding fragment thereof. In some embodiments, the internalizing antibody or internalizing antigen-binding fragment thereof binds to a target cancer antigen expressed on the surface of a cell and enters the cell upon binding. In some embodiments, the eribulin drug moiety of the ADC is released from the antibody moiety of the ADC after the ADC enters and is present in a cell expressing the target cancer antigen (i.e., after the ADC has been internalized).

In various embodiments, the antibody or antigen-binding fragment disclosed herein may comprise a paired set of heavy and light chain variable domains taken from those listed in Tables 3-5, or the set of six CDR sequences from the paired heavy and light chain set, e.g., a set of CDRs listed in Tables 1-2. In some embodiments, the antibody or antigen-binding fragment further comprises human heavy and light chain frameworks (optionally with one or more back-mutations to improve binding affinity) and/or human heavy and light chain constant domains or fragments thereof. For instance, the antibody or antigen-binding fragment may comprise a human IgG heavy chain constant domain (such as an IgG1) and a human kappa or lambda light chain constant domain. In some embodiments, the antibody or antigen-binding fragment comprises a human immunoglobulin G subtype 1 (IgG1) heavy chain constant domain with a human Ig kappa light chain constant domain.

Amino acid and nucleic acid sequences of exemplary antibodies of the present disclosure are set forth in Tables 1-10.

TABLE 1

Amino acid sequences of Kabat CDRs for an anti-mesothelin antibody

| mAb | IgG chain | SEQ ID | Amino acid sequence |
|---|---|---|---|
| 345A12-<br>HC15-LC4 | HC CDR1 | 1 | SYAMS |
|  | HC CDR2 | 2 | VIDISGNRFYADWVKG |
|  | HC CDR3 | 3 | VDSRAWGPFNL |
|  | LC CDR1 | 4 | QASQSIFSYLA |
|  | LC CDR2 | 5 | DASDLAS |
|  | LC CDR3 | 6 | QQGYTRSDVDNA |

TABLE 2

Amino acid sequences of IMGT CDRs for an anti-mesothelin antibody

| mAb | IgG chain | SEQ ID | Amino acid sequence |
|---|---|---|---|
| 345A12-HC15-LC4 | HC CDR1 | 7 | GIDLSSYA |
| | HC CDR2 | 8 | IDISGNR |
| | HC CDR3 | 9 | ARVDSRAWGPFNL |
| | LC CDR1 | 10 | QSIFSY |
| | LC CDR2 | 11 | DAS |
| | LC CDR3 | 12 | QQGYTRSDVDNA |

TABLE 3

Amino acid sequences of variable regions for an anti-mesothelin antibody

| mAb | IgG chain | SEQ ID | Amino acid sequence |
|---|---|---|---|
| 345A12-HC15-LC4 | Heavy chain | 13 | QVQLVESGGGVVQPGRSLRLSCAASGIDL SSYAMSWVRQAPGKGLEWIGVIDISGNRF YADWVKGRFTISRDNSKNTLYLQMSSLRA EDTAVYYCARVDSRAWGPFNLWGQGTLVT VSS |
| | Light chain | 14 | DYQMTQSPSSLSASVGDRVTITCQASQSI FSYLAWYQQKPGKAPKLLIYDASDLASGV PSRFSGSGSGTDFTLTISSLQCEDAATYY CQQGYTRSDVDNAFGGGTKVEIK |

TABLE 4

Amino acid sequences of constant regions for an anti-mesothelin antibody

| mAb | IgG chain | Constant region | SEQ ID | Amino acid sequence |
|---|---|---|---|---|
| 345A12-HC15-LC4 | Heavy chain | Human IgG1 | 15 | ASTKGPSVFPLAPSSKSTSGGT AALGCLVKDYFPEPVTVSWNSG ALTSGVHTFPAVLQSSGLYSLS SVVTVPSSSLGTQTYICNVNHK PSNTKVDKKVEPKSCDKTHTCP PCPAPELLGGPSVFLFPPKPKD TLMISRTPEVTCVVVDVSHEDP EVKFNWYVDGVEVHNAKTKPRE EQYNSTYRVVSVLTVLHQDWLN GKEYKCKVSNKALPAPIEKTIS KAKGQPREPQVYTLPPSRDELT KNQVSLTCLVKGFYPSDIAVEW ESNGQPENNYKTTPPVLDSDGS FFLYSKLTVDKSRWQQGNVFSC SVMHEALHNHYTQKSLSLSPGK |
| | Light chain | Human Ig kappa | 16 | RTVAAPSVFIFPPSDEQLKSGT ASVVCLLNNFYPREAKVQWKVD NALQSGNSQESVTEQDSKDSTY SLSSTLTLSKADYEKHKVYACE VTHQGLSSPVTKSFNRGEC |

TABLE 5

Amino acid sequences of full-length antibody Ig chains for an anti-mesothelin antibody

| mAb | IgG chain | SEQ ID | Amino acid sequence |
|---|---|---|---|
| 345A12-HC15-LC4 | Heavy chain | 17 | QVQLVESGGGVVQPGRSLRLSCAASGIDL SSYAMSWVRQAPGKGLEWIGVIDISGNRF YADWVKGRFTISRDNSKNTLYLQMSSLRA EDTAVYYCARVDSRAWGPFNLWGQGTLVT VSSASTKGPSVFPLAPSSKSTSGGTAALG CLVKDYFPEPVTVSWNSGALTSGVHTFPA VLQSSGLYSLSSVVTVPSSSLGTQTYICN VNHKPSNTKVDKKVEPKSCDKTHTCPPCP APELLGGPSVFLFPPKPKDTLMISRTPEV TCVVVDVSHEDPEVKFNWYVDGVEVHNAK TKPREEQYNSTYRVVSVLTVLHQDWLNGK EYKCKVSNKALPAPIEKTISKAKGQPREP QVYTLPPSRDELTKNQVSLTCLVKGFYPS DIAVEWESNGQPENNYKTTPPVLDSDGSF FLYSKLTVDKSRWQQGNVFSCSVMHEALH NHYTQKSLSLSPGK |
| | Light chain | 18 | DYQMTQSPSSLSASVGDRVTITCQASQSI FSYLAWYQQKPGKAPKLLIYDASDLASGV PSRFSGSGSGTDFTLTISSLQCEDAATYY CQQGYTRSDVDNAFGGGTKVEIKRTVAAP SVFIFPPSDEQLKSGTASVVCLLNNFYPR EAKVQWKVDNALQSGNSQESVTEQDSKDS TYSLSSTLTLSKADYEKHKVYACEVTHQG LSSPVTKSFNRGEC |

TABLE 6

Nucleic acid sequences encoding Kabat CDRs for an anti-mesothelin antibody

| mAb | IgG chain | SEQ ID | Nucleic acid sequence |
|---|---|---|---|
| 345A12-HC15-LC4 | HC CDR1 | 19 | TCCTACGCCATGTCC |
| | HC CDR2 | 20 | GTGATCGACATCTCCGGCAACCGG TTCTACGCCGACTGGGTGAAGGGC |
| | HC CDR3 | 21 | GTGGACTCTAGAGCCTGGGGCCCC TTCAACCTG |
| | LC CDR1 | 22 | CAGGCCTCCCAGTCCATCTTCTCC TACCTGGCC |
| | LC CDR2 | 23 | GACGCCTCTGATCTGGCCTCC |
| | LC CDR3 | 24 | CAGCAGGGCTACACCAGATCCGAC GTGGACAACGCC |

TABLE 7

Nucleic acid sequences encoding IMGT CDRs for an anti-mesothelin antibody

| mAb | IgG chain | SEQ ID | Nucleic acid sequence |
|---|---|---|---|
| 345A12-HC15-LC4 | HC CDR1 | 25 | GGAATCGACCTGTCCTCCTACGCC |
| | HC CDR2 | 26 | ATCGACATCTCCGGCAACCGG |
| | HC CDR3 | 27 | GCCAGAGTGGACTCTAGAGCCTGG GGCCCCTTCAACCTG |

TABLE 7-continued

Nucleic acid sequences encoding IMGT CDRs for an anti-mesothelin antibody

| mAb | IgG chain | SEQ ID | Nucleic acid sequence |
|---|---|---|---|
| | LC CDR1 | 28 | CAGTCCATCTTCTCCTAC |
| | LC CDR2 | 29 | GACGCCTCT |
| | LC CDR3 | 30 | CAGCAGGGCTACACCAGATCCGAC GTGGACAACGCC |

TABLE 8

Nucleic acid sequences encoding variable regions for an anti-mesothelin antibody

| mAb | IgG chain | SEQ ID | Nucleic acid sequence |
|---|---|---|---|
| 345A12-HC15-LC4 | Heavy chain | 31 | CAGGTGCAGCTGGTGGAATCTGGTGGCGGA GTGGTGCAGCCTGGCAGATCCCTGAGACTG TCTTGTGCCGCCTCCGGAATCGACCTGTCC TCCTACGCCATGTCCTGGGTGCGACAGGCT CCTGGCAAGGGCCTGGAATGGATCGGCGTG ATCGACATCTCCGGCAACCGGTTCTACGCC GACTGGGTGAAGGGCCGGTTCACCATCTCC AGAGACAACTCCAAGAACACCCTGTACCTC CAGATGTCCTCCCTGCGGGCCGAGGATACC GCCGTGTACTACTGCGCCAGAGTGGACTCT AGAGCCTGGGGCCCCTTCAACCTGTGGGC CAGGGAACACTCGTGACCGTGTCCTCT |
| | Light chain | 32 | GATTACCAGATGACCCAGTCCCCCTCCAGC CTGTCCGCTTCTGTGGGCGACAGAGTGACC ATCACCTGTCAGGCCTCCCAGTCCATCTTC TCCTACCTGGCTGGTATCAGCAGAAGCCC GGCAAGGCCCCCAAGCTGCTGATCTACGAC GCCTCTGATCTGGCCTCCGGCGTGCCCTCT AGATTCTCCGGCTCTGGCTCTGGCACCGAC TTTACCCTGACCATCAGCTCCCTCCAGTGC GAGGATGCCGCCACCTACTGCCAGCAG GGCTACACCAGATCCGACGTGGACAACGCC TTTGGCGGAGGCACCAAGGTGGAAATCAAA |

TABLE 9

Nucleic acid sequences encoding constant regions for an anti-mesothelin antibody

| mAb | IgG chain | Constant region | SEQ ID | Nucleic acid sequence |
|---|---|---|---|---|
| 345A12-HC15-LC4 | Heavy chain | Human IgG1 | 33 | GCATCCACCAAGGGCCCATCGGTC TTCCCCCTGGCACCCTCCTCCAAG AGCACCTCTGGGGGCACAGCGGCC CTGGGCTGCCTGGTCAAGGACTAC TTCCCCGAACCGGTGACGGTGTCG TGGAACTCAGGCGCCCTGACCAGC GGCGTGCACACCTTCCCGGCTGTC CTACAGTCCTCAGGACTCTACTCC CTCAGCAGCGTGGTGACCGTGCCC TCCAGCAGCTTGGGCACCCAGACC TACATCTGCAACGTGAATCACAAG CCCAGCAACACCAAGGTGGACAAG AAAGTTGAGCCCAAATCTTGTGAC AAAACTCACACATGCCCACCGTGC CCAGCACCTGAACTCCTGGGGGGA CCGTCAGTCTTCCTCTTCCCCCCA AAACCCAAGGACACCCTCATGATC TCCCGGACCCCTGAGGTCACATGC GTGGTGGTGGACGTGAGCCACGAA GACCCTGAGGTCAAGTTCAACTGG TACGTGGACGGCGTGGAGGTGCAT AATGCCAAGACAAAGCCGCGGGAG GAGCAGTACAACAGCACGTACCGT GTGGTCAGCGTCCTCACCGTCCTG CACCAGGACTGGCTGAATGGCAAG GAGTACAAGTGCAAGGTCTCCAAC AAAGCCCTCCCAGCCCCCATCGAG AAAACCATCTCCAAAGCCAAAGGG CAGCCCCGAGAACCACAGGTGTAC ACCCTGCCCCCATCCCGGGATGAG CTGACCAAGAACCAGGTCAGCCTG ACCTGCCTGGTCAAAGGCTTCTAT CCCAGCGACATCGCCGTGGAGTGG GAGAGCAATGGGCAGCCGGAGAAC AACTACAAGACCACGCCTCCCGTG CTGGACTCCGACGGCTCCTTCTTC TTATATTCAAAGCTCACCGTGGAC AAGAGCAGGTGGCAGCAGGGGAAC GTCTTCTCATGCTCCGTGATGCAT GAGGCTCTGCACAACCACTACACG CAGAAGAGCCTCTCCCTGTCTCCC GGGAAATGA |
| | Light chain | Human Ig kappa | 34 | CGAACTGTGGCTGCACCATCTGTC TTCATCTTCCCGCCATCTGATGAG CAGTTGAAATCTGGAACTGCCTCT GTTGTGTGCCTGCTGAATAACTTC TATCCCAGAGAGGCCAAAGTACAG TGGAAGGTGGATAACGCCCTCCAA TCGGGTAACTCCCAGGAGAGTGTC ACAGAGCAGGACAGCAAGGACAGC ACCTACAGCCTCAGCAGCACCCTG ACGCTGAGCAAAGCAGACTACGAG AAACACAAAGTCTACGCCTGCGAA GTCACCCATCAGGGCCTGAGCTCG CCCGTCACAAAGAGCTTCAACAGG GGAGAGTGTTGA |

TABLE 10

Nucleic acid sequences encoding full-length antibody Ig chains for an anti-mesothelin antibody*

| mAb | IgG chain | SEQ ID | Nucleic acid sequence |
|---|---|---|---|
| 345A12-HC15-LC4 | Heavy chain | 35 | CAGGTGCAGCTGGTGGAATCTGGTGGC GGAGTGGTGCAGCCTGGCAGATCCCTG AGACTGTCTTGTGCCGCCTCCGGAATC GACCTGTCCTCCTACGCCATGTCCTGG GTGCGACAGGCTCCTGGCAAGGGCCTG GAATGGATCGGCGTGATCGACATCTCC GGCAACCGGTTCTACGCCGACTGGGTG AAGGGCCGGTTCACCATCTCCAGAGAC AACTCCAAGAACACCCTGTACCTCCAG ATGTCCTCCCTGCGGGCCGAGGATACC GCCGTGTACTACTGCGCCAGAGTGGAC TCTAGAGCCTGGGGCCCCTTCAACCTG TGGGGCCAGGGAACACTCGTGACCGTG TCCTCTGCATCCACCAAGGGCCCATCG GTCTTCCCCCTGGCACCCTCCTCCAAG AGCACCTCTGGGGGCACAGCGGCCCTG GGCTGCCTGGTCAAGGACTACTTCCCC GAACCGGTGACGGTGTCGTGGAACTCA GGCGCCCTGACCAGCGGCGTGCACACC TTCCCGGCTGTCCTACAGTCCTCAGGA CTCTACTCCCTCAGCAGCGTGGTGACC GTGCCCTCCAGCAGCTTGGGCACCCAG ACCTACATCTGCAACGTGAATCACAAG |

TABLE 10-continued

Nucleic acid sequences encoding full-length antibody Ig chains for an anti-mesothelin antibody⁺

| mAb | IgG chain | SEQ ID | Nucleic acid sequence |
|---|---|---|---|
| | | | CCCAGCAACACCAAGGTGGACAAGAAA<br>GTTGAGCCCAAATCTTGTGACAAAACT<br>CACACATGCCCACCGTGCCCAGCACCT<br>GAACTCCTGGGGGGACCGTCAGTCTTC<br>CTCTTCCCCCCAAAACCCAAGGACACC<br>CTCATGATCTCCCGGACCCCTGAGGTC<br>ACATGCGTGGTGGTGGACGTGAGCCAC<br>GAAGACCCTGAGGTCAAGTTCAACTGG<br>TACGTGGACGGCGTGGAGGTGCATAAT<br>GCCAAGACAAAGCCGCGGGAGGAGCAG<br>TACAACAGCACGTACCGTGTGGTCAGC<br>GTCCTCACCGTCCTGCACCAGGACTGG<br>CTGAATGGCAAGGAGTACAAGTGCAAG<br>GTCTCCAACAAAGCCCTCCCAGCCCCC<br>ATCGAGAAAACCATCTCCAAAGCCAAA<br>GGGCAGCCCCGAGAACCACAGGTGTAC<br>ACCCTGCCCCCATCCCGGGATGAGCTG<br>ACCAAGAACCAGGTCAGCCTGACCTGC<br>CTGGTCAAAGGCTTCTATCCCAGCGAC<br>ATCGCCGTGGAGTGGGAGAGCAATGGG<br>CAGCCGGAGAACAACTACAAGACCACG<br>CCTCCCGTGCTGGACTCCGACGGCTCC<br>TTCTTCTTATATTCAAAGCTCACCGTG<br>GACAAGAGCAGGTGGCAGCAGGGGAAC<br>GTCTTCTCATGCTCCGTGATGCATGAG<br>GCTCTGCACAACCACTACACGCAGAAG<br>AGCCTCTCCCTGTCTCCCGGGAAATGA |
| | Light chain | 36 | GATTACCAGATGACCCAGTCCCCCTCC<br>AGCCTGTCCGCTTCTGTGGGCGACAGA<br>GTGACCATCACCTGTCAGGCCTCCCAG<br>TCCATCTTCTCCTACCTGGCCTGGTAT<br>CAGCAGAAGCCCGGCAAGGCCCCCAAG<br>CTGCTGATCTACGACGCCTCTGATCTG<br>GCCTCCGGCGTGCCCTCTAGATTCTCC<br>GGCTCTGGCTCTGGCACCGACTTTACC<br>CTGACCATCAGCTCCCTCCAGTGCGAG<br>GATGCCGCCACCTACTACTGCCAGCAG<br>GGCTACACCAGATCCGACGTGGACAAC<br>GCCTTTGGCGGAGGCACCAAGGTGGAA<br>ATCAAACGAACTGTGGCTGCACCATCT<br>GTCTTCATCTTCCCGCCATCTGATGAG<br>CAGTTGAAATCTGGAACTGCCTCTGTT<br>GTGTGCCTGCTGAATAACTTCTATCCC<br>AGAGAGGCCAAAGTACAGTGGAAGGTG<br>GATAACGCCCTCCAATCGGGTAACTCC<br>CAGGAGAGTGTCACAGAGCAGGACAGC<br>AAGGACAGCACCTACAGCCTCAGCAGC<br>ACCCTGACGCTGAGCAAAGCAGACTAC<br>GAGAAACACAAAGTCTACGCCTGCGAA<br>GTCACCCATCAGGGCCTGAGCTCGCCC<br>GTCACAAAGAGCTTCAACAGGGGAGAG<br>TGTTGA |

⁺Nucleic acid sequences listed do not include leader sequences.

In some embodiments, an antibody or antigen-binding fragment disclosed herein binds to human mesothelin and comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3), as defined by the Kabat numbering system (Kabat, Sequences of Proteins of Immunological Interest.

In some embodiments, an antibody or antigen-binding fragment disclosed herein binds to human mesothelin and comprises three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3), as defined by the IMGT numbering system.

In various embodiments, the anti-mesothelin antibody or antigen-binding fragment comprises three heavy chain CDRs and three light chain CDRs, wherein the CDRs include no more than one, two, three, four, five, or six amino acid additions, deletions or substitutions of HCDR1 (SEQ ID NO: 1 according to Kabat, or SEQ ID NO: 7 according to IMGT), HCDR2 (SEQ ID NO: 2 according to Kabat, or SEQ ID NO: 8 according to IMGT), HCDR3 (SEQ ID NO: 3 according to Kabat, or SEQ ID NO: 9 according to IMGT); and LCDR1 (SEQ ID NO: 4 according to Kabat, or SEQ ID NO: 10 according to IMGT), LCDR2 (SEQ ID NO: 5 according to Kabat, or SEQ ID NO: 11 according to IMGT), and LCDR3 (SEQ ID NO: 6 according to Kabat, or SEQ ID NO: 12 according to IMGT).

In some embodiments, the anti-mesothelin antibody or antigen-binding fragment is humanized. In some embodiments, the anti-mesothelin antibody or antigen-binding fragment contains minimal sequence derived from a non-human immunoglobulin and retains the reactivity of a non-human (e.g., rabbit) antibody while being less immunogenic in human. In some embodiments, the anti-mesothelin antibody or antigen-binding fragment provides one or more of improved stability, formulatability, binding affinity, therapeutic efficacy, and/or decreased aggregation levels as compared to one or more alternate anti-mesothelin antibodies.

In various embodiments, the anti-mesothelin antibody or antigen-binding fragment comprises a heavy chain variable region comprising an amino acid sequence of SEQ ID NO: 13 or a sequence that is at least 90% identical to SEQ ID NO: 13, and/or a light chain variable region comprising an amino acid sequence of SEQ ID NO: 14 or a sequence that is at least 90% identical to SEQ ID NO: 14. In various embodiments, the anti-mesothelin antibody or antigen-binding fragment comprises a heavy chain constant region comprising an amino acid sequence of SEQ ID NO: 15 or a sequence that is at least 90% identical to SEQ ID NO: 15, and/or a light chain constant region comprising an amino acid sequence of SEQ ID NO: 16 or a sequence that is at least 90% identical to SEQ ID NO: 16.

In various embodiments, the anti-mesothelin antibody or antigen-binding fragment comprises a heavy chain amino acid sequence of SEQ ID NO: 17 or a sequence that is at least 90% identical to SEQ ID NO: 17, and/or a light chain amino acid sequence of SEQ ID NO: 18 or a sequence that is at least 90% identical to SEQ ID NO: 18.

In some embodiments, the anti-mesothelin antibody or antigen-binding fragment comprises a human IgG1 heavy chain constant domain and a human Ig kappa light chain constant domain.

In various embodiments, the anti-mesothelin antibody or antigen-binding fragment comprises three heavy chain complementarity determining regions (HCDRs) comprising amino acid sequences encoded by nucleic acid sequences of SEQ ID NO: 19 (HCDR1), SEQ ID NO: 20 (HCDR2), and SEQ ID NO: 21 (HCDR3); and three light chain complementarity determining regions (LCDRs) comprising amino acid sequences encoded by nucleic acid sequences of SEQ ID NO: 22 (LCDR1), SEQ ID NO: 23 (LCDR2), and SEQ ID NO: 24 (LCDR3), as defined by the Kabat numbering system; or three heavy chain complementarity determining regions (HCDRs) comprising amino acid sequences encoded by nucleic acid sequences of SEQ ID NO: 25 (HCDR1), SEQ ID NO: 26 (HCDR2), and SEQ ID NO: 27 (HCDR3); and three light chain complementarity determining regions (LCDRs) comprising amino acid sequences encoded by nucleic acid sequences of SEQ ID NO: 28 (LCDR1), SEQ ID NO: 29 (LCDR2), and SEQ ID NO: 30 (LCDR3), as defined by the IMGT numbering system.

In various embodiments, the anti-mesothelin antibody or antigen-binding fragment comprises a heavy chain variable region comprising an amino acid sequence encoded by the nucleic acid sequence of SEQ ID NO: 31, and a light chain variable region comprising an amino acid sequence encoded by the nucleic acid sequence of SEQ ID NO: 32.

In various embodiments, the anti-mesothelin antibody or antigen-binding fragment comprises a heavy chain constant region comprising an amino acid sequence encoded by the nucleic acid sequence of SEQ ID NO: 33 and a light chain constant region comprising an amino acid sequence encoded by the nucleic acid sequence of SEQ ID NO: 34.

In various embodiments, the anti-mesothelin antibody or antigen-binding fragment comprises a heavy chain comprising an amino acid sequence encoded by the nucleic acid sequence of SEQ ID NO: 35, and a light chain comprising an amino acid sequence encoded by the nucleic acid sequence of SEQ ID NO: 36.

In various embodiments, the anti-mesothelin antibody or antigen-binding fragment is 345A12-HC15-LC4.

The anti-mesothelin antigen-binding domains described herein may be useful alone (e.g., as an antibody or antigen-binding fragment), linked to one or more additional agents (e.g., as ADCs), or as part of a larger macromolecule (e.g., a bispecific antibody or multispecific antibody).

In some embodiments, the antibody or antigen-binding fragment is conjugated to a therapeutic agent. In some embodiments, the chemotherapeutic agent is eribulin. In some embodiments, the chemotherapeutic agent is an eribulin dimer.

In some embodiments, the antibody or antigen-binding fragment is an antigen-binding domain in and/or is part of a bispecific or multispecific antibody. In some embodiments, the bispecific or multispecific antibody comprises an antigen-binding domain that is capable of binding to mesothelin and comprises three HCDRs comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO:5 (LCDR2), and SEQ ID NO: 6 (LCDR3), as defined by the Kabat numbering system; or three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3), as defined by the IMGT numbering system. In some embodiments, the multispecific antibody comprises one or more additional antigen binding domains, e.g., for the same antigen (i.e., mesothelin) or for other antigens.

In some embodiments, an antigen-binding domain is an antigen-binding fragment. In some embodiments, the antigen-binding domain and/or antigen-binding fragment is a single chain variable fragment (scFv) or a Fab fragment.

In some embodiments, the antigen-binding domains (e.g., the anti-mesothelin antigen-binding domains) disclosed herein, for use alone or as part of a larger macromolecule, may include further modifications (e.g., one or more amino acid substitutions, deletions, and/or insertions) while retaining mesothelin-binding function.

Antibody-Drug Conjugates

Further provided herein, in various embodiments, are antibody-drug conjugate (ADC) compounds comprising a linker that attaches a chemotherapeutic drug moiety, e.g., eribulin, to an anti-mesothelin antibody disclosed herein. Antibody-drug conjugate (ADC) compounds may be represented by Formula I:

$$Ab-(L-D)_p \qquad (I)$$

wherein Ab is an internalizing anti-mesothelin antibody disclosed herein or an internalizing antigen-binding fragment thereof;

D is eribulin;

L is a cleavable linker that covalently attaches Ab to D; and p is an integer from 1 to 8.

The ADC compounds of the present disclosure include an antibody moiety (including an antigen-binding fragment thereof) conjugated (e.g., covalently attached by a linker) to a drug moiety (e.g., an eribulin), wherein the drug moiety when not conjugated to an antibody moiety has a cytotoxic or cytostatic effect. In various embodiments, the drug moiety exhibits reduced or no cytotoxicity when bound in a conjugate but resumes cytotoxicity after cleavage from the linker and antibody moiety. In various embodiments, the drug moiety exhibits reduced or no bystander killing when bound in a conjugate but exhibits increased bystander killing after cleavage from a conjugate.

In some embodiments, the ADC compounds disclosed herein can selectively deliver an effective dose of a drug moiety (e.g., eribulin) to cancer cells or to tumor tissues that express an antigen targeted by the antibody moiety of the ADC (e.g., mesothelin). In some embodiments, the disclosed ADC compounds specifically target a cancer by delivering eribulin to cells or tissues that express mesothelin while sparing normal cells or tissues that either do not express mesothelin or express mesothelin at much lower levels. In some embodiments, the disclosed ADC compounds have improved on-target killing and/or reduced off-target killing, as compared to an ADC comprising an alternate antibody, linker, and/or drug moiety, e.g., BAY 94-9343. In some embodiments, the disclosed ADC compounds have improved ADCC activity retention by the ADC, as compared to an ADC comprising an alternate antibody, linker, and/or drug moiety, e.g., BAY 94-9343. In some embodiments, the disclosed ADC compounds have improved stability (e.g., plasma stability), as compared to an ADC comprising an alternate antibody, linker, and/or drug moiety, e.g., BAY 94-9343. In some embodiments, the disclosed ADC compounds have improved anti-tumor efficacy, as compared to an ADC comprising an alternate antibody, linker, and/or drug moiety, e.g., BAY 94-9343.

In some embodiments, the ADC compounds disclosed herein can provide favorable anti-tumor efficacy with a lower dose of eribulin, as compared to the dose of eribulin when evaluated as a stand-alone drug (i.e., not conjugated to an antibody moiety). In some embodiments, the tumor-specific targeting of the ADC compounds disclosed herein increases anti-tumor activity and/or decreases off-target cytotoxicity of the ADC, as compared to eribulin when evaluated as a stand-alone drug. For instance, in some embodiments, the ADC compounds disclosed herein show favorable anti-tumor activity with a dose of eribulin that is at least 10-fold lower, at least 15-fold lower, at least 20-fold lower, or at least 30-fold lower than the dose of eribulin when evaluated as a stand-alone drug. In some embodiments, the disclosed ADC compounds demonstrate anti-tumor activity that is comparable to or superior to the activity of eribulin when evaluated as a stand-alone drug, while providing an improved toxicologic or safety profile over that of the eribulin on its own.

In some embodiments, the linker is stable outside a cell, such that the ADC remains intact when present in extracellular conditions but is capable of being cleaved on internalization in a cell, e.g., a cancer cell. In some embodiments, an eribulin drug moiety is cleaved from an anti-mesothelin antibody moiety when the ADC enters a cell that expresses mesothelin, and cleavage releases an unmodified form of eribulin.

In some embodiments, the linker comprises a cleavable moiety that is positioned such that no part of the linker or the antibody moiety remains bound to the eribulin drug moiety upon cleavage. In some embodiments, the cleavable moiety in the linker is a cleavable peptide moiety. In some embodiments, an ADC that comprises a cleavable peptide moiety demonstrates lower aggregation levels, improved antibody: drug ratio, increased on-target killing of cancer cells, decreased off-target killing of non-cancer cells, and/or higher drug loading (p) relative to an ADC that comprises an alternate linker moiety. In some embodiments, the increased potency and/or cytotoxicity is provided in a cancer expressing moderate levels of mesothelin. In some embodiments, the cleavable peptide moiety is cleavable by an enzyme, and the linker is an enzyme-cleavable linker. In some embodiments, the enzyme is cathepsin B, and the linker is a cathepsin-cleavable linker. In some embodiments, the enzyme-cleavable linker (e.g., the cathepsin-cleavable linker) exhibits one or more of the improved properties mentioned above, as compared to an alternate cleavage mechanism.

In some embodiments, the cleavable peptide moiety in the linker comprises an amino acid unit. In some embodiments, the amino acid unit comprises valine-citrulline (Val-Cit). In some embodiments, an ADC that comprises Val-Cit demonstrates increased stability, decreased off-target cell killing, increased on-target cell killing, lower aggregation levels, and/or higher drug loading relative to an ADC that comprises an alternate amino acid unit or alternate cleavable moiety.

In some embodiments, the linker comprises at least one spacer unit joining the antibody moiety to the cleavable moiety. In some embodiments, the spacer unit in the linker may comprise at least one polyethylene glycol (PEG) moiety. The PEG moiety may, for example, comprise —(PEG)$_m$-, wherein m is an integer from 1 to 10. In some embodiments, the spacer unit in the linker comprises (PEG)$_2$. In some embodiments, an ADC that comprises a shorter spacer unit (e.g., (PEG)$_2$) demonstrates lower aggregation levels and/or higher drug loading relative to an ADC that comprises a longer spacer unit (e.g., (PEG)$_8$) despite the shorter linker length.

In some embodiments, the spacer unit in the linker attaches to the antibody moiety of the ADC via a maleimide moiety (Mal). In some embodiments, an ADC that comprises a linker attached to the antibody moiety via a Mal demonstrates higher drug loading relative to an ADC that comprises a linker attached to the antibody moiety via an alternate moiety. In some embodiments, the Mal in the linker is joined to the antibody moiety via a cysteine residue (e.g., LCcys80). In some embodiments, the Mal in the linker is joined to a cysteine residue (e.g., LCcys80) of a light chain variable region on the antibody or antigen-binding fragment.

In some embodiments, p is 2 and two -L-D moieties are attached to the antibody or antigen-binding fragment. In some embodiments, each -L-D moiety is attached to a cysteine residue (e.g., LCcys80) of a light chain variable region on the antibody or antigen-binding fragment. In some embodiments, the cysteine residue is a LCcys80. In some embodiments, the Mal-spacer unit comprises a PEG moiety. In some embodiments, the linker comprises Mal-(PEG)$_m$, e.g., Mal-(PEG)$_2$. In some embodiments, the Mal-spacer unit attaches the antibody moiety to the cleavable moiety in the linker. In some embodiments, the cleavable moiety in the linker is a cleavable peptide moiety, e.g., an amino acid unit. In some embodiments, the linker comprises Mal-(PEG)$_2$-Val-Cit.

In some embodiments, the cleavable moiety in the linker is directly joined to the eribulin drug moiety of the ADC, and the cleavable moiety is either directly connected to the antibody moiety or connected through a spacer unit. In some embodiments, a spacer unit also attaches the cleavable moiety in the linker to the eribulin drug moiety. In some embodiments, the spacer unit that attaches the cleavable moiety in the linker to the eribulin drug moiety is self-immolative. In some embodiments, the self-immolative spacer is capable of releasing unmodified eribulin in a target cell. In some embodiments, the self-immolative spacer unit comprises a p-aminobenzyl alcohol e.g., p-aminobenzyloxycarbonyl (pAB). The pAB in the linker, in some embodiments, attaches the cleavable moiety to the eribulin drug moiety. In some embodiments, the cleavable moiety is a cleavable peptide moiety, e.g., an amino acid unit. In some embodiments, the linker comprises Val-Cit-pAB. In some embodiments, the linker comprises Val-Cit-pAB and a PEG spacer unit joining the linker to the antibody moiety through a Mal.

In some embodiments, p is an integer from 1 to 8, or from 2 to 6. In some embodiments, p is 2 or 6. In some embodiments, the linker comprises Mal-(PEG)$_2$-Val-Cit-pAB. In some embodiments, the linker comprises Mal-(PEG)$_2$-Val-Cit-pAB and p is 2. In some embodiments, the linker comprises Mal-(PEG)$_2$-Val-Cit-pAB and p is 6.

In some embodiments, the antibody moiety is conjugated to eribulin drug moiety via a linker comprising a Mal moiety, a PEG moiety, Val-Cit, and a pAB. In these embodiments, the maleimide moiety covalently attaches the linker-drug moiety to the antibody moiety, and the pAB acts as a self-immolative spacer unit. Such linker may be referred to as the "Mal-VC-pAB" linker, the "Mal-VCP", "maleimide-VCP", or "VCP" linker, the "Mal-(PEG)$_2$-VCP" linker, or the "Mal-(PEG)$_2$-Val-Cit-pAB" linker. In some embodiments, the eribulin drug moiety is eribulin covalently linked at the C-35 position. In some embodiments, the pAB of the Mal-(PEG)$_2$-Val-Cit-pAB linker is attached to the C-35 amine on the eribulin drug moiety.

345A12-HC15-LC4 is an exemplary anti-mesothelin antibody comprising or encoded by the sequences shown above in Tables 1-10, e.g., comprising a heavy chain variable region comprising an amino acid sequence of SEQ ID NO: 13 and a light chain variable region comprising an amino acid sequence of SEQ ID NO: 14. In some embodiments, the antibody moiety of the ADCs disclosed herein comprises a heavy chain variable region comprising an amino acid sequence of SEQ ID NO: 13 and a light chain variable region comprising an amino acid sequence of SEQ ID NO: 14. In some embodiments, the antibody moiety of the ADCs disclosed herein is 345A12-HC15-LC4.

In some embodiments, an ADC disclosed herein comprises 345A12-HC15-LC4-VCP-eribulin. In these embodiments, an antibody moiety comprising 345A12-HC15-LC4 is joined to an eribulin drug moiety via a linker comprising Mal-(PEG)$_2$-Val-Cit-pAB. Such ADC may be referred to as "MORAb-109." In some embodiments, an ADC disclosed herein is MORAb-109.

In some embodiments, an ADC disclosed herein is MORAb-109 and has a p of 2. In some embodiments, when p is 2, the ADC may be referred to as "MORAb-109 (DAR2)." In other embodiments, an ADC disclosed herein is MORAb-109 and has a p of 6. In some embodiments, when p is 6, the ADC may be referred to as "MORAb-109 (DAR6)."

In various embodiments, the linker is designed to facilitate bystander killing (the killing of neighboring cells, e.g., those that do not express mesothelin) through cleavage after cellular internalization and diffusion of the linker-drug moiety and/or the drug moiety alone to neighboring cells. In some embodiments, the linker promotes cellular internalization. In some embodiments, the linker is designed to minimize cleavage in the extracellular environment and thereby reduce toxicity to off-target tissue (e.g., non-cancerous tissue), while preserving ADC binding to target tissue and bystander killing of cancerous tissue that does not express an antigen targeted by the antibody moiety of an ADC, but surrounds target cancer tissue expressing that antigen. In some embodiments, a linker comprising a maleimide (Mal) moiety, a polyethylene glycol (PEG) moiety, valine-citrulline (Val-Cit or "VC"), and a pAB provides these functional features. In some embodiments, a linker comprising Mal-(PEG)$_2$-Val-Cit-pAB is particularly effective in providing these functional features when joining an antibody moiety and an eribulin drug moiety. In some embodiments, a linker comprising Mal-(PEG)$_2$-Val-Cit-pAB is effective in providing some or all of these functional features when joining an anti-mesothelin antibody moiety such as 345A12-HC15-LC4 and an eribulin drug moiety.

In some embodiments, an anti-mesothelin antibody or antigen-binding fragment comprises sequences disclosed herein (e.g., comprising the six CDRs and/or heavy and light chain variable domains disclosed in Tables 1-3). In some embodiments, the antibody or antigen-binding fragment is a full-length antibody. In some embodiments, the antibody or antigen-binding fragment is a monospecific antibody or antigen-binding fragment, a bispecific antibody or antigen-binding fragment, or a multispecific antibody or antigen-binding fragment. In some embodiments, the antibody or antigen-binding fragment is a single chain variable fragment (scFv) or a Fab fragment.

In some embodiments, an ADC comprising an anti-mesothelin antibody (Ab) moiety and a cleavable peptide moiety demonstrates lower aggregation levels, improved antibody:drug ratio, increased on-target killing of cancer cells, decreased off-target killing of non-cancer cells, higher drug loading (p), increased cytotoxicity, and/or potency relative to an ADC comprising an alternate antibody or antigen-binding fragment. In some embodiments, the ADC is an ADC of Formula (I):

$$Ab-(L-D)_p \qquad (I)$$

wherein Ab is an antibody or antigen-binding fragment, wherein the antibody or antigen-binding fragment is capable of binding to mesothelin and comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO: 5 (LCDR2), and SEQ ID NO: 6 (LCDR3), as defined by the Kabat numbering system; or three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3), as defined by the IMGT numbering system;

D is a chemotherapeutic agent (e.g., eribulin);
L is a cleavable linker that covalently attaches Ab to D; and
p is an integer from 1 to 8.

In some embodiments, the antibody or antigen-binding fragment comprises a heavy chain variable region comprising an amino acid sequence of SEQ ID NO: 13, and a light chain variable region comprising an amino acid sequence of SEQ ID NO: 14. In some embodiments, the antibody or antigen-binding fragment comprises a human IgG1 heavy chain constant domain and a human Ig kappa light chain constant domain. In some embodiments, the antibody or antigen-binding fragment comprises a heavy chain constant region comprising an amino acid sequence of SEQ ID NO: 15, and a light chain constant region comprising an amino acid sequence of SEQ ID NO: 16. In some embodiments, the antibody or antigen-binding fragment comprises a heavy chain comprising an amino acid sequence of SEQ ID NO: 17, and a light chain comprising an amino acid sequence of SEQ ID NO: 18.

In some embodiments, the ADC has Formula (I):

$$Ab-(L-D)_p \qquad (I)$$

wherein:
Ab is an antibody or antigen-binding fragment, wherein the antibody or antigen-binding fragment is capable of binding to mesothelin and/or a mesothelin-expressing cell and comprises three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO:5 (LCDR2), and SEQ ID NO: 6 (LCDR3), as defined by the Kabat numbering system; or three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3), as defined by the IMGT numbering system;

D is an eribulin;
L is a cleavable linker that covalently attaches Ab to D; and
p is an integer from 1 to 8.

In some embodiments, the antibody or antigen-binding fragment that targets mesothelin and/or a mesothelin-expressing cell comprises a heavy chain variable region comprising an amino acid sequence of SEQ ID NO: 13, and a light chain variable region comprising an amino acid sequence of SEQ ID NO: 14. In some embodiments, the antibody or antigen-binding fragment comprises a human IgG1 heavy chain constant domain and a human Ig kappa light chain constant domain. In some embodiments, the antibody or antigen-binding fragment comprises a heavy chain constant region comprising an amino acid sequence of SEQ ID NO: 15, and a light chain constant region comprising an amino acid sequence of SEQ ID NO: 16. In some embodiments, the antibody or antigen-binding fragment comprises a heavy chain comprising an amino acid sequence of SEQ ID NO: 17, and a light chain comprising an amino acid sequence of SEQ ID NO: 18.

In some embodiments, the ADC has Formula (I):

$$Ab-(L-D)_p \qquad (I)$$

wherein:
Ab is an antibody or antigen-binding fragment thereof that targets mesothelin and/or a mesothelin-expressing cell comprising three heavy chain complementarity determining regions (HCDRs) comprising amino acid sequences of SEQ ID NO: 1 (HCDR1), SEQ ID NO: 2 (HCDR2), and SEQ ID NO: 3 (HCDR3); and three light chain complementarity determining regions (LCDRs) comprising amino acid sequences of SEQ ID NO: 4 (LCDR1), SEQ ID NO:5 (LCDR2), and SEQ ID NO: 6 (LCDR3), as defined by the Kabat numbering system; or three heavy chain complementarity determining regions (HCDRs) comprising amino acid sequences of SEQ ID NO: 7 (HCDR1), SEQ ID NO: 8 (HCDR2), and SEQ ID NO: 9 (HCDR3); and three light chain complementarity determining regions (LCDRs) comprising amino acid sequences of SEQ ID NO: 10 (LCDR1), SEQ ID NO: 11 (LCDR2), and SEQ ID NO: 12 (LCDR3), as defined by the IMGT numbering system;
D is an eribulin;
L is a cleavable linker comprising Mal-(PEG)$_2$-Val-Cit-pAB; and
p is an integer from 1 to 8.

In some embodiments, the antibody or antigen-binding fragment that targets mesothelin and/or a mesothelin-expressing cell comprises a heavy chain variable region comprising an amino acid sequence of SEQ ID NO: 13, and a light chain variable region comprising an amino acid sequence of SEQ ID NO: 14. In some embodiments, the antibody or antigen-binding fragment comprises a human IgG1 heavy chain constant domain and a human Ig kappa light chain constant domain. In some embodiments, the antibody or antigen-binding fragment comprises an IgG1 heavy chain constant region comprising an amino acid sequence of SEQ ID NO: 15, and an Ig kappa light chain constant region comprising an amino acid sequence of SEQ ID NO: 16. In some embodiments, the antibody or antigen-binding fragment comprises a heavy chain comprising an amino acid sequence of SEQ ID NO: 17, and a light chain comprising an amino acid sequence of SEQ ID NO: 18.

In some embodiments, the ADC has Formula (I):

$$Ab-(L-D)_p \qquad (I)$$

wherein:
Ab is an antibody or antigen-binding fragment, wherein the antibody or antigen-binding fragment is capable of binding to mesothelin and comprises a heavy chain variable region comprising an amino acid sequence of SEQ ID NO: 13, and a light chain variable region comprising an amino acid sequence of SEQ ID NO: 14;
D is an eribulin;
L is a cleavable linker comprising Mal-(PEG)$_2$-Val-Cit-pAB; and
p is an integer from 1 to 8.

In some embodiments, the antibody or antigen-binding fragment comprises a human IgG1 heavy chain constant region, and a human Ig kappa light chain constant region. In some embodiments, the antibody or antigen-binding fragment comprises a heavy chain constant region comprising an amino acid sequence of SEQ ID NO: 15, and a light chain constant region comprising an amino acid sequence of SEQ ID NO: 16. In some embodiments, the antibody or antigen-binding fragment comprises a heavy chain comprising an amino acid sequence of SEQ ID NO: 17, and a light chain comprising an amino acid sequence of SEQ ID NO: 18.

In some embodiments, the antibody or antigen-binding fragment of the ADC is 345A12-HC15-LC4. In some embodiments, p is 1 to 8. In some embodiments, p is 2 or 6. In some embodiments, p is 2.

In some embodiments, an ADC disclosed herein (e.g., one comprising an anti-mesothelin antibody and linker disclosed herein) with a lower level of eribulin drug loading (e.g., a p of 2) can deliver the same or similar levels of eribulin to a cancer cell or to a tumor tissue as an ADC with a higher level of drug loading (e.g., a p of 6). In some embodiments, an ADC with a lower level of drug loading (e.g., a p of 2) can provide tumor growth inhibition and/or in vivo anti-cancer treatment efficacy approximately comparable to or superior to that of an ADC with a higher level of drug loading (e.g., a p of 6).

In some embodiments, each eribulin moiety is joined by a cleavable linker to the mesothelin-targeting antibody or antigen-binding fragment via a cysteine residue on the antibody or fragment (e.g., LCcys80). In some embodiments, a total of two linker-eribulin moieties are attached to the mesothelin-targeting antibody or antigen-binding fragment, e.g., via two cysteine residues on the antibody or antigen-binding fragment (i.e., such that the ADC has a DAR2). In some embodiments, the cysteine residue(s) is/are LCcys80.

The development and production of an ADC for use as a human therapeutic agent, e.g., as an oncologic agent, may require more than the identification of an antibody capable of binding to a desired target or targets and attaching to a drug used on its own to treat cancer. Linking the antibody to the drug may have significant and unpredictable effects on the activity of one or both the antibody and the drug, effects which will vary depending on the antibody and/or type of linker and/or drug chosen. In some embodiments, therefore, the components of the ADC are selected to (i) retain one or more therapeutic properties exhibited by the antibody and drug moieties in isolation, (ii) maintain the specific binding properties of the antibody moiety; (iii) optimize drug loading and drug-to-antibody ratios; (iv) allow delivery, e.g., intracellular delivery, of the drug moiety via stable attachment to the antibody moiety; (v) retain ADC stability as an intact conjugate until transport or delivery to a target site; (vi) minimize aggregation of the ADC prior to or after administration; (vii) allow for the therapeutic effect, e.g., cytotoxic effect, of the drug moiety after cleavage in the cellular environment; (viii) exhibit in vivo anti-cancer treatment efficacy comparable to or superior to that of the antibody and drug moieties in isolation; (ix) minimize off-target killing by the drug moiety; and/or (x) exhibit desirable pharmacokinetic and pharmacodynamics properties, formulatability, and toxicologic/immunologic profiles. Screening each of these properties may be needed to identify an improved ADC for therapeutic use (Ab et al. (2015) Mol. Cancer Ther. 14:1605-13).

In some embodiments, an ADC disclosed herein comprising an anti-mesothelin antibody or antigen-binding fragment joined to a chemotherapeutic, e.g., eribulin, demonstrates a particular combination of desirable properties. These properties include, but are not limited to, effective levels of drug loading, low aggregation levels, stability under storage conditions and/or when in circulation in the body (e.g., serum and matrix stability), retained affinity for target-expressing cells comparable to unconjugated antibody, potent cytotoxicity against target-expressing cells, high levels of bystander killing, and/or effective in vivo anti-cancer activity, all as compared to ADCs using other antibody moieties. In some embodiments, the high anti-cancer activities of these conjugates are seen even when tested in cell lines having moderate antigen expression, demonstrating potent sensitivity to toxin payload delivered by the ADC. In some embodiments, an ADC comprising an anti-mesothelin antibody or antigen-binding fragment disclosed herein exhibits particularly favorable anti-tumor cytotoxicity and/or potency, and improved off-target toxicity and drug metabolism and pharmacokinetic (DMPK) profiles as compared to an ADC comprising an alternate antibody moiety. In some embodiments, an ADC comprising a humanized anti-mesothelin antibody disclosed herein and eribulin provides surprisingly favorable pharmacological and toxicological properties as compared to an ADC comprising an alternate antibody moiety and/or conjugate.

The ADC compounds of the present disclosure may selectively deliver an effective dose of a cytotoxic or cytostatic agent to cancer cells or to tumor tissue. In some embodiments, the cytotoxic and/or cytostatic activity of the ADC is dependent on the target antigen expression level in a cell. In some embodiments, the disclosed ADCs are particularly effective at killing cancer cells expressing a high level of target antigen, as compared to cancer cells expressing the same antigen at a low level. In some embodiments, the disclosed ADCs are particularly effective at killing cancer cells expressing the target antigen at a moderate level, as compared to cancer cells expressing the same antigen at a low level.

Exemplary high mesothelin-expressing cancers include but are not limited to ovarian cancer (e.g., serous ovarian cancer, clear cell ovarian cancer), pancreatic cancer, mesothelioma, endometrial cancer, non-small cell lung cancer (e.g., adenocarcinoma), and colorectal cancer. Exemplary moderate mesothelin-expressing cancers include but are not limited to gastric cancer, thymic carcinoma, and cholangiocellular carcinoma. Exemplary low mesothelin-expressing cancers include but are not limited to melanoma and lymphoma. In some embodiments, mesothelin-expressing cancers may include cancers harboring mutations and/or drug resistance, e.g., KRAS/STK11 mutated lung cancer (non-small cell lung adenocarcinoma), for example those mutated lung cancers that exhibit resistance to treatment with PD-1 checkpoint blockade.

Drug Moieties

The drug moiety (D) of the ADCs described herein can be any chemotherapeutic agent. Useful classes of chemotherapeutic agents include, for example, anti-tubulin agents. In certain embodiments, the drug moiety is an anti-tubulin agent. One exemplary drug moiety for use in the described ADCs and compositions is eribulin. Another exemplary drug moiety for use in the described ADCs and compositions is an eribulin dimer.

In various embodiments, the structure of eribulin used in its natural form in the disclosed ADCs is as shown in Formula (II):

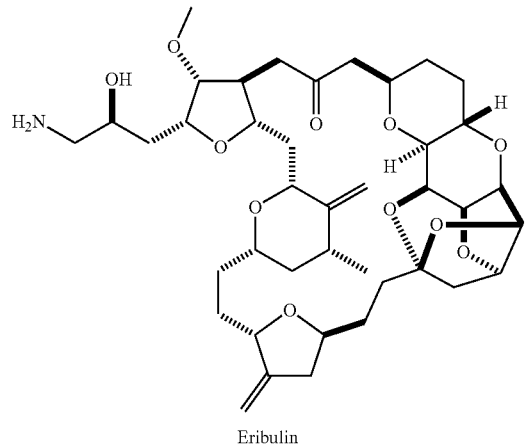

Eribulin

In various other embodiments, the structure of the eribulin used in the disclosed ADCs is as shown in Publ. No. US 20180193478, which is incorporated herein by reference for all eribulin structures and methods of synthesizing those structures.

Drug Loading

Drug loading may be represented by p, and is also referred to herein as the drug-to-antibody ratio (DAR). Drug loading may range from, e.g., 1 to 10 drug moieties per antibody moiety. In some embodiments, p is an integer from 1 to 10. In some embodiments, p is an integer from 1 to 10, 1 to 9, 1 to 8, 1 to 7, 1 to 6, 1 to 5, 1 to 4, 1 to 3, or 1 to 2. In some embodiments, p is an integer from 2 to 10, 2 to 9, 2 to 8, 2 to 7, 2 to 6, 2 to 5, 2 to 4, or 2 to 3. In some embodiments, p is an integer from 1 to 8. In some embodiments, p is an integer from 1 to 6. In some embodiments, p is an integer from 2 to 6. In some embodiments, p is 2. In some embodiments, p is 6.

Drug loading may be limited, in some embodiments, by the number of attachment sites on the antibody moiety. In some embodiments, the linker moiety (L) of the ADC attaches to the antibody moiety through a chemically active group on one or more amino acid residues on the antibody moiety. For example, the linker may be attached to the antibody moiety via a free amino, imino, hydroxyl, thiol, or carboxyl group (e.g., to the N- or C-terminus, to the epsilon amino group of one or more lysine residues, to the free carboxylic acid group of one or more glutamic acid or aspartic acid residues, or to the sulfhydryl group of one or more cysteine residues). The site to which the linker is attached can be a natural residue in the amino acid sequence of the antibody moiety, or it can be introduced into the antibody moiety, e.g., by DNA recombinant technology (e.g., by introducing a cysteine residue into the amino acid sequence) or by protein biochemistry (e.g., by reduction, pH adjustment, or hydrolysis).

In some embodiments, the number of drug moieties that can be conjugated to an antibody moiety is limited by the number of free cysteine residues. For example, where the attachment is a cysteine thiol group, an antibody may have only one or a few cysteine thiol groups, or may have only one or a few sufficiently reactive thiol groups through which a linker may be attached. Generally, antibodies do not contain many free and reactive cysteine thiol groups that may be linked to a drug moiety. Indeed, most cysteine thiol residues in antibodies are involved in either interchain or intrachain disulfide bonds. Conjugation to cysteines can therefore, in some embodiments, require at least partial reduction of the antibody. Over-attachment of linker-toxin to an antibody may destabilize the antibody by reducing the cysteine residues available to form disulfide bonds. Thus, in some embodiments, an optimal drug:antibody ratio should increase potency of the ADC (by increasing the number of attached drug moieties per antibody) without destabilizing the antibody moiety. In some embodiments, an optimal ratio may be 2 or 6. In some embodiments, an optimal ratio is 2.

In some embodiments, one or more site-specific conjugation technologies are used to produce a homogeneous ADC product with a defined drug loading, i.e., a defined drug-to-antibody ratio (DAR). In some embodiments, free cysteine residues can be generated in the light chain or heavy chain of antibodies for site-specific conjugation via Residue-SPEcific Conjugation Technology (RESPECT). Exemplary protocols for the generation of RESPECT-formatted antibodies are described in Albone et al. (2017) Cancer Biol. Ther. 18(5):347-57, and in Intl. Pub. Nos. WO/2016205618 and WO/2017106643, each of which is incorporated herein by reference for methods of performing site-specific conjugation. In some embodiments, an ADC is produced using site-specific conjugation to covalently attach an antibody moiety to a drug moiety via a linker (e.g., a Mal-(PEG)$_2$-Val-Cit-pAB linker). In some embodiments, site-specific conjugation is used to target a DAR of about 2 for ADCs or compositions comprising an eribulin drug moiety.

Rabbit monoclonal antibodies chimerized or humanized to human constant regions may produce unpaired cysteines within the light chain, leaving those residues available for conjugation (Albone et al. (2017) Cancer Biol. Ther. 18(5): 347-57; Intl. Pub. No. WO/2016205618). In some embodiments, the antibody moiety used for site-specific conjugation is a RESPECT-L-formatted antibody. Exemplary RESPECT-L-formatted antibodies with an unpaired cysteine at light chain position 80 (LCcys80) are described herein. As used herein, "LCcys80" or "Cys80" refers to a cysteine residue at amino acid position 80 of a light chain variable region on an antibody or an antigen-binding fragment according to the Kabat numbering system. For example, in some embodiments, in the light chain variable regions disclosed herein, LCcys80 occurs at amino acid position 80. RESPECT-L-derived antibodies can yield an ADC with a DAR of about 2. In some embodiments, a drug loading and/or an average drug loading of about 2 is achieved, e.g., using site-specific conjugation.

Pharmaceutical Compositions

In some embodiments, the present disclosure further provides pharmaceutical compositions comprising one or more antibodies, antigen-binding fragments, conjugates, and/or ADCs disclosed herein and a pharmaceutically acceptable carrier. In some embodiments, the pharmaceutical compositions described herein comprise at least one additional agent.

In some embodiments, the present disclosure further provides pharmaceutical compositions comprising multiple copies of an antibody, antigen-binding fragment, conjugate, and/or ADC disclosed herein. In some embodiments, the present disclosure further provides pharmaceutical compositions comprising multiple copies of an ADC disclosed herein. In some embodiments, the average p of the ADCs in a composition is from about 1 to about 8. In some embodiments, the average p of the ADCs in the composition is about 2 or about 6. In some embodiments, the average p of the ADCs in the composition is about 1.3, about 1.4, about 1.5, about 1.6, about 1.7, about 1.8, about 1.9, about 2.0, about 2.1, about 2.2, or about 2.3. In some embodiments, the average p of the ADCs in the composition is about 5.5, 5.6, 5.7, 5.8, 5.9, 6.0, 6.1, 6.2, 6.3, 6.4, or 6.5.

In some embodiments, a pharmaceutical composition may further comprise one or more additional therapeutic agents, e.g., one or more agents capable of treating a mesothelin-expressing cancer, a steroid, and the like.

Therapeutic Uses and Methods of Treatment

Disclosed herein are methods of using the disclosed antibodies, antigen-binding fragments, conjugates, ADCs and/or pharmaceutical compositions in treating a subject for a disorder, e.g., an oncologic disorder. The antibodies, antigen-binding fragments, conjugates, and/or ADCs may be administered alone or in combination with a second therapeutic agent, and may be administered in any pharmaceutically acceptable formulation, dosage, and dosing regimen. The antibodies, antigen-binding fragments, and/or ADC treatment efficacy may be evaluated for toxicity as well as indicators of efficacy and adjusted accordingly. Efficacy measures include, but are not limited to, a cytostatic and/or cytotoxic effect observed in vitro or in vivo, reduced tumor volume, tumor growth inhibition, and/or prolonged survival.

Methods of determining whether an antibody, antigen-binding fragment, and/or ADC exerts a cytostatic and/or cytotoxic effect on a cell are known. For example, the cytotoxic or cytostatic activity of an antibody, antigen-binding fragment, and/or ADC can be measured by exposing mammalian cells expressing a target protein of the antibody, antigen-binding fragment, and/or ADC in a cell culture medium; culturing the cells for a period from about 6 hours to about 5 days; and measuring cell viability. Cell-based in vitro assays may also be used to measure viability (proliferation), cytotoxicity, and induction of apoptosis (caspase activation) of the ADC.

For determining whether an antibody, antigen-binding fragment, and/or ADC exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of 3H-thymidine during the final 8 hours of the 72-hour period. The incorporation of 3H-thymidine into cells of the culture is measured in the presence and absence of the antibody, antigen-binding fragment, and/or ADC.

For determining cytotoxicity, necrosis or apoptosis (programmed cell death) may be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an ADC is useful in the treatment of cancers.

Cell viability may be measured, e.g., by determining in a cell the uptake of a dye such as neutral red, trypan blue, Crystal Violet, or ALAMAR™ blue (see, e.g., Page et al. (1993) Intl. J. Oncology 3:473-6). In such an assay, the cells are incubated in media containing the dye, the cells are washed, and the remaining dye, reflecting cellular uptake of the dye, is measured spectrophotometrically. In certain embodiments, in vitro potency and/or cytotoxicity of prepared ADCs is assessed using a Crystal Violet assay. Crystal Violet is a triarylmethane dye that accumulates in the nucleus of viable cells. In this assay, cells are exposed to the ADCs or control agents for a defined period of time, after which, cells are stained with Crystal Violet, washed copiously with water, then solubilized with 1% SDS and read spectrophotometrically. The protein-binding dye sulforhodamine B (SRB) can also be used to measure cytotoxicity (Skehan et al. (1990) J. Natl. Cancer Inst. 82:1107-12).

Apoptosis can be quantitated, for example, by measuring DNA fragmentation. Commercial photometric methods for the quantitative in vitro determination of DNA fragmentation are available. Examples of such assays, including TUNEL (which detects incorporation of labeled nucleotides in fragmented DNA) and ELISA-based assays, are described in Biochemica (1999) No. 2, pp. 34-37 (Roche Molecular Biochemicals).

Apoptosis may also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al., eds. (1992) pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The disclosed ADCs may also be evaluated for bystander killing activity. Bystander killing activity may be determined, e.g., by an assay employing two cell lines, one positive for target antigen and one negative for target antigen. The cell lines may be labeled to differentiate them. For example, target-positive cells labeled with Nuclight™ Green (NLG) and target-negative cells labeled with Nuclight™ Red (NLR) may be co-cultured, treated with an ADC followed by monitoring of cytotoxicity. Killing of the target-negative cells when mixed with target-positive cells is indicative of bystander killing, whereas killing of the target-negative cells in the absence of the target-positive cells is indicative of off-target killing.

In some embodiments, the present disclosure features a method of killing, inhibiting or modulating the growth of, or interfering with the metabolism of, a cancer cell or tissue by disrupting tubulin. The method may be used with any subject where disruption of tubulin provides a therapeutic benefit. Subjects that may benefit from disrupting tubulin include, but are not limited to, those having or are at risk of having a gastric cancer, ovarian cancer (e.g., epithelial ovarian cancer), lung cancer (e.g., non-small cell lung cancer), breast cancer, endometrial cancer (e.g., serous endometrial carcinoma), osteosarcoma, Kaposi's sarcoma, testicular germ cell cancer, head and neck cancer, liver cancer, renal cancer, urothelial cancer, uterine cancer, bile duct cancer, leukemia (e.g., acute myeloid leukemia), lymphoma (e.g., Hodgkin's disease, non-Hodgkin's lymphoma), myeloma, head and neck cancer, esophageal cancer, pancreatic cancer, prostate cancer, brain cancer (e.g., glioblastoma), thyroid cancer, colorectal cancer, and/or skin cancer (e.g., melanoma), or any metastases thereof (Dumontet and Jordan (2010) Nat. Rev. Drug Discov. 9:790-803).

In various embodiments, the disclosed antibodies, antigen-binding fragments, and/or ADCs may be administered in any cell or tissue that expresses mesothelin, such as a mesothelin-expressing cancer cell or tissue. An exemplary embodiment includes a method of inhibiting mesothelin-mediated cell signaling or a method of killing a cell. The method may be used with any cell or tissue that expresses mesothelin, such as a cancerous cell or a metastatic lesion.

Non-limiting examples of mesothelin-expressing cancers include mesothelioma, pancreatic cancer (e.g., pancreatic adenocarcinoma), ovarian cancer (e.g., serous ovarian cancer, clear cell ovarian cancer, epithelial ovarian cancer), and lung cancer (e.g., non-small cell lung cancer, lung adenocarcinoma) (Wang et al. (2012) PLoS ONE 7:e33214). Other exemplary mesothelin-cancers include endometrial cancer, colorectal cancer, gastric cancer, leukemia, breast cancer, cervical cancer, head and neck cancer, liver cancer, prostate cancer, renal cancer, thyroid cancer, urothelial cancer, uterine cancer, and bile duct cancer. Non-limiting examples of mesothelin-expressing cells include OVCAR3 human ovarian carcinoma cells, HEC-251 human endometrioid cells, H226 human lung squamous cell mesothelioma cells, and cells comprising a recombinant nucleic acid encoding mesothelin or a portion thereof.

Exemplary methods include the steps of contacting a cell with an antibody, antigen-binding fragment, and/or ADC, as described herein, in an effective amount, i.e., amount sufficient to kill the cell. The method can be used on cells in culture, e.g., in vitro, in vivo, ex vivo, or in situ. For example, cells that express mesothelin (e.g., cells collected by biopsy of a tumor or metastatic lesion; cells from an established cancer cell line; or recombinant cells), can be cultured in vitro in culture medium and the contacting step can be affected by adding the antibody, antigen-binding fragment, and/or ADC to the culture medium. The method will result in killing of cells expressing mesothelin, including in particular tumor cells expressing mesothelin. Alternatively, the antibody, antigen-binding fragment, and/or ADC can be administered to a subject by any suitable administration route (e.g., intravenous, subcutaneous, or direct contact with a tumor tissue) to have an effect in vivo. This approach can also be used for antibodies and ADCs targeting other cell surface antigens.

The in vivo effect of a disclosed antibody, antigen-binding fragment, and/or ADC therapeutic composition can be evaluated in a suitable animal model. For example, xenogeneic cancer models can be used, wherein cancer explants or passaged xenograft tissues are introduced into immune compromised animals, such as nude or SCID mice (Klein et al. (1997) Nature Med. 3:402-8). Efficacy may be predicted using assays that measure inhibition of tumor formation, tumor regression or metastasis, and the like.

In vivo assays that evaluate the promotion of tumor death by mechanisms such as apoptosis may also be used. In some embodiments, xenografts from tumor bearing mice treated with the therapeutic composition can be examined for the presence of apoptotic foci and compared to untreated control xenograft-bearing mice. The extent to which apoptotic foci are found in the tumors of the treated mice provides an indication of the therapeutic efficacy of the composition.

Further provided herein are methods of treating cancer. The antibodies, antigen-binding fragments, and/or ADCs disclosed herein can be administered to a non-human mammal or human subject for therapeutic purposes. The therapeutic methods entail administering to a mammal having a tumor a biologically effective amount of an antibody, antigen-binding fragment, and/or ADC comprising eribulin linked to a targeting antibody that binds to an antigen expressed, is accessible to binding, or is localized on a cancer cell surface.

An exemplary embodiment is a method of delivering eribulin to a cell expressing mesothelin, comprising conjugating eribulin to an antibody that immune-specifically binds to a mesothelin epitope and exposing the cell to the antibody, antigen-binding fragment, and/or ADC. Exemplary tumor cells that express mesothelin for which the antibodies, antigen-binding fragments, and/or ADCs of the present disclosure are indicated include ovarian carcinoma cells, endometrioid cells, and lung squamous cell mesothelioma cells.

Another exemplary embodiment is a method of reducing or inhibiting growth of a target antigen-expressing tumor (e.g., a mesothelin-expressing tumor), comprising administering a therapeutically effective amount of an antibody, antigen-binding fragment, and/or ADC. In some embodiments, the treatment is sufficient to reduce or inhibit the growth of the patient's tumor, reduce the number or size of metastatic lesions, reduce tumor load, reduce primary tumor load, reduce invasiveness, prolong survival time, and/or maintain or improve the quality of life. In some embodiments, the tumor is resistant or refractory to treatment with the antibody or antigen-binding moiety of the ADC when administered alone, and/or the tumor is resistant or refractory to treatment with eribulin when administered alone.

Moreover, antibodies of the present disclosure may be administered to a non-human mammal expressing mesothelin for veterinary purposes or as an animal model of human disease. Regarding the latter, such animal models may be useful for evaluating the therapeutic efficacy of the disclosed antibodies, antigen-binding fragments, and/or ADCs (e.g., testing of dosages and time courses of administration).

Further provided herein are therapeutic uses of the disclosed antibodies, antigen-binding fragments, and/or ADCs. An exemplary embodiment is the use of an antibody, antigen-binding fragment, and/or ADC in the treatment of a target antigen-expressing cancer (e.g., a mesothelin-expressing cancer) are also disclosed. Methods for identifying subjects having cancers that express a target antigen (e.g., mesothelin) are known in the art and may be used to identify suitable patients for treatment with a disclosed antibody, antigen-binding fragment, and/or ADC.

Another exemplary embodiment is the use of an antibody, antigen-binding fragment, and/or ADC in a method of manufacturing a medicament for the treatment of a target antigen-expressing cancer (e.g., a mesothelin-expressing cancer).

The therapeutic compositions used in the practice of the foregoing methods may be formulated into pharmaceutical compositions comprising a pharmaceutically acceptable carrier suitable for the desired delivery method. An exemplary embodiment is a pharmaceutical composition comprising an antibody, antigen-binding fragment, and/or ADC of the present disclosure and a pharmaceutically acceptable carrier. Suitable carriers include any material that, when combined with the therapeutic composition, retains the anti-tumor function of the therapeutic composition and is generally non-reactive with the patient's immune system.

Pharmaceutically acceptable carriers include any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol, mesylate salt, and the like, as well as combinations thereof. In many cases, isotonic agents are included, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the ADC.

Therapeutic formulations may be solubilized and administered via any route capable of delivering the therapeutic composition to the tumor site. Potentially effective routes of administration include, but are not limited to, intravenous, parenteral, intraperitoneal, intramuscular, intratumor, intradermal, intraorgan, orthotopic, and the like. Therapeutic protein preparations can be lyophilized and stored as sterile powders, e.g., under vacuum, and then reconstituted in bacteriostatic water (containing for example, benzyl alcohol preservative) or in sterile water prior to injection. Therapeutic formulations may comprise an antibody, antigen-binding fragment, and/or ADC or a pharmaceutically acceptable salt thereof, e.g., a mesylate salt.

The antibodies, antigen-binding fragments, and/or ADCs disclosed herein may be administered at a dosage ranging from about 0.2 mg/kg to about 10 mg/kg to a patient in need thereof. In some embodiments, an antibody, antigen-binding fragment, and/or ADC is administered to the patient daily, bimonthly, or any time period in between. Dosages and administration protocols for the treatment of cancers using the foregoing methods will vary with the method and the target cancer, and will generally depend on a number of other factors appreciated in the art.

Various delivery systems are known and may be used to administer one or more antibodies, antigen-binding fragments, and/or ADCs of the present disclosure. Methods of administering the antibodies, antigen-binding fragments, and/or ADCs include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration may be employed, e.g., by use of an inhaler or nebulizer, and formulation with an aerosolizing agent. See, e.g., the compositions and methods for pulmonary administration described in U.S. Pat. Nos. 6,019,968, 5,985,320, 5,985,309, 5,934,272, 5,874,064, 5,855,913, 5,290,540, and 4,880,078; and Intl. Publ. Nos. WO 1992/019244, WO 1997/032572, WO 1997/044013, WO 1998/031346, and WO 1999/066903. The ADCs may be administered by any convenient route, for example, by infusion or bolus injection, or by absorption through epithelial or mucocutaneous linings (e.g., oral mucosa, rectal and intestinal mucosa, etc.). Administration can be either systemic or local.

Therapeutic compositions disclosed herein may be sterile and stable under the conditions of manufacture and storage. In some embodiments, one or more of the antibodies, antigen-binding fragments, and/or ADCs, or pharmaceutical compositions, is supplied as a dry sterilized lyophilized powder or water free concentrate in a hermetically sealed container and can be reconstituted (e.g., with water or saline) to the appropriate concentration for administration to a subject. In some embodiments, one or more of the prophylactic or therapeutic agents or pharmaceutical compositions is supplied as a dry sterile lyophilized powder in a hermetically sealed container at a unit dosage of at least 5 mg, at least 10 mg, at least 15 mg, at least 25 mg, at least 35 mg, at least 45 mg, at least 50 mg, at least 75 mg, or at least 100 mg, or any amount in between. In some embodiments, the lyophilized antibodies, antigen-binding fragments, and/or ADCs or pharmaceutical compositions is stored at between 2° C. and 8° C. in the original container. In some embodiments, one or more of the antibodies, antigen-binding fragments, and/or ADCs or pharmaceutical compositions described herein is supplied in liquid form in a hermetically sealed container, e.g., a container indicating the quantity and concentration of the agent. In some embodiments, the liquid form of the administered composition is supplied in a hermetically sealed container of at least 0.25 mg/mL, at least 0.5 mg/mL, at least 1 mg/mL, at least 2.5 mg/mL, at least 5 mg/mL, at least 8 mg/mL, at least 10 mg/mL, at least 15 mg/mL, at least 25 mg/mL, at least 50 mg/mL, at least 75 mg/mL, or at least 100 mg/mL ADC. The liquid form may be stored at between 2° C. and 8° C. in the original container.

In some embodiments, the disclosed antibodies, antigen-binding fragments, and/or ADCs can be incorporated into a pharmaceutical composition suitable for parenteral administration. The injectable solution may be composed of either a liquid or lyophilized dosage form in a flint or amber vial, ampule, or pre-filled syringe, or other known delivery or storage device.

The compositions described herein may be in a variety of forms. These include, for example, liquid, semi-solid, and solid dosage forms, such as liquid solutions (e.g., injectable and infusible solutions), dispersions or suspensions, tablets, pills, powders, liposomes, and suppositories. The form depends on the intended mode of administration and therapeutic application.

In various embodiments, treatment involves single bolus or repeated administration of the antibody, antigen-binding fragment, and/or ADC preparation via an acceptable route of administration.

Patients may be evaluated for the levels of target antigen in a given sample (e.g., the levels of target antigen expressing cells) in order to assist in determining the most effective dosing regimen, etc. An exemplary embodiment is a method of determining whether a patient will be responsive to treatment with an antibody, antigen-binding fragment, and/or ADC of the present disclosure, comprising providing a biological sample from the patient and contacting the biological sample with the antibody, antigen-binding fragment, and/or ADC. Exemplary biological samples include tissue or body fluid, such as an inflammatory exudate, blood, serum, bowel fluid, stool sample, or tumor biopsy (e.g., a tumor biopsy derived from a patient having or at risk of a target antigen-expressing cancer, e.g., a mesothelin-expressing cancer). In some embodiments, a sample (e.g., a tissue and/or body fluid) can be obtained from a subject, and a suitable immunological method can be used to detect and/or measure protein expression of the target antigen (e.g., mesothelin). Such evaluations are also used for monitoring purposes throughout therapy, and are useful to gauge therapeutic success in combination with the evaluation of other parameters.

In some embodiments, the efficacy of an antibody, antigen-binding fragment, and/or ADC may be evaluated by contacting a tumor sample from a subject with the antibody, antigen-binding fragment, and/or ADC and evaluating tumor growth rate or volume. In some embodiments, when an antibody, antigen-binding fragment, and/or ADC has been determined to be effective, it may be administered to the subject.

The above therapeutic approaches can be combined with any one of a wide variety of additional surgical, chemotherapy, or radiation therapy regimens. In some embodiments, the antibodies, antigen-binding fragments, and/or ADCs or compositions disclosed herein are co-formulated and/or co-administered with one or more additional therapeutic agents, e.g., one or more chemotherapeutic agents. Non-limiting examples of chemotherapeutic agents include alkylating agents, for example, nitrogen mustards, ethyleneimine compounds, and alkyl sulphonates; antimetabolites, for example, folic acid, purine or pyrimidine antagonists; anti-mitotic agents, for example, anti-tubulin agents such as eribulin or eribulin mesylate (Halaven™), vinca alkaloids, and auristatins; cytotoxic antibiotics; compounds that damage or interfere with DNA expression or replication, for example, DNA minor groove binders; and growth factor receptor antagonists. In some embodiments, a chemotherapeutic agent may be a cytotoxic or cytostatic agent. Examples of cytotoxic agents include, but are not limited to, anti-mitotic agents, such as eribulin or eribulin mesylate (Halaven™), auristatins (e.g., monomethyl auristatin E (MMAE), monomethyl auristatin F (MMAF)), maytansinoids (e.g., maytansine), dolastatins, duostatins, cryptophycins, vinca alkaloids (e.g., vincristine, vinblastine), taxanes, taxols, and colchicines; anthracyclines (e.g., daunorubicin, doxorubicin, dihydroxyanthracindione); cytotoxic antibiotics (e.g., mitomycins, actinomycins, duocarmycins (e.g., CC-1065), auromycins, duomycins, calicheamicins, endomycins, phenomycins); alkylating agents (e.g., cisplatin); intercalating agents (e.g., ethidium bromide); topoisomerase inhibitors (e.g., etoposide, tenoposide); radioisotopes, such as At211, I131, I125, Y90, Re186, Re188, Sm153, Bi212 or 213, P32, and radioactive isotopes of lutetium (e.g., Lu177); and toxins of bacterial, fungal, plant or animal origin (e.g., ricin (e.g., ricin A-chain), diphtheria toxin, *Pseudomonas* exotoxin A (e.g., PE40), endotoxin, mitogellin, combrestatin, restrictocin, gelonin, alpha-sarcin, abrin (e.g., abrin A-chain), modeccin (e.g., modeccin A-chain), curicin, crotin, *Sapaonaria officinalis* inhibitor, glucocorticoid).

Also disclosed herein are uses of one or more of the disclosed antibodies, antigen-binding fragments, and/or ADCs in the manufacture of a medicament for treating cancer, e.g., according to the methods described above. In some embodiments, the ADCs disclosed herein are used for treating cancer, e.g., according to the methods described above.

In various embodiments, kits for use in the laboratory and therapeutic applications described herein are within the scope of the present disclosure. Such kits may comprise a carrier, package, or container that is compartmentalized to receive one or more containers such as vials, tubes, and the like, each of the container(s) comprising one of the separate elements to be used in a method disclosed herein, along with a label or insert comprising instructions for use, such as a use described herein. Kits may comprise a container comprising a drug moiety. The present disclosure also provides one or more of the antibodies, antigen-binding fragments, and/or ADCs, or pharmaceutical compositions thereof, packaged in a hermetically sealed container, such as an ampoule or sachette, indicating the quantity of the agent.

Kits may comprise the container described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label may be present on or with the container to indicate that the composition is used for a specific therapy or non-therapeutic application, such as a prognostic, prophylactic, diagnostic, or laboratory application. A label may also indicate directions for either in vivo or in vitro use, such as those described herein. Directions and or other information may also be included on an insert(s) or label(s), which is included with or on the kit. The label may be on or associated with the container. A label may be on a container when letters, numbers, or other characters forming the label are molded or etched into the container itself. A label may be associated with a container when it is present within a receptacle or carrier that also holds the container, e.g., as a package insert. The label may indicate that the composition is used for diagnosing or treating a condition, such as a cancer a described herein.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

Example 1: Chimeric Antibody Generation Against Human Mesothelin

Chimeric antibodies containing rabbit and human immunoglobulin sequences were generated according to the procedures described below. Antibodies were analyzed for binding to human mesothelin and epitope binding. Initial ADC cytotoxicity of the recombinant chimeric anti-mesothelin antibodies was evaluated in human cell lines expressing varying levels of mesothelin. Lead antibodies for humanization and ADC development are described in Examples 2-3.

1.1 Reagents and Materials
1.1.1 Antibodies

The antibodies used in the following studies are the rabbit-human chimeric (-xi) form of anti-human mesothelin antibodies and have an unpaired cysteine at light chain position 80 (LCcys80). The antibodies were purified and decysteinylated as described below in Section 1.5. Final protein content was assessed by BCA assay and SDS-PAGE.

1.1.2 Conjugatable Cytotoxins and LCcys80 ADCs

Linker-cytotoxin compounds used in the following studies include Mal-PEG$_2$-Auristatin F. The antibodies were conjugated with Mal-PEG$_2$-Auristatin F at a molar ratio of 1:5 (mAb:payload). Conjugated LCcys80 antibodies were purified using desalting chromatography with 2×5 mL HiTrap desalting columns (GE Healthcare) on an AKTA FPLC, using 1×DPBS as running buffer. Final protein content was determined by BCA assay.

1.1.3 Tumor Cell Lines

Human tumor cell lines used in the analyses of rabbit-human chimeric ADCs included A431-K5 (human melanoma cells A431 stably transfected with human mesothelin, MSLN$^{hi}$), A431 (MSLN$^{lo}$), and OVCAR3 (human ovarian carcinoma, MSLN$^{hi}$). A431-K5 cells were obtained from the National Cancer Institute. Cell lines used were obtained directly from the American Type Culture Collection (ATCC).

1.1.4 Other Reagents

All reagents used were obtained from commercial suppliers at research-grade or higher, unless otherwise indicated.

1.2 Generation of Antibodies in Rabbits Against Human Mesothelin

Human mesothelin cDNA from vector p0301 was cloned into an Aldevron expression vector (pB8-Mesothelin-hum). Two rabbits were then immunized with the immunization vector pB8-mesothelin-human. After four genetic applications, immune sera were taken at day 52 of the immunization protocol. Rabbit immune sera was diluted 1:1000 or 1:5000 in PBS containing 1% BSA, and was tested by flow cytometry using mammalian cells previously transiently transfected with the human mesothelin cDNA cloned into an Aldevron expression vector (pB1-mesothelin-hum) and mammalian cells transiently transfected with an irrelevant cDNA cloned into the same vector. Antibodies from the immune sera were then detected with 10 µg/mL goat anti-rabbit IgG R-phycoerythrin (Southern Biotech, #4030-09). Immunization, flow cytometry, and cryo-conserving cells were performed by Aldevron (Dreiburg, Germany).

1.3 High Throughput Screening of Cultures Producing Anti-Mesothelin Antibodies
1.3.1 Cell Culture Cryo-conserved rabbit lymph node cells (2.0×10$^7$ cells) were thawed then activated with 2.5 µg/mL of lectin from *Phytolacca americana* and recovered with DNAse I for one hour at 37° C. with 5% CO$_2$. The cells were seeded at 5 cells per well on a 384 well plate with feeder cells (CHOs expressing rabbit CD154) and cultured in complete IMDM (IMDM supplemented with 10% FBS, 2 mM L-glutamine, 1×MEM NEAA, 1 mM Sodium Pyruvate, 50 U/mL Penicillin, 50 µg/mL Streptomycin, 55 µM 2-Me) that contained 10.5 ng/mL human IL2 and 10.5 ng/mL human IL21 cytokines (PeproTech).

1.3.2 Isolation of Rabbit IgG and Polyclonal Antibodies Against Human Mesothelin On week 2, the wells producing rabbit IgG antibody were identified by IgG FRET using europium cryptate. Wells producing IgG were screened for the presence of rabbit IgG Fcγ antibody by ELISA against plates coated with 1 µg/mL of CHO-MT40 mesothelin. The cultures producing mesothelin specific rabbit IgG were confirmed by ELISA screening against 1 µg/mL of mesothelin and counter screened against 1 µg/mL of CD73-his. FRET and ELISA were performed on the Biomek® FX robotic system (Beckman).

1.3.3 mRNA Gene Rescue of Rabbit Antibodies Against Human Mesothelin

Total RNA was isolated from wells producing rabbit IgG anti-mesothelin antibodies using RNAqueous™-96 Total RNA Isolation Kit (Ambion). cDNA was synthesized and light and heavy chain variable regions were amplified by PCR using Platinum Taq one step RT-PCR kit (Invitrogen) using in-house primers (Table 11). The light and heavy chain variable regions were amplified with nested primers (Table 12) using Platinum Taq Amplification Kit and a thermocycler (40 cycles, 1 min 94° C., 1 min 54° C., 1.5 min 68° C.). Amplified DNA template was visualized by gel electrophoresis, purified by QIAquick 96 PCR Purification Kit (Qiagen) and DNA sequence was determined by GeneWiz (South Plainfield, N.J.) using in-house primers (Table 13). DNA Sequences were analyzed against V-gene and J-gene rabbit families (IMGT/V-QUEST) and against in-house In-Fusion primer database (Blastn). In-Fusion primers (Table 14) were either identified or designed containing a human Fc linker added to the 5' end for the V and J gene primer. Primers were synthesized by IDT (Coralville, Iowa).

TABLE 11

Primer sequences used for one step RT-PCR

| Gene | 5' Primer | 3' Primer |
| --- | --- | --- |
| Heavy | TYCTCCTGGTCRCTSYGCTC (SEQ ID NO: 37) | TTGGTGTTGGTGGCTGGGTG (SEQ ID NO: 38) |

TABLE 11-continued

Primer sequences used for one step RT-PCR

| Gene | 5' Primer | 3' Primer |
|---|---|---|
| Light | GGGCCCCCACTCAGCTGCTG (SEQ ID NO: 39) | GTTBTACTGKTMTYGATGCC (SEQ ID NO: 40) |

TABLE 12

Primer sequences used for PCR

| Gene | 5' Primer | 3' Primer |
|---|---|---|
| Heavy | TYCTCCTGGTCRCTSYGCTC (SEQ ID NO: 41) | TTGGTGTTGGTGGCTGGGTG (SEQ ID NO: 42) |
| Light | ACTCAGCTGCTGGGGCTCCT (SEQ ID NO: 43) | GTTBTACTGKTMTYGATGCC (SEQ ID NO: 44) |

TABLE 13

Primer sequences used for DNA template sequencing

| Gene | 3' Primer |
|---|---|
| Heavy | TTGGTGTTGGTGGCTGGGTG (SEQ ID NO: 45) |
| Light | GTTBTACTGKTMTYGATGCC (SEQ ID NO: 46) |

TABLE 14

Primer sequences used for In-Fusion PCR for sample 345A12

| Gene | 5' Primer | 3' Primer |
|---|---|---|
| Heavy | gccaccggcgtgcactccCAG TCGYTGGAGGAGTCCGGGGG (SEQ ID NO: 47) | gggcccttggtggatgcTGAR GAGACRGTGACSAGGGTSCC (SEQ ID NO: 48) |
| Light | gccaccggcgtgcactccGCC TATGATATGACCCAGACTCCA (SEQ ID NO: 49) | agccacagttcgTTTGACSAC CACCTCGGTCCC (SEQ ID NO: 50) |

1.3.4 PCR Fragments

PCR-amplified variable domains included 15 base-pairs at the 5' and 3' ends homologous to the cloning site within the subcloning vector. PCR fragments were subcloned into an expression plasmid containing a human gamma (p1974 pC+75IZ-ldr-InFusion-hugamma) or kappa constant region (p1975 pC+75IB-ldr-InFusion-hukappa) using an In-Fusion HD cloning kit (Clontech) according to the manufacturer's protocol. 1 µL of the In-Fusion reaction was transformed into Stellar Competent Cells (Clontech) according to manufacturer's protocol. Transformants were grown in 1 mL TB medium (Teknova) overnight at 37° C. on a microtiter plate shaker. The next day, cultures were miniprepped with a QIAprep 96 Turbo miniprep kit (Qiagen) using an epMotion 5075 according to the manufacturer's protocol.

1.3.5 Gene Synthesis Fragments

Humanized heavy and light variable domains were codon-optimized for expression in Chinese hamster ovary (CHO) cells and were synthesized by GeneArt. The variable domains were synthesized with a Kozak translation initiation sequence and an Ig secretion leader sequence, and included 15 base-pairs at the 5' and 3' ends homologous to the cloning site within the subcloning vector. PCR fragments synthesized by GeneArt were subcloned into an expression plasmid containing a human gamma (p1974 pC+75IZ-ldr-InFusion-hugamma) or kappa constant region (p1975 pC+75IB-ldr-InFusion-hukappa) using an InFusion HD cloning kit (Clontech). All clones were sequenced to confirm the presence and fidelity of the inserts.

1.4 Transient mAb Production

1.4.1 HEK Cells

For each milliliter of $3 \times 10^6$ cells to be transfected with ExpiFectamine (ThermoFisher), 333.3 ng HC plasmid and 333.3 ng LC plasmid were incubated for 5-10 min in 50 µL Opti-MEM (ThermoFisher). Likewise, 2.67 µL ExpiFectamine was incubated in 50 µL Opti-MEM. The ExpiFectamine solution was added to the DNA mixture, and incubated for 20-30 min at room temperature. The DNA:ExpiFectamine mixture was added to the cells while swirling and incubated at 37° C., 8% $CO_2$, shaking at 125 rpm. The following day, 5 µL of enhancer 1 and 50 µL of enhancer 2 per mL of cells were added to the transfection with continued incubation for another 7-10 days. After 48-72 hours, cells were fed at a final concentration of 10 g/L Yeastolate (BD Biosciences), 5 mM valeric acid (Sigma-Aldrich), and 1:100 CD Lipid Concentrate (ThermoFisher).

1.4.2 CHO Cells

For each milliliter of $6 \times 10^6$ cells to be transfected with ExpiFectamine CHO (ThermoFisher), 500 ng HC plasmid and 500 ng LC plasmid were mixed in Opti-PRO (ThermoFisher) in 40 µL total volume. Likewise, 3.2 µL ExpiFectamine CHO was mixed in 36.8 µL Opti-PRO. The ExpiFectamine CHO solution was added to the DNA mixture, and incubated for 1-5 min at room temperature. The DNA:ExpiFectamine CHO mixture was added to the cells while swirling and incubated at 37° C., 8% $CO_2$, shaking at 125 rpm. The following day, 6 µL of enhancer and 160 µL of feed per mL of cells were added to the transfection, and cells were transferred to 32° C., 5% $CO_2$. At day 5, an additional 160 µL of feed per mL of cells was added. At days 12 to 14, the supernatants were harvested.

1.5 mAb Purification and Decysteinylation

1.5.1 Antibody Purification

Prosep-vA High Capacity Protein A resin (Millipore) was equilibrated with DPBS, and 50 µL were added to 2 mL of sample. Following incubation at room temperature for 1 hour, the medium and resin were added to a filter plate and washed twice with 1 mL DPBS. The sample was eluted from the resin by addition of 400 µL 0.1 M Glycine, pH 2.9 followed by centrifugation at 15,000×g for 30 sec. The sample was neutralized with 20 µL of 1 M Tris, pH 8.0. The samples were concentrated to approximately 100 µL by centrifugation at 15,000×g for 5 min using 0.5 mL Amicon Ultra, 10 k cutoff filters (Millipore) and were buffer-exchanged into DPBS using 0.5 mL Zeba desalting columns, 7K MWCO, according to the manufacturer's protocol. mAb concentration was determined by measuring AU280 and converted to mg/mL using the mAb's extinction coefficient.

1.5.2 Cysteine Decapping

Purification was performed using an AKTA Xpress purification platform (GE Healthcare). Up to 1 L of conditioned medium was loaded onto a 5 mL MabSelect column (GE Healthcare) equilibrated in 20 mM sodium phosphate, 150 mM NaCl, pH 7.0. The column was washed extensively with equilibration buffer following loading until a stable baseline was observed. Bound material was eluted using 100 mM glycine, pH 2.9. Eluted material was immediately injected on to a 26/10 HiPrep desalting column (GE Healthcare)

equilibrated in 1x phosphate-buffered saline (PBS) and eluted in the same buffer. Peak fractions were pooled. Material was analyzed for protein content by BCA assay (ThermoFisher) and electrophoresis by reducing and non-reducing SDS-PAGE.

1.6 Initial Screening and Characterization of Recombinant Chimeric Anti-Mesothelin Antibodies for ADC Development Anti-mesothelin antibodies were transiently expressed and cultured in 96 deep-well plates using Expi-293 medium. Antibodies from the supernatant were purified and decysteinylated as described above. The antibodies were conjugated using Mal-PEG$_2$-Auristatin F as payload using a molar ratio of 1:5 (mAb:payload). Conjugated antibodies were desalted to remove extra free payload using Thermo Zeba spin desalting plates.

1.7 Binding Characterization 1.7.1 Anti-Mesothelin Epitope Binning Using Octet

The antibody binding epitope to mesothelin was initially characterized using Octet, with Streptavidin tip, using a customized binding assay. Epitope binding of the anti-mesothelin antibodies were normalized to the epitope bound by a known anti-mesothelin antibody, MORAb-009 (Amatuximab). Antibodies were grouped based on their binding to the same, nearby, or different epitope as MORAb-009. Steps were repeated until all antibodies aligned with different epitope binning. Binding affinity was ranked as high, medium and low based on the Octet results. All binding steps were conducted in the PBST buffer containing 0.2% BSA.

1.7.2 Surface Plasmon Resonance (BIAcore) Binding Analysis

Anti-mesothelin antibody binding affinity to mesothelin was measured by BIAcore (BIAcore T-100, GE healthcare, #1426075), using a series S CMS chip. Antibody concentrations were adjusted to 1 µg/mL and mesothelin (50 µg) to 100 nM in 1xHBS-P+ buffer (GE Healthcare). Anti-human antibody capture chip was prepared according to the manufacturer's protocol using a CMS chip with immobilization wizard. Final capture antibody levels were 8000-9000 RU, in HBS-P+. Chip was prepared for assay with five cycles of 300 sec buffer injection followed by 30 sec regeneration, all at 30 µL/min across all four flow cells. Antibodies were captured on flow cells 2-4 by sequential injections of individual ligand solutions for 90 sec at 10 µL/min. Analyte injection was done in a single-cycle kinetics manner by sequential injections of analyte solutions from low to high concentration for 240 sec each at 30 µL/min. Detection was 2-1, 3-1, 4-1. Double-referencing was performed by a sequence of identical ligand capture injections, followed by 5 buffer-only injections for 240 sec each, dissociation for 1800 sec, and regeneration as above. All ligands were analyzed for binding to mesothelin in duplicate. Kinetic analysis was performed using BIAEvaluations software using a 1:1 Langmuir fitting model. On-rate, off-rate, and affinity constants were averaged from duplicate runs.

1.8 In Vitro Cytotoxicity Analysis

A431, A431-K5, and OVCAR3 cells were sub-cultured and seeded at 5,000 cells/well in complete growth medium in 96-well tissue culture plates, and incubated at 37° C., 5% CO$_2$ overnight (16 hours). Test reagents were serially diluted 1:3 in 2 mL deep-well dilution plates, starting at 200 nM (10 dilutions total). Diluted samples (100 µL) were added to the cell plates (starting concentration of test samples at 100 nM). Plates were incubated at 37° C., 5% CO$_2$ for an additional 5 days. Medium was then discarded, and plates were washed once with 200 µL DPBS, stained with 50 µL of 0.2% Crystal Violet solution at room temperature for 15 min, and then washed extensively with tap water. Plates were air-dried, and Crystal Violet was dissolved with 200 µL of 1% SDS solution. Plates were read at 570 nm. Data was analyzed using GraphPad Prism 6.

1.9 Results 1.9.1 Rabbit Immunization

Two rabbits were DNA immunized with the plasmid pB8-mesothelin-human for four genetic applications. Immune sera were taken at day 52 of the immunization protocol, diluted 1:1000 or 1:5000 in PBS containing 1% BSA, and was tested by flow cytometry using mesothelin-expressing cells. Sera from both immunized rabbits bound the mesothelin-expressing cells, which were cells transfected with pB1-mesothelin-hu (FIG. 1, lower curves). Conversely, sera from immunized rabbits did not bind cells transfected with an irrelevant cDNA (FIG. 1, upper curves).

Figure 2:
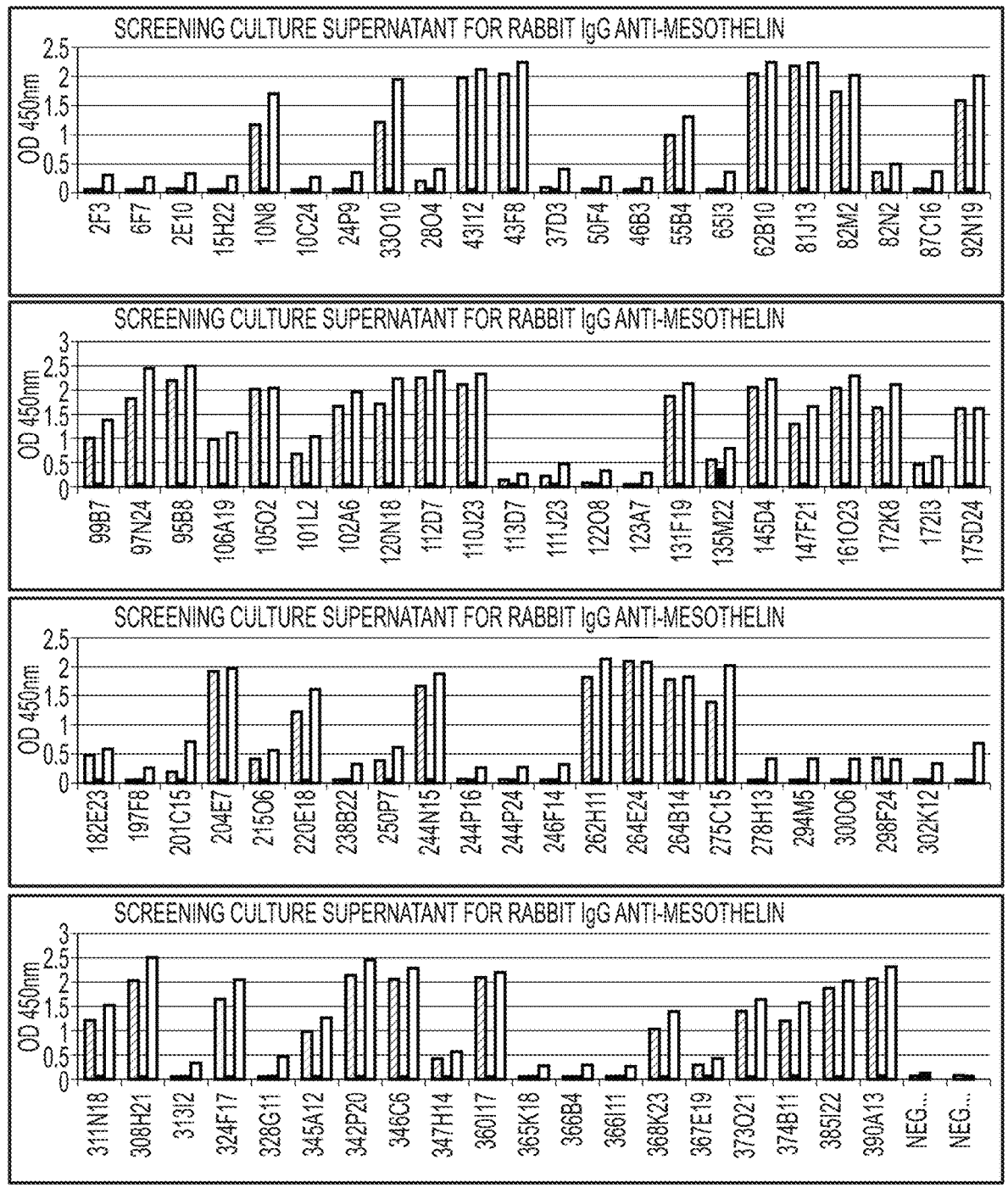
FIG. 2 shows detection of the specific reactivity of culture supernatants to human mesothelin by ELISA.

1.9.2 High Throughput Screening of Cultures Producing Rabbit Polyclonal Antibodies Against Human Mesothelin Rabbit lymph node cells were harvested and cryo-preserved. Cells (2×10$^7$ cells) from thawed lymph node were seeded at 5 cells per well on a 384 well plate with feeder cells and cultured in complete IMDM containing 10.5 ng/mL human IL-2 and 10.5 ng/mL human IL-21 cytokines. Wells producing rabbit IgG antibody were identified two weeks following seeding via IgG FRET using europium cryptate and 18,715 IgG-producing cultures were screened by ELISA for human mesothelin reactivity. Eighty-five mesothelin-specific cultures were re-confirmed for reactivity to mesothelin and counter-screened against reactivity to human CD73. There were 54 confirmed cultures producing rabbit Fcγ antibody that bound mesothelin above 0.2 OD$_{450}$ with no cross reactivity to CD73 (FIG. 2). Primary ELISA results are shown by the right-most set of bars, secondary ELISA results are shown by the left-most set of bars, and human CD73 binding is shown by the middle set of bars.

1.9.3 RT-PCR, Sequencing, and Cloning of Variable Regions

Figure 3:
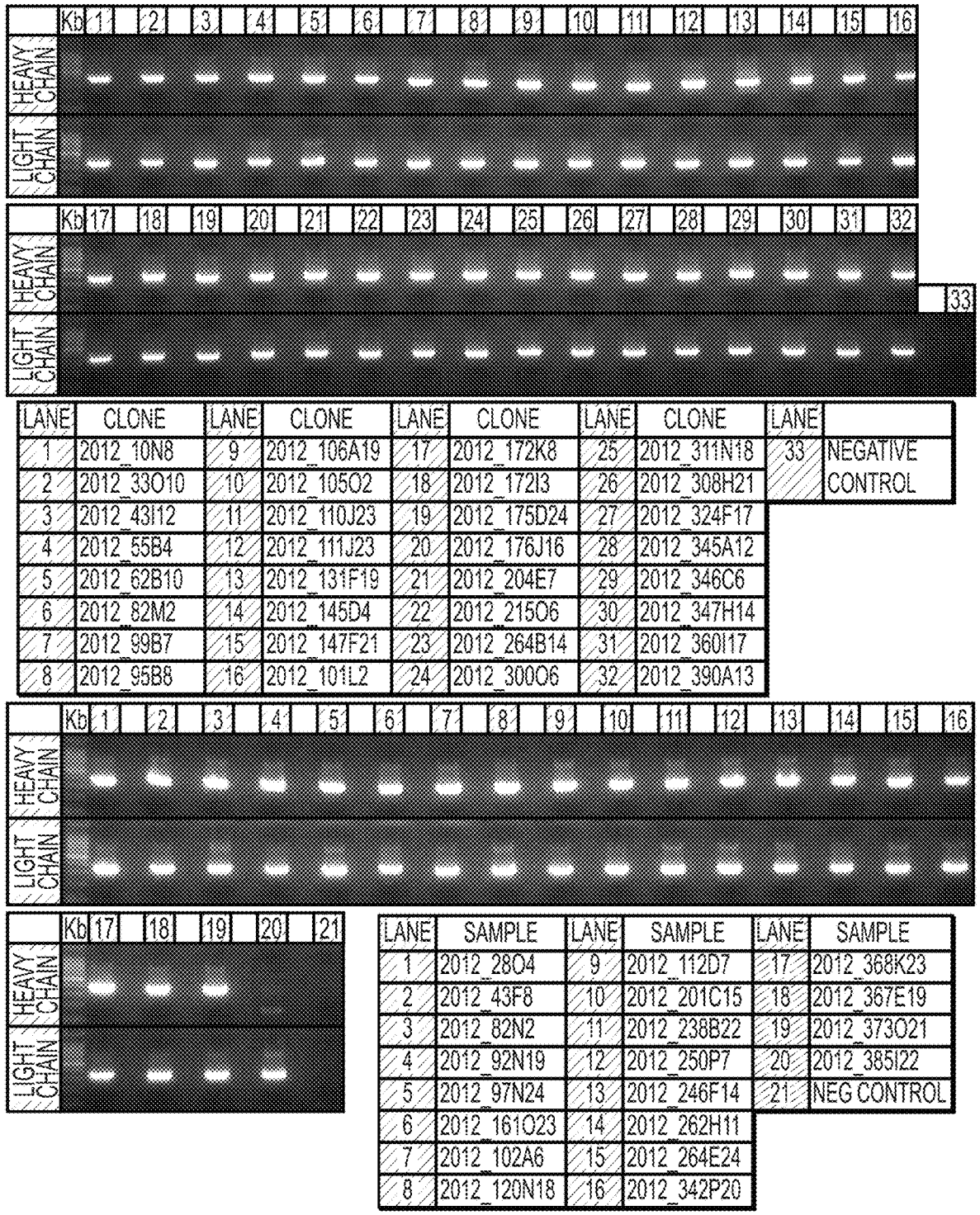
FIG. 3 shows In-Fusion PCR amplification of anti-mesothelin antibodies by gel electrophoresis.

Total RNA was isolated from 54 confirmed cultures producing rabbit IgG anti-mesothelin antibodies, cDNA was synthesized by RT-PCR, and light and heavy chain variable regions were PCR amplified. Fifty-two DNA sequences were analyzed using V-gene and J-gene rabbit families (IMGT/V-QUEST) and 51 were PCR amplified with primers specific for In-Fusion cloning into constant region expression vectors (FIG. 3). A total of 48 antibodies were cloned into human constant region expression vectors and were subsequently transfected into expi293F cells. Antibody was detected in 45 of the 51 transfectants (FIG. 4), rabbit variable regions were In-Fusion cloned into human constant region expression vectors.

1.9.4 Initial Screening of ADCs Against Mesothelin-Expressing Cells

Chimeric rabbit anti-human mesothelin (rb-hu-xi anti-MSLN) antibodies were purified according to method described in Section 1.5. The protein concentration of purified antibodies were determined (FIG. 5). To complete the screening of anti-mesothelin antibody for ADC development, micro-conjugation of anti-mesothelin antibody with Mal-PEG$_2$ Auristatin F was performed, and ADCs were characterized in the in-vitro cell based potency assay using OVCAR3, A431-K5 and A431 cell lines, where OVCAR3 and A431-K5 expressed high level of mesothelin, and A431 (MSLN$^-$) was used as control cell line for evaluating off-target killing and specificity of ADCs (FIG. 6).

1.9.5 Epitope Binding of Anti-Mesothelin Antibodies

Figure 7:
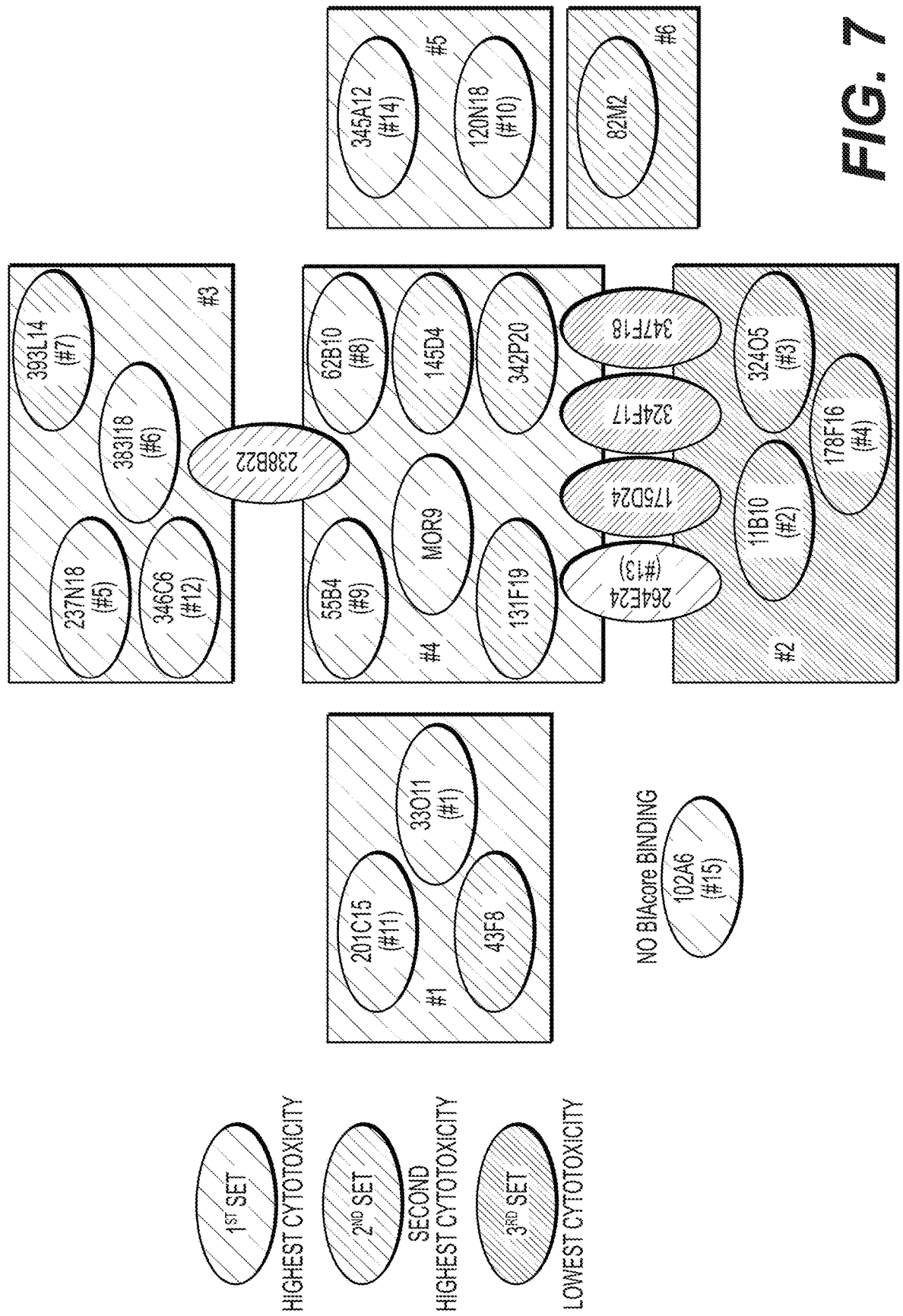
FIG. 7 shows epitope binning characterization of anti-mesothelin antibodies.

The binding epitope to mesothelin of the 48 anti-mesothelin antibodies were characterized using Octet as indicated in Section 1.7.1. Six different epitopes were identified for the antibodies, and 102A6 observed no binding in the current format by Octet (FIG. 7). Antibody binding affinity to mesothelin was measured by BIAcore, as indicated in Section 1.7.2. The binding affinity results are summarized in Table 15.

serum and matrix stability. Lead humanized antibodies and ADCs were evaluated in vivo, as described in Example 3.

2.1 Reagents and Materials 2.1.1 Antibodies

The antibodies used in the following studies have an unpaired cysteine at light chain position 80 (LCcys80) and

TABLE 15

Anti-mesothelin antibody binding affinity to mesothelin

| Epitope Bin | Curve | $k_a$ (1/Ms) | $k_d$ (1/s) | $K_D$ (M) | Rmax (RU) | Chi$^2$ (RU$^2$) |
|---|---|---|---|---|---|---|
| | M09-3 | 1.95E+06 | 2.92E−04 | 1.50E−10 | 40.19 | 0.646 |
| | 55B4-1 | 1.67E+06 | 8.32E−03 | 4.98E−09 | 42.33 | 1.72 |
| | 55B4-2 | 1.04E+06 | 5.52E−03 | 5.33E−09 | 42.6 | 0.586 |
| MORAb-009 | 62B10-1 | 2.10E+06 | 8.57E−03 | 4.08E−09 | 47.6 | 3.54 |
| | 62B10-2 | 9.91E+05 | 6.71E−03 | 6.77E−09 | 46.58 | 0.398 |
| | 131F9-1 | 8.36E+05 | 7.23E−03 | 8.65E−09 | 48.89 | 0.458 |
| | 131F9-2 | 8.71E+05 | 6.79E−03 | 7.79E−09 | 48.71 | 0.639 |
| | 145D4-1 | 8.05E+05 | 6.83E−03 | 8.48E−09 | 50.61 | 0.489 |
| | 145D4-2 | 8.69E+05 | 6.90E−03 | 7.95E−09 | 51.21 | 0.681 |
| | 342P20-1 | 1.74E+06 | 2.27E−04 | 1.30E−10 | 29.15 | 0.498 |
| | 342P20-2 | 2.32E+06 | 2.51E−04 | 1.08E−10 | 27.51 | 0.447 |
| | Xi-33O11 | 1.99E+06 | 6.68E−04 | 3.35E−10 | 35.89 | 0.169 |
| | 43F8-1 | 7.10E+05 | 6.37E−03 | 8.97E−09 | 35.29 | 0.48 |
| #1 | 43F8-2 | 7.77E+05 | 5.82E−03 | 7.48E−09 | 36.43 | 0.78 |
| | 201C15-1 | 2.74E+05 | 1.29E−04 | 4.70E−10 | 63.95 | 0.75 |
| | 201C15-2 | 2.64E+06 | 3.45E−04 | 1.31E−10 | 58.09 | 0.568 |
| | X-237N18 | 1.27E+06 | 4.28E−03 | 3.38E−09 | 41.45 | 0.295 |
| | Xi-393L14 | 1.10E+06 | 2.57E−04 | 2.33E−10 | 46.47 | 0.627 |
| #3 | Xi-383I18(AuF) | 1.01E+06 | 2.81E−04 | 2.80E−10 | 43.9 | 0.494 |
| | 346C6-1 | 6.82E+05 | 4.81E−04 | 7.06E−10 | 44.85 | 0.218 |
| | 346C6-2 | 1.15E+06 | 6.09E−04 | 5.29E−10 | 45.06 | 0.503 |
| | 345A12-1 | 2.89E+06 | 4.12E−04 | 1.43E−10 | 39 | 0.793 |
| #5 | 345A12-2 | 2.85E+06 | 3.89E−04 | 1.36E−10 | 38.63 | 0.833 |
| | 120N18-1 | 6.26E+05 | 5.26E−04 | 8.41E−10 | 50.28 | 0.323 |
| | 120N18-2 | 6.57E+05 | 5.13E−04 | 7.80E−10 | 50.89 | 0.395 |
| | 82M2-1 | 7.18E+05 | 4.35E−04 | 6.06E−10 | 47.12 | 0.493 |
| #6 | 82M2-2 | 8.98E+05 | 4.74E−04 | 5.28E−10 | 48.64 | 0.961 |
| M09/#2 | 264E24-1 | 4.01E+05 | 5.81E−05 | 1.45E−10 | 48.8 | 0.347 |
| hybrid | 264E24-2 | 4.10E+05 | 5.47E−05 | 1.34E−10 | 49.33 | 0.423 |
| M09/#3 | 238B22-1 | 2.60E+05 | 3.03E−03 | 1.17E−08 | 153.1 | 6.95 |
| hybrid | 238B22-2 | 4.31E+05 | 6.03E−03 | 1.40E−08 | 57.04 | 0.318 |

Based on the results above, fifteen antibodies that cover all epitope bins were selected for scale-up conjugation and characterization, as indicated in Table 16. 102A6A was also selected based on favorable in-vitro potency when conjugated to auristatin F.

TABLE 16

Fifteen selected anti-mesothelin antibodies and their epitope bins

| Epitope Bin | Lead Antibodies |
|---|---|
| Bin #1 | 33O11, 210C15 |
| Bin #2 | 111B10, 324O5, 178F16, 264E24 |
| Bin #3 | 237N18, 383I18, 393L14, 346C6 |
| Bin #4 | 62B10, 55B4, MORAb009 |
| Bin #5 | 120N18, 345A12 |
| No binding | 102A6A |

Example 2: Humanization of Anti-Mesothelin ADCs

Humanized anti-mesothelin antibodies were generated according to the procedures described below. Antibodies and ADCs were analyzed for retained binding activity to human mesothelin and cell killing potency toward cells expressing mesothelin. Antibodies were also biophysically characterized for drug loading, aggregation, thermal stability, and include both the rabbit-human chimeric (-xi) and humanized (-zu) forms of the anti-human mesothelin antibodies 33O11, 201C15, 111B10, 324O5, 178F16, 264E24, 237N18, 383I18, 393L14, 346C6, 62B10, 55B4, MORAb009, 120N18, 345A12, and 102A6A2. The antibodies were batch purified using a Prosep-vA High Capacity Protein A resin and Zeba desalting columns. Conditioned medium was purified and decysteinylated as described in Section 1.5 (Example 1). Final protein content was assessed via BCA assay and SDS-PAGE.

2.1.2 Conjugatable Cytotoxins and LCcys80 ADCs

Linker-cytotoxin compounds used in the following studies include maleimide-VCP-eribulin, maleimide-VCP-cryptophycin, and maleimide-VCP-eribulin dimer. Conjugated antibodies were purified using desalting chromatography with HiTrap desalting columns (GE Healthcare) equilibrated in 1×DPBS. Final protein content was determined by BCA assay.

2.1.3 Tumor Cell Lines

Human tumor cell lines used in the analyses of rabbit-human chimeric ADCs included A431 (human melanoma cells, MSLN$^{neg}$), A3 (A431 stably transfected with human mesothelin, MSLN$^{hi}$) OVCAR3 (human ovarian carcinoma cells, MSLN$^{hi}$), HEC-251 (human endometrioid, MSLN$^{med}$), and H226 (human lung squamous cell mesothelioma, MSLN$^{lo}$). All cell lines used were obtained directly from the American Type Culture Collection (ATCC), with the exception of A3, which was generated at Morphotek from the A431 parental cell line and HEC-251, which was obtained from JCRB.

2.1.4 Other Reagents

All reagents used were obtained from commercial suppliers at research-grade or higher, unless otherwise indicated.

2.2 Biophysical Characterization of ADCs 2.2.1 SEC-HPLC Aggregation Analysis

SEC-HPLC analysis was conducted using Agilent 1200 HPLC system. AdvanceBio SEC 300A (2.7 µm, 7.8×50 mm, serial no. 0006344424-13, batch no. 0006344424) guard column was connected to AdvanceBio SEC 300A analytical column (2.7 µm, 7.8×300 mm, serial no. 0006336837-4, batch no. 0006336837), equilibrated in 0.1 M sodium phosphate, 0.15 M sodium chloride, 5% IPA, pH 7.4, at flow rate of 0.5 mL/min.

Aggregation of LCcys80 ADCs was analyzed by size-exclusion, high-performance liquid chromatography (SEC-HPLC) using an Agilent 1200 HPLC. Antibodies and ADCs were prepared at 2 mg/mL in 1×DPBS, 8 µL (16 µg) of each sample was injected and run for 36 min. All data were analyzed using Agilent ChemStation software. Percent aggregation, percent monomer, and percent fragmentation were reported.

2.2.2 Hydrophobic Interaction Chromatography (HIC-HPLC) DAR Analysis

DAR was analyzed using hydrophobic interaction chromatography (HIC-HPLC) on an Agilent HPLC 1260 system. Samples were injected onto a TSKgel Ethyl-5PW column (TOSOH Bioscience, 7.5 mm ID×7.5 cm, 10 µm, nonporous size), and eluted from the column with a 3 min equilibration in 100% of mobile phase A, a 15 min gradient (0-100% B), a 5 min hold in 100% B, a 1 min change to 100% A, and a 5 min re-equilibration in 100% of mobile phase A, at 0.7 mL/min. Mobile phase A was 25 mM sodium phosphate, 1.5 M ammonium sulfate, pH 7.0. Mobile phase B was 25 mM sodium phosphate, 25% isopropanol, pH 7.0. Detection was performed at 280 nm (reference 320 nm). DAR was determined by the formula:

$$[AUC+1+2(AUC+2)+3(AUC+3)+\ldots n(AUC+n)]/\Sigma AUCtot$$

where AUC+1 is the area under the curve for the antibody peak corresponding to ADC conjugated with one cytotoxin, and AUC+2 is the area under the curve for the antibody peak corresponding to ADC conjugated with two cytotoxins. $\Sigma AUCtot$ is the combined area under the curve for the conjugated and unconjugated peaks (DAR=0, 1, and 2).

2.2.3 Liquid Chromatography/Mass Spectrometry (LC-MS) DAR Analysis

DAR was also analyzed using an LC-MS method with a Waters Alliance HPLC with SQD/PDA detection. Samples were injected onto a Proteomix RP-1000 column (5 µm, 1000 Å, 4.6 mm×15 cm, Sepax) at 65° C., and eluted with a 3 min equilibration in 25% B, a 27 min linear gradient from 25%-55% B, a 5 min hold in 55% B, a 1 min change to 90% B, a 5 min hold at 90% B, a 1 min change back to 25% B, and a 5 min re-equilibration at 25% B. Mobile phase A was 0.1% TFA in water, and mobile phase B was 0.1% TFA in acetonitrile. Elute was then 10:1 split into PDA and SQD detectors. SQD detector was set up as ES positive, capillary voltage at 3.5 KV, cone voltage at 50 V, extractor at 5 V, and RF lens at 0.3 V, source temperature at 150° C., desolvation temperature at 350° C. Mass data was acquired at 200-2000 m/z for 40 min, continuum mode, and scan time 1 sec. Data was analyzed and deconvoluted offline using MassLynx and MaxEnt1. DAR was calculated using the formula:

$$2[[AUCLC+1+2(AUCLC+2)+3(AUCLC+3)+\ldots n(AUCLC+n)]/\Sigma ILCtot]+2[[AUCHC+1+2(AUCHC+2)+3(AUCHC+3)+\ldots n(AUCHC+n)]/\Sigma AUCHCtot]$$

where AUCLC+1 is area under the curve of the light chain peak conjugated with one cytotoxin, AUCLC+2 is area under the curve of the light chain peak conjugated with two cytotoxins, etc. AUCHC are the area under the curve of the corresponding heavy chains, and $\Sigma AUCLCtot$ and $\Sigma AUCHCtot$ are the combined area under the curve of all unconjugated and conjugated light chains and heavy chains, respectively.

2.3 Binding Characterization 2.3.1 Anti-Mesothelin Epitope Binning Using Octet

The antibody binding epitope to mesothelin was initially characterized using Octet, with Streptavidin tip, using a customized binding assay. Epitope binding of the anti-mesothelin antibodies were normalized to the epitope bound by a known anti-mesothelin antibody, MORAb-009. Antibodies were grouped based on their binding to the same, nearby, or different epitope as MORAb-009. Steps were repeated until all antibodies aligned with different epitope binning. Binding affinity was ranked as high, medium and low based on the octet results. All binding steps were conducted in the PBST buffer containing 0.2% BSA.

2.3.2 Surface Plasmon Resonance (BIAcore) Binding Analysis

Anti-mesothelin antibody binding affinity to mesothelin was measured by BIAcore (BIAcore T-100, GE healthcare, #1426075), using a series S CM5 chip. Antibody concentrations were adjusted to 1 µg/mL and mesothelin (50 µg) to 100 nM in 1×HBS-P+ buffer (GE Healthcare). Anti-human antibody capture chip was prepared according to the manufacturer's protocol using a CM5 chip with immobilization wizard. Final capture antibody levels were 8000-9000 RU, in HBS-P+. Chip was prepared for assay with five cycles of 300 sec buffer injection followed by 30 sec regeneration, all at 30 µL/min across all four flow cells. Antibodies were captured on flow cells 2-4 by sequential injections of individual ligand solutions for 90 sec at 10 µL/min. Analyte injection was done in a single-cycle kinetics manner by sequential injections of analyte solutions from low to high concentration for 240 sec each at 30 µL/min. Detection was 2-1, 3-1, 4-1. Double-referencing was performed by a sequence of identical ligand capture injections, followed by 5 buffer-only injections for 240 sec each, dissociation for 1800 sec, and regeneration as above. All ligands were analyzed for binding to mesothelin in duplicate. Kinetic analysis was performed using BIAEvaluations software using a 1:1 Langmuir fitting model. On-rate, off-rate, and affinity constants were averaged from duplicate runs.

2.4 Differential Scanning Calorimetry (DSC) Thermal Stability Analysis

VP Capillary Differential Scanning Calorimeter (VP-CapDSC; Microcal, VP-CapDSC, #12-07-149 with Origin-7 graphing and MicroCal VP-Capillary DSC Software v.2.0) was used to decipher and compare the higher order structure and thermal stability of various F(ab')2 fragments and controls. Samples were prepared on 96-well assay plates (Microliter Analytical Supply) using 20% Contrad solution and analyzed in auto-sampler at 10° C.

2.5 Capillary Isoelectric Focusing (cIEF) Analysis

Auto-sampler reagents were filled according to the CFR installation and start-up procedures. Hemoglobin was used as system stability standard. Default settings for batch data analysis was used. Focus period #1 was performed for 1 min at 1,500 V for both the system suitability standards and samples. Focus period #2 was performed for 5 min at 3,000 V for the system suitability standards and 11 min at 3,000 V for the TIGC samples and matched buffer controls. Duplicate TIGC samples used Focus period #2 at 4.5 min and all samples were bracketed with a system suitability standard. Samples were automatically integrated using a peak width parameter of 0.1 and threshold of 5 and integrated between pI 7.5-9.4.

2.6 Preparation of DAR2 and DAR6 MORAb-109 ADCs

The 345A12-HC15-LC4 CHOZN cell line was cultured in a wave bag (20 L) until viability <30% and concentrated to 2 L using TFF. Antibody was captured on Amosphere A3 resin preequilibrated in 20 mM sodium phosphate, 10 mM EDTA, pH 7.2, washed in the same buffer until a stable baseline was achieved (to remove unbound material), then reduced on-column for 8 hours using 20 mM sodium phosphate, 10 mM EDTA, 10 mM cysteine, pH 7.2 at low flow rate, then re-oxidized on-column for 60 hours using 20 mM Tris, pH 7.5. Bound material was eluted in 0.1 M glycine, pH 3.0, then diafiltered into 1×PBS, 2 mM EDTA, pH 7.4 and concentrated to >10 mg/mL. Final recovery was 100%.

For DAR2 MORAb-109, maleimide-VCP-eribulin was added (in DMSO) at a molar ratio of 1:2.5 (mAb:payload) for 1 hour at room temperature. Following conjugation, material was diluted to 2 mg/mL, diafiltered into 1×PBS, 2 mM EDTA to remove unconjugated linker-payload and concentrated to 5 mg/mL. DAR2 material was purified by preparative Ether-5PW HIC chromatography. Final material was characterized by SEC-HPLC, RP-HPLC, and HIC-HPLC.

For DAR6 MORAb-109, purified/decysteinylated antibody was diluted to 7.5 mg/mL in 1×PBS, 2 mM EDTA and further reduced by adding an equal volume of 250 µM TCEP in the same buffer for 50 min, then an equal total volume of 50% Propylene glycol in 1×DPBS/1 mM EDTA was added, then finally maleimide-VCP-eribulin at molar ratio of 1:8 (mAb:payload), incubated at room temperature for 1 hour. ADC was purified by G-25 chromatography to remove unconjugated payload and formulated into 1×PBS, 2 mM EDTA. Final material was characterized by SEC-HPLC, RP-HPLC, and HIC-HPLC.

2.7 In Vitro Serum Stability

Anti-mesothelin ADCs (maleimide-VCP-eribulin as payload) were prepared at 0.5 mg/mL either in PBS or human serum. Samples were incubated at 37° C. for 0, 24, 48, 72, 96, or 240 hours, then transferred to −80° C. for storage. All samples thawed to ambient temperature, and single dilution of 1:2,000 for testing. Samples were tested for total mAb, total ADC, and in cell based potency. Total mAb assay was developed as stepwise sandwich format on Gyrolab XP, captured with biotinylated mesothelin, and detected with Alexa Fluor 647 anti-IgG1 Fc. Quantifiable ranges for the total mAb and the intact ADC assays were 6.25-800 ng/mL and 6.25-800 ng/mL, respectively. Standard curve and QCs were made with MORAb-109 (345A12-HC15-LC4-VCP-eribulin).

2.8 In Vitro DAR-Sensitive Matrix Stability of MORAb-109 ADCs

MORAb-109 (345A12-HC15-LC4-VCP-eribulin) DAR 2 was prepared at 0.1 mg/mL in either PBS or human, monkey, rat, or mouse serum in triplicate. Samples were incubated at 37° C. for 0, 24, 48, 72, 96, or 240 hours. Samples removed from each time point were transferred to −80° C. for storage. Analysis was performed using a label-free bio-layer interferometry assay. Matrix samples were diluted to 1:20 in 1×PBS containing 0.05% Tween-20 and 1% BSA (assay buffer). Control samples of MORAb-109 DAR 0, DAR 1, DAR 2, and DAR 6 were diluted to 0.1 mg/mL in matched matrix. Negative control samples were 5% matrix-alone. Biotinylated mesothelin at 5 µg/mL in assay buffer was captured on SA streptavidin biosensor tips (300 sec; Pall-ForteBio), followed by capture of diluted stability samples and controls (300 sec). Payload was then quantitated by binding of rabbit-human chimeric anti-eribulin antibody 5E4 at 100 mg/mL. Association was monitored for 300 sec, at which point binding had reached equilibrium. Binding level at the end of dissociation phase ($R_{eq}$) was determined for each sample at 295 sec of association. Stability was determined by plotting percent $R_{eq}$ relative to $t_0$, where:

percent $R_{eq} = R_{eq}t_x / R_{eq}t_0 [100]$ and $t_x = 0\text{-}240$ hours.

2.9 In Vitro Cytotoxicity Analysis

A431, A3, OVCAR3, HEC-251, and H226 cells were sub-cultured and seeded at 5,000 cells/well in complete growth medium in 96-well tissue culture plates, and incubated at 37° C., 5% $CO_2$ overnight (16 hours). Test reagents were serially diluted 1:3 in 2 mL deep-well dilution plates, starting at 200 nM (10 dilutions total). Diluted samples (100 µL) were added to the cell plates (starting concentration of test samples at 100 nM). Plates were incubated at 37° C., 5% $CO_2$ for an additional 5 days. Medium was then discarded, and plates were washed once with 200 µL DPBS, stained with 50 µL of 0.2% Crystal Violet solution at room temperature for 15 min, and then washed extensively with tap water. Plates were air-dried, and Crystal Violet was dissolved with 200 µL of 1% SDS solution. Plates were read at 570 nm. Data was analyzed using GraphPad Prism 6.

2.10 Results 2.10.1 Initial Screening of Humanized Anti-Mesothelin Eribulin ADCs Fifteen anti-mesothelin antibodies were sub-cloned, scale-up expressed and purified, and conjugated using maleimide-VCP-eribulin as payload at the Cys80 position. All ADCs were purified and characterized using SEC-HPLC for aggregation analysis, HIC-HPLC for DAR analysis, and cell-based assay with A431-A3 ($MSLN^{hi}$), A431 ($MSLN^{lo}$), and OVCAR3 ($MSLN^{hi}$) cell lines. The cells were treated with ADC for 6 hours then washed off, or treated for 48 hours (A431-A3 and A431 cells) or 72 hours (OVCAR3 cells) for the potency comparison. Characterization data is summarized in Table 17. Based on the characterization data below, six antibodies (bolded) were selected for humanization.

TABLE 17

Characterization of fifteen anti-mesothelin eribulin ADCs

| No. | Sample Name | Conc. (mg/mL) | Lot | DAR | SEC-HPLC % Monomer mAb | SEC-HPLC 15% IPA % Monomer ADC | Cell based Cytotoxicity assay, EC50 (nM) | | | | | |
|---|---|---|---|---|---|---|---|---|---|---|---|---|
| | | | | | | | A3-6 hr | A3-48 hr | A431-6 hr | A431-48 hr | OVCAR3-6 hr | OVCAR3-72 hr |
| 1 | 33O11-VCP-Eribulin | 0.46 | 02750-83G | 2.00 | 95.4 | 97.58 | 0.90 | 0.50 | >100 | >100 | 2.74 | 4.59 |
| 2 | 111B10-VCP-Eribulin | 0.98 | 02750-83H | 2.00 | 89.9 | 93.69 | 0.30 | 0.14 | >100 | >100 | 3.11 | 3.15 |
| 3 | 324O5-VCP-Eribulin | 0.97 | 02750-83I | 2.00 | 83.5 | 85.92 | 1.15 | 0.72 | >100 | >100 | 3.33 | 2.40 |
| 4 | 178F16-VCP-Eribulin | 0.99 | 02750-83J | 2.00 | 81.4 | 84.54 | 0.65 | 0.38 | >100 | >100 | 1.36 | 0.08 |
| 5 | 237N18-VCP-Eribulin | 0.83 | 02750-83K | 2.00 | 92.8 | 95.84 | 0.51 | 0.24 | >100 | >100 | 14.65 | 4.41 |
| 6 | 383I18-VCP-Eribulin | 0.71 | 02750-84I | 1.83 | 93.5 | 95.80 | 1.06 | 0.83 | >100 | >100 | 16.25 | 2.16 |
| 7 | 393L14-VCP-Eribulin | | | | 93.0 | 93.88 | 1.70 | 1.18 | >100 | >100 | 13.37 | 4.04 |
| 8 | 62B10-VCP-Eribulin | 0.48 | 02750-84J | 2.00 | 98.7 | 46.84 | 0.64 | 0.33 | >100 | >100 | 11.70 | 1.84 |
| 9 | 55B4-VCP-Eribulin | 0.42 | 02750-84K | 2.00 | 98.4 | 73.44 | 0.55 | 0.27 | >100 | >100 | 32.17 | 1.33 |
| 10 | 120N18-VCP-Eribulin | 0.3 | 02750-83G | 2.00 | 97.4 | 61.42 | 1.67 | 0.98 | >100 | >100 | 2.16 | 0.20 |
| 11 | 201C15-VCP-Eribulin | 0.61 | 02750-83H | 2.00 | 94.3 | 95.84 | 0.71 | 0.54 | >100 | >100 | 2.83 | 0.05 |
| 12 | 346C6-VCP-Eribulin | 0.9 | 02750-83I | 2.00 | 91.4 | 92.28 | 0.95 | 0.29 | >100 | >100 | 8.20 | 0.49 |
| 13 | 264E24-VCP-Eribulin | 0.66 | 02750-83J | 1.63 | 46.2? | 73.67 | 1.04 | 0.74 | >100 | >100 | 1.71 | 0.14 |
| 14 | 345A12-VCP-Eribulin | 0.4 | 02750-83K | 2.00 | 95.7 | 98.53 | 0.95 | 0.80 | >100 | >100 | 0.66 | 0.09 |
| 15 | 102A6A-VCP-Eribulin | 0.19 | 02750-83D | 2.00 | 98.1 | 67.87 | 0.38 | 0.21 | >100 | >100 | 1.92 | 0.12 |
| 16 | 102A6B-VCP-Eribulin | 0.31 | 02750-83L | 2.00 | 97.9 | 19.02 | 0.84 | 0.53 | >100 | >100 | 1.85 | 0.14 |
| 17 | 1552-VCP-Eribulin | 0.63 | 02750-83F | 1.89 | 97.1 | 97.20 | >100 | 58.78 | >100 | >100 | >100 | 10.60 |
| 18 | Eribulin | 6 mM | | | | | 4.08 | 1.09 | 2.86 | 0.00 | 2.81 | 0.25 |

2.10.2 HC1-LC1 Humanization and In Vitro Cytotoxicity of ADCs

The sequences for the rabbit 102A6A2, 11B10, 201C15, 345A12, and 346C6 Fv regions were BLASTed for the closest homology to human germline variable domain protein sequences using IGBLAST (National Center for Biotechnology Information (NCBI)) and IMGT/DomainGapAlign (International ImMunoGeneTics Information System (IMGT®)) tools. Rabbit framework sequences were replaced with the closest homologous human germline sequences to generate CDR-grafted humanized variants (HC1 and LC1). The final two residues of Kabat-defined FWRH2 were retained as rabbit residues. The final Kabat defined FWRH3 residue was retained for 111B10. The RESPECT-L motif Cys80 and Ala83 in the Vκ region was retained for all clones. After the humanized antibodies were generated, both chimeric and humanized antibodies were conjugated with three different payloads (maleimide-VCP-eribulin, maleimide-VCP-cryptophycin, and maleimide-VCP-eribulin dimer) varying the hydrophobicity. Binding affinity to mesothelin was measured by BIAcore for all antibodies, and ADCs were characterized for percent (%) aggregation, DAR and in-vitro potency, as summarized in Table 18. Potency payloads of humanized anti-mesothelin ADCs were also measured and are summarized in Table 19. ADCs had low nanomolar cell killing EC50 values in all five cell lines tested.

TABLE 18

Characterization summary for lead chimeric and humanized anti-mesothelin ADCs

| | Parental mAb | | | | ADC | |
|---|---|---|---|---|---|---|
| | | Affinity | | | | |
| | Epitope Bin | $k_a$ ($10^5$ M$^{-1}$ sec$^{-1}$) | $k_d$ ($10^{-3}$ sec$^{-1}$) | $K_D$ ($10^{-9}$ M) | Payload Drug-linker | HIC-Ethyl DAR |
| 33O11 | xi | 1 | | | VCP-eribulin | 1.92 |
| | | | | | VCP-cryptophycin | 1.87 |
| | | | | | VCP-eribulin dimer | 1.17 |

TABLE 18-continued

Characterization summary for lead chimeric and humanized anti-mesothelin ADCs

| Antibody | Type | | | | | Payload | |
|---|---|---|---|---|---|---|---|
| | zu | | 2.2 | 0.65 | 3.4 | VCP-eribulin | 1.69 |
| | | | | | | VCP-cryptophycin | 1.33 |
| | | | | | | VCP-eribulin dimer | 1.63 |
| 111B10 | xi | 2 | 6.5 | 3.9 | 6.3 | VCP-eribulin | 1.90 |
| | | | | | | VCP-cryptophycin | 1.86 |
| | | | | | | VCP-eribulin dimer | 1.85 |
| | zu | | 5.1 | 3 | 6.5 | VCP-eribulin | 1.81 |
| | | | | | | VCP-cryptophycin | 1.76 |
| | | | | | | VCP-eribulin dimer | 1.78 |
| 201C15 | xi | 1 | 2.4 | 0.26 | 1.1 | VCP-eribulin | 1.85 |
| | | | | | | VCP-cryptophycin | 1.75 |
| | | | | | | VCP-eribulin dimer | 0.96 |
| | zu | | 3.1 | 1.1 | 4.2 | VCP-eribulin | 1.80 |
| | | | | | | VCP-cryptophycin | 1.74 |
| | | | | | | VCP-eribulin dimer | 1.75 |
| 346C6 | xi | 3 | 3.8 | 0.49 | 1.4 | VCP-eribulin | 1.56 |
| | | | | | | VCP-cryptophycin | 1.52 |
| | | | | | | VCP-eribulin dimer | 1.60 |
| | zu | | 133 | 93 | 8.9 | VCP-eribulin | 1.63 |
| | | | | | | VCP-cryptophycin | 1.65 |
| | | | | | | VCP-eribulin dimer | 1.68 |
| 345A12 | xi | 5 | 26 | 0.42 | 0.12 | VCP-eribulin | n/a |
| | | | | | | VCP-cryptophycin | n/a |
| | | | | | | VCP-eribulin dimer | n/a |
| | zu | | 35 | 2.1 | 0.2 | VCP-eribulin | 1.72 |
| | | | | | | VCP-cryptophycin | 1.60 |
| | | | | | | VCP-eribulin dimer | 1.59 |
| 102A6A2 | xi | 7 | n.b. | n.b | n.b | VCP-eribulin | n/a |
| | | | | | | VCP-cryptophycin | n/a |
| | | | | | | VCP-eribulin dimer | n/a |
| | zu | | n.b. | n.b | n.b | VCP-eribulin | 1.87 |
| | | | | | | VCP-cryptophycin | 1.87 |
| | | | | | | VCP-eribulin dimer | 1.68 |
| 155D5 | xi | | | | | VCP-eribulin dimer | 1.62 |
| | | | | | | Eribulin | n/a |
| | | | | | | Cryptophycin | n/a |
| | | | | | | VCP-DiOH Eribulin Dimer | n/a |

| | | | ADC | | | | | |
|---|---|---|---|---|---|---|---|---|
| | | | SEC-HPLC | | Cell-Based Cytotoxicity Assay, EC50 (nM) | | | | |
| | | | % aggregate | % monomer | A431 | OVCAR3 | HEC-251 | H226 | A3 |
| 33O11 | xi | | 8.97 | 91.03 | 40.67 | 0.008 | 3.950 | >100 | 0.14 |
| | | | 12.74 | 87.26 | 6.79 | 0.010 | 0.110 | 0.06 | 0.03 |
| | | | 32.70 | 67.30 | 1.40 | 0.030 | 0.33 | 0.93 | 0.05 |
| | zu | | 1.42 | 98.58 | ~100 | 0.064 | 26.500 | >100 | 0.28 |
| | | | 0.90 | 99.10 | 22.50 | 0.066 | 5.35 | 5.81 | 0.04 |
| | | | 1.08 | 98.92 | 2.01 | 0.025 | 0.31 | 0.22 | 0.04 |
| 111B10 | xi | | 4.25 | 95.75 | 38.10 | 0.004 | 13.960 | ~100 | 0.05 |
| | | | 8.83 | 91.17 | 10.93 | 0.011 | 1.600 | 2.66 | 0.016 |
| | | | 9.25 | 90.75 | 0.96 | 0.007 | 0.06 | 0.71 | 0.011 |
| | zu | | 3.64 | 96.36 | 68.92 | 0.014 | 27.42 | >100 | 0.12 |
| | | | 1.80 | 98.20 | 4.30 | 0.011 | 0.820 | 1.36 | 0.015 |
| | | | 4.47 | 95.53 | 1.68 | 0.007 | 0.13 | 1.15 | 0.025 |
| 201C15 | xi | | 1.62 | 98.38 | 48.50 | 0.004 | 14.82 | ~100 | 0.27 |
| | | | 2.10 | 97.90 | 8.08 | 0.012 | 0.540 | 1.02 | 0.12 |
| | | | 0.00 | 100.00 | 0.63 | <0.003 | 0.10 | 0.64 | 0.065 |
| | zu | | 5.84 | 94.16 | 68.88 | 0.290 | 20.42 | >100 | 0.41 |
| | | | 11.51 | 88.49 | 2.55 | 0.120 | 0.600 | 1.73 | 0.037 |
| | | | 9.94 | 90.06 | 1.12 | 0.063 | 0.28 | 1.26 | 0.082 |
| 346C6 | xi | | 5.28 | 94.72 | 34.49 | 0.087 | 5.73 | ~100 | 0.11 |
| | | | 8.28 | 91.72 | 4.18 | 0.042 | 0.190 | 1.21 | 0.043 |
| | | | 10.43 | 89.57 | 1.32 | 0.026 | 0.09 | 0.99 | 0.035 |
| | zu | | 4.48 | 95.52 | 72.86 | 1.180 | 32.54 | >100 | 0.55 |
| | | | 13.70 | 86.30 | 2.30 | 0.380 | 0.800 | 2.21 | 0.13 |
| | | | 4.86 | 95.14 | 1.36 | 0.140 | 0.34 | 1.86 | 0.13 |
| 345A12 | xi | | n/a | n/a | n/a | n/a | n/a | n/a | n/a |
| | | | n/a | n/a | n/a | n/a | n/a | n/a | n/a |
| | | | n/a | n/a | n/a | n/a | n/a | n/a | n/a |
| | zu | | 4.24 | 95.76 | 63.49 | 0.004 | 20.70 | >100 | 0.091 |
| | | | 6.17 | 93.83 | 3.03 | <0.003 | 0.350 | 0.69 | 0.01 |
| | | | 5.05 | 94.95 | 1.04 | <0.003 | 0.06 | 0.79 | 0.016 |
| 102A6A2 | xi | | 89.50 | 10.50 | 36.18 | 0.024 | 2 | >100 | 0.12 |
| | | | 100.00 | 0.00 | 9.52 | 0.110 | 0.280 | 0.21 | 0.11 |
| | | | n/a | n/a | n/a | n/a | n/a | n/a | n/a |

TABLE 18-continued

Characterization summary for lead chimeric and humanized anti-mesothelin ADCs

|  |  |  |  |  |  |  |  |  |
|---|---|---|---|---|---|---|---|---|
|  | zu | 3.60 | 96.40 | 57.44 | 0.046 | 8.67 | >100 | 3.02 |
|  |  | 3.64 | 96.36 | 3.54 | 0.021 | 0.054 | 0.08 | 0.0092 |
|  |  | 1.74 | 98.26 | 1.40 | 0.047 | 0.05 | 0.50 | 0.018 |
| 155D5 | xi | 14.42 | 81.63 | 1.20 | 0.210 | 0.47 | 1.50 | 1.41 |
|  |  | n/a | n/a | 0.47 | 0.11 | 0.2 | 5.3 | 1.03 |
|  |  | n/a | n/a | 0.8 | 0.24 | 0.43 | 1.94 | 1.01 |
|  |  | n/a | n/a | 0.03 | <0.003 | 0.003 | 0.32 | 0.08 |

TABLE 19

In-vitro cell based potency of payloads

| | Cell-Based Cytotoxicity Assay EC50 (nM) | | | | |
|---|---|---|---|---|---|
| | A431 | OVCAR3 | HEC-251 | H226 | A3 |
| Eribulin | 0.47 | 0.11 | 0.2 | 5.3 | 1.03 |
| Cryptophycin | 0.8 | 0.24 | 0.43 | 1.94 | 1.01 |
| VCP-DiOH Eribulin Dimer | 0.03 | <0.003 | 0.003 | 0.32 | 0.08 |

2.10.3 Humanization Refinement

Due to loss of mesothelin binding for 201C15, 345A12, and 346C6 clones, subsequent mutations were required to retain binding to mesothelin. The rabbit and CDR-grafted Fv sequences were used to generate in silico models of the variable domains. The theoretical structure of the rabbit and humanized models were superimposed, and residues in close proximity to the CDRs were analyzed for potential structural influence on the overall structure of the CDR loops. The residues differing between the rabbit and humanized sequences were identified. Most of the differing residues were not located at the dimer interface or were distal to the CDRs. Several residues in the VH and Vκ regions were found to be in close proximity (within 5 Å) of the CDRs, and were further analyzed.

Two humanized regions in the VH region were identified as possibly interfering with antigen-binding in clones 201C15, 345A12, and 346C6. The N terminus for all clones was one amino acid longer in HC1 than in the rabbit sequence. Also, each had a 2-amino acid deletion in FWRH3 (residues 72-73). For each of these clones, the first five amino acids and the six amino acids surrounding the FWRH3 deletion (residues 71-76) of HC1 were reverted to the rabbit sequences. Residue 93 of 345A12 was also reverted to rabbit in HC5. Regarding LC1, the N termini of 201C15, 345A12, and 346C6 were reverted to the rabbit sequence. One residue in FWRL3 of 20105 (residue 67) and 345A12 (residue 70) was identified as potentially interacting with the CDRs and one residue in FWRL2 of 346C6 (residue 36) was likewise identified.

2.10.4 Super-Humanizing 345A12

With the identification of additional rabbit residues in Vκ as critical for antigen-binding, further mutants of 345A12 were generated to introduce increasing numbers of human residues throughout the VH and Vκ regions. Analysis of the in silico model identified residues 35, 48, 49, 57, 58, 61, 62, 63, and 64 in VH and residues 1, 3, 24, 55, and 70 in VK.

2.10.5 Biophysical Characterization of Super-Humanized 345A12 Antibodies

The super-humanized 345A12 antibodies were purified from 350 mL of scale-up cell culture and formulated in 1×DPBS. The antibodies were concentrated for physical-chemical property evaluation. As shown in Table 20, the combination of HC10-LC7 and HC15-LC7 were precipitated during concentration step, potentially due to relative low pI or poor solubility. Purified antibodies were analyzed by BIAcore for mesothelin binding affinity, and the data are summarized in Table 21 below.

TABLE 20

Summary of purified humanized 345A12 antibodies

| mAbs | Supernatant Volume (mL) | Purification Yield | mAb-VCP-DiOH Eribulin Dimer, yield | mAb-VCP-Eribulin, Yield | Concentration to 5 mg/mL |
|---|---|---|---|---|---|
| 345A12-HC10-LC4 | 350 mL | 77.5 mg @ 5.1 mg/mL | 3.9 mg @ 1.3 mg/mL, 78% | 11 mg @ 5.0 mg/mL, 73% | Yes |
| 345A12-HC10-LC7 | 350 mL | 78 mg @ 5.2 mg/mL | 4.5 mg @ 1.6 mg/mL, 90% | 8.1 mg at 2.7 mg/mL, 54% | No, precipitated |
| 345A12-HC15-LC4 | 350 mL | 191 mg @ 8.3 mg/mL | 4.2 mg @ 1.4 mg/mL, 84% | 11 mg @4.85 mg/mL, 73% | Yes |
| 345A12-HC15-LC7 | 350 mL | 87.2 mg @ 4.0 mg/mL | 3.3 mg @1.1 mg/mL, 66% | 4.6 mg @ 1.54 mg/mL, 31% | No, precipitated |

TABLE 21

Binding affinity to mesothelin for humanized 345A12

| | Aggregation | Conjugation | Affinity | | | | |
|---|---|---|---|---|---|---|---|
| | | | Run 1 | | | Run 2 | |
| | % Monomer | % Conjugation | $k_a$ | $k_d$ | $K_D$ | $k_a$ | $k_d$ |
| Chimeric HC1-LC2 | 88.85 | 1.6 | 2.63E+06 | 4.64E−04 | 1.76E−10 | | |
| | | | 2.59E+06 | 4.32E−04 | 1.67E−10 | 2.47E+06 | 3.04E−04 |

TABLE 21-continued

Binding affinity to mesothelin for humanized 345A12

| | | | | | |
|---|---|---|---|---|---|
| HC1-LC4 | 82.96 | 1.33 | | 2.35E+06 | 2.57E−04 |
| HC1-LC7 | 87.23 | 1.29 | | | |
| HC10-LC4 | 80.73 | 1.32 | | | |
| HC10-LC7 | 82.75 | 1.21 | | | |
| HC15-LC4 | 86.56 | 1.3 | | | |
| HC15-LC7 | 92.7 | 1.42 | | | |

| | Affinity | | | | | |
|---|---|---|---|---|---|---|
| | Run 2 | Run 3 | | | Run 4 | | |
| | $K_D$ | $k_a$ | $k_d$ | $K_D$ | $k_a$ | $k_d$ | $K_D$ |
| Chimeric | | | | | | | |
| HC1-LC2 | 1.13E−10 | | | | | | |
| HC1-LC4 | 1.18E−10 | 1.96E+06 | 1.30E−04 | 6.61E−11 | 1.35E+06 | 1.61E−04 | 1.19E−10 |
| HC1-LC7 | | 1.83E+06 | 1.40E−04 | 7.66E−11 | 1.38E+06 | 1.79E−04 | 1.29E−10 |
| HC10-LC4 | | 1.80E+06 | 1.52E−04 | 8.47E−11 | 1.21E+06 | 1.80E−04 | 1.49E−10 |
| HC10-LC7 | | | | | 1.26E+06 | 1.89E−04 | 1.50E−10 |
| HC15-LC4 | | | | | 1.44E+06 | 1.12E−04 | 7.79E−11 |
| HC15-LC7 | | | | | 1.49E+06 | 1.16E−04 | 7.82E−11 |

2.10.6 DSC and cIEF Analyses

Figure 8:
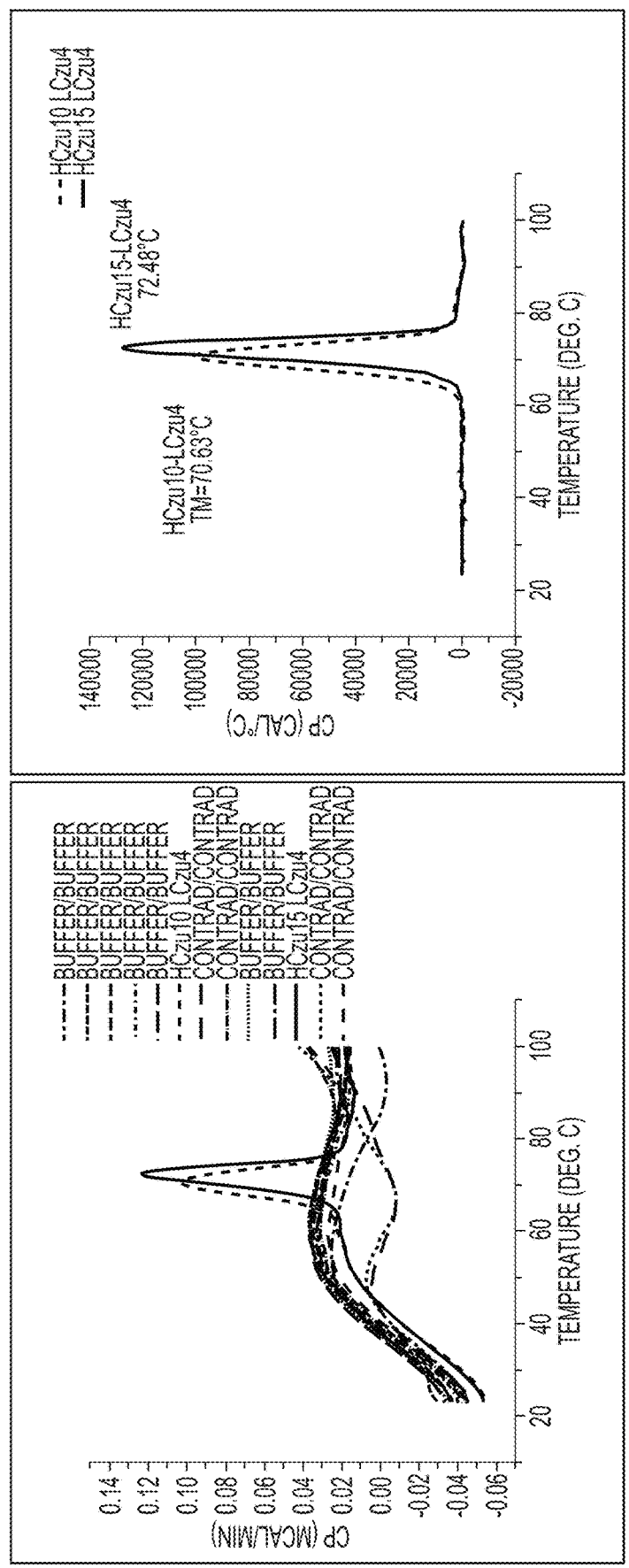
FIG. 8 shows DSC analysis results for humanized 345A12 antibodies. 345A12 F(ab')2 fragments were subject to thermal analysis ranging from 25-100° C. using a scan rate of 100° C./hour.

The thermal melting curves of F(ab')2 fragments were analyzed by DSC. The profiles of the HC15-LC4 F(ab')2 and HC10-LC4 F(ab')2 are shown in FIG. 8.

The pI of 345A12-HC10-LC4 and 345A12-HC15-LC4 mAbs were analyzed by cIEF. The pI varied within 0.06 pH units between each mAb, 8.19 for 345A12-HC10-LC4 and 8.25 for 345A12-HC15-LC4 (Table 22).

TABLE 22 cIEF analysis

| Sample Name | pI | % Acidic Peaks | % Neutral Peak | % Basic Peaks |
|---|---|---|---|---|
| 345A12-HC10-LC4 | 8.19 | 24.412 | 57.171 | 18.417 |
| 345A12-HC15-LC4 | 8.25 | 34.787 | 50.790 | 14.424 |

2.10.7 Serum Stability

PBS/human serum stability evaluation of 345A12-HC10-LC4 and 345A12-HC15-LC4 ADCs were tested for up to 10 days, as described in Section 2.7. Data are summarized in Table 23 below.

TABLE 23

In vitro PBS/human serum stability of zu345A12-VCP-eribulin ADCs, HC15-LC4 vs. HC10-LC4

| | | | Total Ab | | | | Intact ADC | | | |
|---|---|---|---|---|---|---|---|---|---|---|
| Sample # | Sample Description | Dilution | Mean Conc. (ng/mL) | % CV | Adjusted Result (µg/mL) | % Difference from T = 0 | Mean Conc. (ng/mL) | % CV | Adjusted Result (µg/mL) | % Difference from T = 0 |
| 1 | Zu345A12-HC10LC4-VCP-Eribulin T = 0, in human serum | 1:2,000 | 231 | 2.14 | 462 | N/A | 258 | 1.42 | 516 | N/A |
| 2 | Zu345A12-HC10LC4-VCP-Eribulin T = 24, in human serum | 1:2,000 | 221 | 4.59 | 442 | −4.3 | 190 | 1.70 | 380 | −26.4 |
| 3 | Zu345A12-HC10LC4-VCP-Eribulin T = 48, in human serum | 1:2,000 | 208 | 0.840 | 416 | −10.0 | 154 | 3.19 | 308 | −40.3 |

TABLE 23-continued

In vitro PBS/human serum stability of zu345A12-VCP-eribulin ADCs, HC15-LC4 vs. HC10-LC4

| | | | Total Ab | | | | Intact ADC | | | |
|---|---|---|---|---|---|---|---|---|---|---|
| Sample # | Sample Description | Dilution | Mean Conc. (ng/mL) | % CV | Adjusted Result (µg/mL) | % Difference from T = 0 | Mean Conc. (ng/mL) | % CV | Adjusted Result (µg/mL) | % Difference from T = 0 |
| 4 | Zu345A12-HC10LC4-VCP-Eribulin T = 72, in human serum | 1:2,000 | 213 | 1.46 | 426 | −7.8 | 142 | 1.66 | 284 | −45.0 |
| 5 | Zu345A12-HC10LC4-VCP-Eribulin T = 96, in human serum | 1:2,000 | 210 | 2.55 | 420 | −9.1 | 105 | 21.5 | 210 | −59.3 |
| 6 | Zu345A12-HC10LC4-VCP-Eribulin T = 240, in human serum | 1:2,000 | 207 | 4.27 | 414 | −10.4 | 97.0 | 6.31 | 194 | −62.4 |
| 7 | Zu345A12-HC15LC4-VCP-Eribulin T = 0, in human serum | 1:2,000 | 284 | 0.387 | 568 | N/A | 278 | 4.84 | 556 | N/A |
| 8 | Zu345A12-HC15LC4-VCP-Eribulin T = 24, in human serum | 1:2,000 | 282 | 4.19 | 564 | −0.7 | 229 | 2.71 | 458 | −17.6 |
| 9 | Zu345A12-HC15LC4-VCP-Eribulin T = 48, in human serum | 1:2,000 | 273 | 0.103 | 546 | −3.9 | 180 | 1.87 | 360 | −35.3 |
| 10 | Zu345A12-HC15LC4-VCP-Eribulin T = 72, in human serum | 1:2,000 | 258 | 0.744 | 516 | −9.2 | 144 | 0.436 | 288 | −48.2 |
| 11 | Zu345A12-HC15LC4-VCP-Eribulin T = 96, in human serum | 1:2,000 | 270 | 0.669 | 540 | −4.9 | 135 | 3.13 | 270 | −51.4 |
| 12 | Zu345A12-HC15LC4-VCP-Eribulin T = 240, in human serum | 1:2,000 | 270 | 1.48 | 540 | −4.9 | 111 | 0.669 | 222 | −60.1 |
| 13 | Zu345A12-HC10LC4-VCP-Eribulin T = 0, in PBS | 1:2,000 | 180 | 1.03 | 360 | N/A | 229 | 1.40 | 458 | N/A |
| 14 | Zu345A12-HC10LC4-VCP-Eribulin T = 24, in PBS | 1:2,000 | 184 | 0.583 | 368 | 2.2 | 187 | 2.07 | 374 | −18.3 |
| 15 | Zu345A12-HC10LC4-VCP-Eribulin T = 48, in PBS | 1:2,000 | 166 | 3.12 | 332 | −7.8 | 177 | 1.64 | 354 | −22.7 |
| 16 | Zu345A12-HC10LC4-VCP-Eribulin T = 72,in PBS | 1:2,000 | 180 | 0.829 | 360 | 0.0 | 177 | 2.00 | 354 | −22.7 |
| 17 | Zu345A12-HC10LC4-VCP-Eribulin T = 96, in PBS | 1:2,000 | 179 | 1.73 | 358 | −0.6 | 174 | 3.87 | 348 | −24.0 |
| 18 | Zu345A12-HC10LC4-VCP-Eribulin T = 240, in PBS | 1:2,000 | 171 | 0.915 | 342 | −5.0 | 131 | 6.24 | 262 | −42.8 |
| 19 | Zu345A12-HC15LC4-VCP-Eribulin T = 0, in PBS | 1:2,000 | 225 | 1.14 | 450 | N/A | 233 | 0.325 | 466 | N/A |
| 20 | Zu345A12-HC15LC4-VCP-Eribulin T = 24, in PBS | 1:2,000 | 226 | 1.45 | 452 | 0.4 | 209 | 3.53 | 418 | −10.3 |
| 21 | Zu345A12-HC15LC4-VCP-Eribulin T = 48, in PBS | 1:2,000 | 233 | 0.754 | 466 | 3.6 | 210 | 0.942 | 420 | −9.9 |
| 22 | Zu345A12-HC15LC4-VCP-Eribulin T = 72, in PBS | 1:2,000 | 210 | 4.03 | 420 | −6.7 | 186 | 2.11 | 372 | −20.2 |

TABLE 23-continued

In vitro PBS/human serum stability of zu345A12-VCP-eribulin ADCs, HC15-LC4 vs. HC10-LC4

| Sample # | Sample Description | Dilution | Total Ab | | | | Intact ADC | | | |
| | | | Mean Conc. (ng/mL) | % CV | Adjusted Result (µg/mL) | % Difference from T = 0 | Mean Conc. (ng/mL) | % CV | Adjusted Result (µg/mL) | % Difference from T = 0 |
|---|---|---|---|---|---|---|---|---|---|---|
| 23 | Zu345A12-HC15LC4-VCP-Eribulin T = 96, in PBS | 1:2,000 | 247 | 10.4 | 494 | 9.8 | 182 | 0.0585 | 364 | −21.9 |
| 24 | Zu345A12-HC15LC4-VCP-Eribulin T = 240, in PBS | 1:2,000 | 226 | 0.514 | 452 | 0.4 | 145 | 6.91 | 290 | −37.8 |

2.10.8 Matrix Stability of 345A12-HC15-LC4-VCP-Eribulin in Various Matrices Using a DAR-Sensitive Octet Assay 345A12-HC15-LC4-VCP-eribulin (DAR2) was analyzed for in vitro stability in mouse, rat, cynomolgus monkey, and human plasma and serum. ADC was incubated in matrix at 0.1 mg/mL for 1 week, and time points were removed after 1, 2, 3, 4, and 10 days. Analysis was done using a DAR-sensitive Octet (biolayer inferometry)-based assay as described in Section 2.3.1. Results are shown in FIG. 9. 345A12-HC15-LC4-VCP-eribulin (DAR2) demonstrated a time-dependent release of payload, with an average of 20% release after a 10 day incubation at 37° C.

2.10.9 Cultures Producing Rabbit IgG and Polyclonal Antibodies Against Human Mesothelin On week 2, the wells producing rabbit IgG antibody were identified by IgG FRET using europium cryptate. Wells producing IgG were screened for the presence of rabbit IgG Fcγ antibody by ELISA against plates coated with 1 µg/mL of CHO-MT40 mesothelin. The cultures producing mesothelin specific rabbit IgG were confirmed by ELISA screening against 1 µg/mL of mesothelin and counter screened against 1 µg/mL of CD73-his. FRET and ELISA were performed on the Biomek® FX robotic system (Beckman).

Example 3: In Vivo Studies

ADCs comprising lead humanized anti-mesothelin antibodies and eribulin conjugates were evaluated in mice using human lung and gastric cancer xenograft models and a human mesothelioma patient-derived xenograft (PDX) model according to the protocol described below. The anticancer activity and off-target toxicity of different DAR species of the ADCs was assessed.

3.1 Reagents and Materials
3.1.1 Antibodies

The antibodies used in the following studies have an unpaired cysteine at light chain position 80 (LCcys80) and include both the rabbit-human chimeric (-xi) and humanized (-zu) forms of the anti-human mesothelin antibodies xi345A12-HC1-LC2, xi102A6A2-HC1-LC2, zu345A12-HC1-LC2, zu345A12-HC10-LC4, and zu345A12-HC15-LC4.

3.1.2 Conjugatable Cytotoxins and LCcys80 ADCs

Linker-cytotoxin compounds used in the following studies include maleimide-VCP-eribulin and maleimide-VCP-diOH eribulin dimer.

3.1.3 Tumor Cell Lines

Human NSCLC cell line NCI-H2110, human gastric cancer cell line NCI-N87, and human mesothelioma cancer cell line HAY were used in the following studies. All cell lines used were obtained directly from the American Type Culture Collection (ATCC), with the exception of HAY cells, which were obtained from NCI.

3.1.4 Other Reagents

All reagents used were obtained from commercial suppliers at research-grade or higher, unless otherwise indicated.

3.2 In Vivo Screening and Efficacy Studies in Human Cancer Xenograft Models 3.2.1 Study Animals Female CD-1 IGS mice (Charles River, 7-9 weeks old) were used for the maximum tolerated dose (MTD) study, female NOD.CB17-SCID mice (Jackson Laboratory) were used for the NCI-H2110 and HAY xenograft studies, and female NCr nude mice (Taconic, 5 weeks old) were used for the NCI-N87 xenograft studies. Upon arrival, animals were acclimated for 5-7 days prior to inoculation. Animals were housed 3-5 mice per ventilated cage with sterilized food pellets and water bottle available ad lib. Animals were ear tagged and weighed prior to study initiation.

3.2.2 Cell Culture

Cryopreserved NCI-H2110, NCI-N87, or HAY cells from frozen stocks were cultured in medium containing necessary supplements. Cells were sub-cultured in complete medium for 2 passages before being used for in vivo inoculation.

3.2.3 Tumor Implantation, Enrollment Process, and Treatment

Cells were suspended in PBS mixed with ice-cold Matrigel at 1:1 (vol:vol) to a final concentration of $1.0 \times 10^8$ cells/mL or $5.0 \times 10^7$ cells/mL for the NCI-H2110 and HAY cells. Mice were injected subcutaneously with 100 µL/mouse of cell mixture and monitored for body weight and tumor growth. Measurements were taken by digital caliper 3 times weekly beginning on day 3 post-implantation.

3.2.4 Tumor Measurement and Treatment

Tumor volume was calculated using the formula: W (mm)×L (mm)×D (mm)×π/6. Mice were randomized to five mice per group once tumor implants reached an average volume of 100 mm³. Treatment was given intravenously at a volume of 200 µL. Terminal body weight was measured and recorded at the end of each study.

3.2.5 Statistical Analysis

Tumor volumes of animals from each treatment group were compared with a control group by a repeated-measures two-way ANOVA, followed by a Bonferroni post-test. Comparison of tumor growth within each experimental group was also performed using the same statistical analysis.

3.3 In Vivo Efficacy Studies in a Human Mesothelioma PDX Model

3.3.1 Study Animals

NMRI nu/nu female mice (Janvier Labs, 5-6 weeks) were acclimated for at least 4 days upon arrival prior to inoculation. Animals was housed 3-5 mice per ventilated cage with sterilized food pellets and water bottle available ad lib. Animals were ear marked and weighed prior to study initiation.

3.3.2 Xenotransplantation

On day 0 of the study, Meso 7212 tumors were removed from five donor mice under sterile conditions. Donor tumor tissue was cut into 2×2 mm fragments and placed in a sterile Petri dish covered with 0.9% saline. In parallel, the receptor animals were subcutaneously treated with the analgesic Metacam® (2 mg/kg) and then anaesthetized by a single intravenous injection (0.15 mL/mouse) with Etomidat-Lipuro® (12 mg/kg). A superficial vertical incision in the skin of 5-8 mm on the left flank was performed. The tip of a surgical scissor was inserted into the incision, directly over the flank, and was used to form a pocket in the subcutaneous space. One tumor fragment per mouse was implanted into the pocket using surgical tweezers. The incision was closed with a metal clip and the animals were placed back into a clean cage.

3.3.3 Experimental Procedure

During tumor propagation, tumor diameters were measured using a digital caliper (Mitutoyo). Animals were randomly assigned into experimental groups according to their tumor volume (inclusion criteria for tumor volume, 0.1-0.3 $cm^3$). Tumor volumes and body weights were recorded twice weekly.

3.3.4 Treatment

Eribulin was administered intravenously at doses of 0.2, 0.3, and 3.2 mg/kg on the day of randomization. MORAb-109 (DAR 0, 2, and 6) was administered intravenously at a dose of 10.0 mg/kg on the day of randomization or a dose of 2.5 mg/kg on four consecutive days. The administration volume was 10 mL/kg for intravenous injections throughout all experimental groups.

3.3.5 Statistical Analyses

Descriptive statistics were performed on the data for tumor volume and body weight. Tumor volumes of animals from each treatment group were compared with the control group by using a repeated-measures two-way ANOVA, followed by a Bonferroni post-test. Additionally, the comparison of tumor growth of animals within each group was also performed with the same statistical analysis.

3.4 Results—In Vivo Screening and Efficacy Studies

Figure 10A:
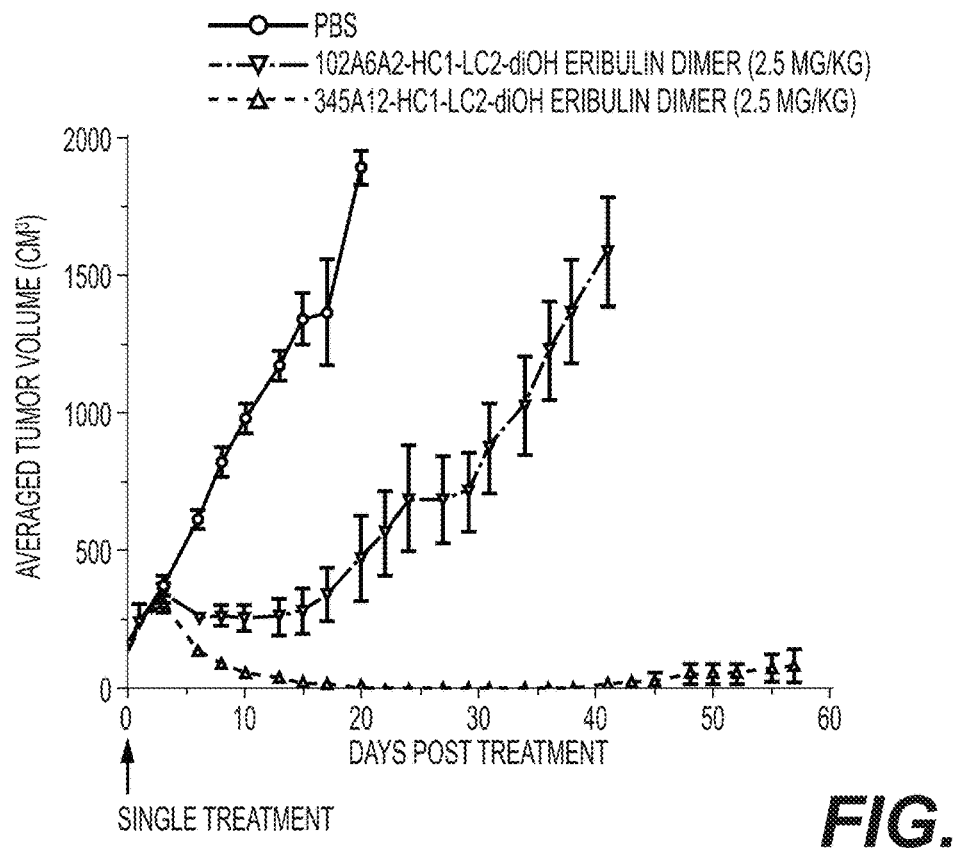
FIG. 10A and FIG. 10B show the anti-tumor effect (FIG. 10A) and body weight change (FIG. 10B) in a human non-small cell lung cancer (NSCLC)NCI-H2110 xenograft model treated with 345A12-HC1-LC2-diOH eribulin dimer ADC at 2.5 mg/kg or 102A6A2-HC1-LC2-diOH eribulin dimer ADC at 2.5 mg/kg (Study M109-004-2016).
Figure 10B:
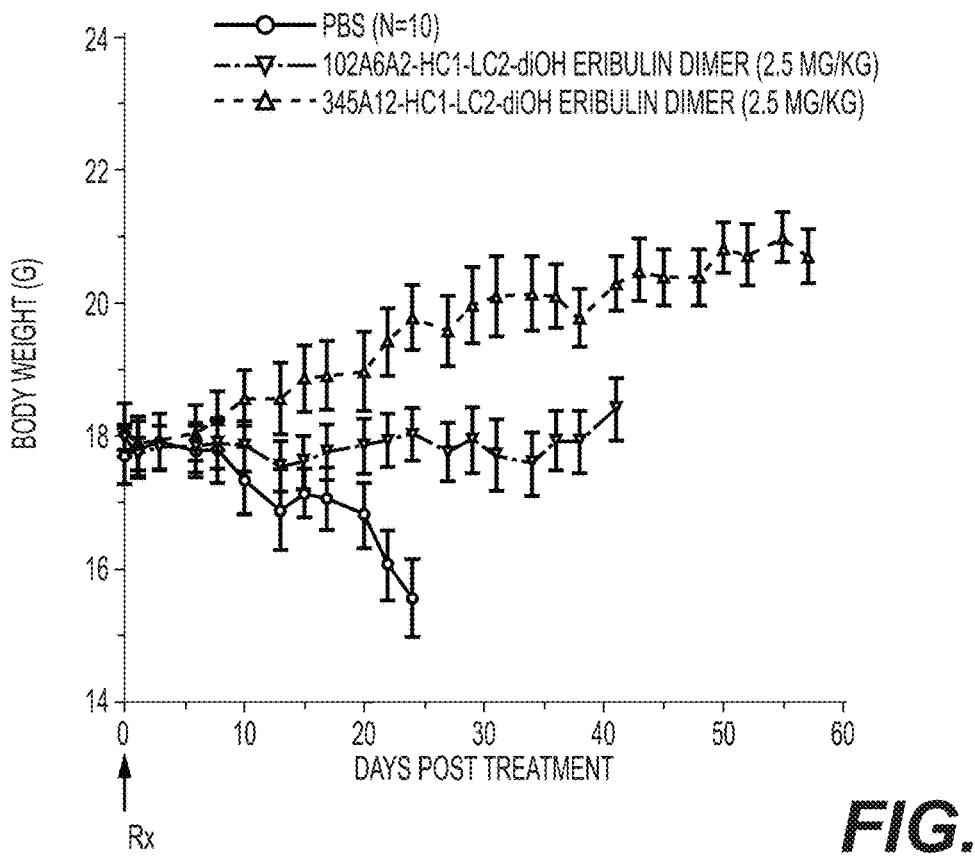

3.4.1 Study M109-004-2016: In Vivo Screening of 345A12-HC1-LC2 and 102A6A2 HC1-LC2 Eribulin Dimer ADCs in a Human NSCLC Xenograft Model Comparative in vivo screening of two clones of anti-mesothelin antibodies (345A12-HC1-LC2 and 102A6A2-HC1-LC2) was performed in a human non-small cell lung cancer (NSCLC) NCI-H2110 xenograft model. Mice were treated with 345A12-HC1-LC2-diOH eribulin dimer ADC at 2.5 mg/kg or 102A6A2-HC1-LC2-diOH eribulin dimer ADC at 2.5 mg/kg. Anti-tumor activity and body weight changes for both ADCs are shown in FIG. 10A and FIG. 10B, respectively.

Figure 11A:
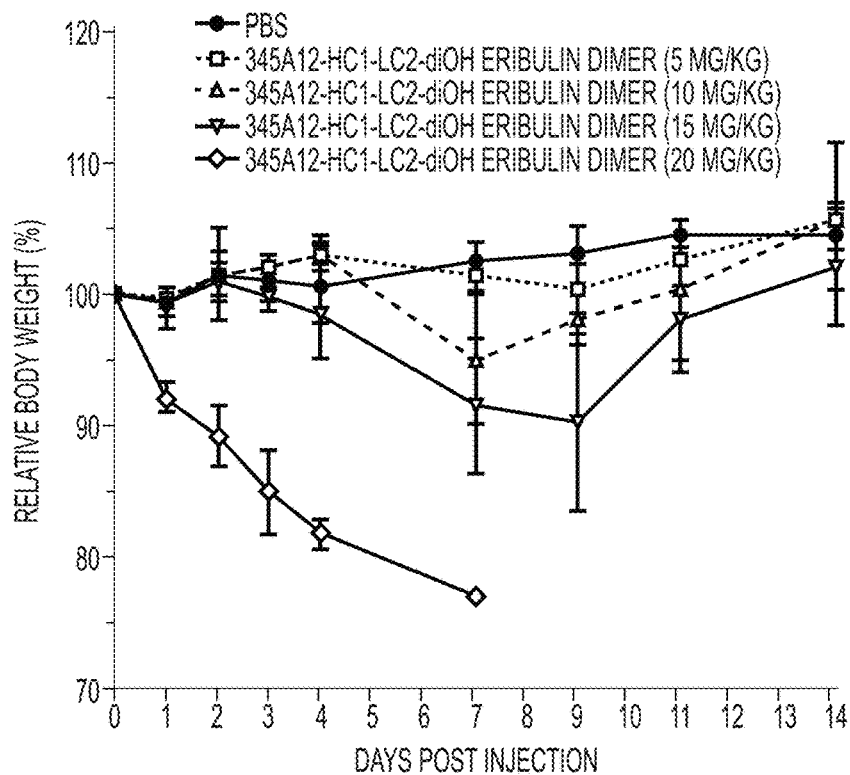
FIG. 11A and FIG. 11B show body weight change of female CD-1 mice treated with 345A12-HC1-LC2-diOH eribulin dimer ADC (5, 10, 15, or 20 mg/kg) (FIG. 11A) or 345A12-HC15-LC4-diOH eribulin dimer ADC (5, 10, or 20 mg/kg) (FIG. 11B) (Study M109-006-2017).
Figure 11B:
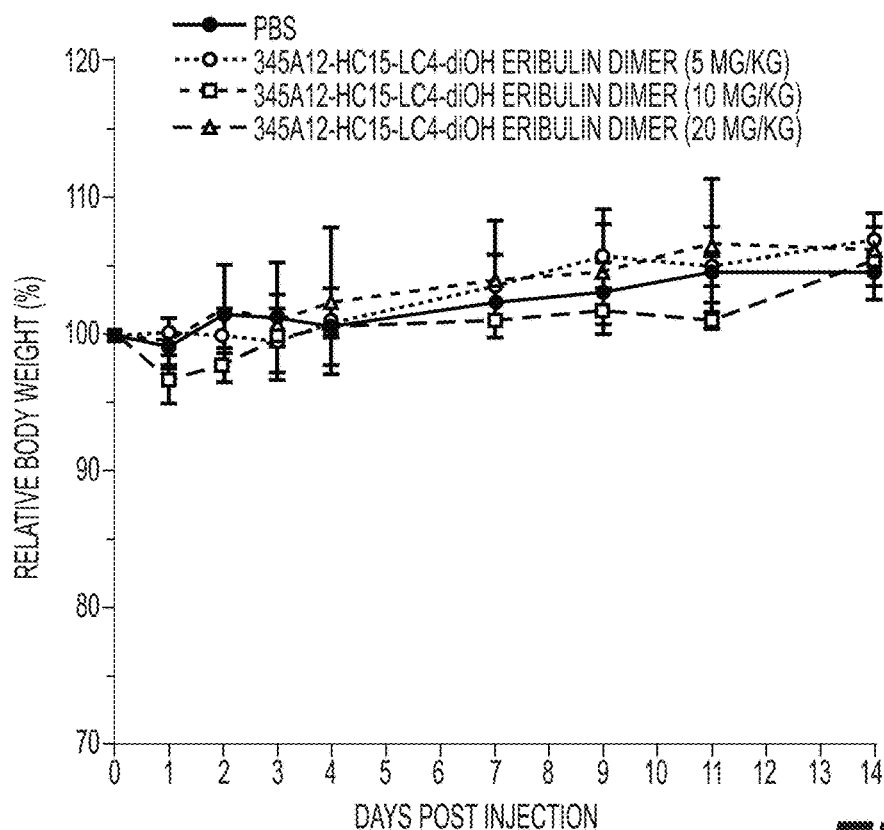

3.4.2 Study M109-006-2017: Preliminary Evaluation of Maximum Tolerance Dose (MTD) of 345A12-HC1-LC2 and 345A12-HC15-LC4 Eribulin Dimer ADCs in CD-1 Mice Body weight changes of female CD-1 mice were measured following administration of 5, 10, 15, or 20 mg/kg of 345A12-HC1-LC2-diOH eribulin dimer ADC, or 5, 10, or 20 mg/kg of 345A12-HC15-LC4-diOH eribulin dimer ADC. Body weight changes for each ADC are shown in FIG. 11A and FIG. 11B, respectively.

Figure 12A:
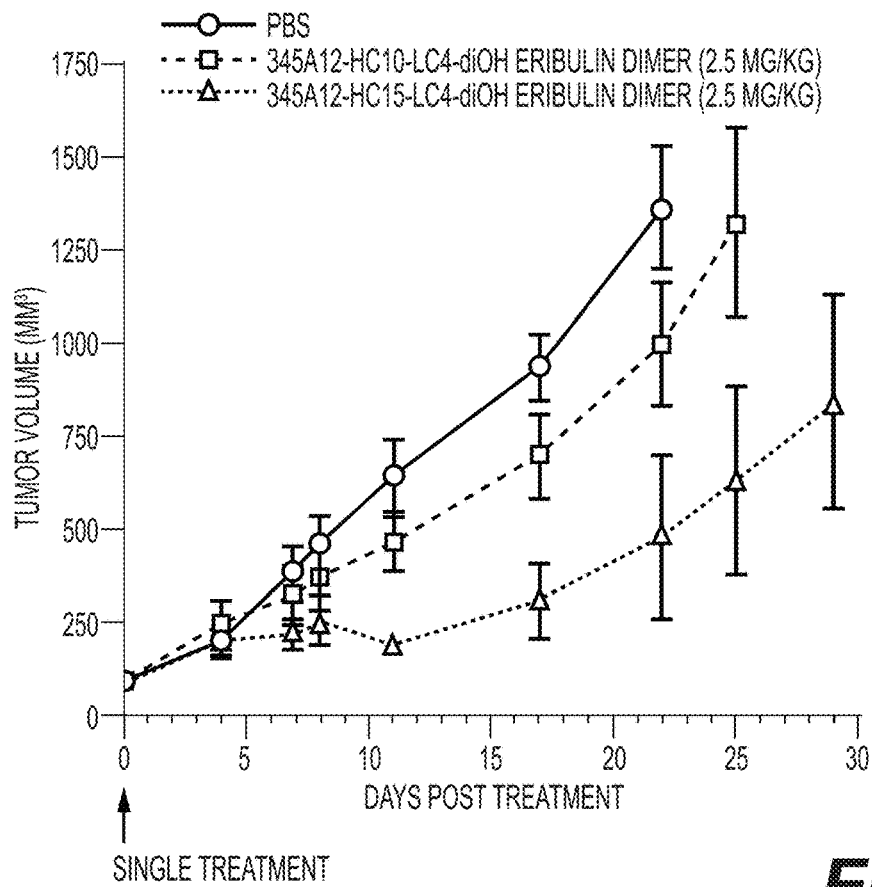
FIG. 12A and FIG. 12B show the anti-tumor effect (FIG. 12A) and body weight change (FIG. 12B) in a human NSCLC NCI-H2110 xenograft model treated with 345A12-HC10-LC4-diOH eribulin dimer ADC at 2.5 mg/kg or 345A12-HC15-LC4-diOH eribulin dimer ADC at 2.5 mg/kg (Study M109-007-2017).
Figure 12B:
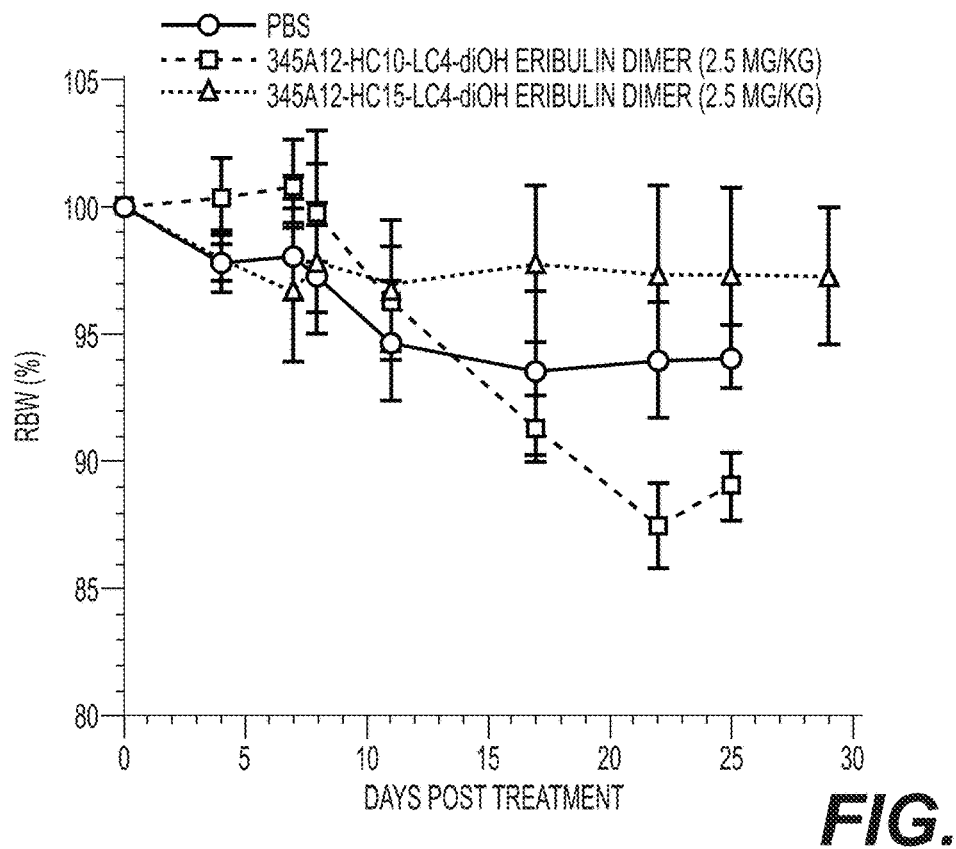

3.4.3 Study M109-007-2017: In Vivo Screening of 345A12-HC10-LC4 and 345A12-HC15-LC4 Eribulin Dimer ADCs in a Human NSCLC Xenograft Model Comparative in vivo screening of two additional clones of anti-mesothelin antibodies (345A12-HC10-LC4 and 345A12-HC15-LC4) was performed in a human NSCLC NCI-H2110 xenograft model. Mice were treated with 345A12-HC10-LC4-diOH eribulin dimer ADC at 2.5 mg/kg or 345A12-HC15-LC4-diOH eribulin dimer ADC at 2.5 mg/kg. Anti-tumor activity and body weight changes for both ADCs are shown in FIG. 12A and FIG. 12B, respectively.

The 345A12-HC15-LC4 clone was selected based on its anti-tumor activity and toxicity profile as the candidate clone for the antibody used in the MORAb-109 ADC.

Figure 13A:
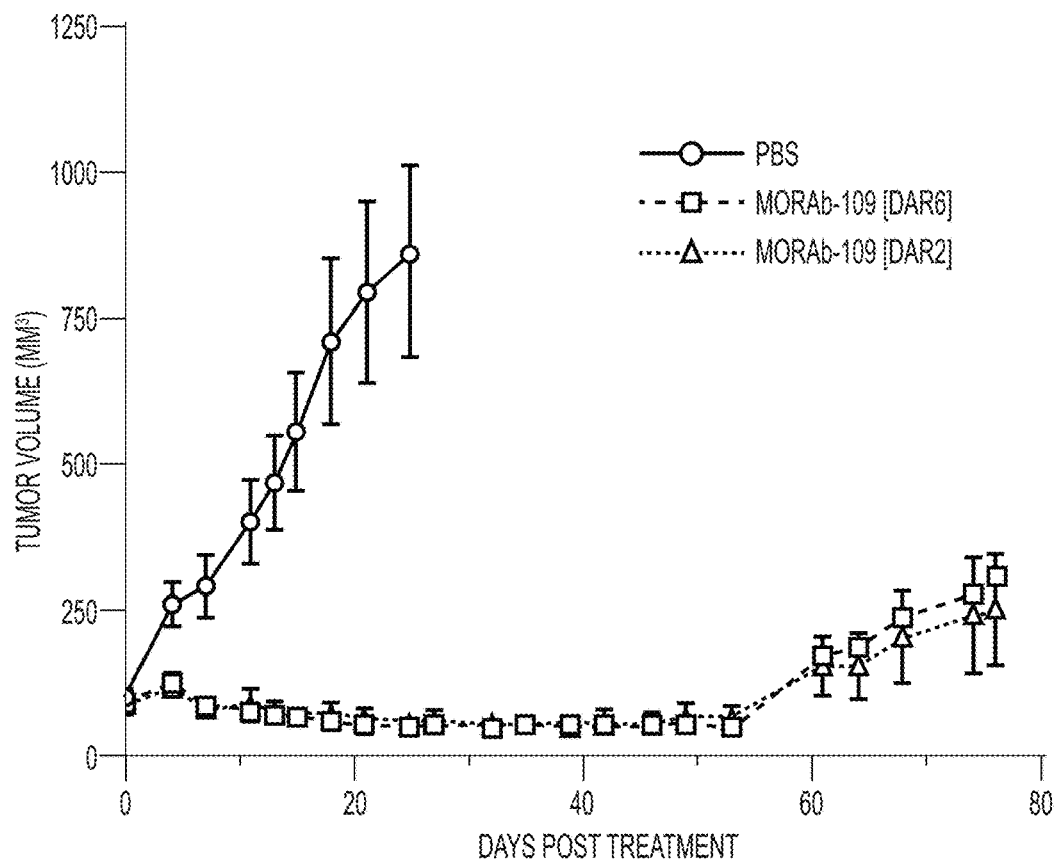
FIG. 13A and FIG. 13B show the anti-tumor effect (FIG. 13A) and body weight change (FIG. 13B) in a human gastric cancer NCI-N87 xenograft model treated with MORAb-109 (DAR2 or DAR6) (Study M109-010-2018).
Figure 13B:
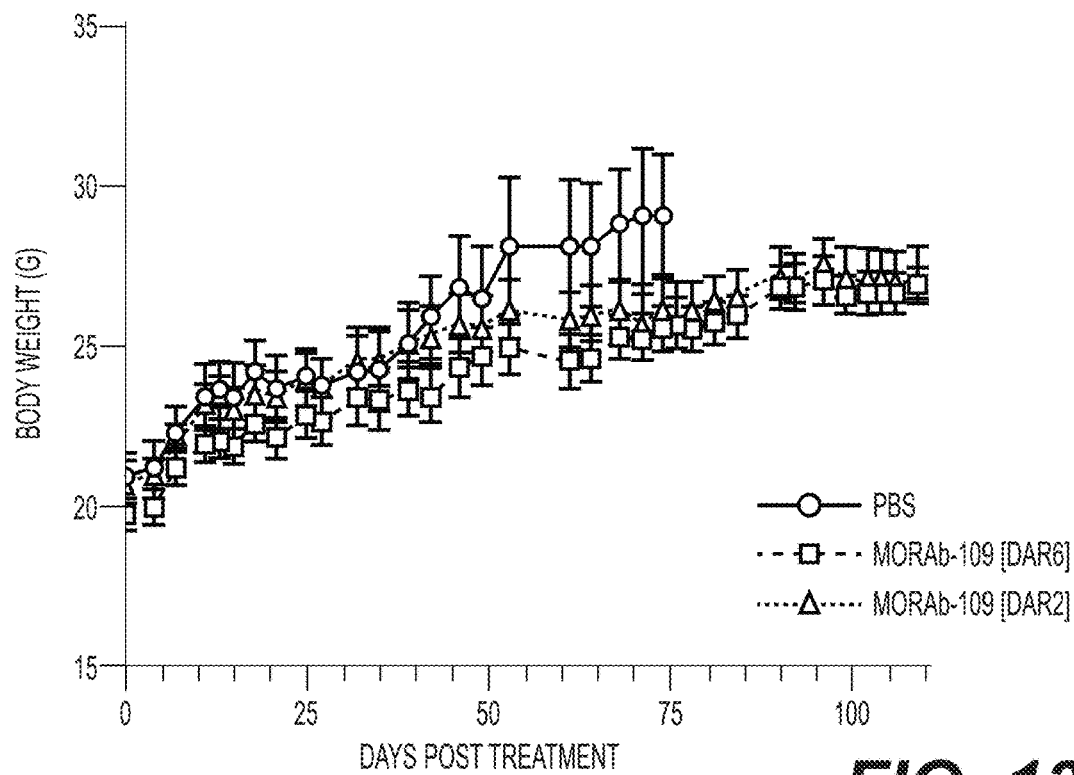

3.4.4 Study M109-010-2018: Anti-Tumor Effect of DAR2 and DAR6 Species of the 345A12-HC15-LC4-VCP-Eribulin ADC (MORAb-109) in a Human Gastric Cancer Xenograft Model Two DAR species (DAR2 and DAR6) of the 345A12-HC15-LC4-VCP-eribulin ADC (MORAb-109) were compared in a human gastric cancer NCI-N87 xenograft model at a dose of 10 mg/kg. Both DAR2 and DAR6 ADC species demonstrated durable and similar anti-tumor responses (FIG. 13A), with little to no weight loss observed following administration of either DAR species (FIG. 13B).

Figure 14A:
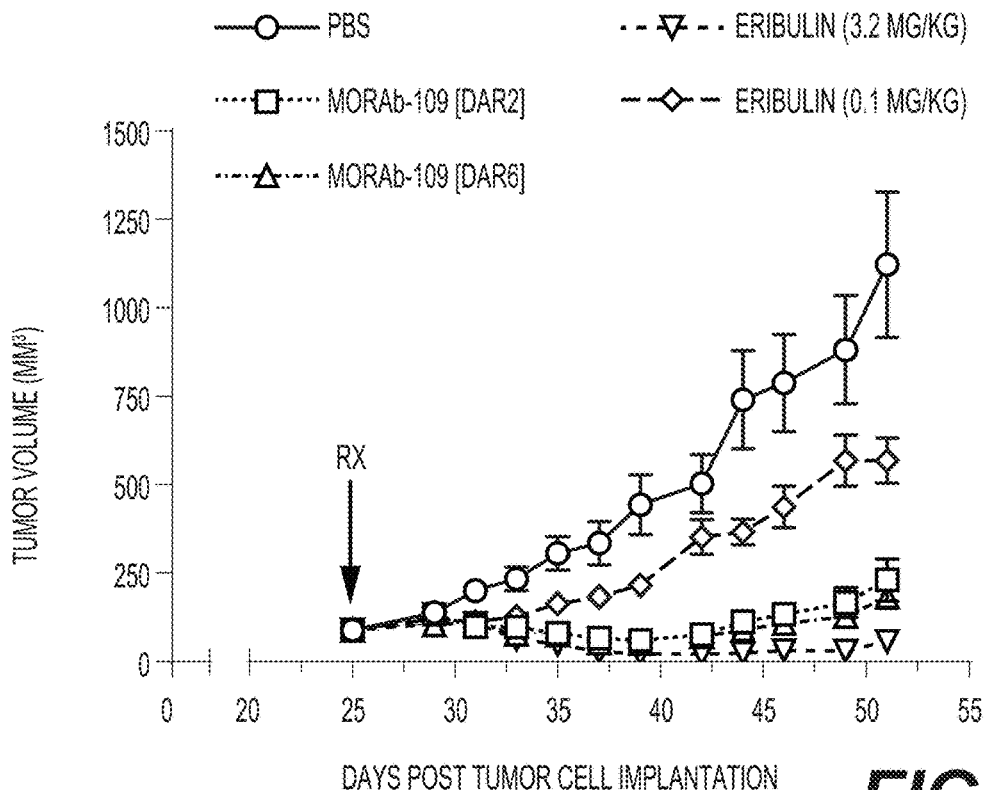
FIG. 14A and FIG. 14B show the anti-tumor effect (FIG. 14A) and body weight change (FIG. 14B) in a human mesothelioma HAY xenograft model treated with MORAb-109 (DAR2 or DAR6) or eribulin (Study M109-010-2018).
Figure 14B:
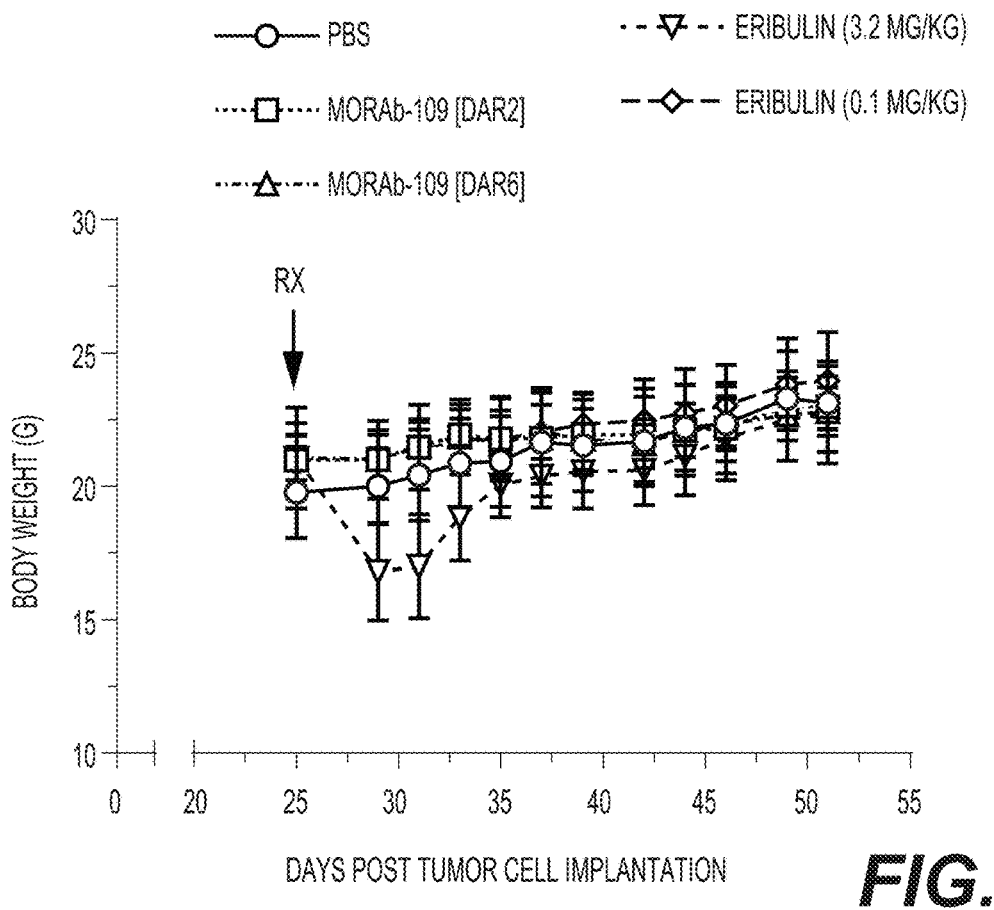

3.4.5 Study M109-010-2018: Anti-Tumor Effect of DAR2 and DAR6 Species of the 345A12-HC15-LC4-VCP-Eribulin ADC (MORAb-109) in a Human Mesothelioma Xenograft Model Two DAR species (DAR2 and DAR6) of the 345A12-HC15-LC4-VCP-eribulin ADC (MORAb-109) were compared in a human mesothelioma HAY xenograft model. Both DAR2 and DAR6 ADC species demonstrated durable and similar anti-tumor responses in mice treated with a single dose (5 mg/kg) of MORAb-109, while eribulin alone (administered at the MTD (3.2 mg/kg) or at an equivalent molar amount of eribulin as found in MORAb-109 (0.1 mg/kg)) showed limited anti-tumor effects (FIG. 14A). Acute and temporary body weight loss was observed in mice treated with the MTD dose of eribulin, while no body weight loss was observed in mice treated with either ADC (FIG. 14B).

Figure 15A:
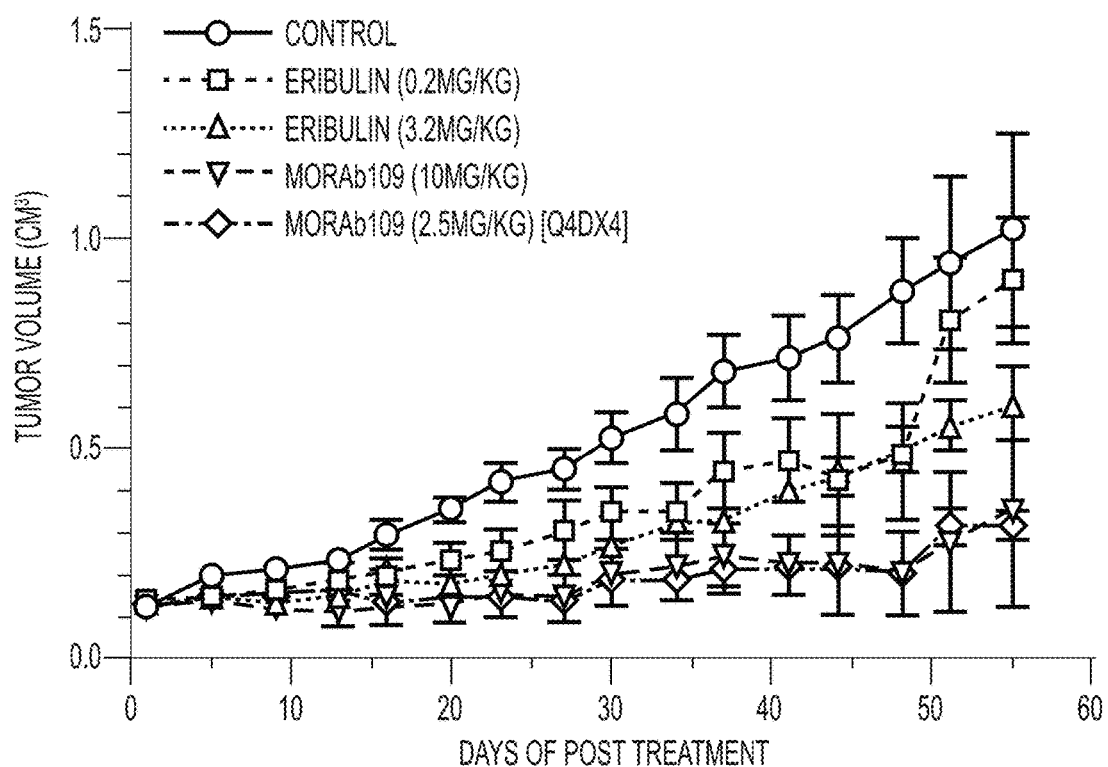
FIG. 15A and FIG. 15B show the anti-tumor effect (FIG. 15A) and body weight change (FIG. 15B) in a human mesothelioma PDX model (Meso7212) treated with MORAb-109 (DAR6) or eribulin.
Figure 15B:
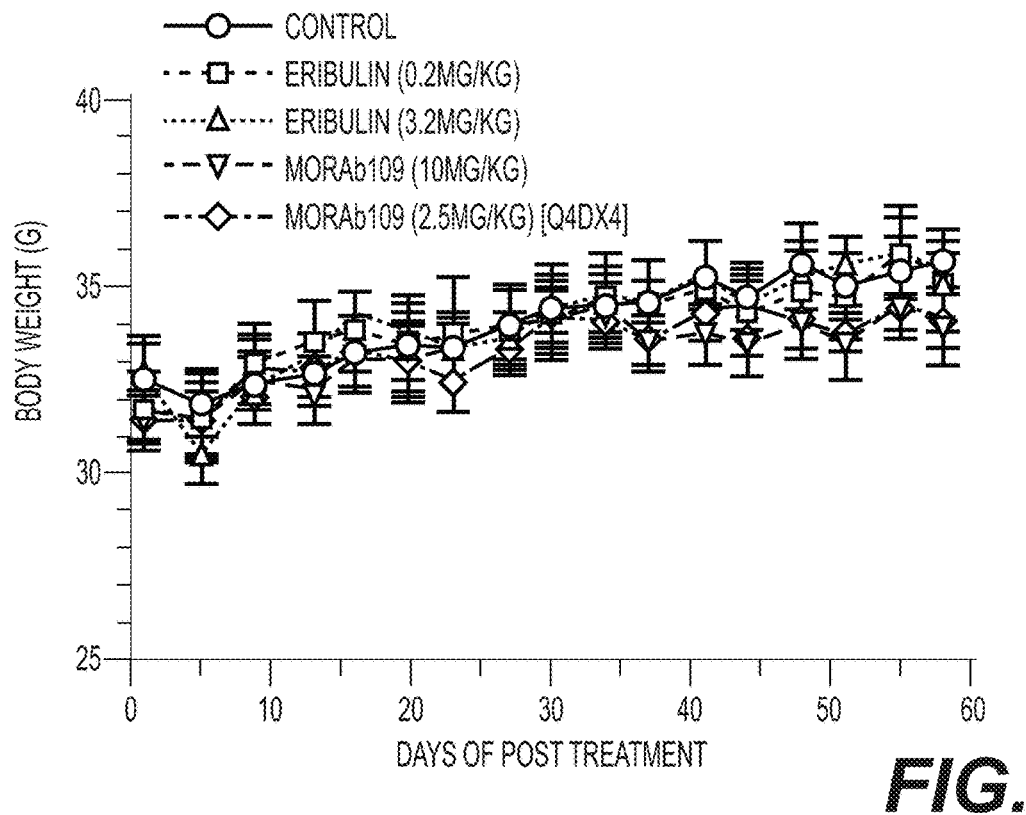

3.4.6 Anti-Tumor Effect of MORAb-109 (DAR6) in a Human Mesothelioma PDX Model The anti-tumor effect of the 345A12-HC15-LC4-VCP-eribulin ADC (MORAb-109) (DAR6) were investigated in a human mesothelioma PDX model, Meso7212 (MV15369). Two different treatment regimens were tested: a single administration of 10 mg/kg MORAb-109 or four consecutive daily administrations of 2.5 mg/kg. Both treatment regimens of MORAb-109 demonstrated durable and comparable anti-tumor responses, while the equivalent molar amount of eribulin alone (0.2 mg/kg) showed limited anti-tumor effects (FIG. 15A). Both MORAb-109 ADC treatments showed significantly increased anti-tumor activity as compared to the MTD dose of eribulin alone (P<0.05). Body weight changes for all treatments are shown in FIG. 15B.

Figure 16A:
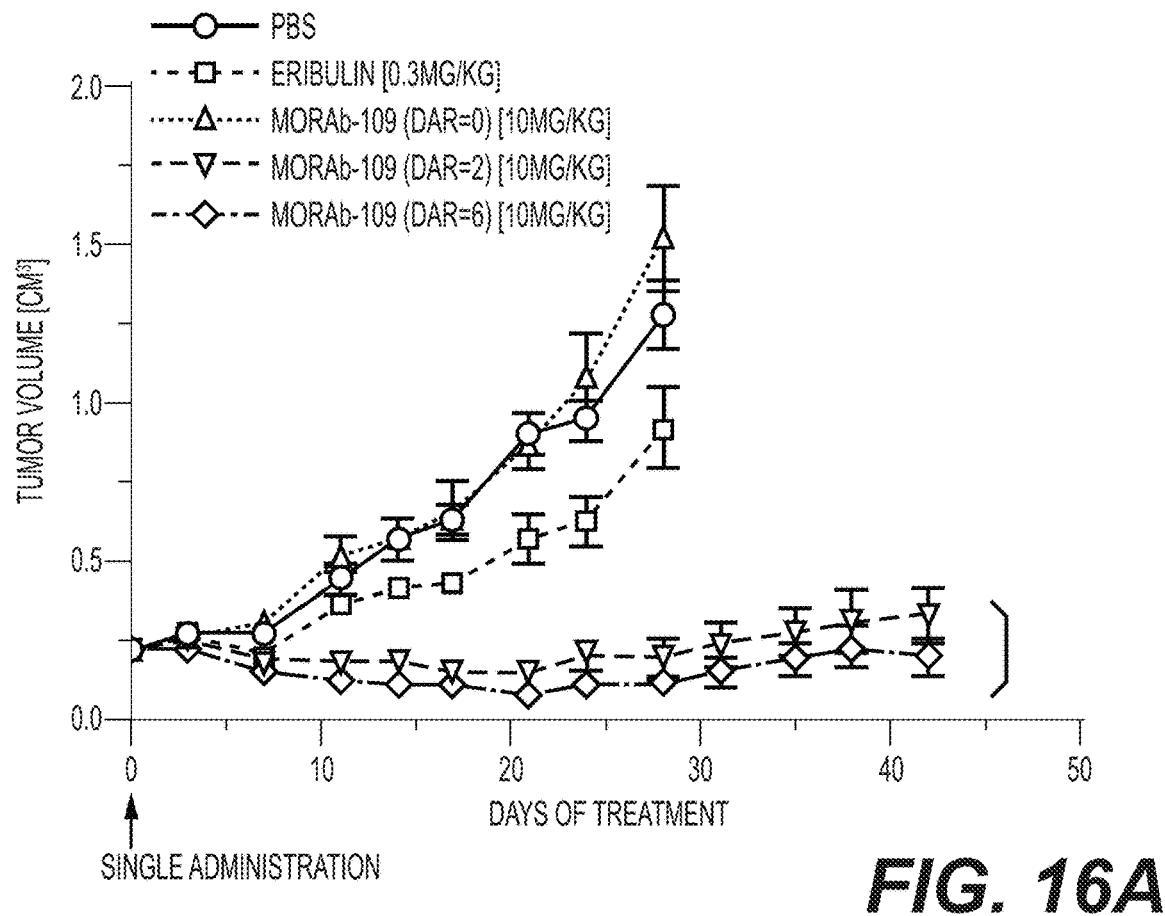
FIG. 16A and FIG. 16B show the anti-tumor effect (FIG. 16A) and body weight change (FIG. 16B) in a human mesothelioma PDX model (Meso7212) treated with different DAR species of MORAb-109 or eribulin.
Figure 16B:
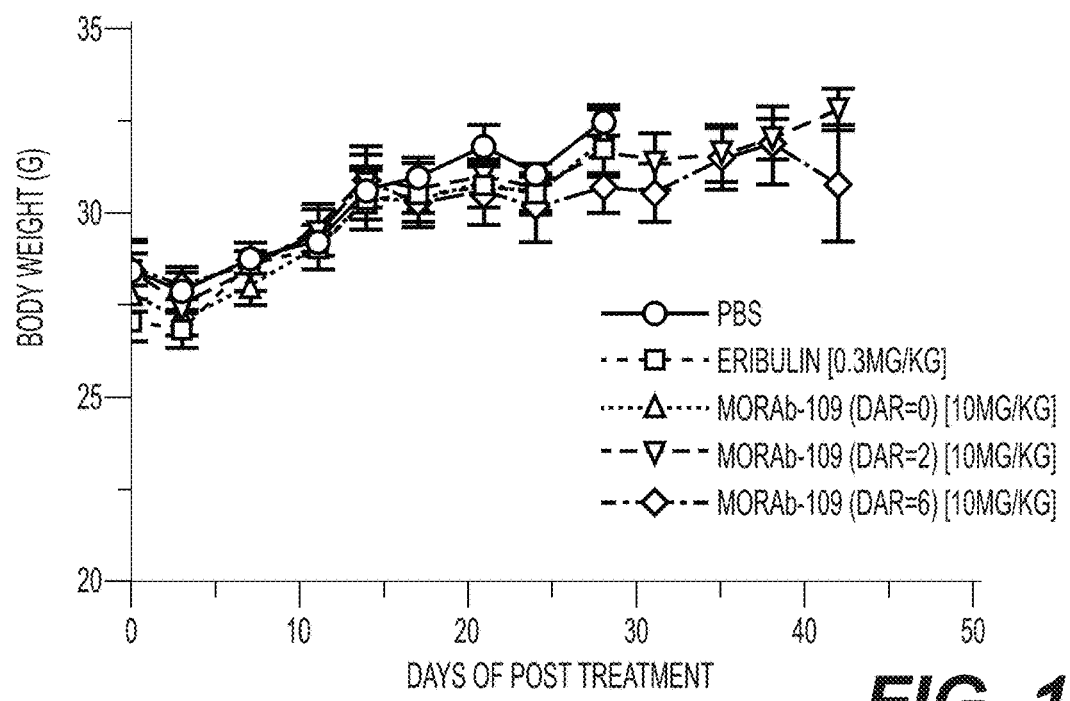

3.4.7 Anti-Tumor Effect of MORAb-109 (DAR2 and DAR6) in a Human Mesothelioma PDX Model The anti-tumor effect of two DAR species (DAR2 and DAR6) of the 345A12-HC15-LC4-VCP-eribulin ADC (MORAb-109) were investigated in a human mesothelioma PDX model, Meso7212 (MV16071), at a single administration of 10 mg/kg. Both DAR2 and DAR6 species of MORAb-109 demonstrated durable and comparable anti-tumor responses, while the equivalent molar amount of eribulin alone (0.3 mg/kg) and the no-eribulin conjugated MORAb-109 species (DAR0) showed limited or no anti-tumor effects (FIG. 16A). No body weight loss observed in any group (FIG. 16B). There was no statistical difference of anti-tumor effect between the DAR2 and DAR6 species of MORAb-109.

Example 4: Mesothelin (MSLN) Expression and In Vitro Potency 4.1 Methods

Cytotoxicity: Cells were sub-cultured and seeded at 5,000 cells/well in complete growth medium in 96-well tissue culture plates, and incubated at 37° C., 5% $CO_2$ overnight (16 hours). Test reagents were serially diluted 1:3 in 2 mL deep-well dilution plates, starting at 200 nM (10 dilutions total). Diluted samples (100 μL) were added to the cell plates (starting concentration of test samples at 100 nM). Plates were incubated at 37° C., 5% $CO_2$ for an additional 5 days. Medium was then discarded, and plates were washed once with 200 μL DPBS, stained with 50 μL of 0.2% Crystal Violet solution at room temperature for 15 min, and then washed extensively with tap water. Plates were air-dried, and Crystal Violet was dissolved with 200 μL of 1% SDS solution. Plates were read at 570 nm. Data was analyzed for $IC_{50}$ determination using GraphPad Prism 6. Correlation analysis was performed in GraphPad Prism using a non-parametric Spearman analysis.

4.2 Results

Figure 17:
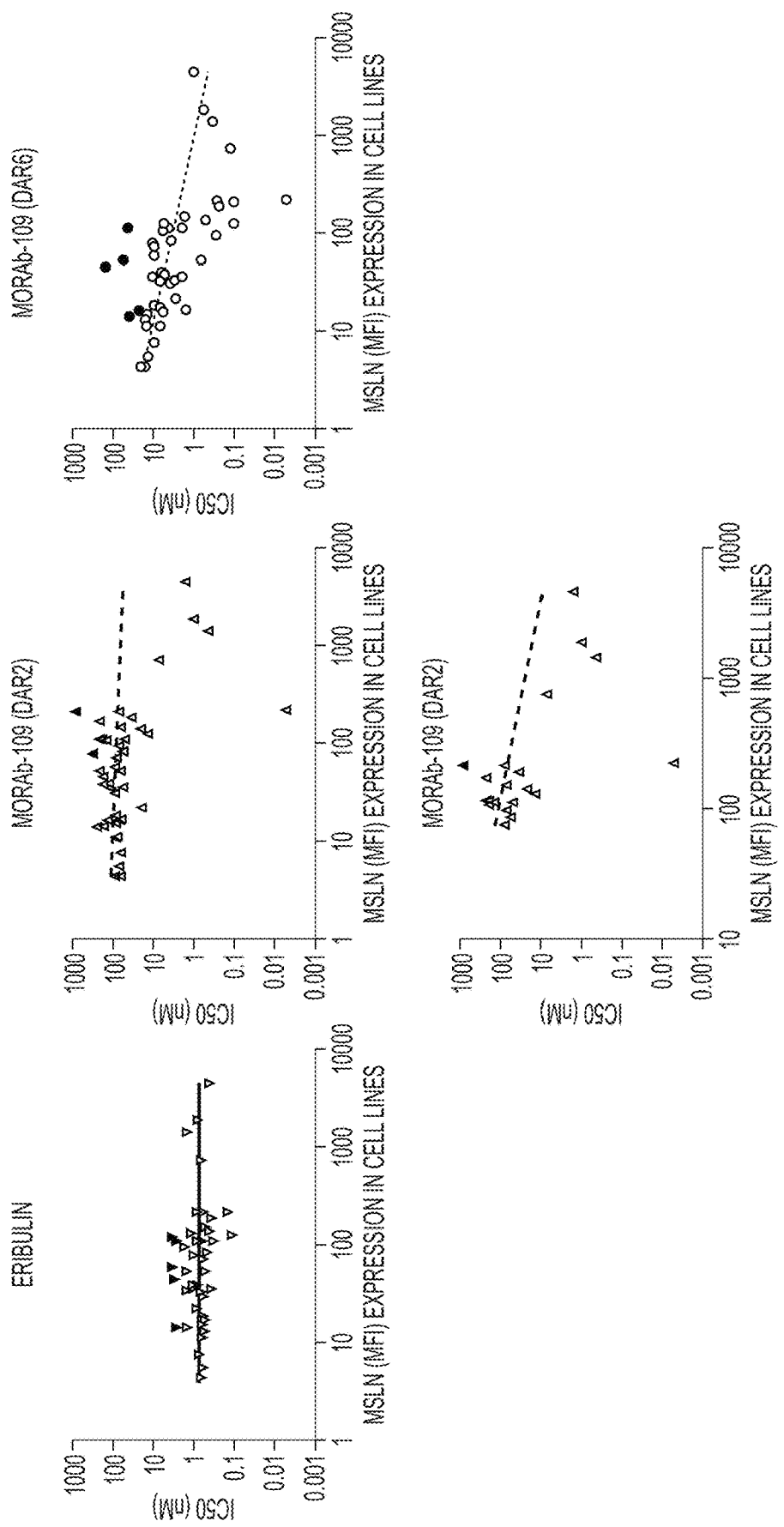
FIG. 17 shows a correlation analysis between mesothelin (MSLN) expression and in vitro potency ($IC_{50}$) of eribulin and MORAb-109 (DAR2 and DAR6) in various cell lines. The correlation for MORAb-109 (DAR2) was analyzed in all 51 cell lines and in a subset of cell lines with higher mesothelin expression levels (FACS staining of mean fluorescence intensity (MFI) equal to or >80). The subset excluded cell lines with lower mesothelin expression levels (FACS staining of MFI<80).

A correlation between potency of MORAb-109 (DAR6) and mesothelin expression was observed for all cell lines (FIG. 17; Tables 24 and 25).

For MORAb-109 (DAR2), when cell lines having lower mesothelin expression (FACS staining of mean fluorescence intensity (MFI)<80) were excluded from the analysis, a significant correlation between potency and mesothelin expression was observed (FIG. 17; Tables 24 and 25). Potency of MORAb-109 (DAR2) correlated with mesothelin expression at higher mesothelin expression levels.

TABLE 25

Cell lines used in mesothelin expression and potency correlation analysis

| | | In-vitro potency, IC50, nM | | |
|---|---|---|---|---|
| Cell lines | MSLN (MFI) | Eribulin | MORAb109 (DAR2) | MORAb109 (DAR6) |
| EGI-1 | 14.8 | 1.48 | 187.8 | 15.45 |
| TFK1 | 132.81 | 1.27 | | 5.65 |
| SNU-245 | 23.9 | 78.24 | 355.8 | |
| SNU-478 | 53.8 | 1.58 | 227.5 | 55.16 |
| SNU-1196 | 40.2 | 1.14 | 128.4 | 6.49 |
| T-47D | 4.4 | 0.68 | 95.86 | 22.04 |
| JIMT-1 | 36.4 | 0.39 | 61.8 | 11.4 |
| HCC1806 | 189.3 | 0.37 | 35.54 | 0.24 |
| HEC-1-A | 16.5 | 0.68 | 140.7 | 23.7 |
| HEC-1-B | 16.9 | 0.54 | 66.29 | 1.6 |
| HEC-251 | 53.3 | 0.5 | 67.15 | 0.67 |
| MFE-280 | 45.1 | 3.24 | 196.5 | 164.9 |
| NCI-H292 | 108.6 | 0.58 | 147.3 | 6.37 |
| NCI-H322 | 83.9 | 0.46 | 62.84 | 3.62 |
| NCI-H1355 | 11.5 | 0.67 | 79.77 | 7.09 |
| NCI-H1355-Sorted | 32.7 | 0.7 | 96.92 | 6.48 |
| NCI-H1573 | 17.4 | | 60.41 | 6.46 |
| NCI-H1568/MSLN | 4474 | 0.44 | 1.69 | 1.08 |
| NCI-H1650 | 31.5 | 0.61 | 92.2 | 4.09 |
| NCI-H1650/MSLN | 1865.5 | 0.84 | 1 | 0.57 |
| NCI-H2110 | 112.2 | 0.32 | 52.23 | 4.17 |
| NCI-H2126 | 73.6 | 0.53 | 87.89 | 10.82 |
| PC9 | 11.24 | 0.56 | 85.14 | 15.22 |
| H226 | 725.3 | 0.66 | 7.46 | 0.13 |
| NCI-H23 | 4.42 | 0.6 | 66.74 | 17.31 |
| Lu65 | 13.13 | 0.56 | | 15.85 |
| NCI-H460 | 8.56 | 35.29 | | |
| MOR/CPR | 120.79 | 3.69 | | 5.68 |
| A549 | 14.2 | 2.72 | 276 | 41.33 |
| CNE2 | 147.7 | 0.49 | 69.55 | 1.64 |
| HK1 | 39.2 | 0.89 | 197.5 | 5.88 |
| HNE-1 | 110.8 | 0.87 | 239.2 | 2.03 |
| HNE-1-T1 | 79.3 | 1.03 | 347 | 11.28 |
| HONE1 | 108.6 | 0.89 | 197.5 | 5.88 |
| SUNE1 | 212.4 | 0.56 | 77.8 | 0.27 |
| CaOV-3 | 137.6 | 0.44 | 20.93 | 0.51 |
| COV362 | 113.5 | 2.78 | 193 | 45.29 |
| HAC-2 | 172.3 | 26.65 | 228 | 320 |
| Kuramochi | 211.2 | 0.89 | 897.8 | 0.1 |
| OVCAR3 A1 | 220 | 0.15 | 0.005 | 0.005 |

TABLE 24

Mesothelin expression and potency correlation analysis (DAR2 and DAR6)

| | MSLN (MFI) vs. Eribulin | MSLN (MFI) vs. MORAb109 | MSLN (MFI) vs MORAb109(DAR6) | MSLN (MFI) vs MORAb109_MSLN high |
|---|---|---|---|---|
| Spearman r | | | | |
| r | −0.1113 | −0.2906 | −0.6773 | −0.6267 |
| 95% confidence interval | −0.3935 to 0.1902 | −0.5472 to 0.01591 | −0.8093 to −0.4803 | −0.8502 to −0.2118 |
| P value | | | | |
| P (two-tailed) | 0.4566 | 0.0557 | <0.0001 | 0.0054 |
| P value summary | ns | ns | **** | ** |
| Exact or approximate P value? | Approximate | Approximate | Approximate | Approximate |
| Significant? (alpha = 0.05) | No | No | Yes | Yes |
| Number of XY Pairs | 47 | 44 | 48 | 18 |

TABLE 25-continued

Cell lines used in mesothelin expression and potency correlation analysis

| Cell lines | MSLN (MFI) | In-vitro potency, IC50, nM | | |
|---|---|---|---|---|
| | | Eribulin | MORAb109 (DAR2) | MORAb109 (DAR6) |
| AsPC1 | 33.47 | 1.62 | | 3.13 |
| BxPC3 | 15.59 | 0.66 | 86.2 | 5.88 |
| Capan-2 | 36 | 1.21 | 138 | 1.99 |
| A431 | 5.6 | 0.55 | 71.51 | 14.17 |
| A431-K5 | 1430.3 | 1.5 | 0.45 | 0.35 |
| NCI-N87 | 125.8 | 0.11 | 14.7 | 0.1 |
| MKN1 | 22.06 | 0.96 | 20.14 | 2.89 |
| MKN74 | 7.73 | 0.78 | 66.96 | 9.62 |
| SNU216 | 94.91 | 1.78 | 73.42 | 0.29 |
| MKN45 | 57.94 | 3.65 | 100 | 10.39 |
| MKN7 | 18.48 | 0.58 | 86.53 | 10.39 |

Example 5: Dose-Response of MORAb-109 in Human Gastric Cancer (NCI-N87) Xenograft Model 5.1 Methods 5.1.1 In Vivo Efficacy Animals: Female NCr nude mice (Taconic), 5 weeks old at the time of arrival were acclimated for 5-7 days prior to inoculation. Animals were housed 3-5 mice per ventilated cage with sterilized food pellets and water bottle available ad lib. Animals were ear tagged and weighed prior to study initiation.

Cell culture: Cryopreserved NCI-N87 cells were thawed and grown in medium containing necessary supplements. Cells were sub-cultured in complete medium for 2 passages before being used for in vivo inoculation.

Tumor implantation, enrollment process, and treatment: The cell suspension in PBS was mixed with ice-cold Matrigel at 1:1 (vol:vol) to a final concentration of $1.0 \times 10^8$ cells/mL. 100 µL/mouse of the mixture was injected subcutaneously. The mice were monitored for clinical well-being with body weights and tumors measurements by digital caliper, 3 times weekly, beginning on day 3 post-implantation.

Tumor measurement and treatment: Tumor volume (TV) ($mm^3$) was calculated using the formula: W (mm)×L (mm)×D (mm)×n/6. When the tumors reached around 100 $mm^3$ in an average, the animals were randomized to 5 per group. Treatment was given intravenously in a volume of 200 µL of test article. At the end of the study, the terminal body weight was measured and recorded.

Statistical analysis: Descriptive statistics were performed on the data of tumor volume and body weight. Tumor volumes of animals from each treatment group were compared with the control group by using the repeated-measures two-way ANOVA followed by the Bonferroni post-test. Additionally, the comparison of tumor growth of animals within each group was performed with the same statistical analysis.

5.1.2 Pharmacokinetics (PK)

PK analysis was performed using both an intact ADC assay and a total antibody assay. Total antibody refers to the sum total of all species, including conjugated and unconjugated species (i.e., DAR0+DAR1+DAR2+ . . . +DARn), whereas intact ADC refers to all conjugated species (i.e., DAR1+DAR2+ . . . +DARn). Total antibody assay used biotinylated mesothelin for capture. Intact ADC assay used biotinylated anti-eribulin 5E4 Fab fragment for capture and AlexaFluor647-labelled anti-human Fc for detection. Sample analysis was performed on a Gyros analyzer. Data analysis was performed in WatsonLIMS 7.4.1 and plotted in Microsoft Excel.

5.2 Results

Figure 18A:
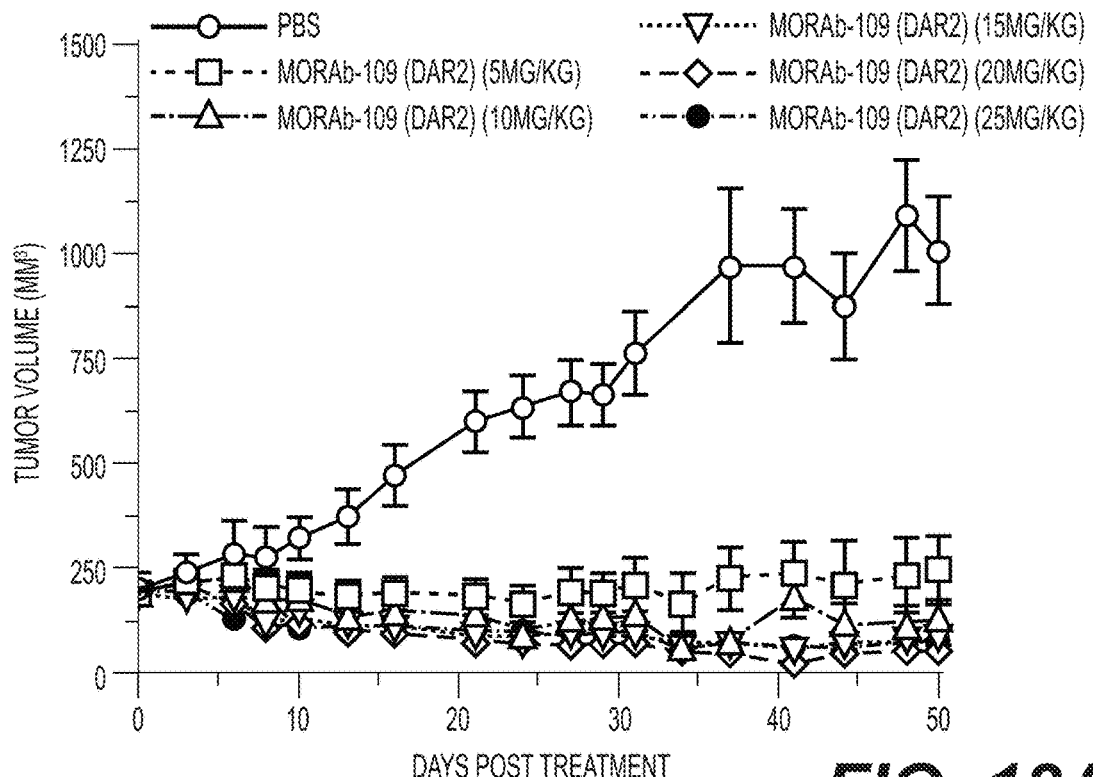
FIG. 18A-C show the anti-tumor effect (FIG. 18A and FIG. 18B) and body weight change (FIG. 18C) in a human gastric cancer NCI-N87 xenograft model treated with different doses of MORAb-109 (DAR2) ranging from 5 mg/kg to 25 mg/kg.
Figure 18B:
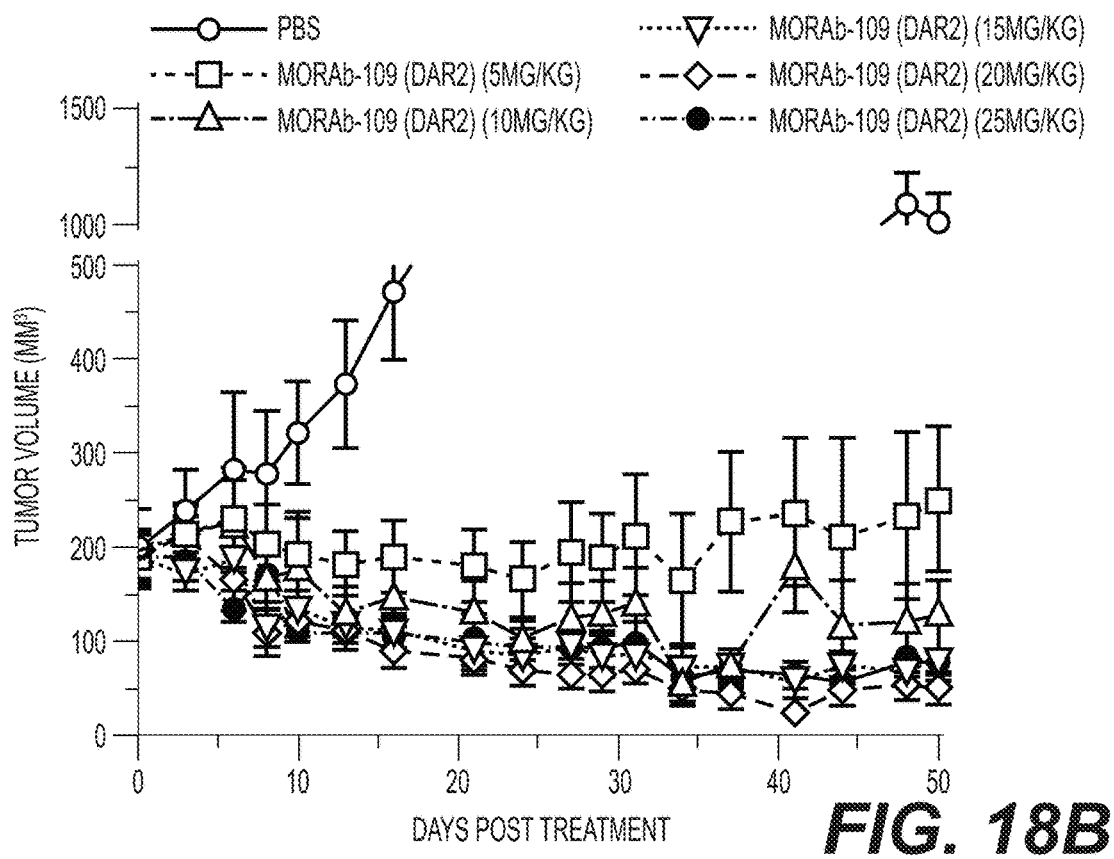
Figure 18C:
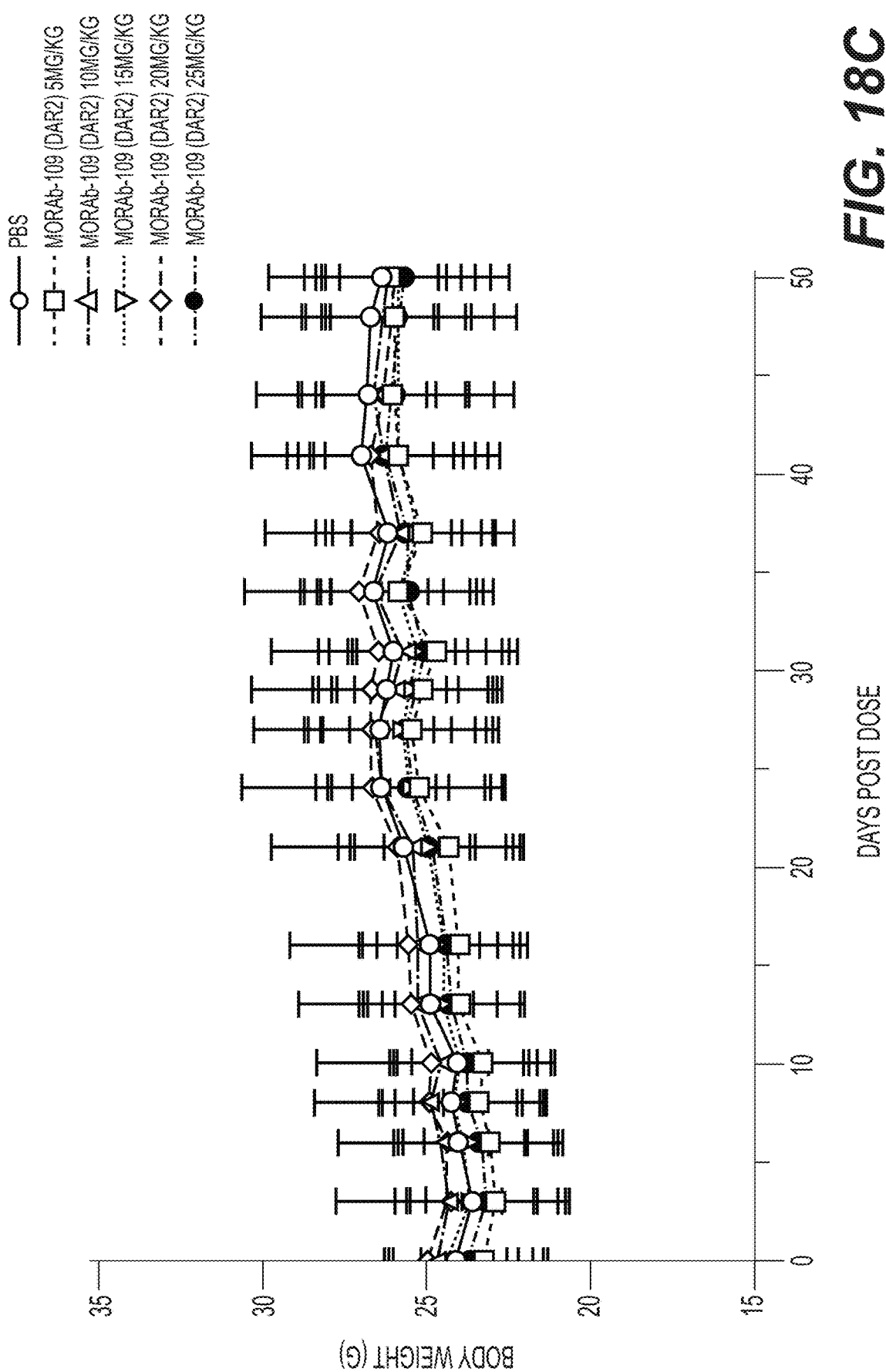

Dose-dependent efficacy was observed for dose ranges of MORAb-109 (DAR2) from 5 mg/kg to 25 mg/kg (FIGS. 18A and 18B). No body weight loss was observed in any dose group (FIG. 18C). A dose-dependent exposure of ADC was observed in treated animals, as indicated by dose-dependent increases in AUC (FIG. 19 and Table 26).

TABLE 26

PK of MORAb-109 (dose-titration) in NCI-N87 tumor-bearing mice

| Dose (mg/kg) | Intact ADC or Total Ab | $T_{1/2}$ (hr) | $V_{dss}$ (mL/kg) | CL (mL/kg/hr) | AUC (µg*hr/kg) | $C_{max}$ (µg/mL) |
|---|---|---|---|---|---|---|
| 5 | Intact | 125.1 | 78.7 | 0.509 | 9512 | 62.9 |
| | Total | 173.9 | 75.1 | 0.316 | 14375 | 73.2 |
| 10 | Intact | 148.2 | 99.5 | 0.475 | 19559 | 105 |
| | Total | 231.6 | 89.6 | 0.259 | 31631 | 123 |
| 15 | Intact | 142.1 | 81.1 | 0.414 | 34557 | 169 |
| | Total | 209.2 | 68.8 | 0.236 | 56134 | 205 |
| 20 | Intact | 151.5 | 90.9 | 0.429 | 43852 | 214 |
| | Total | 218.6 | 70.6 | 0.230 | 75718 | 270 |
| 25 | Intact | 143.5 | 91.1 | 0.463 | 51253 | 271 |
| | Total | 226.1 | 78.2 | 0.240 | 88099 | 322 |

Example 6: In Vivo Anti-Tumor Efficacy of MORAb-109 in Human Ovarian Cancer (OVCAR-3-A1-T1) Xenograft Model 6.1 Methods Animals: Female NOD.CB17-SCID mice (Jackson Laboratory), 5 weeks old at the time of arrival were acclimated for 5-7 days prior to inoculation. Animals were housed 3-5 mice per ventilated cage with sterilized food pellets and water bottle available ad lib. Animals were ear tagged and weighed prior to study initiation.

Cell culture: Cryopreserved OVCAR-3-A1-T1 cells were thawed and grown in medium containing necessary supplements. Cells were sub-cultured in complete medium for 2 passages before being used for in vivo inoculation.

Tumor implantation, enrollment process, and treatment: The cell suspension in PBS was mixed with ice-cold Matrigel at 1:1 (vol:vol) to a final concentration of $5.0 \times 10^7$ cells/mL. 100 µL/mouse of the mixture was injected subcutaneously. The mice were monitored for clinical well-being with body weights and tumors measurements by digital caliper, 3 times weekly, beginning on day 3 post-implantation.

Tumor measurement and treatment: Tumor volume (TV) (mm$^3$) was calculated using the formula: W (mm)×L (mm)×D (mm)×n/6. When the tumors reached around 100 mm$^3$ in an average, the animals were randomized to 5 per group. Treatment was given intravenously in a volume of 200 µL of test article. At the end of the study, the terminal body weight was measured and recorded.

Statistical analysis: Descriptive statistics were performed on the data of tumor volume and body weight. Tumor volumes of animals from each treatment group were compared with the control group by using the repeated-measures two-way ANOVA followed by the Bonferroni post-test. Additionally, the comparison of tumor growth of animals within each group was performed with the same statistical analysis.

6.2 Results

Figure 20A:
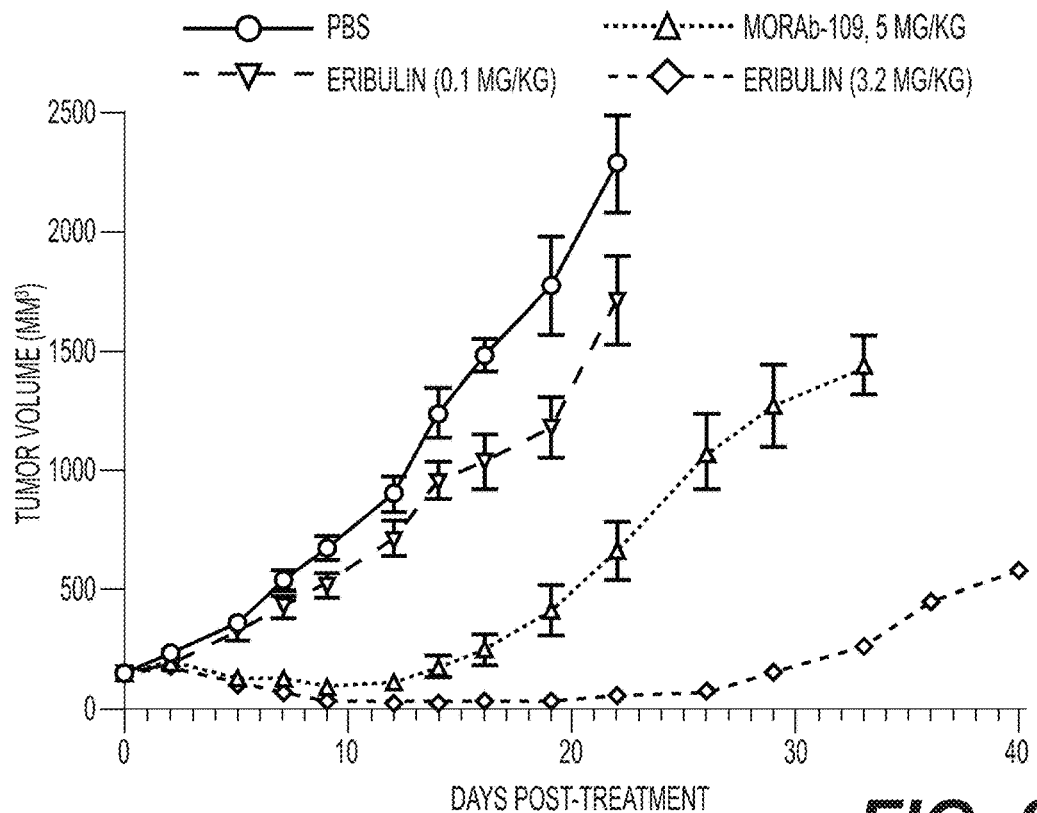
FIG. 20A and FIG. 20B show the anti-tumor effect (FIG. 20A) and body weight change (FIG. 20B) in a human ovarian cancer OVCAR-3-A1-T1 xenograft model treated with MORAb-109 (DAR2) (5 mg/kg) or eribulin (0.1 or 3.2 mg/kg).
Figure 20B:
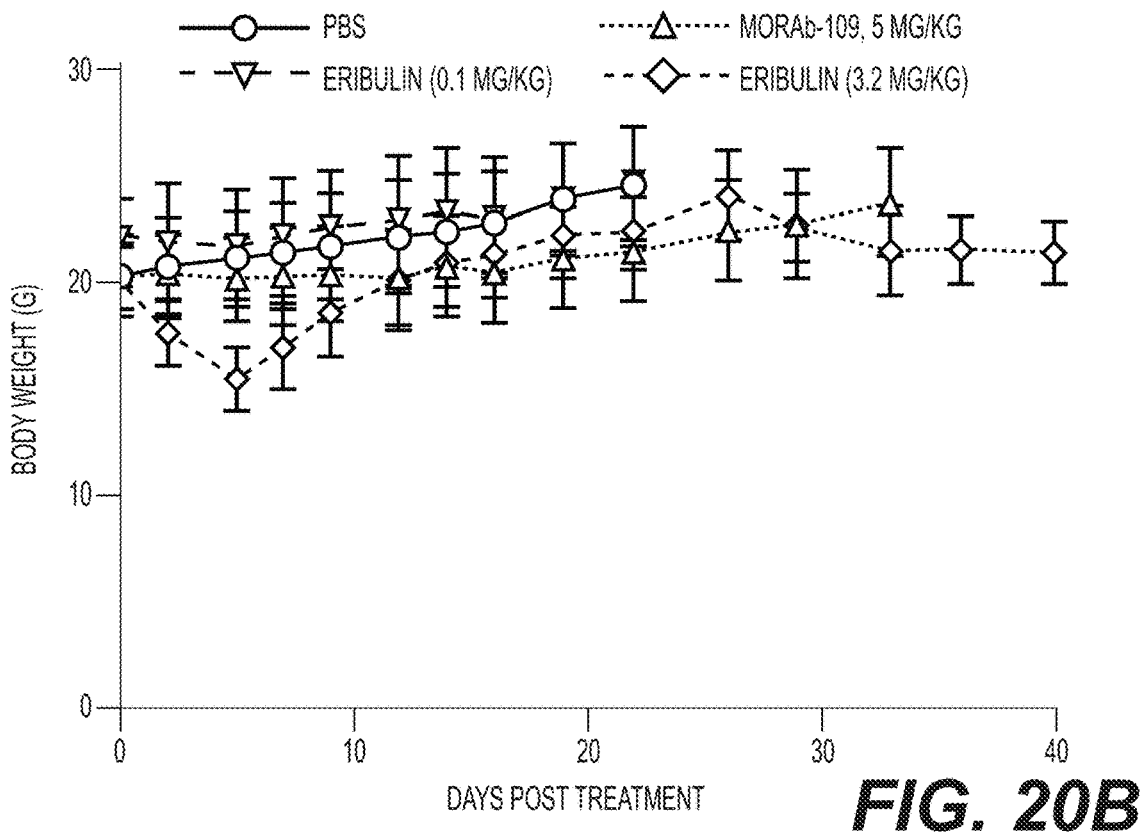

MORAb-109 (DAR2) demonstrated tumor growth delay in a human ovarian cancer OVCAR-3-A1-T1 xenograft model (FIG. 20A and FIG. 20B).

Example 7: In Vivo Anti-Tumor Efficacy of MORAb-109 in Human NSCLC PDX Model (LC-F-25)

7.1 Methods

Animals: Outbred athymic (nu/nu) female mice (HSD: Athymic Nude-Foxn1nu), 5 weeks old at the time of arrival were acclimated for at least 4 days prior to inoculation. Animals were housed 3-5 mice per ventilated cage with sterilized food pellets and water bottle available ad lib. Animals were ear marked and weighed prior to study initiation.

Xenotransplantation: LC-F-25 was established as a growing tumor (P9.1.1/0) from a primary non-small cell lung adenocarcinoma from a human patient. LC-F-25 has lower MSLN expression in terms of percent positivity and overall intensity, based on immunohistochemistry (IHC) analysis, relative to other tumor types (such as, e.g., LXFA-737 (Example 8)).

Experimental procedure: Thirty one (31) mice with an established growing LC-F-25 tumor (P9.1.1/0) between 108 and 288 mm$^3$ were allocated to treatment when the mean and median tumor volume reached 153.5 and 126 mm$^3$, respectively.

Treatment: Efficacy was evaluated in 4 groups of 7 to 8 mice each:
In group 1, vehicle was dosed at 5 mL/kg, i.v., single dose on day 1.
In groups 2 and 3, eribulin was dosed respectively at 0.1 mg/kg (5 mL/kg) and 3.2 mg/kg (6.4 mL/kg), i.v., single dose on day 1.
In group 4, MORAb-109 was dosed at 10 mg/kg (5 mL/kg), i.v., single dose on day 1.

Tumors were measured and mice were weighed twice a week during the experimental period.

Statistical analysis: Statistical analysis was performed for each measurement by a Mann-Whitney non-parametric comparison test. Each treated group was compared with the control group.

7.2 Results

Figure 21A:
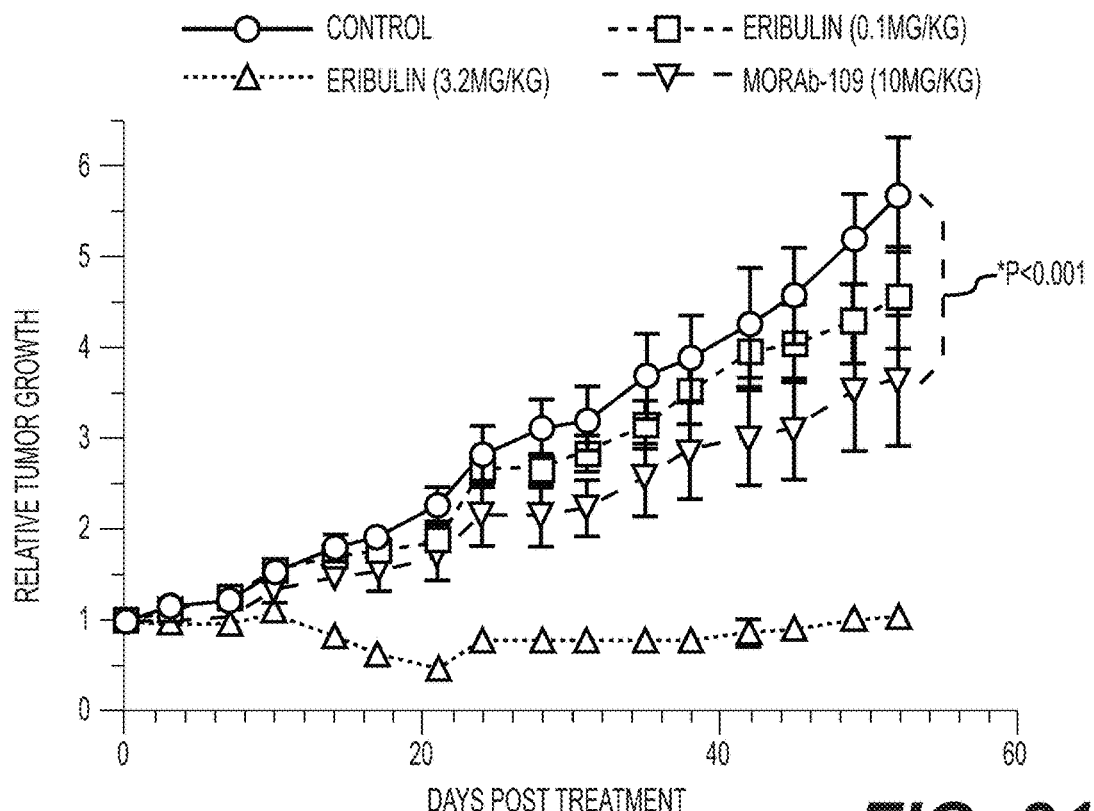
FIG. 21A and FIG. 21B show the anti-tumor effect (FIG. 21A) and body weight change (FIG. 21B) in a human NSCLC PDX model (LC-F-25) treated with MORAb-109 (DAR2) (10 mg/kg) or eribulin (0.1 or 3.2 mg/kg).
Figure 21B:
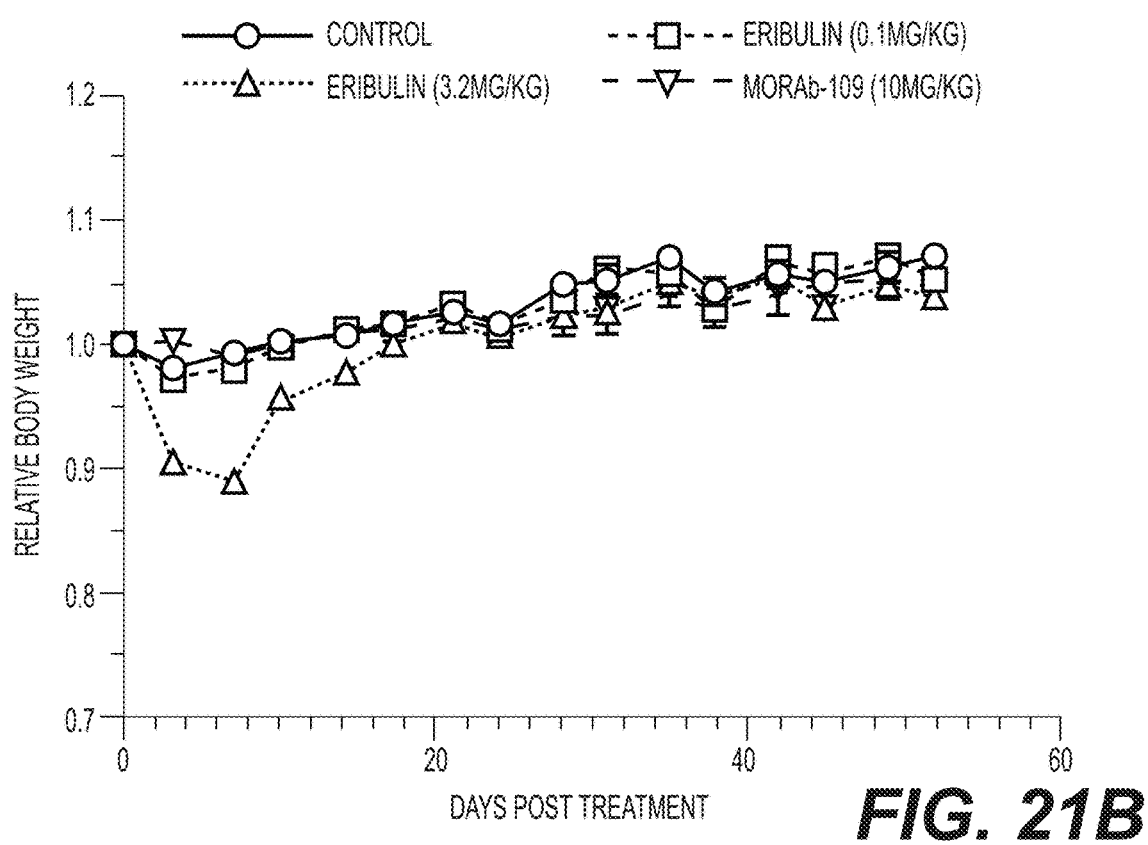

MORAb-109 (DAR2) given at a single dose of 10 mg/kg by intravenous route was well tolerated without bodyweight loss by LC-F-25 tumor-bearing mice (FIG. 21B). MORAb-109 (DAR2) demonstrated tumor growth delay at 10 mg/kg in the LC-F-25 NSCLC PDX model (FIG. 21A).

Eribulin given at a single dose of 0.1 mg/kg (the equivalent molar amount of payload in MORAb-109 when administered at 10 mg/kg) by intravenous route was well tolerated by LC-F-25 tumor-bearing mice but did not induce statistically significant tumor growth inhibition (FIG. 21A and FIG. 21B).

Eribulin given at a single dose of 3.2 mg/kg (mouse MTD dosage or 32 times higher than the molar amount of eribulin in MORAb-109 when administered at 10 mg/kg) by intravenous route was well tolerated by LC-F-25 tumor-bearing mice, but induced slight and transient bodyweight loss from 3 to 10 days after administration (FIG. 21B). At this dose, eribulin induced statistically significant tumor growth inhibition, with partial tumor regressions in 6 out of 8 mice (FIG. 21A).

Example 8: In Vivo Anti-Tumor Efficacy of MORAb-109 in Human NSCLC PDX Model (LXFA-737)

8.1 Methods

Animals: Female NMRI nu/nu mice (Crl:NMRI-Foxn1nu), 4 to 6 weeks of age.

Xenotransplantation: LXFA-737 was established as a growing tumor (P14N4) from a primary non-small cell lung adenocarcinoma from a human patient. LXFA-737 has moderate MSLN expression in terms of overall intensity and higher percent positivity, based on IHC analysis, relative to other tumor types (such as, e.g., LC-F-25 (Example 7)).

Experimental procedure: Animals were monitored until the tumor implants reached the study volume criteria of 50-250 mm$^3$ (e.g., 80-200 mm$^3$) in a sufficient number of animals. Mice were assigned to groups, aiming at comparable group median and mean tumor volumes. The day of randomization was designated as day 0.

Treatment: Efficacy was evaluated in 4 groups of 6 to 7 mice each:
In group 1, vehicle was dosed at 5 mL/kg, i.v., single dose on day 1.
In groups 2 and 3, eribulin was dosed respectively at 0.2 mg/kg and 3.2 mg/kg, i.v., single dose on day 1.
In group 4, MORAb-109 was dosed at 10 mg/kg, i.v., single dose on day 1.

Tumors were measured and mice were weighed twice a week during the experimental period. The first day of dosing was day 1, one day after randomization (day 0).

Statistical analysis: Inhibition of Tumor Growth, Test/Control Value in % (Min. T/C): The test versus control value (T/C in %) was calculated from the ratio of the median residual tumor volume (RTV) values of test versus control groups on day X multiplied by 100. Tumor volume doubling and quadrupling time (Td, Tq) for test and control groups was defined as the time interval (in days) required for a group to reach a median RTV of 200% or 400%.

8.2 Results

Figure 22A:
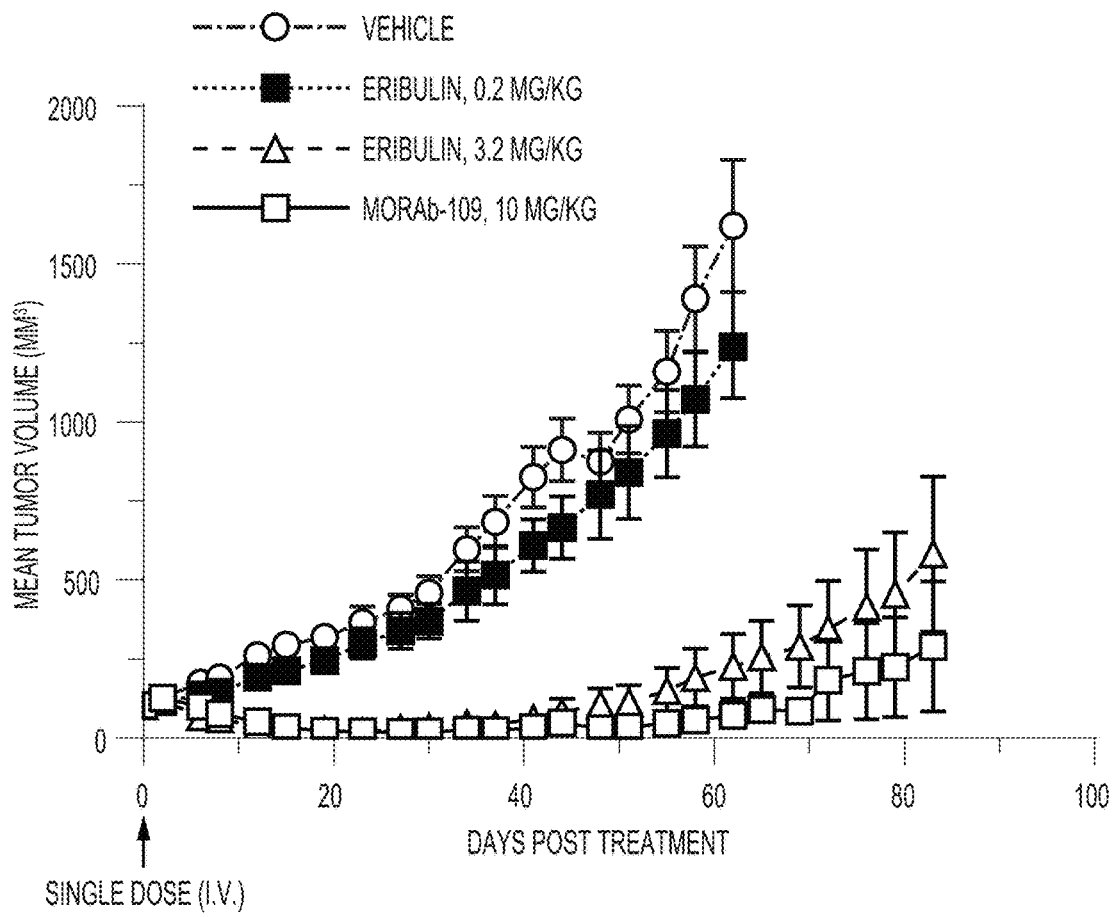
FIG. 22A and FIG. 22B show the anti-tumor effect (FIG. 22A) and body weight change (FIG. 22B) in a human NSCLC PDX model (LXFA-737) treated with MORAb-109 (DAR2) (10 mg/kg) or eribulin (0.2 or 3.2 mg/kg).
Figure 22B:
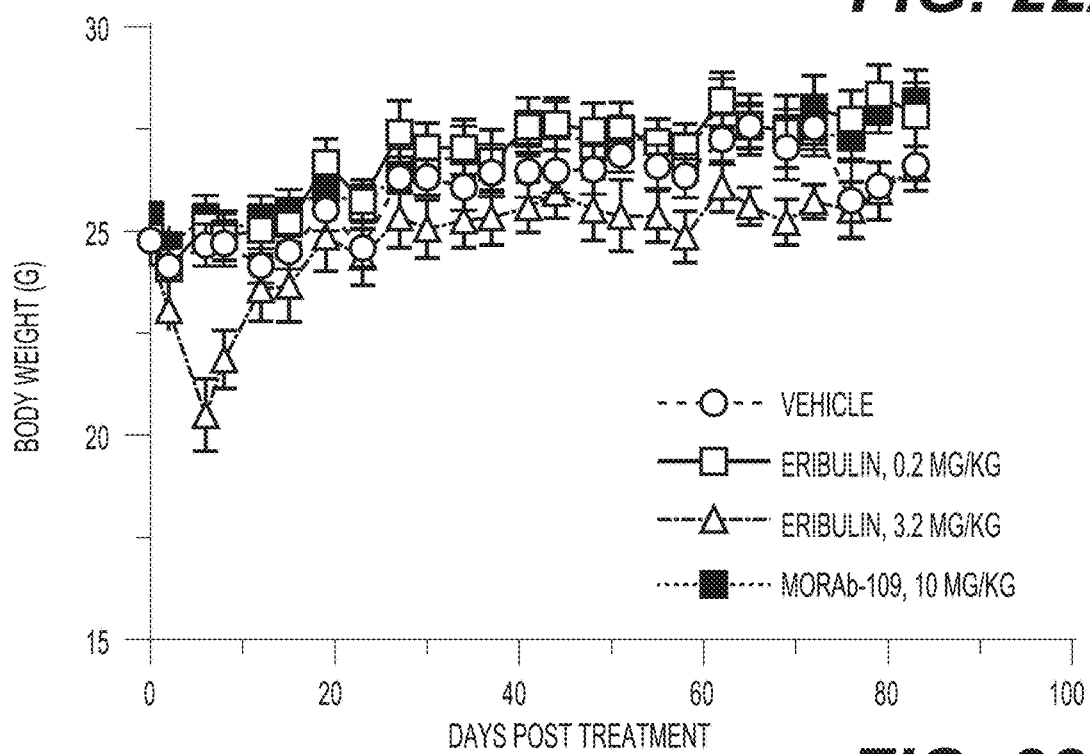

MORAb-109 (DAR2) demonstrated robust anti-tumor efficacy (minimum T/C, 2.3% on day 41) at 10 mg/kg in the LXFA-737 NSCLC PDX model (FIG. 22A) and its Tq was not reached during the study. MORAb-109 given at the single dose was also well tolerated without bodyweight loss by LXFA-737 tumor-bearing mice (FIG. 22B).

Eribulin given at a single dose of 3.2 mg/kg (mouse MTD dosage or 32 times higher than the molar amount of eribulin in MORAb-109 when administered at 10 mg/kg) by intravenous route was well tolerated by LXFA-737 tumor-bearing mice, showed anti-tumor efficacy (minimum T/C, 4.2% on day 27), and its Tq was 80.1%. However, eribulin induced slight and transient bodyweight loss after administration (FIG. 22A and FIG. 22B). A single dose of 0.2 mg/kg, double the molar amount of eribulin in MORAb-109 when administered at 10 mg/kg, showed limited anti-tumor efficacy (minimum T/C, 51.1% on day 44).

Example 9: Dose-Response of MORAb-109 in Human Gastric Cancer (NCI-N87) Xenograft Model 9.1 Methods
9.1.1 In Vivo Efficacy Animals: Female NCr nude mice (Taconic), 5 weeks old at the time of arrival were acclimated for 5-7 days prior to inoculation. Animals was housed 3-5 mice per ventilated cage with sterilized food pellets and water bottle available ad lib. Animals were ear tagged and weighed prior to study initiation.

Cell culture: Cryopreserved NCI-N87 cells were thawed and grown in medium containing necessary supplements. Cells were sub-cultured in complete medium for 2 passages before being used for in vivo inoculation.

Tumor implantation, enrollment process, and treatment: The cell suspension in PBS was mixed with ice-cold Matrigel at 1:1 (vol:vol) to a final concentration of $1.0 \times 10^8$ cells/mL. 100 µL/mouse of the mixture was injected subcutaneously. The mice were monitored for clinical well-being with body weights and tumors measurements by digital caliper, 3 times weekly, beginning on day 3 post-implantation.

Tumor measurement and treatment: Tumor volume (TV) ($mm^3$) was calculated using the formula: W (mm)×L (mm)×D (mm)×n/6. When the tumors reached around 100 $mm^3$ in an average, the animals were randomized to 5 per group. Treatment was given intravenously in a volume of 200 µL of test article. At the end of the study, the terminal body weight was measured and recorded.

Statistical analysis: Descriptive statistics were performed on the data of tumor volume and body weight. Tumor volumes of animals from each treatment group were compared with the control group by using the repeated-measures two-way ANOVA followed by the Bonferroni post-test. Additionally, the comparison of tumor growth of animals within each group was performed with the same statistical analysis.

9.1.2 Pharmacokinetics (PK)

PK analysis was performed using both an intact ADC assay and a total antibody assay. Total antibody refers to the sum total of all species, including conjugated and unconjugated species (i.e., DAR0+DAR1+DAR2+ . . . +DARn), whereas intact ADC refers to all conjugated species (i.e., DAR1+DAR2+ . . . +DARn). Total antibody assay used biotinylated mesothelin for capture and AlexaFluor647-labelled anti-human Fc for detection. Intact ADC assay used biotinylated anti-eribulin 5E4 for capture and AlexaFluor647-labelled anti-human Fc for detection. Sample analysis was performed on a Gyros analyzer. Data analysis was performed in WatsonLIMS 7.4.1 and plotted in Microsoft Excel. Eribulin was quantitated using LC-MS from plasma, tumor, and bone marrow samples.

9.1.3 LC-MS 20-50 µL of MORAb-109 (DAR2) plasma from individual mice or 50 µL of equally pooled plasma from MORAb-109 (DAR6)-dosed mice was used for analysis. Dynabeads M-280 streptavidin (100 µL) were incubated with 3 µg of capture select human IgG-Fc PK biotin conjugate for 1 hour at room temperature, then washed with HBS-EP buffer. Plasma samples diluted in HBS-EP buffer were then mixed with the complexed/washed beads for capture of MORAb-109 complexes, incubated for 1 hour at room temperature, then washed twice in HBS-EP buffer. Washed beads containing complex were deglycosylated with Rapid PNGaseF (1 µL) in PNGase buffer for 1 hour at 37° C., then washed once in HBS-EP buffer. Elution of captured/deglycosylated MORAb-109 was done with 10% acetonitrile w/0.1% formic acid (30 µL). Samples were analyzed for intact or reduced mass with Synapt G2/M-class UPLC analysis.

9.2 Results

Figure 23A:
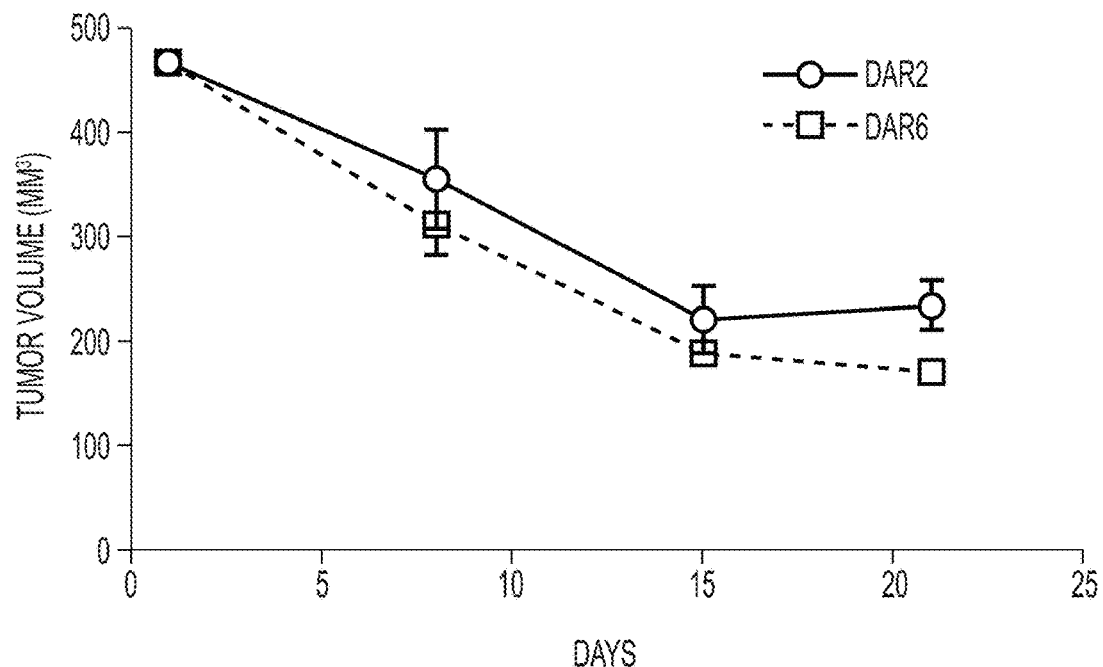
FIG. 23A and FIG. 23B show the anti-tumor effect (FIG. 23A) and body weight change (FIG. 23B) in a human gastric cancer NCI-N87 xenograft model treated with a single dose of MORAb-109 (DAR2 or DAR6) at 10 mg/kg (3 mice per group).
Figure 23B:
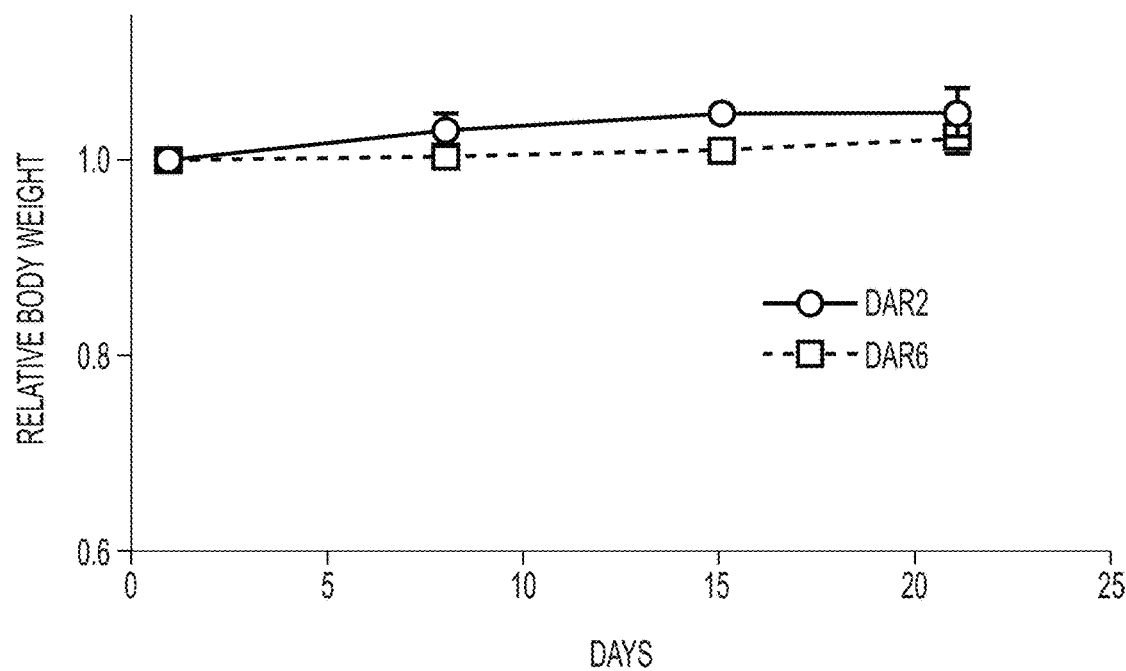
Figure 24A:
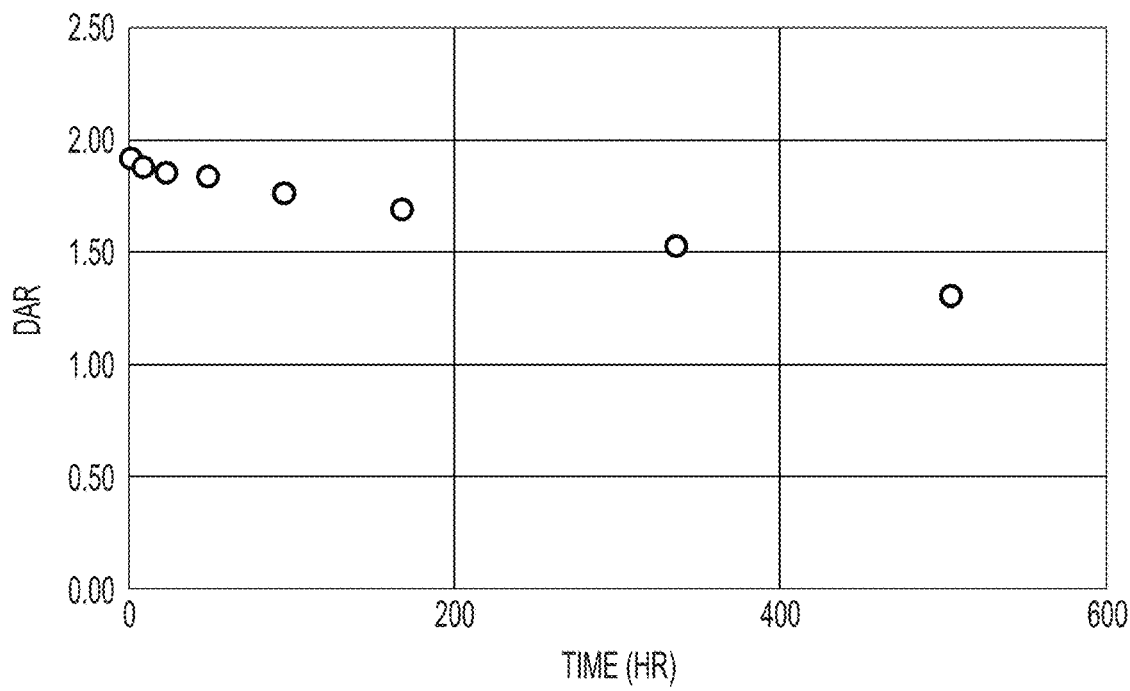
FIG. 24A and FIG. 24B show the DAR of MORAb-109 (DAR2) (FIG. 24A) or MORAb-109 (DAR6) (FIG. 24B) in plasma samples from NCI-N87 tumor-bearing mice after treatment with a single dose of MORAb-109 (DAR2 or DAR6) at 10 mg/kg.
Figure 24B:
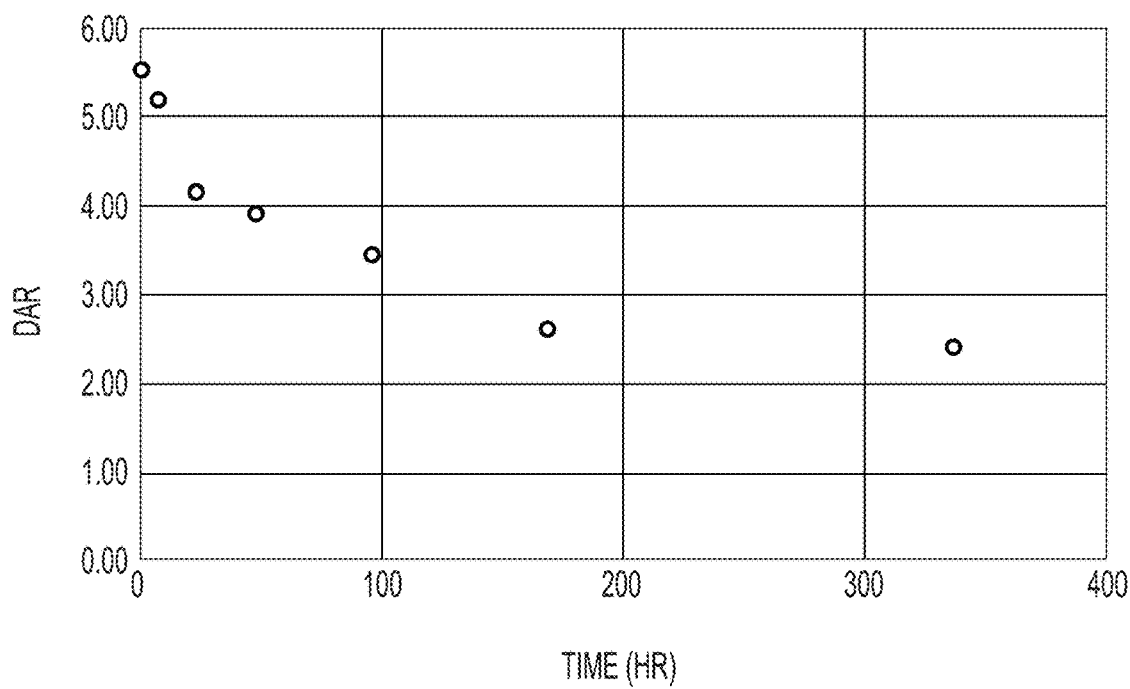

The anti-tumor effect and body weight change in a human gastric cancer NCI-N87 xenograft model treated with a single dose of MORAb-109 (DAR2 or DAR6) at 10 mg/kg are shown in FIG. 23A and FIG. 23B, respectively.

PK analysis of MORAb-109 (DAR2), MORAb-109 (DAR6), and unconjugated antibody is shown in Table 27. Total antibody for unconjugated and MORAb-109 (DAR2) was similar, while MORAb-109 (DAR6) was lower, indicating that MORAb-109 (DAR2) is stable in circulation.

DAR analysis of ADCs from plasma samples indicated that the payload release rate was higher for the DAR6 species and contributed to higher plasma levels of eribulin (Tables 28 and 29).

TABLE 27

PK profile of MORAb-109 (DAR2 and DAR6) in NCI-N87-tumor-bearing mice

| Parameters | Unit | ADC | Total Ab | Plasma ERI | Tumor ERI | Bone marrow ERI |
|---|---|---|---|---|---|---|
| DAR2 | | | | | | |
| $CL_{tot}$ | mL/hr/kg | 0.71 | N/A | N/A | N/A | N/A |
| $V_dss$ | mL/kg | 121 | N/A | N/A | N/A | N/A |
| $AUC_0$-inf | mg × hr/mL | 14.2 | 20.9 | 44.0 (ng × hr/mL) | 17.8 (µg × hr/mL) | 9.9 (µg × hr/mL) |
| $T_{max}$ | hr | N/A | 0.17 | 0.17 | 24 | 1 |
| $C_{max}$ | µg/mL | N/A | 137 | 0.65 (ng/mL) | 64 (ng/g) | 121 (ng/g) |
| $T_{1/2}$ | hr | 134 | 191 | 59 | 162 | 151 |
| DAR6 | | | | | | |
| $CL_{tot}$ | mL/hr/kg | 0.73 | N/A | N/A | N/A | N/A |
| $V_dss$ | mL/kg | 100 | N/A | N/A | N/A | N/A |
| $AUC_0$-inf | mg × hr/mL | 13.7 | 14.4 | 121 (ng × hr/mL) | 16.0 (µg × hr/mL) | 6.7 (µg × hr/mL) |
| $T_{max}$ | hr | N/A | 0.17 | 1 | 24 | 3 |
| $C_{max}$ | µg/mL | N/A | 148 | 2.6 (ng/mL) | 96 (ng/g) | 94 (ng/g) |
| $T_{1/2}$ | hr | 103 | 129 | 33 | 98 | 76 |

TABLE 27-continued

PK profile of MORAb-109 (DAR2 and DAR6) in NCI-N87-tumor-bearing mice

| Parameters | Unit | ADC | Total Ab | Plasma ERI | Tumor ERI | Bone marrow ERI |
|---|---|---|---|---|---|---|
| | | | Naked Ab | | | |
| $CL_{tot}$ | mL/hr/kg | | 0.54 | | | |
| $V_dss$ | mL/kg | | 126 | | | |
| $AUC_0$-inf | mg × hr/mL | | 18.5 | | | |
| $C_{max}$ | µg/mL | | 183 | | | |
| $T_{1/2}$ | hr | | 164 | | | |

TABLE 28

DAR of MORAb-109 (DAR2) in plasma

| Hours | 1 | 2 | 3 | Averaged DAR |
|---|---|---|---|---|
| 0.167 | 1.92 | 1.93 | 1.94 | 1.93 |
| 8 | 1.88 | 1.86 | 1.92 | 1.89 |
| 24 | 1.83 | 1.86 | 1.90 | 1.86 |
| 48 | 1.87 | 1.82 | 1.83 | 1.84 |
| 96 | 1.83 | 1.65 | 1.78 | 1.75 |
| 168 | 1.69 | 1.75 | 1.63 | 1.69 |
| 336 | 1.38 | 1.54 | 1.64 | 1.52 |
| 504 | 1.08 | 1.18 | 1.63 | 1.30 |

TABLE 29

DAR of MORAb-109 (DAR6) in plasma

| Time (hr) | L-chain | H-chain | Averaged DAR |
|---|---|---|---|
| 0.167 | 1.52 | 1.23 | 5.52 |
| 8 | 1.46 | 1.13 | 5.18 |
| 24 | 1.26 | 0.81 | 4.15 |
| 48 | 1.25 | 0.71 | 3.91 |
| 96 | 1.27 | 0.44 | 3.42 |
| 168 | 0.93 | 0.38 | 2.61 |
| 336 | 0.86 | 0.35 | 2.41 |
| 504 | N.D. | N.D. | N.A. |

Example 10: Comparison of 345A12 HC15 LC4 with Anetumab—Binding Affinity 10.1 Methods Antibodies: 345A12 HC15 LC4 (the anti-mesothelin antibody in MORAb-109) and anetumab. Sequences for anetumab, a human anti-mesothelin antibody, are set forth in Table 30.

Binding affinity: Binding measurements were performed in HBS-P+ buffer on a BIAcore T-100 instrument. Antibodies were diluted to 1 µg/mL in HBS-P+. Samples were centrifuged at 14,000×g for 5 min at room temperature and then supernatants were transferred to a new 1.5 mL BIAcore tube and capped. Mesothelin (50 µg) was diluted to 100 nM in 1×HBS-P+ buffer, then serial diluted 5-fold at 100, 20, 4, 0.8, and 0.16 nM in BIAcore tubes and capped. Anti-human antibody capture chip was prepared according to the manufacturer's protocol using a CM5 chip with immobilization wizard. Final capture antibody levels were 8000-9000RU, in HBS-P+. Chip was prepared for assay with five cycles of 300 sec buffer injection followed by 30 sec regeneration, all at 304/min across all four flow cells.

Antibodies were captured on flow cells 2-4 by sequential injections of individual ligand solutions for 90 sec at 10 µL/min. Analyte injection was done in a single-cycle kinetics manner by sequential injections of analyte solutions from low to high concentration for 240 sec each at 30 µL/min. Detection was 2-1, 3-1, 4-1. Double-referencing was performed by a sequence of identical ligand capture injections, followed by 5 buffer-only injections for 240 sec each, dissociation for 1800 sec, and regeneration as above. All ligands were analyzed for binding to mesothelin in duplicate. Kinetic analysis was performed using BIAEvaluations software using a 1:1 Langmuir fitting model. On-rate, off-rate, and affinity constants were averaged from duplicate runs.

10.2 Results

345A12 HC15 LC4 exhibited 40-fold higher affinity than anetumab (Table 31). 345A12 HC15 LC4 retained binding affinity to cynomolgus monkey mesothelin, while anetumab did not bind cynomolgus monkey mesothelin. Nether antibody bound rat mesothelin.

TABLE 30

Anetumab sequences

| IgG chain | NA/AA | SEQ ID | Sequence |
|---|---|---|---|
| Heavy chain | Amino acid | 51 | QVELVQSGAEVKKPGESLKISCKGSGYSFT SYWIGWVRQAPGKGLEWMGIIDPGDSRTRY SPSFQGQVTISADKSISTAYLQWSSLKASD TAMYYCARGQLYGGTYMDGWGQGTLVTVSS ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSRDE LTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| | Nucleic acid | 52 | CAGGTTGAACTGGTTCAGTCTGGCGCCGAA GTGAAGAAGCCTGGCGAGAGCCTGAAGATC AGCTGCAAAGGCAGCGGCTACAGCTTCACC AGCTATTGGATCGGCTGGGTTCGACAGGCC CCTGGCAAAGGACTGGAATGGATGGGAATC ATCGACCCCGGCGACAGCAGAACCAGATAC AGCCCTAGCTTTCAGGGCCAAGTGACCATC AGCGCCGACAAGAGCATCAGCACAGCCTAC CTGCAGTGGTCTAGCCTGAAAGCCAGCGAC ACCGCCATGTACTATTGTGCCAGAGGCCAG CTGTACGGCGGCACCTATATGGATGGATGG GGCCAGGGCACACTGGTCACAGTGTCTAGC GCCTCTACAAAGGGCCCTAGCGTTTTCCCA CTGGCTCCTAGCAGCAAGAGCACATCTGGT GGAACAGCCGCTCTGGGCTGCCTGGTCAAG GATTACTTTCCTGAGCCTGTGACCGTGTCC TGGAATAGCGGAGCACTGACAAGCGGCGTG CACACATTTCCAGCTGTGCTGCAGAGCAGC GGCCTGTACTCTCTGTCTAGCGTCGTGACA |

TABLE 30-continued

Anetumab sequences

| IgG chain | NA/AA | SEQ ID | Sequence |
|---|---|---|---|
| | | | GTGCCTAGCAGCTCTCTGGGCACCCAGACC
TACATCTGCAACGTGAACCACAAGCCTAGC
AACACCAAGGTGGACAAGAAGGTGGAACCC
AAGAGCTGCGACAAGACCCACACCTGTCCT
CCATGTCCTGCTCCAGAACTGCTCGGCGGA
CCCTCCGTTTTCCTGTTTCCACCTAAGCCT
AAGGACACCCTGATGATCAGCAGGACCCCT
GAAGTGACCTGTGTGGTGGTGGATGTGTCC
CACGAGGACCCAGAAGTGAAGTTCAATTGG
TACGTGGACGGCGTGGAAGTGCACAACGCC
AAGACCAAGCCTAGAGAGGAACAGTACAAC
AGCACCTACAGAGTGGTGTCCGTGCTGACC
GTGCTGCACCAGGATTGGCTGAACGGCAAA
GAGTACAAGTGCAAGGTGTCCAACAAGGCC
CTGCCTGCTCCTATCGAGAAAACCATCAGC
AAGGCCAAGGGCCAGCCAAGAGAACCCAG
GTTTACACACTGCCTCCAAGCAGGGACGAG
CTGACCAAGAATCAGGTGTCCCTGACCTGC
CTCGTGAAGGGCTTCTACCCTTCCGATATC
GCCGTGGAATGGGAGAGCAATGGCCAGCCT
GAGAACAACTACAAGACAACCCCTCCTGTG
CTGGACAGCGACGGCTCATTCTTCCTGTAC
AGCAAGCTGACAGTGGACAAGTCCAGATGG
CAGCAGGGCAACGTGTTCAGCTGTTCTGTG
ATGCACGAGGCCCTGCACAACCACTACACC
CAGAAAAGCCTGTCTCTGAGCCCCGGCAAA |
| Light chain | Amino acid | 53 | DIALTQPASVSGSPGQSITISCTGTSSDIG
GYNSVSWYQQHPGKAPKLMIYGVNNRPSGV
SNRFSGSKSGNTASLTISGLQAEDEADYYC
SSYDIESATPVFGGGTKLTVLGQPKAAPSV
TLFPPSSEELQANKATLVCLISDFYPGAVT
VAWKGDSSPVKAGVETTTPSKQSNNKYAAS
SYLSLTPEQWKSHRSYSCQVTHEGSTVEKT
VAPTECS |
| | Nucleic acid | 54 | GATATTGCTCTGACACAGCCTGCCAGCGTG
TCCGGATCTCCTGGCCAGAGCATCACAATC
AGCTGTACCGGCACAAGCAGCGACATCGGC
GGCTACAATAGCGTGTCCTGGTATCAGCAG
CACCCCGGAAAGGCCCCTAAGCTGATGATC
TACGGCGTGAACAACAGACCCAGCGGCGTG
TCCAATAGATTCAGCGGCAGCAAGAGCGGC
AATACCGCCTCTCTGACAATTAGCGGACTG
CAGGCCGAGGACGAGGCCGATTACTACTGC
AGCAGCTACGACATCGAGAGCGCCACACCT
GTGTTTGGCGGCGGAACAAAACTGACAGTG
CTGGGCCAACCTAAGGCCGCTCCTAGCGTT
ACACTGTTCCCACCTAGCAGCGAGGAACTG
CAGGCTAACAAGGCCACACTCGTGTGCCTG
ATCAGCGATTTTTACCCTGGCGCCGTGACA
GTGGCCTGGAAAGGCGATAGTTCTCCTGTG
AAGGCCGGCGTGGAAACCACCACACCTAGC
AAGCAGAGCAACAACAAATACGCCGCCAGC
TCCTACCTGAGCCTGACACCTGAGCAGTGG
AAGTCCCACAGATCCTACAGCTGCCAAGTG
ACCCACGAGGGCAGCACCGTGGAAAAAACA
GTGGCCCCTACCGAGTGCAGC |

TABLE 31

Binding of 345A12 HC15 LC4 and anetumab to human, cynomologus monkey, and rat mesothelin

| | | $k_a$ (M$^{-1}$sec$^{-1}$) | $k_d$ (sec$^{-1}$) | $K_D$ (M) |
|---|---|---|---|---|
| human | 345A12 HC15 LC4 | 1.46 ± 0.05 × 10$^6$ | 2.85 ± 0.14 × 10$^{-4}$ | 1.95 ± 0.16 × 10$^{-10}$ |
| | anetumab | 1.68 ± 0.64 × 10$^5$ | 1.12 ± 1.00 × 10$^{-3}$ | 7.26 ± 2.29 × 10$^{-9}$ |
| cynomolgus | 345A12 HC15 LC4 | 1.05 ± 1.15 × 10$^4$ | 7.51 ± 5.76 × 10$^{-4}$ | 8.86 ± 5.16 × 10$^{-8}$ |
| | anetumab | no binding | no binding | no binding |
| rat | 345A12 HC15 LC4 | no binding | no binding | no binding |
| | anetumab | no binding | no binding | no binding |

Example 11: Comparison of MORAb-109 with BAY 94-9343—In Vitro Potency 11.1 Methods ADCs: MORAb-109 (DAR2 and DAR6) and anetumab ravtansine (BAY 94-9343) were evaluated. Anetumab ravtansine, also referred to as BAY 94-9343, is an ADC comprising anetumab conjugated to the maytansinoid tubulin inhibitor DM4 via a disulfide-containing linker (a reducible SPDB linker [N-succinimidyl 4-(2-pyridyldithio)butanoate]). BAY 94-9343 was generated as described in Example 15.

Cytotoxicity: Cells were sub-cultured and seeded at 5,000 cells/well in complete growth medium in 96-well tissue culture plates, and incubated at 37° C., 5% CO$_2$ overnight (16 hours). Test reagents were serially diluted 1:3 in 2 mL deep-well dilution plates, starting at 200 nM (10 dilutions total). Diluted samples (100 µL) were added to the cell plates (starting concentration of test samples at 100 nM). Plates were incubated at 37° C., 5% CO$_2$ for an additional 5 days. Medium was then discarded, and plates were washed once with 200 µL DPBS, stained with 50 µL of 0.2% Crystal Violet solution at room temperature for 15 min, and then washed extensively with tap water. Plates were air-dried, and Crystal Violet was dissolved with 200 µL of 1% SDS solution. Plates were read at 570 nm. Data was analyzed for IC$_{50}$ determination using GraphPad Prism 6.

11.2 Results

MORAb-109 (DAR2 and DAR6) showed specific cytotoxicity on MSLN-positive cell lines (Table 32). BAY 94-9343, in contrast, demonstrated killing on both MSLN-positive and MSLN-negative cell lines.

TABLE 32

Comparison of in vitro activity on MSLN+ and MSLN− cell lines

| | OVCAR3-A1 | NCI-H1568/MSLN | NCI-H292 | BxPC3 | A431 | SKOV3 |
|---|---|---|---|---|---|---|
| | In vitro cell based potency, IC50, nM | | | | | |
| MORAb109_DAR2 | 0.01 | 2.17 | >300 | 86.24 | 109.30 | 213.80 |
| MORAb109_DAR6 | 0.02 | 1.09 | 4.80 | 2.66 | 20.12 | 21.77 |
| Eribulin | 0.02 | 0.14 | 0.11 | 0.13 | 0.18 | 0.14 |
| BAY 94-9343 | 0.41 | 0.15 | 3.07 | 2.53 | 5.31 | 0.81 |
| DM4 | 0.10 | 0.57 | 0.24 | 0.57 | 0.71 | 0.28 |
| anetumab | >100 | >100 | >300 | >300 | >300 | >300 |
| | % Max Killing | | | | | |
| MORAb109_DAR2 | 98.39 | 73.49 | 56.22 | 90.62 | 84.97 | 58.41 |
| MORAb109_DAR6 | 98.47 | 77.89 | 75.34 | 94.63 | 90.76 | 72.79 |
| Eribulin | 99.31 | 74.39 | 85.37 | 97.28 | 93.04 | 72.82 |
| BAY 94-9343 | 100.00 | 75.10 | 64.15 | 97.33 | 96.82 | 74.99 |
| DM4 | 100.00 | 77.49 | 92.40 | 97.98 | 92.52 | 81.89 |
| anetumab | 19.80 | 5.50 | 15.15 | 25.73 | 18.58 | 31.55 |
| MSLN expression (MFI) | 220.0 | 4474.00 | 108.6 | 15.59 | 5.6 | 20 |

Example 12: Comparison of MORAb-109 with BAY 94-9343—Specificity

12.1 Methods

Cytotoxicity: Cells were sub-cultured and seeded at 5,000 cells/well in complete growth medium in 96-well tissue culture plates, and incubated at 37° C., 5% $CO_2$ overnight (16 hours). Test reagents were serially diluted 1:3 in 2 mL deep-well dilution plates, starting at 200 nM (10 dilutions total). Diluted samples (100 μL) were added to the cell plates (starting concentration of test samples at 100 nM). Plates were incubated at 37° C., 5% $CO_2$ for an additional 5 days. Medium was then discarded, and plates were washed once with 200 μL DPBS, stained with 50 μL of 0.2% Crystal Violet solution at room temperature for 15 min, and then washed extensively with tap water. Plates were air-dried, and Crystal Violet was dissolved with 200 μL of 1% SDS solution. Plates were read at 570 nm. Data was analyzed for $IC_{50}$ determination using GraphPad Prism 6.

12.2 Results

Figure 25B:
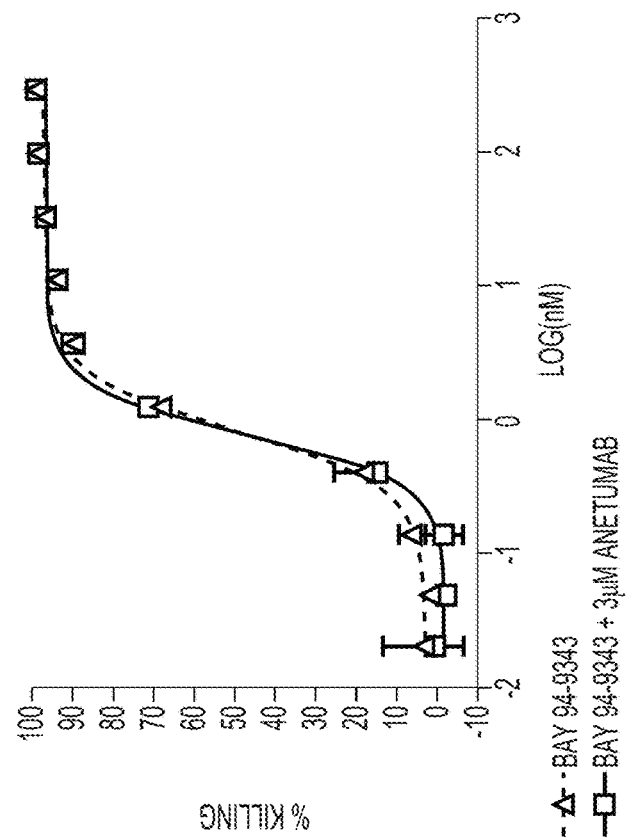
FIG. 25A and FIG. 25B show the cytotoxicity (% killing) of MORAb-109 (DAR2) (FIG. 25A) or BAY 94-9343 (FIG. 25B) on NCI-N87 gastric cancer cells. Both anti-MSLN ADCs were evaluated alone and in the presence of unconjugated antibody.
Figure 25A:
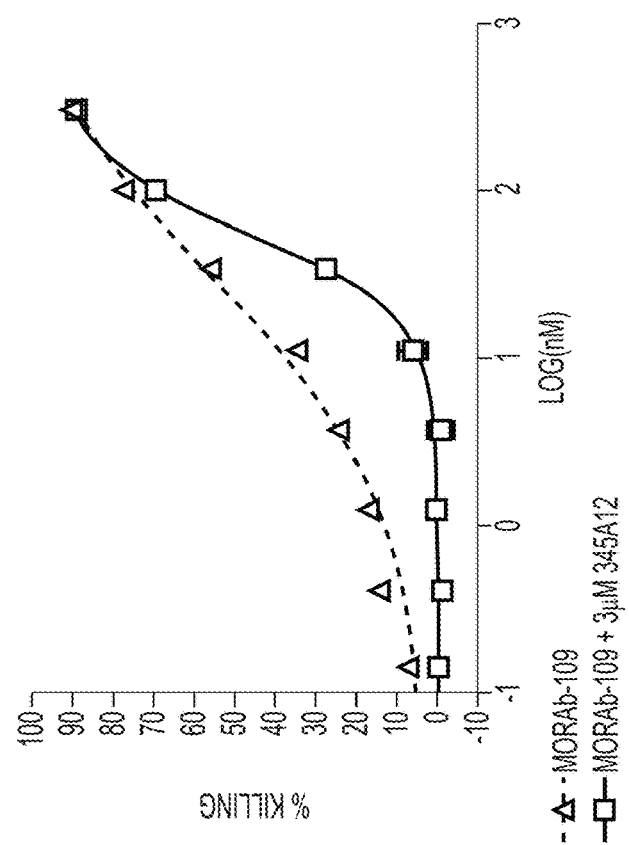

Cytotoxicity assays with unconjugated antibody demonstrated specific killing of mesothelin-expressing cells by MORAb-109 (DAR2) (FIG. 25A), but not BAY 94-9343 (FIG. 25B). Without being bound by theory, the lack of competition by unconjugated antibody observed for BAY 94-9343 suggests release of payload, which can lead to killing even when antibody binding is blocked by an unconjugated competitor. This payload release is consistent with the relatively high levels of cytotoxicity observed for BAY 94-9343 on mesothelin-negative cell lines (Table 32). Payload release is also directly observed in FIG. 27 (plasma stability comparison).

Example 13: Comparison of MORAb-109 with BAY 94-9343—ADCC Activity

13.1 Methods

MSLN-expressing CHO cells were thawed and seeded 1,000 cells/well (25 μL) in 96-well tissue culture plates in complete RPMI-4% Ultralow IgG FBS. Test reagents (345A12 antibody, MORAb-109 (DAR2), and BAY 94-9343) were 1:2.5 serial diluted starting from 20 μg/mL in complete RPMI-4% ultra-low IgG FBS, then transferred (25 μL) to the cell plate, and incubated at 37° C., 5% $CO_2$ for 60 min. 6,000 Jurkat-Effector cells (Promega) were thawed and added (25 μL) to the cell plate, and the plate was incubated at 37° C., 5% $CO_2$ for 18-22 hours.

Luciferase assay reagent was thawed in the dark. 75 μL of luciferase assay reagent was added to each well, plates were shaken for 30 sec on a plate shaker. Plates were read on a luminometer after 5 min incubation.

13.2 Results

Figure 26B:
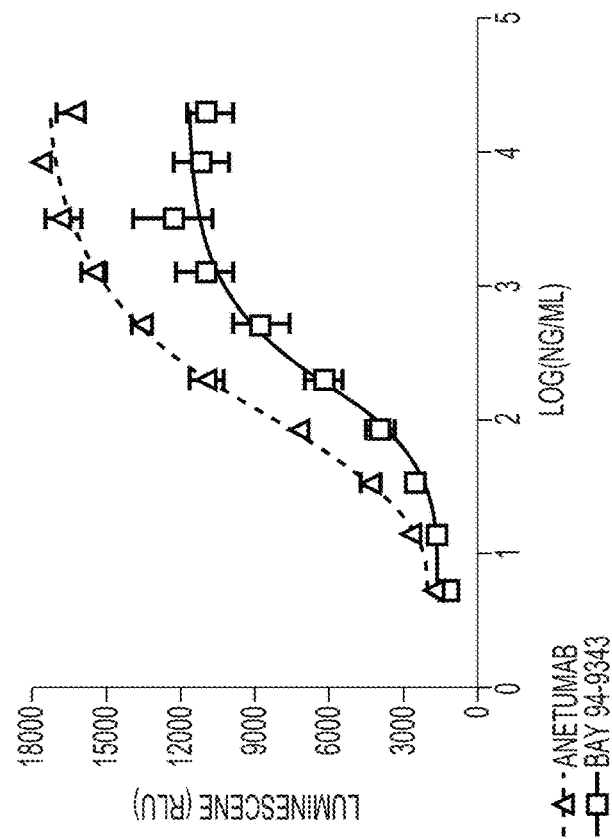
FIG. 26A and FIG. 26B show the ADCC activity of MORAb-109 (DAR2) and 345A12-HC15-LC4 (FIG. 26A) or BAY 94-9343 and anetumab (FIG. 26B), as measured by a luciferase assay. ADCC activity was calculated by relative area under the curve (AUC).
Figure 26A:
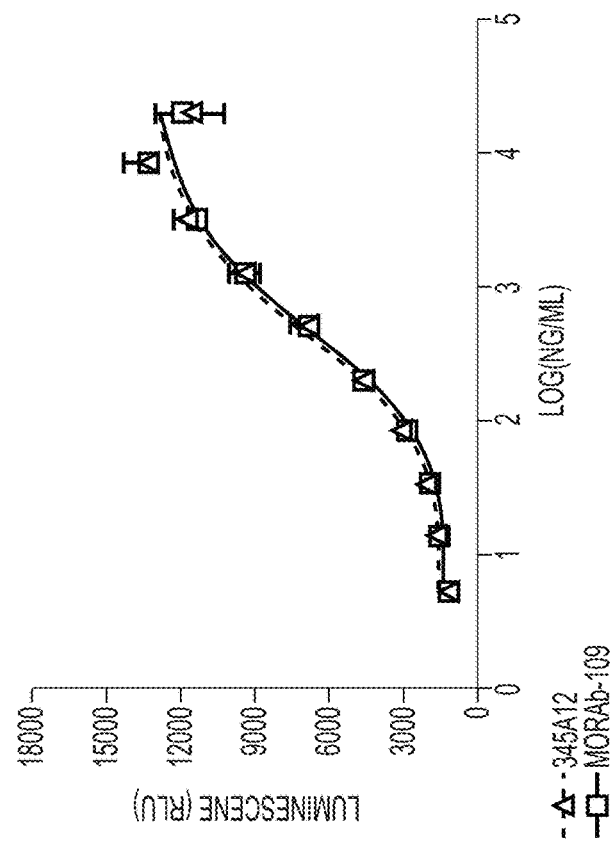

MORAb-109 (DAR2) and 345A12 HC15 LC4 had similar ADCC activity (FIG. 26A and Table 33), while BAY 94-9343 had weaker ADCC activity than anetumab (FIG. 26B and Table 34).

TABLE 33

ADCC activity - MORAb-109 and 345A12 HC15 LC4

| 345A12 | MORAb-109 |
|---|---|
| 100% | 96.9% |

TABLE 34

ADCC activity - BAY 94-9343 and anetumab

| anetumab | BAY 94-9343 |
|---|---|
| 100% | 65.06% |

Example 14: Stability of MORAb-109 and BAY 94-9343 in Matrix

14.1 Methods

Anti-MSLN ADCs were prepared at 0.1 mg/mL either in human or mouse plasma, the samples were incubated at 37° C. for 0, 24, 48, 72, 96 and 240 hours, then transferred to −80° C. for storage when timepoints were achieved. All samples were thawed to ambient temperature and diluted 1:100 for testing. A DAR-sensitive stability assay was developed as stepwise sandwich format on Gyrolab. Assay used biotinylated mesothelin for capture after blocking and sample binding, and Alexa Fluor 647 anti-eribulin 5E4 Fab or Alexa Fluor 647 anti-DM4 (Levena Biopharma) for detection. Standard curve and quality controls were made with MORAb-109 and BAY 94-9343.

14.2 Results

Figure 27:
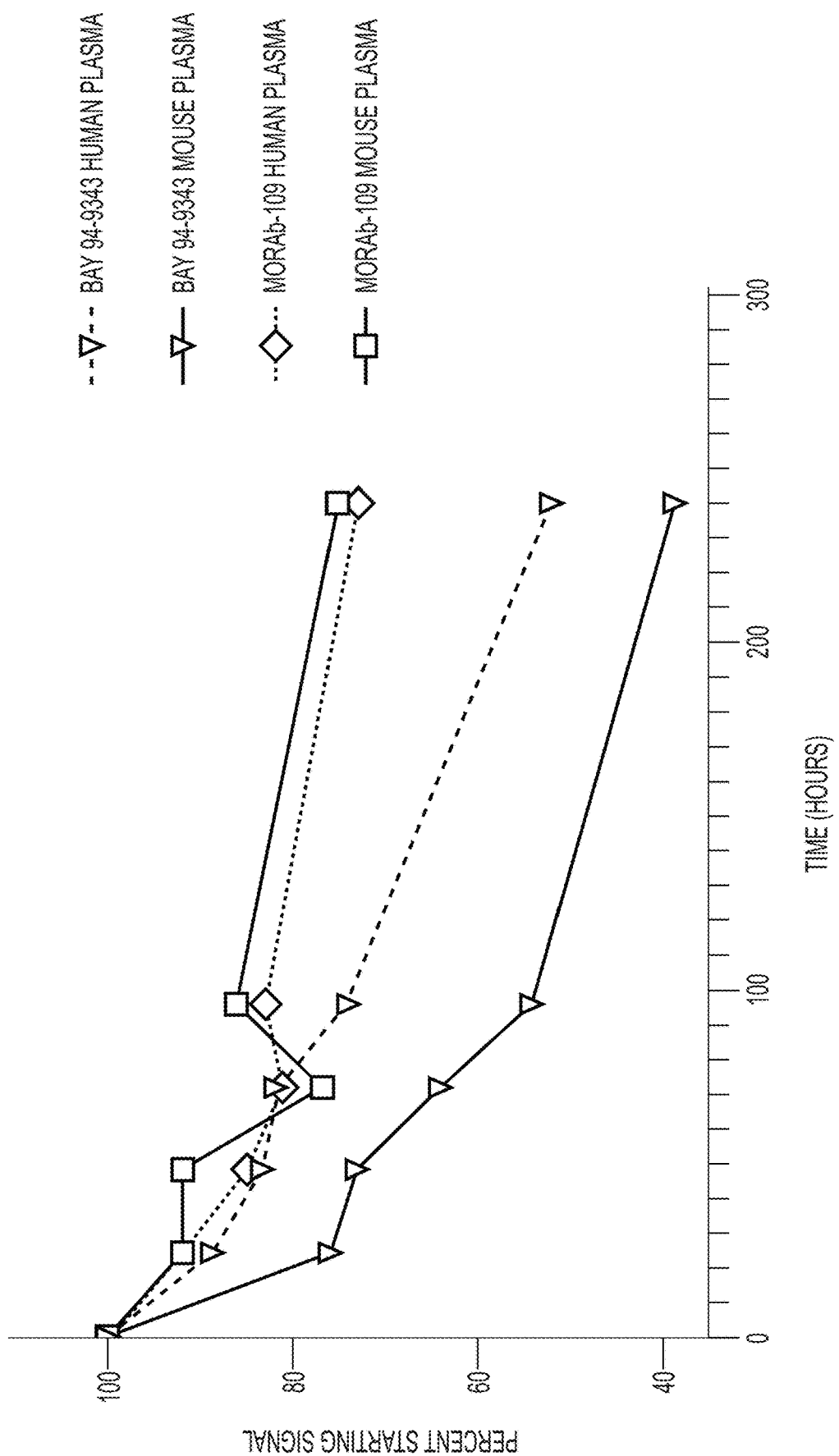
FIG. 27 shows a stability analysis of anti-MSLN ADCs, MORAb-109 (DAR2) and BAY 94-9343, in mouse and human plasma.

MORAb-109 (DAR2) was more stable than BAY 94-9343 in both human and mouse plasma (FIG. 27).

Example 15: Anti-Tumor Efficacy of MORAb-109 and BAY 94-9343 in Human Gastric Cancer (NCI-N87) Xenograft Model 15.1 Methods
15.1.1 Generation of BAY 94-9343

BAY 94-9343 is an ADC comprising anetumab conjugated to the maytansinoid tubulin inhibitor DM4 via a disulfide-containing linker (a reducible SPDB linker [N-succinimidyl 4-(2-pyridyldithio)butanoate]). Sequences from anetumab were obtained from Beacon database (Hanson-Wade). Antibody sequences (Table 30) were generated from overlapping oligonucleotides, PCR-amplified, cloned into expression plasmids, and sequence-confirmed. Stable pools were generated in 293F cells and cells were grown until viability <30%. Anetumab was purified from conditioned medium using protein A affinity chromatography. BAY 94-9343 was generated by lysine-reactive conjugation with SPDB-DM4 (Levena BioPharma) to achieve a DAR of 3.7. Unconjugated payload was removed by desalting chromatography.

15.1.2 In Vivo Efficacy

Animals: Female NCr nude mice (Taconic), 5 weeks old at the time of arrival were acclimated for 5-7 days prior to inoculation. Animals was housed 3-5 mice per ventilated cage with sterilized food pellets and water bottle available ad lib. Animals were ear tagged and weighed prior to study initiation.

Cell culture: Cryopreserved NCI-N87 cells were thawed and grown in medium containing necessary supplements. Cells were sub-cultured in complete medium for 2 passages before being used for in vivo inoculation.

Tumor implantation, enrollment process, and treatment: The cell suspension in PBS were mixed with ice-cold Matrigel at 1:1 (vol:vol) to a final concentration of $1.0 \times 10^8$ cells/mL. 100 μL/mouse of the mixture was injected subcutaneously. The mice were monitored for clinical well-being with body weights and tumors measurements by digital caliper, 3 times weekly, beginning on day 3 post-implantation.

Tumor measurement and treatment: Tumor volume (TV) ($mm^3$) was calculated using the formula: W (mm)×L (mm)×D (mm)×n/6. When the tumors reached around 100 $mm^3$ in an average, the animals were randomized to 5 per group. Treatment was given intravenously in a volume of 200 μL of test article. At the end of the study, the terminal body weight was measured and recorded.

Statistical analysis: Descriptive statistics were performed on the data of tumor volume and body weight. Tumor volumes of animals from each treatment group were compared with the control group by using the repeated-measures two-way ANOVA followed by the Bonferroni post-test. Additionally, the comparison of tumor growth of animals within each group was performed with the same statistical analysis.

15.2 Results

Figure 28A:
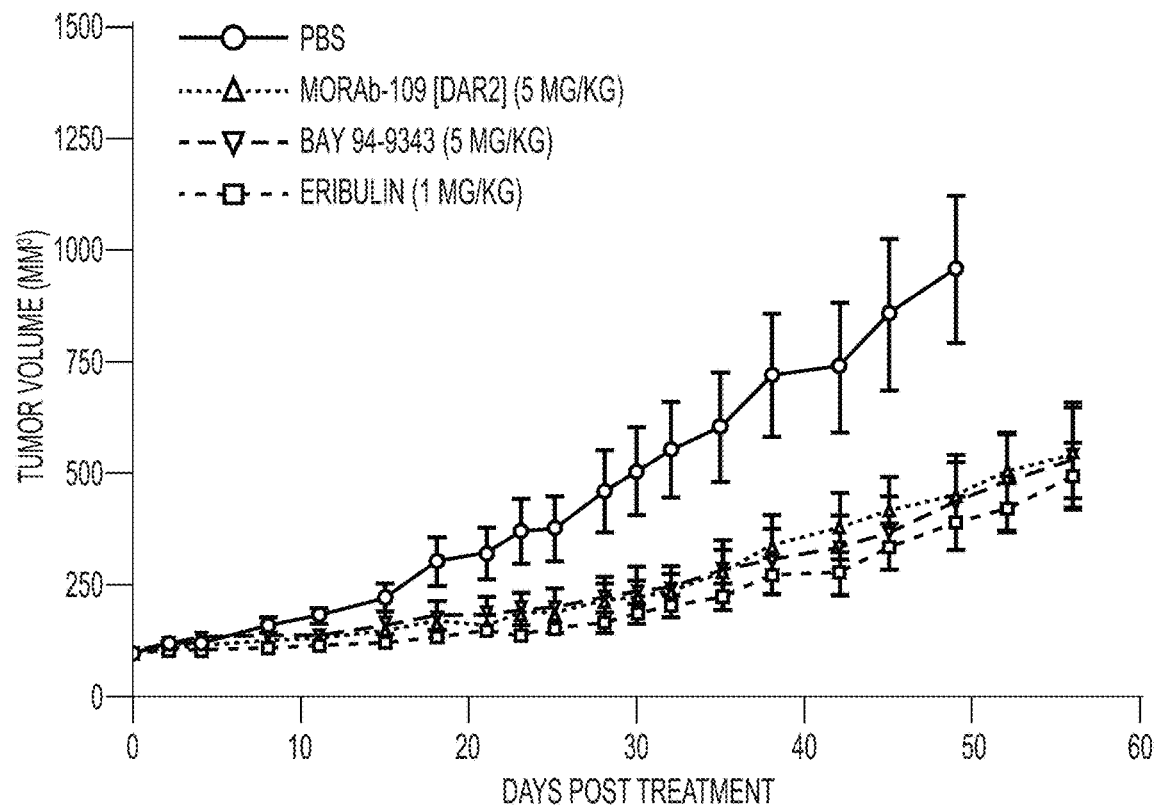
FIG. 28A and FIG. 28B show the anti-tumor effect (FIG. 28A) and body weight change (FIG. 28B) in a human gastric cancer NCI-N87 xenograft model treated with MORAb-109 (DAR2) (5 mg/kg), BAY 94-9343 (5 mg/kg), or eribulin (1 mg/kg).
Figure 28B:
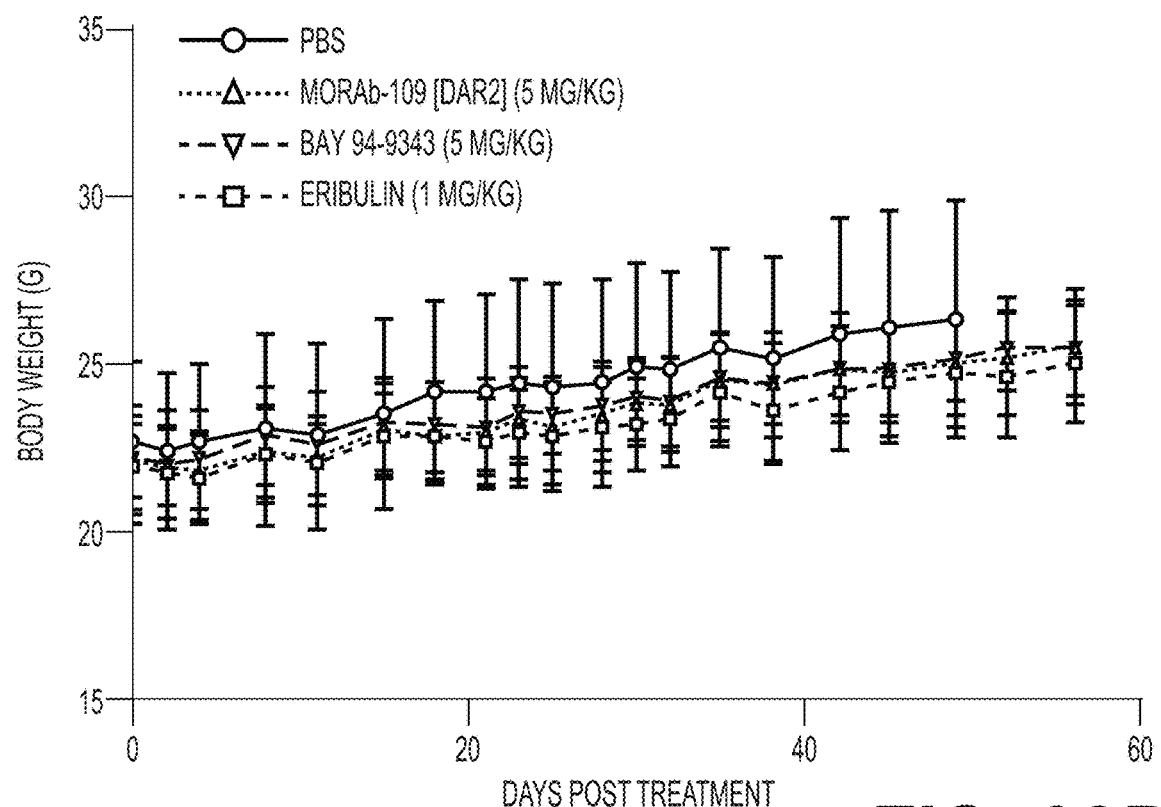

MORAb-109 (DAR2) and BAY 94-9343 both demonstrated similar efficacy in NCI-N87 tumor-bearing mice (FIG. 28A). No body weight loss was observed in either group (FIG. 28B).

Example 16: Anti-Tumor Efficacy of MORAb-109 and BAY 94-9343 in Human Mesothelioma (HAY) Xenograft Model 16.1 Methods Animals: Female NOD.CB17-SCID mice (Jackson Laboratory), 5 weeks old at the time of arrival were acclimated for 5-7 days prior to inoculation. Animals was housed 3-5 mice per ventilated cage with sterilized food pellets and water bottle available ad lib. Animals were ear tagged and weighed prior to study initiation.

Cell culture: Cryopreserved HAY cells were thawed and grown in medium containing necessary supplements. Cells were sub-cultured in complete medium for 2 passages before being used for in vivo inoculation.

Tumor implantation, enrollment process, and treatment: The cell suspension in PBS were mixed with ice-cold Matrigel at 1:1 (vol:vol) to a final concentration of $5.0 \times 10^7$ cells/mL. 100 μL/mouse of the mixture was injected subcutaneously. The mice were monitored for clinical well-being with body weights and tumors measurements by digital caliper, 3 times weekly, beginning on day 3 post-implantation.

Tumor measurement and treatment: Tumor volume (TV) ($mm^3$) was calculated using the formula: W (mm)×L (mm)×D (mm)×n/6. When the tumors reached around 100 $mm^3$ in an average, the animals were randomized to 5 per group. Treatment was given intravenously in a volume of 200 μL of test article. At the end of the study, the terminal body weight was measured and recorded.

Statistical analysis: Descriptive statistics were performed on the data of tumor volume and body weight. Tumor volumes of animals from each treatment group were compared with the control group by using the repeated-measures two-way ANOVA followed by the Bonferroni post-test. Additionally, the comparison of tumor growth of animals within each group was performed with the same statistical analysis.

16.2 Results

Figure 29A:
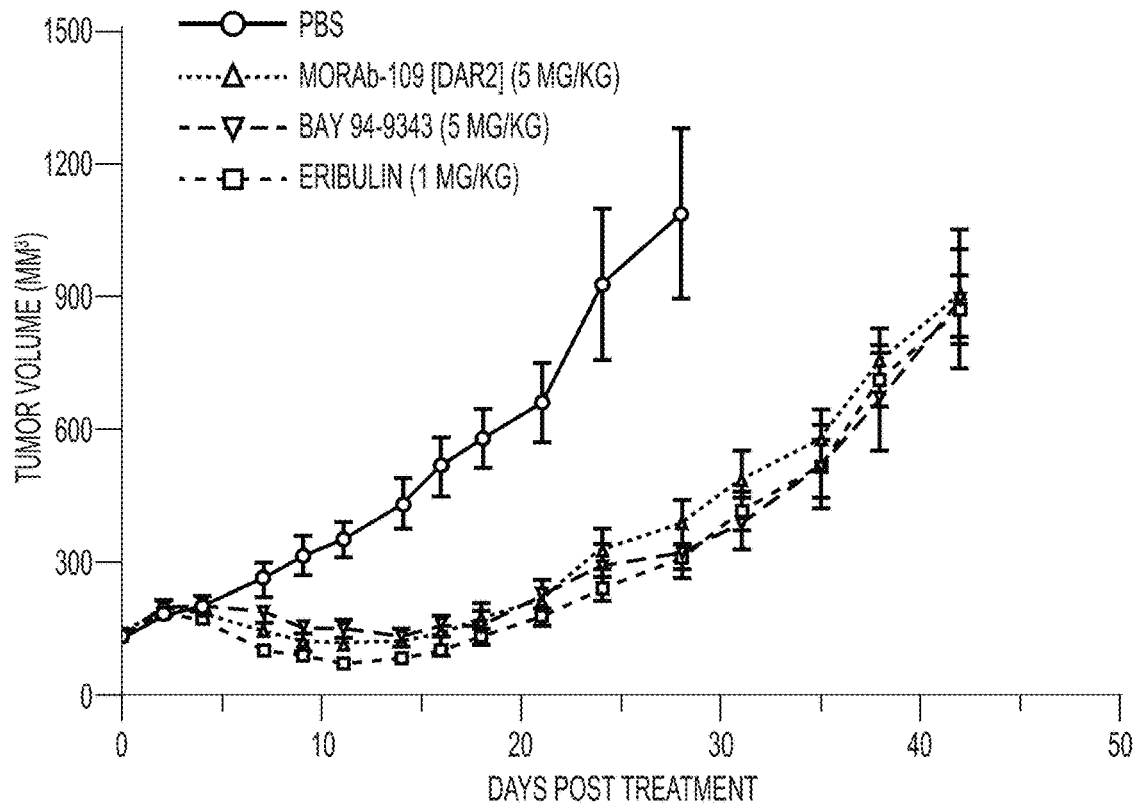
FIG. 29A and FIG. 29B show the anti-tumor effect (FIG. 29A) and body weight change (FIG. 29B) in a human mesothelioma HAY xenograft model treated with MORAb-109 (DAR2) (5 mg/kg), BAY 94-9343 (5 mg/kg), or eribulin (1 mg/kg).
Figure 29B:
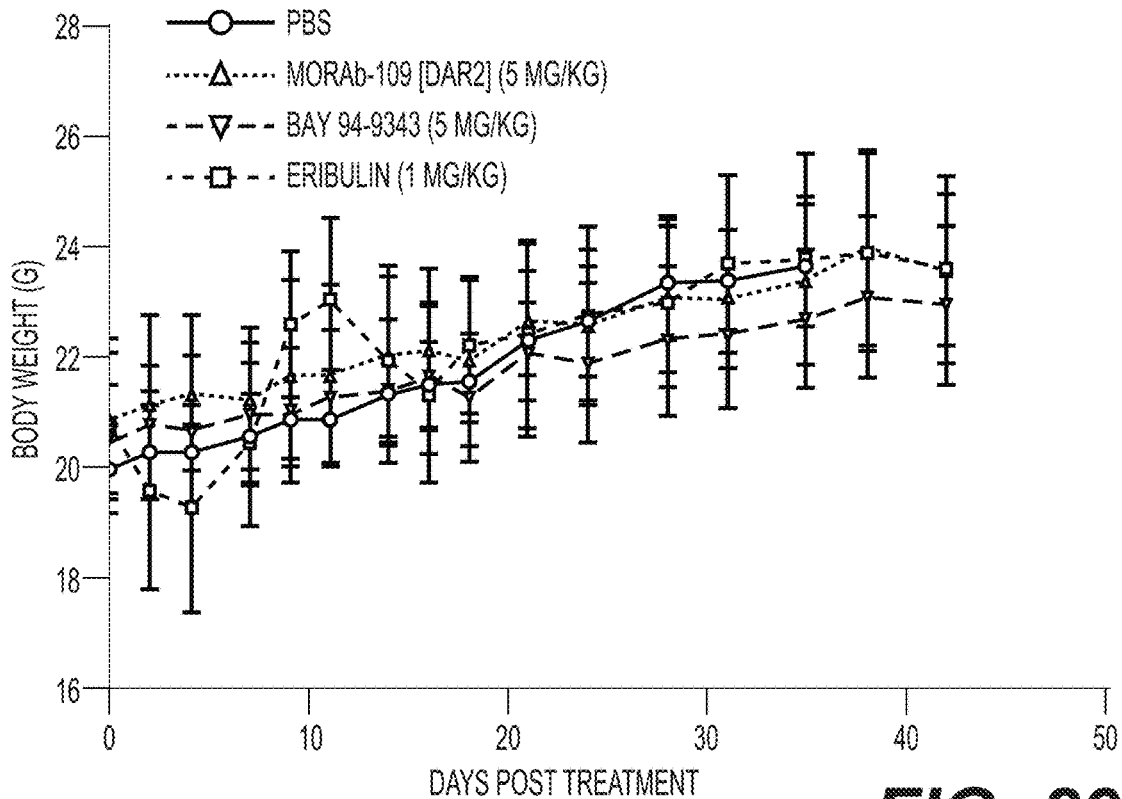

MORAb-109 (DAR2) and BAY 94-9343 both demonstrated similar efficacy in HAY tumor-bearing mice (FIG. 29A). No body weight loss was observed in either group (FIG. 29B).

Example 17: Anti-Tumor Efficacy of MORAb-109 and BAY 94-9343 in Human Mesothelioma PDX Model (Meso7212)

17.1 Methods

Animals: NMRI nu/nu female mice (Janvier Labs), 5 to 6 weeks old at the time of arrival, were acclimated for at least 4 days prior to inoculation. Animals were housed 3-5 mice per ventilated cage with sterilized food pellets and water bottle available ad lib. Animals were ear marked and weighed prior to study initiation Xenotransplantation: On day 0, Meso 7212 tumors were removed from the five donor mice under sterile conditions. The tumor tissue was cut into 2×2 mm fragments and placed in a sterile Petri dish covered with 0.9% saline. In parallel, the receptor animals were subcutaneously analgesic-treated with Metacam® (2 mg/kg) and then anaesthetized by a single intravenous injection (0.15 mL/mouse) with Etomidat-Lipuro® (12 mg/kg). A superficial vertical incision in the skin of 5-8 mm on the left flank was performed. The tip of a surgical scissor was inserted into the incision directly over the flank and was used to form a pocket in the subcutaneous space. One tumor fragment per mouse was implanted into the pocket using surgical tweezers. Finally, the incision was closed with a metal clip and the animal placed in a clean cage.

Experimental procedure: After the xenotransplantation, the engraftment and the propagation of the tumor in the mice were controlled at least twice weekly by palpation. When the tumor was palpable, the measurements of tumor diameters were performed with a digital caliper (Mitutoyo).

Prior starting the treatment, animals were randomly assigned into the experimental groups according to their tumor volume (inclusion criteria for tumor volume, 0.1-0.3 cm$^3$). From the first treatment day onwards, tumor volumes and body weights were recorded twice weekly. The animal welfare was controlled twice daily.

Treatment: All agents were administered intravenously as a single dose on the day of randomization. Animals in the control group were treated with DPBS in the same manner.

Statistical analysis: Descriptive statistics were performed on the data of tumor volume and body weight. Tumor volumes of animals from each treatment group were compared with the control group by using the repeated-measures two-way ANOVA followed by the Bonferroni post-test. Additionally, the comparison of tumor growth of animals within each group was also performed with the same statistical analysis.

17.2 Results

Figure 30A:
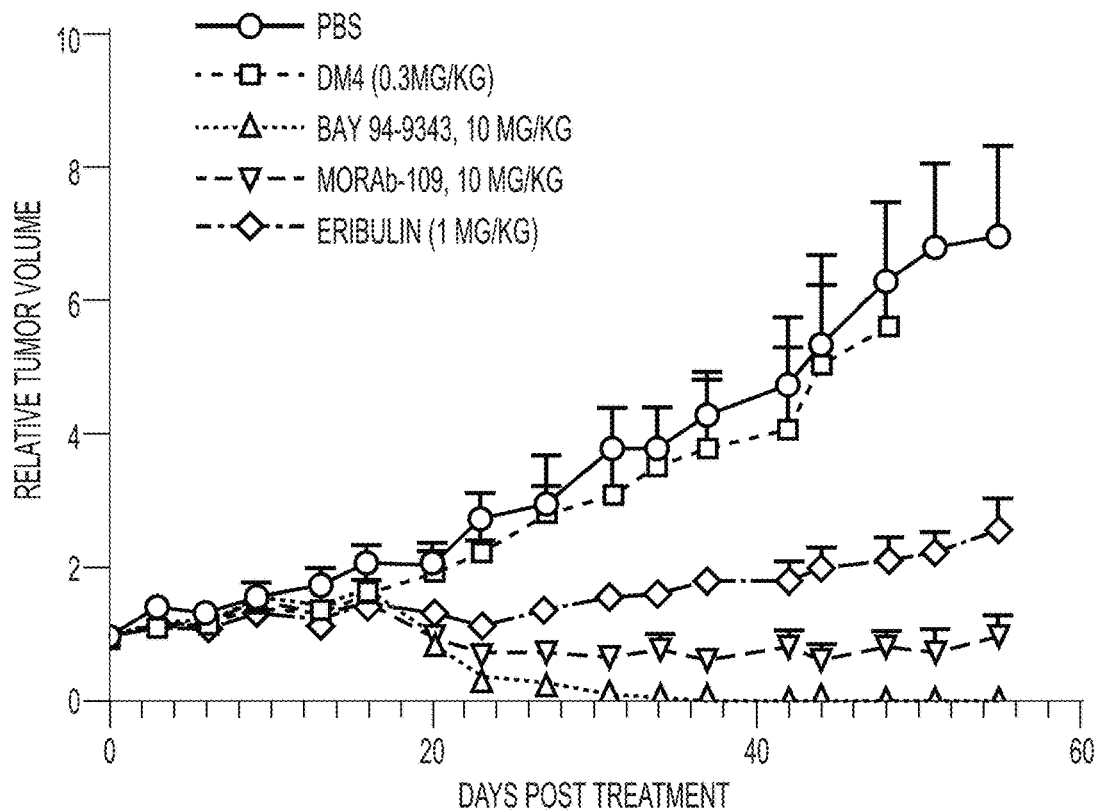
FIG. 30A and FIG. 30B show the anti-tumor effect (FIG. 30A) and body weight change (FIG. 30B) in a human mesothelioma PDX model (Meso7212) treated with MORAb-109 (DAR2) (10 mg/kg), BAY 94-9343 (10 mg/kg), eribulin (1 mg/kg), or DM4 (0.3 mg/kg).
Figure 30B:
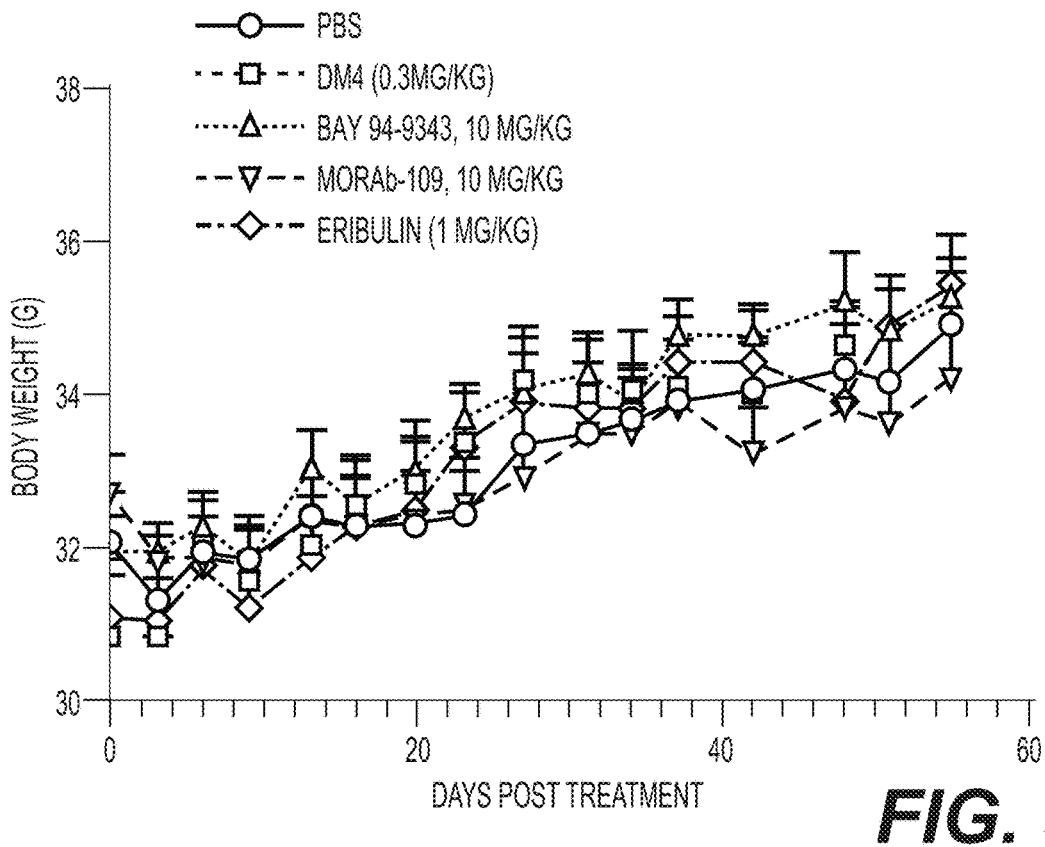

MORAb-109 (DAR2) and BAY 94-9343 both demonstrated tumor regression in Meso7212 tumor-bearing mice (FIG. 30A). No body weight loss was observed in either group (FIG. 30B).

Example 18: Anti-Tumor Efficacy of MORAb-109 and BAY 94-9343 in Human NSCLC PDX Model (LXFA-586)

18.1 Methods

Animals: Female NMRI nu/nu mice, 4 to 6 weeks of age.

Xenotransplantation: LXFA-586 established growing tumor (T2N1M0) from a primary non-small cell lung adenocarcinoma human patient.

Experimental procedure: Animals were monitored until the tumor implants reached the study volume criteria of 50-250 mm$^3$ (e.g., 80-200 mm$^3$) in a sufficient number of animals. Mice were assigned to groups aiming at comparable group median and mean tumor volumes. The process of the assignment to groups (enrollment, stratified randomization) may also be referred to as randomization. The day of randomization was designated as day 0 of the experiment.

Treatment: Efficacy was evaluated in 4 groups of 6 to 7 mice each:
  In group 1, vehicle was dosed at 5 mL/kg, i.v., single dose on day 1.
  In group 2, BAY 94-9343 (DAR~4) was dosed at 25 mg/kg, i.v., single dose on day 1.
  In group 3, MORAb-109 (DAR2) was dosed at 25 mg/kg, i.v., single dose on day 1.
  In group 4, eribulin was dosed at 3.2 mg/kg, i.v., single dose on day 1.

Tumors were measured and mice were weighed twice a week during the experimental period. The first day of dosing was day 1, one day after randomization (day 0).

18.2 Results

Figure 31A:
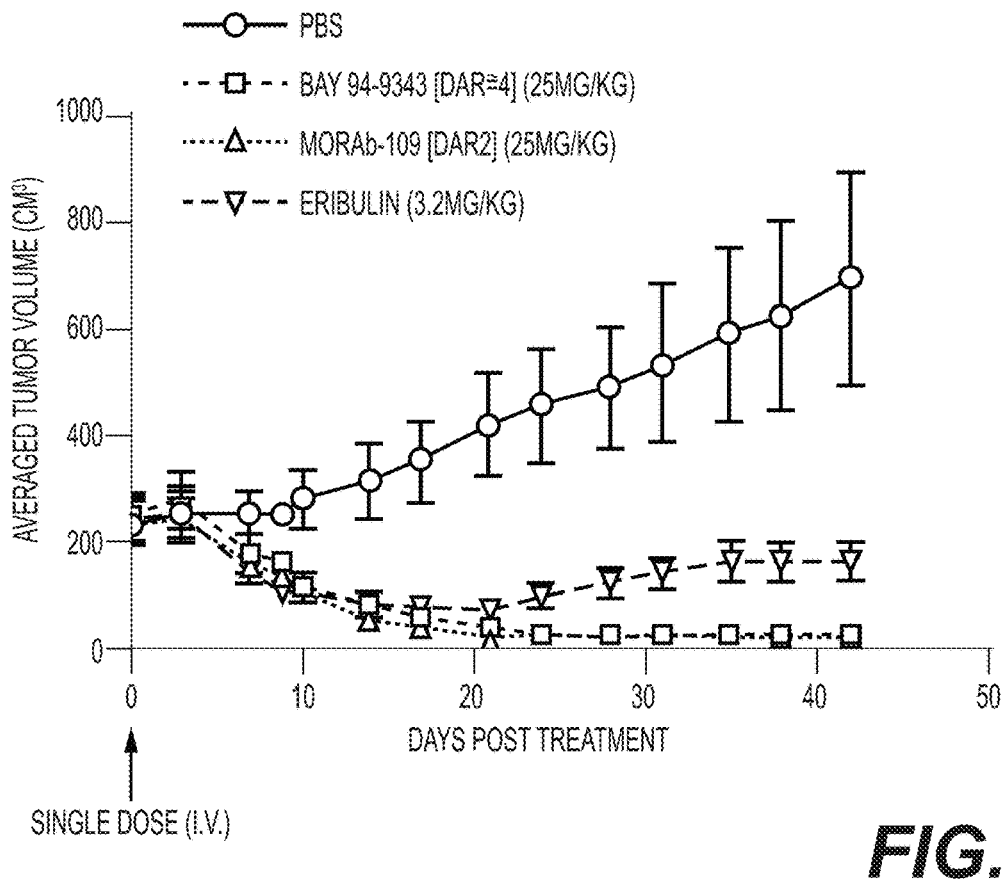
FIG. 31A and FIG. 31B show the anti-tumor effect (FIG. 31A) and body weight change (FIG. 31B) in a human NSCLC PDX model (LXFA-586) treated with MORAb-109 (DAR2) (25 mg/kg), BAY 94-9343 (DAR~4) (25 mg/kg), or eribulin (3.2 mg/kg).
Figure 31B:
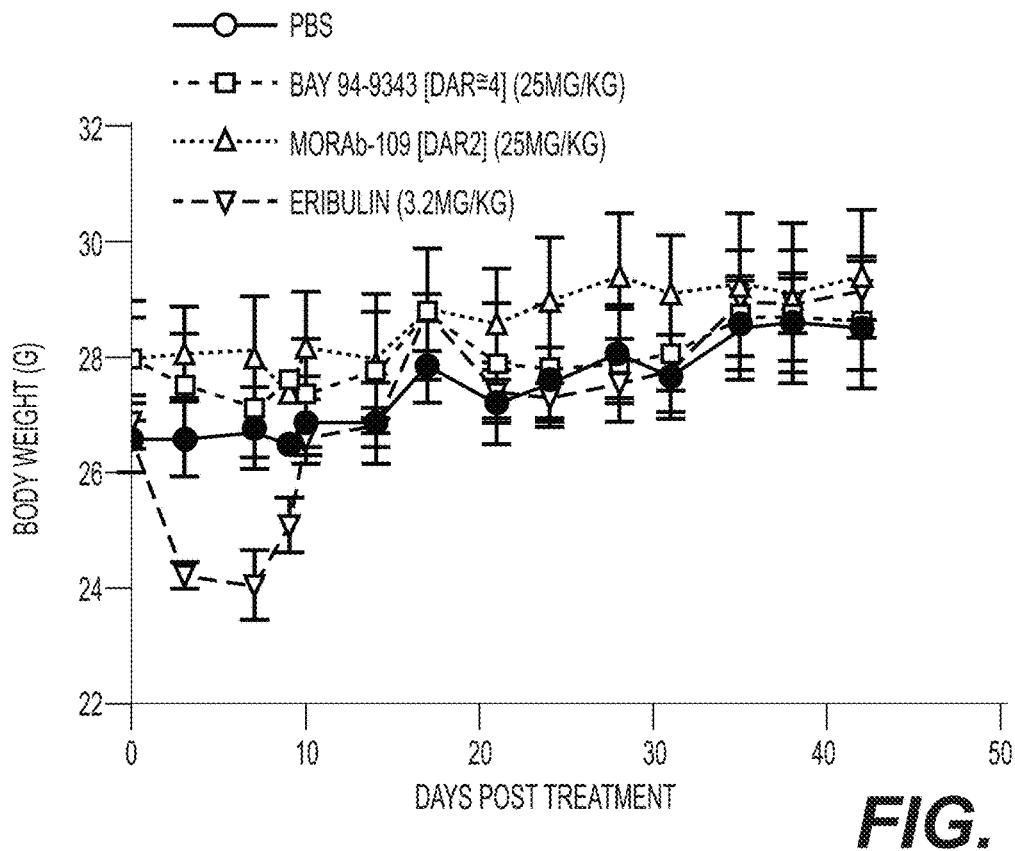

MORAb-109 (DAR2) demonstrated robust anti-tumor efficacy (minimum T/C, 1.8% on day 41) at 25 mg/kg in the LXFA-586 NSCLC PDX model (FIG. 31A) and its Tq was not reached during the study. MORAb-109 given at the single dose was also well tolerated without bodyweight loss by LXFA-586 tumor-bearing mice (FIG. 31B).

BAY 94-9343 (DAR~4) demonstrated robust anti-tumor efficacy similar to MORAb-109 at 25 mg/kg in the LXFA-586 NSCLC PDX model (FIG. 31A) and its Tq was not reached during the study. However, the molar amount of DM4 payload in BAY 94-9343 is approximately twice the amount of eribulin payload in MORAb-109.

Eribulin given at a single dose of 3.2 mg/kg (mouse MTD dosage or 32 times higher than the molar amount of eribulin in MORAb-109 when administered at 10 mg/kg) by intravenous route was well tolerated by LXFA-586 tumor-bearing mice, and showed anti-tumor efficacy (minimum T/C, 14.8% on day 21). However, eribulin induced slight and transient bodyweight loss after administration (FIG. 31A and FIG. 31B).

Example 19: Anti-Tumor Efficacy of MORAb-109 and BAY 94-9343 in Human NSCLC PDX Model (LXFL-529)

19.1 Methods

Animals: Female NMRI nu/nu mice, 4 to 6 weeks of age.

Xenotransplantation: LXFL-529 established growing tumor (T3N1M0) from a primary non-small cell lung adenocarcinoma human patient.

Experimental procedure: Animals were monitored until the tumor implants reached the study volume criteria of 50-250 mm$^3$ (e.g., 80-200 mm$^3$) in a sufficient number of animals. Mice were assigned to groups aiming at comparable group median and mean tumor volumes. The process of the assignment to groups (enrollment, stratified randomization) may also be referred to as randomization. The day of randomization was designated as day 0 of the experiment.

Treatment: Efficacy was evaluated in 6 groups of 6 to 7 mice each:
  In group 1, vehicle was dosed at 5 mL/kg, i.v., single dose on day 1.
  In group 2, BAY 94-9343 (DAR~4) was dosed at 12.5 mg/kg, i.v., single dose on day 1.
  In group 3, eribulin was dosed at 3.2 mg/kg, i.v., single dose on day 1.
  In group 4, MORAb-109 (DAR2) was dosed at 25 mg/kg, i.v., single dose on day 1.
  In group 5, MORAb-109 (DAR2) was dosed at 12.5 mg/kg, i.v., single dose on day 1.
  In group 6, MORAb-109 (DAR2) was dosed at 12.5 mg/kg, i.v., doses on days 1, 8, and 16.

Tumors were measured and mice were weighed twice a week during the experimental period. The first day of dosing was day 1, one day after randomization (day 0).

19.2 Results

Figure 32A:
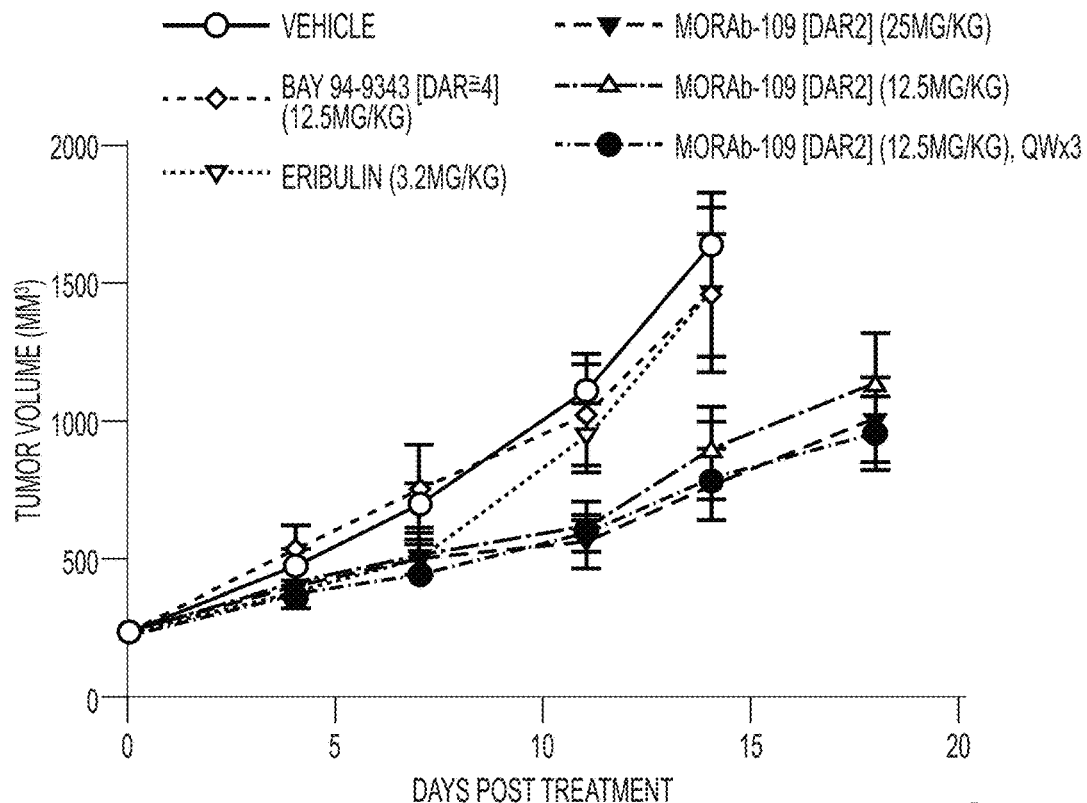
FIG. 32A and FIG. 32B show the anti-tumor effect (FIG. 32A) and body weight change (FIG. 32B) in a human NSCLC PDX model (LXFL-529) treated with MORAb-109 (DAR2) (25 mg/kg), MORAb-109 (DAR2) (12.5 mg/kg), MORAb-109 (DAR2) (12.5 mg/kg, QW×3), BAY 94-9343 (DAR~4) (12.5 mg/kg), or eribulin (3.2 mg/kg).
Figure 32B:
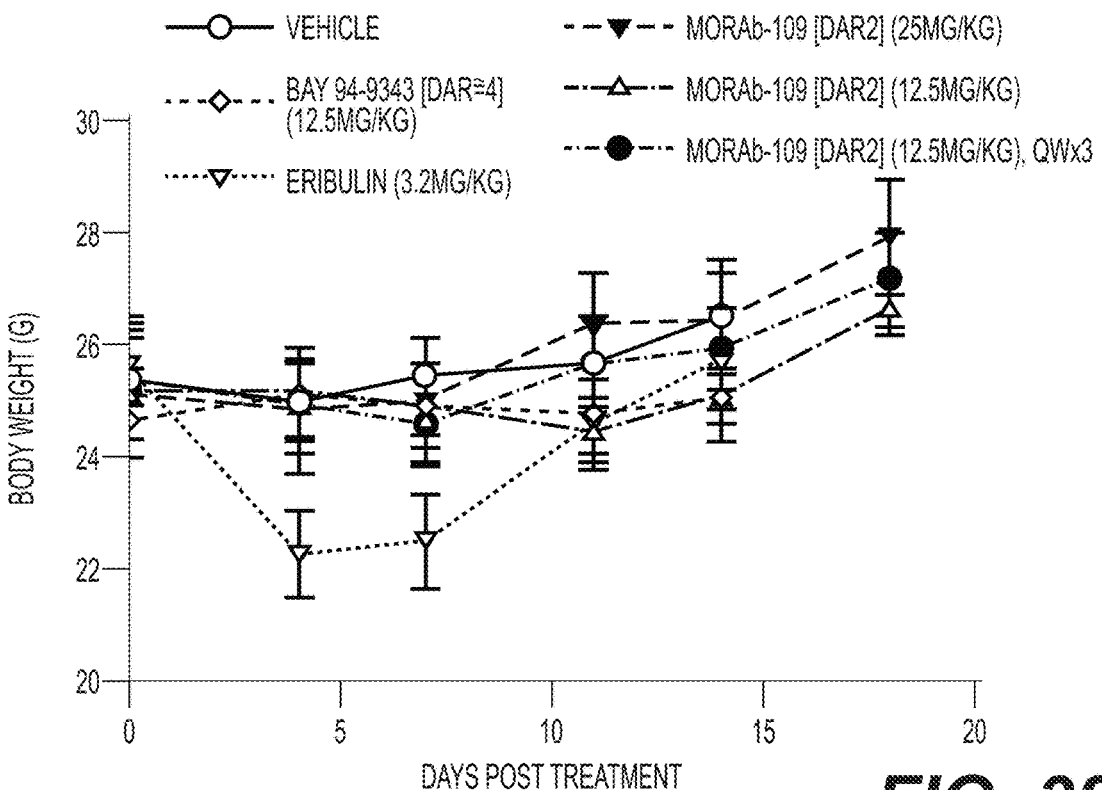

MORAb-109 (DAR2) demonstrated robust anti-tumor efficacy at 12.5 and 25 mg/kg in the LXFL-529 NSCLC PDX model (FIG. 32A). MORAb-109 given at the single dose was also well tolerated without bodyweight loss by LXFL-529 tumor-bearing mice (FIG. 32B).

BAY 94-9343 (DAR~4), however, at 12.5 mg/kg (the equivalent molar amount of DM4 payload as the amount of eribulin payload in MORAb-109 at 25 mg/kg) demonstrated no anti-tumor efficacy (FIG. 32A).

Eribulin given at a single dose of 3.2 mg/kg (mouse MTD dosage) by intravenous route was well tolerated by LXFL-529 tumor-bearing mice, and showed anti-tumor efficacy. However, eribulin induced slight and transient bodyweight loss after administration (FIG. 32A and FIG. 32B).

The invention claimed is:

1. An isolated antibody or antigen-binding fragment, wherein the antibody or antigen-binding fragment is capable of binding to mesothelin and comprises heavy chain complementarity determining regions comprising amino acid sequences of SEQ ID NO: 1 (HCDR1), SEQ ID NO: 2 (HCDR2), and SEQ ID NO: 3 (HCDR3); and light chain complementarity determining regions comprising amino acid sequences of SEQ ID NO: 4 (LCDR1), SEQ ID NO: 5 (LCDR2), and SEQ ID NO: 6 (LCDR3), as defined by the Kabat numbering system; or heavy chain complementarity determining regions comprising amino acid sequences of SEQ ID NO: 7 (HCDR1), SEQ ID NO: 8 (HCDR2), and SEQ ID NO: 9 (HCDR3); and light chain complementarity determining regions comprising amino acid sequences of SEQ ID NO: 10 (LCDR1), SEQ ID NO: 11 (LCDR2), and SEQ ID NO: 12 (LCDR3), as defined by the IMGT numbering system.

2. The antibody or antigen-binding fragment of claim 1, wherein the antibody or antigen-binding fragment comprises a heavy chain variable region comprising the amino acid sequence of SEQ ID NO: 13, and a light chain variable region comprising the amino acid sequence of SEQ ID NO: 14.

3. The antibody or antigen-binding fragment of claim 1, wherein the antibody or antigen-binding fragment comprises a heavy chain comprising the amino acid sequence of SEQ ID NO: 17, and a light chain comprising the amino acid sequence of SEQ ID NO: 18.

4. The antibody or antigen-binding fragment of claim 1, wherein the antibody or antigen-binding fragment is conjugated to a therapeutic agent.

5. The antibody or antigen-binding fragment of claim 4, wherein the therapeutic agent is eribulin.

6. A pharmaceutical composition comprising the antibody or antigen-binding fragment of claim 1, and a pharmaceutically acceptable carrier.

* * * * *

SEQUENCE LISTING

<160> NUMBER OF SEQ ID NOS: 54

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Ala Met Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Ile Asp Ile Ser Gly Asn Arg Phe Tyr Ala Asp Trp Val Lys Gly
1               5                   10                  15

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Asp Ser Arg Ala Trp Gly Pro Phe Asn Leu
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Ala Ser Gln Ser Ile Phe Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Ala Ser Asp Leu Ala Ser
1               5

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic

```
                                          -continued
      peptide

<400> SEQUENCE: 6

Gln Gln Gly Tyr Thr Arg Ser Asp Val Asp Asn Ala
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Ile Asp Leu Ser Ser Tyr Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Asp Ile Ser Gly Asn Arg
1               5

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Arg Val Asp Ser Arg Ala Trp Gly Pro Phe Asn Leu
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Ile Phe Ser Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Ala Ser
1

<210> SEQ ID NO 12
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Gly Tyr Thr Arg Ser Asp Val Asp Asn Ala
1               5                   10

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Val Glu Ser Gly Gly Val Val Gln Pro Gly Arg
1               5                   10                  15

Ser Leu Arg Leu Ser Cys Ala Ala Ser Gly Ile Asp Leu Ser Ser Tyr
                20                  25                  30

Ala Met Ser Trp Val Arg Gln Ala Pro Gly Lys Gly Leu Glu Trp Ile
            35                  40                  45

Gly Val Ile Asp Ile Ser Gly Asn Arg Phe Tyr Ala Asp Trp Val Lys
        50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Val Asp Ser Arg Ala Trp Gly Pro Phe Asn Leu Trp Gly Gln Gly
            100                 105                 110

Thr Leu Val Thr Val Ser Ser
        115

<210> SEQ ID NO 14
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Tyr Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Phe Ser Tyr
                20                  25                  30

Leu Ala Trp Tyr Gln Gln Lys Pro Gly Lys Ala Pro Lys Leu Leu Ile
            35                  40                  45

Tyr Asp Ala Ser Asp Leu Ala Ser Gly Val Pro Ser Arg Phe Ser Gly
        50                  55                  60

Ser Gly Ser Gly Thr Asp Phe Thr Leu Thr Ile Ser Ser Leu Gln Cys
65                  70                  75                  80

Glu Asp Ala Ala Thr Tyr Tyr Cys Gln Gln Gly Tyr Thr Arg Ser Asp
                85                  90                  95

Val Asp Asn Ala Phe Gly Gly Gly Thr Lys Val Glu Ile Lys
            100                 105                 110
```

<210> SEQ ID NO 15
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 16
<211> LENGTH: 107
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 17
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Ile Asp Leu Ser Ser Tyr
            20                  25                  30

Ala Met Ser Trp Val Arg Gln Ala Pro Gly Lys Gly Leu Glu Trp Ile
        35                  40                  45

Gly Val Ile Asp Ile Ser Gly Asn Arg Phe Tyr Ala Asp Trp Val Lys
    50                  55                  60

Gly Arg Phe Thr Ile Ser Arg Asp Asn Ser Lys Asn Thr Leu Tyr Leu
65                  70                  75                  80

Gln Met Ser Ser Leu Arg Ala Glu Asp Thr Ala Val Tyr Tyr Cys Ala
                85                  90                  95

Arg Val Asp Ser Arg Ala Trp Gly Pro Phe Asn Leu Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220
```

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 18
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Tyr Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Phe Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asp Leu Ala Ser Gly Val Pro Ser Arg Phe Ser Gly
    50                  55                  60

Ser Gly Ser Gly Thr Asp Phe Thr Leu Thr Ile Ser Ser Leu Gln Cys
65                  70                  75                  80

Glu Asp Ala Ala Thr Tyr Tyr Cys Gln Gln Tyr Thr Arg Ser Asp
                85                  90                  95

Val Asp Asn Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125
```

Lys Ser Gly Thr Ala Ser Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tcctacgcca tgtcc                                                         15

<210> SEQ ID NO 20
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gtgatcgaca tctccggcaa ccggttctac gccgactggg tgaagggc                     48

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gtggactcta gagcctgggg ccccttcaac ctg                                     33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
caggcctccc agtccatctt ctcctacctg gcc                                     33

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gacgcctctg atctggcctc c                                                 21

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cagcagggct acaccagatc cgacgtggac aacgcc                                 36

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggaatcgacc tgtcctccta cgcc                                              24

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atcgacatct ccggcaaccg g                                                 21

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gccagagtgg actctagagc ctggggcccc ttcaacctg                              39

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
cagtccatct tctcctac                                                     18

<210> SEQ ID NO 29
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 29 gacgcctct                                                                9

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagcagggct acaccagatc cgacgtggac aacgcc                                 36

<210> SEQ ID NO 31
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caggtgcagc tggtggaatc tggtggcgga gtggtgcagc tggcagatc cctgagactg        60 tcttgtgccg cctccggaat cgacctgtcc tcctacgcca tgtcctgggt gcgacaggct      120
cctggcaagg gcctggaatg gatcggcgtg atcgacatct ccggcaaccg gttctacgcc      180
gactgggtga agggccggtt caccatctcc agagacaact ccaagaacac cctgtacctc      240
cagatgtcct ccctgcgggc cgaggatacc gccgtgtact actgcgccag agtggactct      300
agagcctggg gccccttcaa cctgtggggc caggaacac tcgtgaccgt gtcctct         357

<210> SEQ ID NO 32
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
gattaccaga tgacccagtc cccctccagc ctgtccgctt ctgtgggcga cagagtgacc       60
atcacctgtc aggcctccca gtccatcttc tcctacctgg cctggtatca gcagaagccc     120
ggcaaggccc ccaagctgct gatctacgac gcctctgatc tggcctccgg cgtgccctct     180
agattctccg gctctggctc tggcaccgac tttaccctga ccatcagctc cctccagtgc     240
gaggatgccg ccacctacta ctgccagcag ggctacacca gatccgacgt ggacaacgcc     300
tttggcggag gcaccaaggt ggaaatcaaa                                      330

<210> SEQ ID NO 33
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
gcatccacca agggcccatc ggtcttcccc ctggcaccct cctccaagag cacctctggg       60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
```

```
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaact cctgggggga      360
ccgtcagtct tcctcttccc cccaaaaccc aaggacaccc tcatgatctc ccggacccct      420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacaac      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag gcagccccg agaaccacag gtgtacaccc tgcccccatc ccgggatgag       720
ctgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcttatat tcaaagctca ccgtggacaa gagcaggtgg      900
cagcagggga acgtcttctc atgctccgtg atgcatgagg ctctgcacaa ccactacacg      960
cagaagagcc tctccctgtc tcccgggaaa tga                                   993

<210> SEQ ID NO 34
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag      120
tggaaggtgg ataacgccct ccaatcgggt aactcccagg agagtgtcac agagcaggac      180
agcaaggaca gcacctacag cctcagcagc accctgacgc tgagcaaagc agactacgag      240
aaacacaaag tctacgcctg cgaagtcacc catcagggcc tgagctcgcc cgtcacaaag      300
agcttcaaca ggggagagtg ttga                                             324

<210> SEQ ID NO 35
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
caggtgcagc tggtggaatc tggtggcgga gtggtgcagc ctggcagatc cctgagactg      60
tcttgtgccg cctccggaat cgacctgtcc tcctacgcca tgtcctgggt gcgacaggct      120
cctggcaagg gcctggaatg gatcggcgtg atcgacatct ccggcaaccg gttctacgcc      180
gactgggtga agggccggtt caccatctcc agagacaact ccaagaacac cctgtacctc      240
cagatgtcct ccctgcgggc cgaggatacc gccgtgtact actgcgccag agtggactct      300
agagcctggg gccccttcaa cctgtggggc cagggaacac tcgtgaccgt gtcctctgca      360
tccaccaagg gcccatcggt cttccccctg gcaccctcct ccaagagcac ctctgggggc      420
acagcggccc tgggctgcct ggtcaaggac tacttccccg aaccggtgac ggtgtcgtgg      480
```

```
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttccccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cttatattca aagctcaccg tggacaagag caggtggcag    1260
caggggaacg tcttctcatg ctccgtgatg catgaggctc tgcacaacca ctacacgcag    1320
aagagcctct ccctgtctcc gggaaatga                                      1350

<210> SEQ ID NO 36
<211> LENGTH: 654
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
gattaccaga tgacccagtc cccctccagc ctgtccgctt ctgtgggcga cagagtgacc     60
atcacctgtc aggcctccca gtccatcttc tcctacctgg cctggtatca gcagaagccc    120
ggcaaggccc ccaagctgct gatctacgac gcctctgatc tggcctccgg cgtgccctct    180
agattctccg gctctggctc tggcaccgac tttaccctga ccatcagctc cctccagtgc    240
gaggatgccg ccacctacta ctgccagcag ggctacacca atccgacgt ggacaacgcc    300 tttggcggag gcaccaaggt ggaaatcaaa cgaactgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg ttga          654

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tyctcctggt crctsygctc                                                 20

<210> SEQ ID NO 38
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ttggtgttgg tggctgggtg                                              20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39 gggccccccac tcagctgctg                                             20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gttbtactgk tmtygatgcc                                              20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tyctcctggt crctsygctc                                              20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ttggtgttgg tggctgggtg                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
actcagctgc tggggctcct                                              20

<210> SEQ ID NO 44
<211> LENGTH: 20
<212> TYPE: DNA
```

-continued

<213> ORGANISM: Artificial Sequence
<220> FEATURE:
<223> OTHER INFORMATION: Description of Artificial Sequence: Synthetic
      primer

<400> SEQUENCE: 44
gttbtactgk tmtygatgcc                                                   20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttggtgttgg tggctgggtg                                                   20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gttbtactgk tmtygatgcc                                                   20

<210> SEQ ID NO 47
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gccaccggcg tgcactccca gtcgytggag gagtccgggg g                           41

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gggcccttgg tggatgctga rgagacrgtg acsagggtsc c                           41

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gccaccggcg tgcactccgc ctatgatatg acccagactc ca                          42

<210> SEQ ID NO 50
<211> LENGTH: 33
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 50
agccacagtt cgtttgacsa ccacctcggt ccc                                    33

<210> SEQ ID NO 51
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51
```

Gln Val Glu Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Ala Pro Gly Lys Gly Leu Glu Trp Met
        35                  40                  45

Gly Ile Ile Asp Pro Gly Asp Ser Arg Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gln Leu Tyr Gly Gly Thr Tyr Met Asp Gly Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 52
<211> LENGTH: 1350
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
caggttgaac tggttcagtc tggcgccgaa gtgaagaagc tggcgagag  cctgaagatc      60 agctgcaaag gcagcggcta cagcttcacc agctattgga tcggctgggt tcgacaggcc     120
cctggcaaag gactggaatg gatgggaatc atcgaccccg gcgacagcag aaccagatac     180
agccctagct tcagggcca gtgaccatc agcgccgaca gagcatcag cacagcctac       240 ctgcagtggt ctagcctgaa agccagcgac accgccatgt actattgtgc cagaggccag    300
ctgtacggcg gcacctatat ggatggatgg ggccagggca cactggtcac agtgtctagc    360
gcctctacaa agggcctag cgttttccca ctggctccta gcagcaagag cacatctggt    420
ggaacagccg ctctgggctg cctggtcaag gattactttc ctgagcctgt gaccgtgtcc    480
tggaatagcg gagcactgac aagcggcgtg cacacatttc cagctgtgct gcagagcagc    540
ggcctgtact ctctgtctag cgtcgtgaca gtgcctagca gctctctggg cacccagacc    600
tacatctgca acgtgaacca caagcctagc aacaccaagg tggacaagaa ggtggaaccc    660
aagagctgcg acaagaccca cacctgtcct ccatgtcctg ctccagaact gctcggcgga    720
ccctccgttt tcctgtttcc acctaagcct aaggacaccc tgatgatcag caggacccct    780
gaagtgacct gtgtggtggt ggatgtgtcc cacgaggacc cagaagtgaa gttcaattgg    840
tacgtggacg gcgtggaagt gcacaacgcc aagaccaagc ctagagagga acagtacaac    900
agcacctaca gagtggtgtc cgtgctgacc gtgctgcacc aggattggct gaacggcaaa    960
gagtacaagt gcaaggtgtc caacaaggcc ctgcctgctc tatcgagaa aaccatcagc   1020 aaggccaagg gccagccaag agaaccccag gtttacacac tgcctccaag cagggacgag   1080
ctgaccaaga atcaggtgtc cctgacctgc ctcgtgaagg gcttctaccc ttccgatatc   1140
gccgtggaat gggagagcaa tggccagcct gagaacaact acaagacaac ccctcctgtg   1200
ctggacagcg acggctcatt cttcctgtac agcaagctga cagtggacaa gtccagatgg   1260
```
cagcagggca acgtgttcag ctgttctgtg atgcacgagg ccctgcacaa ccactacacc    1320
cagaaaagcc tgtctctgag ccccggcaaa    1350

<210> SEQ ID NO 53
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Gly Tyr
            20                  25                  30

Asn Ser Val Ser Trp Tyr Gln Gln His Pro Gly Lys Ala Pro Lys Leu
        35                  40                  45

Met Ile Tyr Gly Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Asp Ile Glu
                85                  90                  95

Ser Ala Thr Pro Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Gly Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 54
<211> LENGTH: 651
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
gatattgctc tgacacagcc tgccagcgtg tccggatctc ctggccagag catcacaatc     60
agctgtaccg gcacaagcag cgacatcggc ggctacaata gcgtgtcctg gtatcagcag    120
cacccccgga aggccccctaa gctgatgatc tacggcgtga acaacagacc cagcggcgtg    180
tccaatagat tcagcggcag caagagcggc aataccgcct ctctgacaat tagcggactg    240
caggccgagg acgaggccga ttactactgc agcagctacg acatcgagag cgccacacct    300

-continued

| | | | | | |
|---|---|---|---|---|---|
| gtgtttggcg | gcggaacaaa | actgacagtg | ctgggccaac | ctaaggccgc | tcctagcgtt | 360 |
| acactgttcc | cacctagcag | cgaggaactg | caggctaaca | aggccacact | cgtgtgcctg | 420 |
| atcagcgatt | tttaccctgg | cgccgtgaca | gtggcctgga | aaggcgatag | ttctcctgtg | 480 |
| aaggccggcg | tggaaaccac | cacacctagc | aagcagagca | acaacaaata | cgccgccagc | 540 |
| tcctacctga | gcctgacacc | tgagcagtgg | aagtcccaca | gatcctacag | ctgccaagtg | 600 |
| acccacgagg | gcagcaccgt | ggaaaaaaca | gtggcccta | ccgagtgcag | c | 651 |